United States Patent
Nagase et al.

(10) Patent No.: US 10,351,522 B2
(45) Date of Patent: Jul. 16, 2019

(54) SULFONAMIDE DERIVATIVE AND PHARMACEUTICALLY ACCEPTABLE ACID ADDITION SALT THEREOF

(71) Applicants: UNIVERSITY OF TSUKUBA, Tsukuba-shi, Ibaraki (JP); BOARD OF REGENTS, THE UNIVERSITY OF TEXAS SYSTEM, Austin, TX (US)

(72) Inventors: Hiroshi Nagase, Tsukuba (JP); Masashi Yanagisawa, Tsukuba (JP); Tsuyoshi Saitoh, Tsukuba (JP); Noriki Kutsumura, Tsukuba (JP); Yoko Irukayama, Tsukuba (JP)

(73) Assignees: UNIVERSITY OF TSUKUBA, Tsukuba (JP); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/735,835

(22) PCT Filed: Jun. 10, 2016

(86) PCT No.: PCT/JP2016/067405
§ 371 (c)(1),
(2) Date: Dec. 12, 2017

(87) PCT Pub. No.: WO2016/199906
PCT Pub. Date: Dec. 15, 2016

(65) Prior Publication Data
US 2018/0179151 A1 Jun. 28, 2018

(30) Foreign Application Priority Data
Jun. 12, 2015 (JP) ................. 2015-119785

(51) Int. Cl.
C07D 213/81 (2006.01)
C07C 311/29 (2006.01)
A61K 31/18 (2006.01)
A61K 31/341 (2006.01)
A61K 31/36 (2006.01)
A61K 31/381 (2006.01)
A61K 31/4164 (2006.01)
A61K 31/4402 (2006.01)
A61K 31/4406 (2006.01)
A61K 31/4409 (2006.01)
(Continued)

(52) U.S. Cl.
CPC ............ *C07C 311/29* (2013.01); *A61K 31/18* (2013.01); *A61K 31/341* (2013.01); *A61K 31/36* (2013.01); *A61K 31/381* (2013.01); *A61K 31/4164* (2013.01); *A61K 31/4402* (2013.01); *A61K 31/4406* (2013.01); *A61K 31/4409* (2013.01); *A61K 31/4439* (2013.01); *A61P 25/00* (2018.01); *A61P 43/00* (2018.01); *C07C 311/21* (2013.01); *C07C 317/44* (2013.01); *C07C 335/20* (2013.01); *C07D 213/36* (2013.01); *C07D 213/75* (2013.01); *C07D 213/81* (2013.01); *C07D 233/36* (2013.01); *C07D 239/10* (2013.01); *C07D 243/04* (2013.01); *C07D 295/10* (2013.01); *C07D 307/54* (2013.01); *C07D 317/68* (2013.01); *C07D 333/36* (2013.01); *C07D 417/04* (2013.01); *C07C 2601/04* (2017.05)

(58) Field of Classification Search
CPC ...... A61K 31/18; A61K 31/341; A61K 31/36; A61K 31/381; A61K 31/4164; A61K 31/4402; A61K 31/4406; A61K 31/4409; A61K 31/4439; C07D 213/81; C07D 233/36; C07D 295/10; C07D 307/54; C07D 317/68; C07D 333/36; C07D 417/04

See application file for complete search history.

(56) References Cited

U.S. PATENT DOCUMENTS

| | | | |
|---|---|---|---|
| 6,153,585 | A | 11/2000 | Rubenstein et al. |
| 6,630,513 | B1 | 10/2003 | Rubenstein et al. |

(Continued)

FOREIGN PATENT DOCUMENTS

| | | |
|---|---|---|
| JP | 2000-319249 A | 11/2000 |
| JP | 2005-534684 A | 11/2005 |

(Continued)

OTHER PUBLICATIONS

CAS Abstract WO 2006047302 (2006).*

(Continued)

*Primary Examiner* — Alexander R Pagano
(74) *Attorney, Agent, or Firm* — Leydig, Voit & Mayer, Ltd.

(57) ABSTRACT

The present invention aims to provide a novel low-molecular-weight compound exhibiting an orexin receptor agonist activity and expected to be useful as a prophylactic or therapeutic agent for narcolepsy and the like. The present invention provides a compound represented by the formula (I):

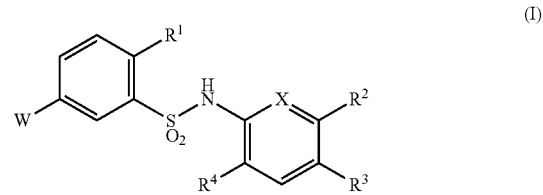

wherein each symbol is as defined in the description, or a pharmaceutically acceptable acid addition salt thereof, which has an orexin receptor agonist activity, and an orexin receptor agonist containing the compound or a pharmaceutically acceptable acid addition salt thereof.

20 Claims, 1 Drawing Sheet

(51) Int. Cl.
| | |
|---|---|
| A61K 31/4439 | (2006.01) |
| C07D 213/75 | (2006.01) |
| C07D 317/68 | (2006.01) |
| C07D 333/36 | (2006.01) |
| C07C 311/21 | (2006.01) |
| C07D 417/04 | (2006.01) |
| C07D 295/10 | (2006.01) |
| C07D 213/36 | (2006.01) |
| C07D 307/54 | (2006.01) |
| A61P 25/00 | (2006.01) |
| C07D 233/36 | (2006.01) |
| C07D 239/10 | (2006.01) |
| C07C 317/44 | (2006.01) |
| C07D 243/04 | (2006.01) |
| C07C 335/20 | (2006.01) |
| A61P 43/00 | (2006.01) |

(56) References Cited

U.S. PATENT DOCUMENTS

| | | | |
|---|---|---|---|
| 8,258,163 | B2 | 9/2012 | Yanagisawa |
| 9,815,787 | B2 * | 11/2017 | Nagase ............... C07D 213/81 |
| 2004/0097547 | A1 | 5/2004 | Taveras et al. |
| 2004/0180892 | A1 | 9/2004 | Wu et al. |
| 2008/0255240 | A1 | 10/2008 | Christiansen et al. |
| 2009/0186920 | A1 | 7/2009 | Knust et al. |
| 2009/0258903 | A1 | 10/2009 | Coleman et al. |
| 2009/0275588 | A1 | 11/2009 | Aissaoui et al. |
| 2016/0362376 | A1 | 12/2016 | Nagase et al. |

FOREIGN PATENT DOCUMENTS

| | | | | |
|---|---|---|---|---|
| JP | 2006-519785 | A | 8/2006 | |
| JP | 2007-536348 | A | 12/2007 | |
| JP | 2009-503106 | A | 1/2009 | |
| JP | 2009-533419 | A | 9/2009 | |
| JP | 2011-510037 | A | 3/2011 | |
| WO | WO 2004/011418 | A1 | 2/2004 | |
| WO | WO-2006047302 | A1 * | 5/2006 | ........... C07C 311/29 |
| WO | WO 2014/006402 | A1 | 1/2014 | |
| WO | WO 2015/088000 | A1 | 6/2015 | |
| WO | WO-2015088000 | A1 * | 6/2015 | ........... C07D 213/81 |
| WO | WO-2016133160 | A1 * | 8/2016 | ............. A61K 31/18 |

OTHER PUBLICATIONS

CAS Abstract, H. Nagase et al., U.S. Pat. No. 9,815,787 (2015).*
CAS Abstract, A. Mjalli et al., WO 2006/047302 (2006).*
Compound Registry Nos. Indexed by CAS (2016).*
I. A. Clark et al., 11 Journal of Neuroinflammation (2014) (Year: 2014).*
D. Smart et al., 440 European Journal of Pharmacology, 199-212 (2002) (Year: 2002).*
T.E. Scammell et al., 51 Annual Review of Pharmacology and Toxicology, 243-266 (2011) (Year: 2011).*
J. Adrien, 6 Sleep Medical Reviews (2002) (Year: 2002).*
Yanagisawa, English-Language Machine Translation of WO 2016/133160 (2016) (Year: 2016).*
Chemelli et al., "Narcolepsy in orexin Knockout Mice: Molecular Genetics of Sleep Regulation," Cell, 98(4): 437-451 (1999).
De Lecea et al., "The hypocretins: Hypothalamus-specific peptides with neuroexcitatory activity," Proc. Natl. Acad. Sci. USA, 95(1): 322-327 (1998).
Deutschman et al., "Orexinergic Activity Modulates Altered Vital Signs and Pituitary Hormone Secretion in Experimental Sepsis," Crit. Care Med., 41(11): e368-e375 (2013).
Funato et al., "Enhanced Orexin Receptor-2 Signaling Prevents Diet-Induced Obesity and Improves Leptin Sensitivity," Cell Metab., 9(1): 64-76 (2009).
Grossberg et al., "Inflammation-Induced Lethargy is Mediated by Suppression of Orexin Neuron Activity," J. Neurosci., 31(31): 11376-11386 (2011).
Lin et al., "The Sleep Disorder Canine Narcolepsy is Caused by a Mutation in the Hypocretin (Orexin) Receptor 2 Gene," Cell, 98(3): 365-376 (1999).
Mignot et al., "The Role of Cerebrospinal Fluid Hypocretin Measurement in the Diagnosis of Narcolepsy and Other Hypersomnias," Arch. Neurol., 59(10): 1553-1562 (2002).
Nagahara et al., "Design and Synthesis of Non-Peptide, Selective Orexin Receptor 2 Agonists," J. Med. Chem., 58(20): 7931-7937 (2015).
Sakurai et al., "Orexins and Orexin Receptors: a Family of Hypothalamic Neuropeptides and G Protein-Coupled Receptors that Regulate Feeding Behavior," Cell, 92(4): 573-585 (1998).
Willie et al., "Distinct Narcolepsy Syndromes in Orexin Receptor-2 and Orexin Null Mice: Molecular Genetic Dissection of Non-REM and REM Sleep Regulatory Processes," Neuron, 38(5): 715-730 (2003).
Yamanaka et al., "Hypothalamic Orexin Neurons Regulate Arousal According to Energy Balance in Mice," Neuron, 38(5): 701-713 (2003).
Japanese Patent Office, International Search Report in International Patent Application No. PCT/JP2016/067405 (dated Aug. 16, 2016).
Japanese Patent Office, Written Opinion of the International Searching Authority in International Patent Application No. PCT/JP2016/067405 (dated Aug. 16, 2016).
Asinex, "Benzamide, 3-(3-aminophenyl)-3-[[(3-aminophenyl)amino]sulfonyl]," Database Z Registry, Chemical Abstracts Service, Database Accession No. RN: 300383-04-04 (Oct. 30, 2000).
Asinex, "Benzamide, 3-[[[4-(benzoylamino)phenyl]amino]sulfonyl]-N-(2-nitrophenyl)," Database Z Registry, Chemical Abstracts Service, Database Accession No. RN: 301656-17-7 (Nov. 8, 2000).
Asinex, "Benzamide, 3-[[[4-(benzoylamino)phenyl]amino]sulfonyl]-N-(4-bromophenyl)," Database Z Registry, Chemical Abstracts Service, Database Accession No. RN: 301656-23-5 (Nov. 8, 2000).
Chembridge Corporation, "Benzamide, 3-[[[4-(benzoylamino)phenyl]amino]sulfonyl]-4-methyl-N-phenyl," Database Z Registry, Chemical Abstracts Service, Database Accession No. Rn: 423726-65-2 (May 31, 2002).
Zelinksy Institute of Organic Chemistry, "Benzamide, 3-[[[4-benzoylamino)phenyl]amino]sulfonyl]-4-chloro-N-phenyl," Database Z Registry, Chemical Abstracts Service, Database Accession No. RN: 350246-87-6 (Aug. 3, 2001).
European Patent Office, Extended European Search Report in European Patent Application No. 16807611.5 (dated Jan. 24, 2019).

* cited by examiner

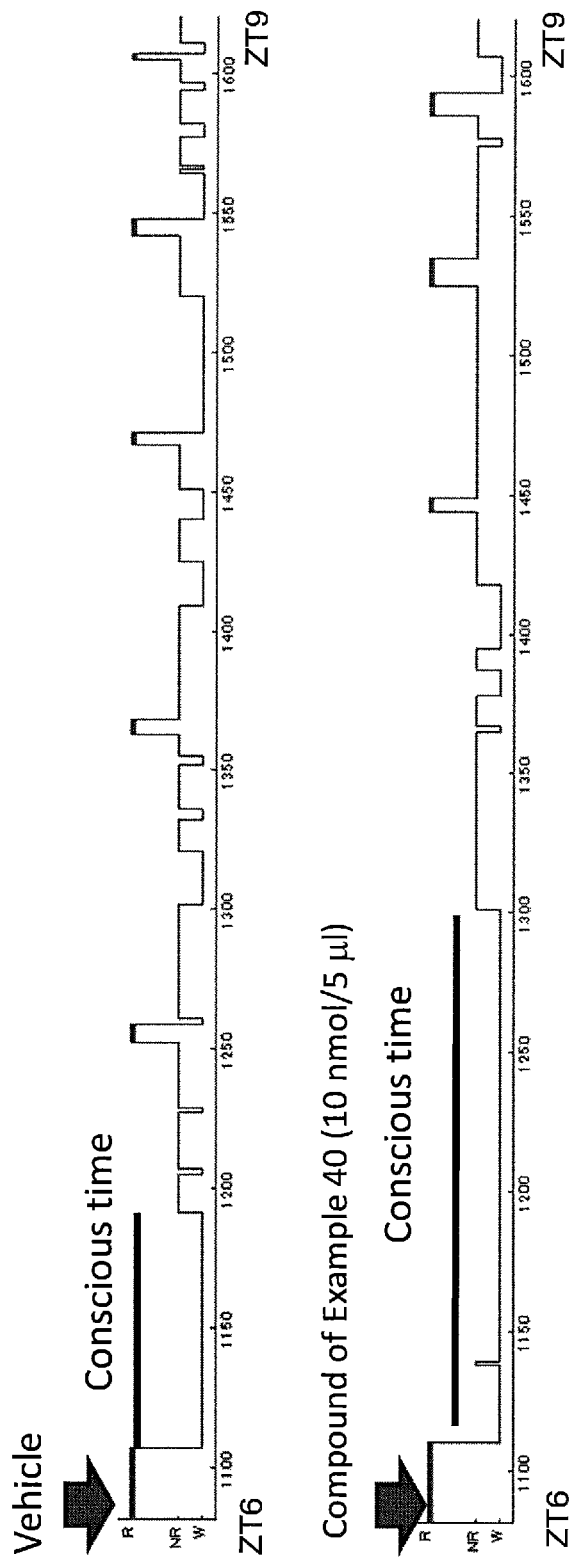

SULFONAMIDE DERIVATIVE AND PHARMACEUTICALLY ACCEPTABLE ACID ADDITION SALT THEREOF

CROSS-REFERENCE TO RELATED APPLICATIONS

This patent application is the U.S. national phase of International Patent Application No. PCT/JP2016/067405, filed Jun. 10, 2016, which claims the benefit of Japanese Patent Application No. 2015-119785, filed on Jun. 12, 2015, which are incorporated by reference in their entireties herein.

TECHNICAL FIELD

The present invention aims to provide a novel compound useful as an excellent orexin receptor agonist.

BACKGROUND ART

Narcolepsy is a sleeping disorder caused by the inability of the brain to control the sleep-wake cycle. The major symptoms of narcolepsy includes, for example, excessive daytime sleepiness, cataplexy induced by emotion (particularly strong joy and surprise), hypnagogic hallucination, and hypnagogic paralysis, and narcolepsy patients are under serious influence in general social life. The prevalence of narcolepsy is assumed to be 0.05-0.2% (0.16-0.18% in Japan), and the prevalence indicates that the disease is not rare.

The therapy of narcolepsy mainly includes a drug therapy and life guidance. For drug therapy, methylphenidate, modafinil and pemoline are used to suppress daytime sleepiness, and tricyclic antidepressant, selective serotonin reuptake inhibitor (SSRI), and serotonin and noradrenaline reuptake inhibitor (SNRI) are used to control cataplexy. While these treatment methods are symptomatic therapy of narcolepsy, they are not basic treatment methods.

In recent years, the relationship between narcolepsy and orexin system dysfunction is attracting attention. Orexins are neuropeptides present in the lateral hypothalamic area, which are two kinds of peptide of orexin-A and orexin-B (hypocretin 1, hypocretin 2 (non-patent document 1)). They bind to orexin 1 receptor (hereinafter to be also referred to as OX1R) and orexin 2 receptor (hereinafter to be also referred to as OX2R), which are G-protein coupled receptors (non-patent document 2). It was suggested from model experiments using mouse and dog that lack of orexin receptor (both OX1R and OX2R are expressed), or lack of OX2R causes narcolepsy (non-patent document 3). Furthermore, it was suggested from model experiments using mouse that the function of OX2R is important for maintaining wakefulness (non-patent document 4, non-patent document 5).

On the other hand, many narcolepsy patients were confirmed to show disappearance of orexin nerves, and decreased orexin concentration (non-patent document 6). Therefore, it is strongly suggested that narcolepsy is highly possibly caused by the lack of orexin.

The orexin receptor is widely expressed in the brain. Orexins are peptides, and are not useful for pharmaceutical use since permeability through the blood-brain barrier is extremely low. Therefore, a low-molecular-weight orexin receptor agonist has been desired. In recent years, a compound with a cyclic guanidine skeleton is reported as a small-molecule OX2R agonist (patent document 1).

In addition, orexin system is considered to not only control the above-mentioned sleep-wake but also appropriately control feeding behavior with emotion and energy balance. A mouse under fasting increases the amount of behavior for searching food by increasing the waking time and decreasing the sleep hours. On the other hand, it was clarified that the waking time and the amount of behavior do not increase in orexin receptor-deficient mouse (non-patent document 7). Moreover, it was suggested that an increase of the leptin sensitivity by OX2R regulates the homeostasis of body weight (non-patent document 8). From these findings, an orexin receptor (particularly OX2R) agonist is a potential therapeutic drug for not only narcolepsy but also diabetes, obesity and metabolic syndrome.

Furthermore, it has been reported that sepsis rats show a decrease in the spontaneous activity and a decrease in the activity of the orexin-containing neurons in the perifornical areas of hypothalamus (non-patent document 9). There is a report that intraventricular administration of orexin to a mouse sepsis model led to an increase in the body temperature and recovery of cardiac function (non-patent document 10). From these, it is possible that an orexin receptor agonist may become a therapeutic drug for sepsis.

DOCUMENT LIST

Patent Document patent document 1: U.S. Pat. No. 8,258,163

Non-Patent Documents non-patent document 1: Proc. Natl. Acad. Sci. USA, 95, 322-327 (1998)
non-patent document 2: Cell, 92, 573-585 (1998)
non-patent document 3: Cell, 98, 365-376 (1999)
non-patent document 4: Cell, 98, 437-451 (1999)
non-patent document 5: Neuron, 38, 715-730 (2003)
non-patent document 6: Arch. Neurol., 59, 1553-1562 (2002)
non-patent document 7: Neuron, 38, 701-713 (2003)
non-patent document 8: Cell Metab., 9, 64-76 (2009)
non-patent document 9: J. Neurosci., 31(31), 11376-11386 (2011)
non-patent document 10: Crit. Care Med., 41, 1-8 (2013)

SUMMARY OF THE INVENTION

Problems to be Solved by the Invention

The present invention aims to provide a novel low-molecular-weight compound showing an orexin agonist activity, which is expected to be useful as an excellent prophylactic or therapeutic agent for narcolepsy and the like.

Means of Solving the Problems

The present inventors have conducted intensive studies in an attempt to solve the aforementioned problems and found a compound represented by the formula (I) or (I') mentioned below and having an excellent OX2R agonist activity, which resulted in the completion of the present invention.

That is, the present invention provides the following.

[1] A compound represented by the formula (I):

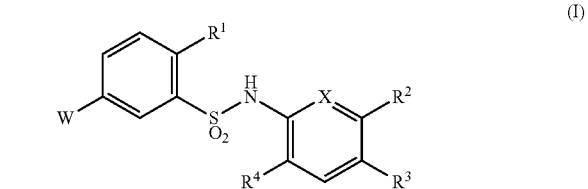

wherein
$R^1$ is a hydrogen atom, $C_{1-6}$ alkoxy, —OH, $C_{1-6}$ alkyl or a halogen atom,
X is —C($R^5$)═ or —N═,
$R^5$ is a hydrogen atom or $C_{1-6}$ alkoxy,
any one of $R^2$, $R^3$ and $R^4$ is $R^6$ and the remaining two are each a hydrogen atom,
$R^6$ is
(1) —NR$^{17}$—Y$^1$—R$^7$
wherein $Y^1$ is —C(═O)NR$^{18}$—, —C(═S)NH—, —C(═NH)NH—, —C(═O)O—, —C(═O)—, —SO$_2$— or —SO$_2$—NR$^8$—,
$R^8$ is a hydrogen atom or $C_{1-6}$ alkyl,
$R^{17}$ is a hydrogen atom or $C_{1-6}$ alkyl,
$R^{18}$ is a hydrogen atom or $C_{1-6}$ alkyl, or
$R^{17}$ and $R^{18}$ are optionally bonded to each other to form, together with the nitrogen atoms bonded thereto and adjacent C(═O), a 5- to 7-membered heterocycle,
$R^7$ is
(a) $C_{6-10}$ aryl,
(b) 5- to 10-membered heteroaryl,
(c) $C_{1-6}$ alkyl, or
(d) $C_{2-6}$ alkenyl
wherein $C_{1-6}$ alkyl and $C_{2-6}$ alkenyl are optionally substituted by one substituent selected from phenyl, furyl and diphenylmethylsulfinyl,
$C_{6-10}$ aryl and 5- to 10-membered heteroaryl are optionally substituted by optionally selected $R^9$ in the number of 1 to 4,
$R^9$ are each independently
a halogen atom,
—NO$_2$,
—OH,
$C_{1-6}$ alkyl,
$C_{1-6}$ haloalkyl,
$C_{1-6}$ alkoxy,
5- to 10-membered heteroaryl,
—NR$^{9a}$R$^{9b}$ wherein $R^{9a}$ is a hydrogen atom, $C_{1-6}$ alkyl or $C_{1-6}$ alkoxy-carbonyl, and $R^{9b}$ is a hydrogen atom or $C_{1-6}$ alkyl,
—C(═O)OR$^{9c}$ wherein $R^{9c}$ is a hydrogen atom or $C_{1-6}$ alkyl,
—C(═O)NR$^{9d}$R$^{9e}$ wherein $R^{9d}$ is a hydrogen atom or $C_{1-6}$ alkyl, and
$R^{9e}$ is a hydrogen atom or $C_{1-6}$ alkyl, or
—NH—C(═NR$^{9f}$)—NHR$^{9g}$ wherein $R^{9f}$ is a hydrogen atom or $C_{1-6}$ alkoxy-carbonyl, and $R^{9g}$ is a hydrogen atom or $C_{1-6}$ alkoxy-carbonyl, or
$R^9$ in the number of 2 are joined to form methylenedioxy,
(2) —NH—Y$^2$—R$^{10}$
wherein $Y^2$ is —CH$_2$— or a single bond, and
$R^{10}$ is
(a) $C_{6-10}$ aryl, or
(b) 5- to 10-membered heteroaryl
wherein $C_{6-10}$ aryl and 5- to 10-membered heteroaryl are optionally substituted by optionally selected $R^9$ in the number of 1 to 4, and $R^9$ is as defined above,
(3) a group represented by the formula (ii):

wherein $R^{11}$ is $C_{1-6}$ alkoxy or $C_{6-10}$ arylamino (wherein $C_{6-10}$ aryl moiety of the $C_{6-10}$ arylamino is optionally substituted by 1 to 3 substituents selected from $C_{1-6}$ alkyl and $C_{1-6}$ alkoxy), (4) —N═N—R$^{12}$
wherein $R^{12}$ is $C_{6-10}$ aryl optionally substituted by 1 to 3 substituents selected from (a) $C_{1-6}$ alkyl optionally substituted by —OH, (b) —OH, (c) di($C_{1-6}$ alkyl)amino and (d) $C_{1-6}$ alkoxy-carbonylamino, or
(5) —NR$^{13}$R$^{14}$
wherein $R^{13}$ is a hydrogen atom, $C_{1-6}$ alkyl, $C_{6-10}$ aryl-$C_{1-6}$ alkyl or $C_{2-6}$ alkenyl-carbonyl, and
$R^{14}$ is a hydrogen atom or $C_{1-6}$ alkyl (wherein $C_{1-6}$ alkyl is optionally substituted by one substituent selected from (a) $C_{1-6}$ alkoxy-carbonylamino, (b) $C_{2-6}$ alkenyl-carbonylamino and (c) $C_{6-10}$ aryl-$C_{1-6}$ alkylaminocarbonyl optionally substituted by $C_{1-6}$ alkyl), or $R^{13}$ and $R^{14}$ are bonded to each other to form, together with the nitrogen atom bonded thereto, a 5- to 7-membered heterocycle further containing one nitrogen atom (wherein 5- to 7-membered heterocycle is optionally substituted by $C_{6-10}$ aryl-carbonyl optionally substituted by $C_{1-6}$ alkyl), provided that when $R^{14}$ is ethyl substituted by $C_{2-6}$ alkenyl-carbonylamino, $R^{13}$ is not a hydrogen atom, and
W is
(1) a group represented by the formula (iii):

wherein $R^{15}$ is $C_{1-6}$ alkyl, and $R^{16}$ is $C_{1-6}$ alkyl, or
(2) —C(═O)NR$^{Wa}$R$^{Wb}$
wherein $R^{Wa}$ is $C_{1-6}$ alkyl (wherein $C_{1-6}$ alkyl is optionally substituted by phenyl, pyridyl, $C_{1-6}$ alkoxy-carbonylamino or di($C_{1-6}$ alkyl)amino) or phenyl (wherein phenyl is optionally substituted by di($C_{1-6}$ alkyl)amino), and $R^{Wb}$ is a hydrogen atom or $C_{1-6}$ alkyl),
or a pharmaceutically acceptable acid addition salt thereof (hereinafter to be also referred to as compound (I)).
[2] The compound of the aforementioned [1] wherein $R^{17}$ and $R^{18}$ are each a hydrogen atom, or a pharmaceutically acceptable acid addition salt thereof.
[3] The compound of the aforementioned [1] that is a compound represented by the formula (I-A):

wherein each symbol is as defined in the aforementioned [1], or a pharmaceutically acceptable acid addition salt thereof.
[4] The compound of the aforementioned [3] wherein $R^{17}$ and $R^{18}$ are each a hydrogen atom, or a pharmaceutically acceptable acid addition salt thereof.
[5] The compound of any one of the aforementioned [1] to [4] wherein X is —C($R^5$)═ (wherein $R^5$ is a hydrogen atom or $C_{1-6}$ alkoxy), or a pharmaceutically acceptable acid addition salt thereof.

[6] The compound of any one of the aforementioned [1] to [5] wherein $R^2$ is $R^6$ (wherein $R^6$ is as defined in the aforementioned [1]), and $R^3$ and $R^4$ are each a hydrogen atom, or a pharmaceutically acceptable acid addition salt thereof.

[7] The compound of any one of the aforementioned [1] to [6] wherein $R^6$ is —$NR^{17}$—$Y^1$—$R^7$ (wherein $R^{17}$, $Y^1$ and $R^7$ are as defined in the aforementioned [1]), or a pharmaceutically acceptable acid addition salt thereof.

[8] The compound of any one of the aforementioned [1] to [6] wherein $R^6$ is —NH—$Y^2$—$R^{10}$ (wherein $Y^2$ and $R^{10}$ are as defined in the aforementioned [1]), or a pharmaceutically acceptable acid addition salt thereof.

[9] The compound of any one of the aforementioned [1] to [6] wherein $R^6$ is a group represented by the formula (ii):

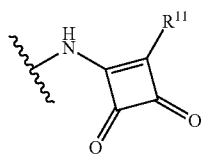

(ii)

wherein $R^{11}$ is as defined in the aforementioned [1], or a pharmaceutically acceptable acid addition salt thereof.

[10] The compound of any one of the aforementioned [1] to [6] wherein $R^6$ is —N=N—$R^{12}$ (wherein $R^{12}$ is as defined in the aforementioned [1]), or a pharmaceutically acceptable acid addition salt thereof.

[11] The compound of any one of the aforementioned [1] to [6] wherein $R^6$ is —$NR^{13}R^{14}$ (wherein $R^{13}$ and $R^{14}$ are as defined in the aforementioned [1]), or a pharmaceutically acceptable acid addition salt thereof.

[12] The compound of the aforementioned [1] wherein W is a group represented by the formula (iii):

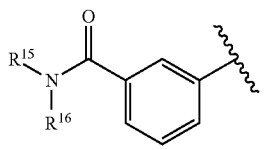

(iii)

wherein $R^{15}$ is $C_{1-6}$ alkyl and $R^{16}$ is $C_{1-6}$ alkyl,

X is —C($R^5$)= wherein $R^5$ is a hydrogen atom or $C_{1-6}$ alkoxy, $R^2$ is —NH—$Y^1$—$R^7$ wherein $Y^1$ and $R^7$ are as defined in the aforementioned [1], and $R^3$ and $R^4$ are each a hydrogen atom, or a pharmaceutically acceptable acid addition salt thereof.

[13] The compound of the aforementioned [12] wherein $Y^1$ is —C(=O)NH—, —C(=S)NH—, —C(=NH)NH— or —C(=O)O—, or a pharmaceutically acceptable acid addition salt thereof.

[14] The compound of the aforementioned [1] that is represented by the formula (I-B):

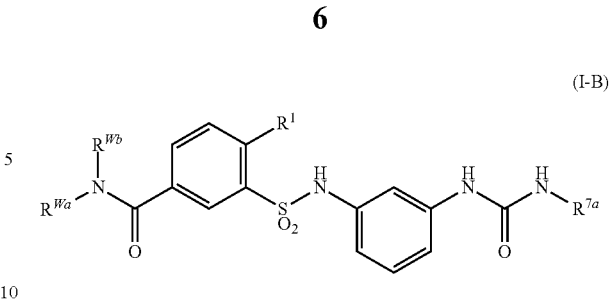

(I-B)

wherein $R^{7a}$ is phenyl substituted by —$NR^{9a}R^{9b}$ (wherein $R^{9a}$ is $C_{1-6}$ alkyl and $R^{9b}$ is $C_{1-6}$ alkyl), and each of other symbols is as defined in the aforementioned [1], or a pharmaceutically acceptable acid addition salt thereof.

[15] A compound represented by the formula (I'):

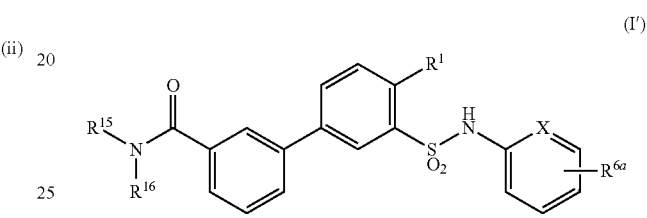

(I')

wherein $R^1$ is a hydrogen atom, $C_{1-6}$ alkoxy, —OH, $C_{1-6}$ alkyl or a halogen atom, X is —C($R^5$)= or —N=, $R^5$ is a hydrogen atom or $C_{1-6}$ alkoxy, $R^{6a}$ is an optionally substituted hydrocarbon group, an optionally substituted heterocyclic group, a group bonded via an oxygen atom, or a group bonded via a sulfur atom, $R^{15}$ is $C_{1-6}$ alkyl, and $R^{16}$ is $C_{1-6}$ alkyl, or a pharmaceutically acceptable acid addition salt thereof.

[16] A medicament comprising the compound of any one of the above-mentioned [1] to [15] or a pharmaceutically acceptable acid addition salt thereof.

[17] An orexin receptor agonist comprising the compound of any one of the above-mentioned [1] to [15] or a pharmaceutically acceptable acid addition salt thereof.

[18] An anti-narcolepsy agent comprising the compound of any one of the above-mentioned [1] to [15] or a pharmaceutically acceptable acid addition salt thereof.

[19] An agent for improving sleepiness comprising the compound of any one of the above-mentioned [1] to [15] or a pharmaceutically acceptable acid addition salt thereof.

[20] A prophylactic or therapeutic agent for obesity, diabetes or depression comprising the compound of any one of the aforementioned [1] to [15] or a pharmaceutically acceptable acid addition salt thereof.

[21] A prophylactic or therapeutic agent for sepsis, severe sepsis or septic shock comprising the compound of any one of the aforementioned [1] to [15] or a pharmaceutically acceptable acid addition salt thereof.

[22] A method of treating or preventing narcolepsy comprising administering an effective amount of the compound of any one of the above-mentioned [1] to [15] or a pharmaceutically acceptable acid addition salt thereof.

[23] A method of improving sleepiness comprising administering an effective amount of the compound of any one of the aforementioned [1] to [15] or a pharmaceutically acceptable acid addition salt thereof.

[24] A method of treating or preventing obesity, diabetes or depression comprising administering an effective amount of the compound of any one of the aforementioned [1] to [15] or a pharmaceutically acceptable acid addition salt thereof.

[25] A method of treating or preventing sepsis, severe sepsis or septic shock comprising administering an effective amount of the compound of any one of the aforementioned [1] to [15] or a pharmaceutically acceptable acid addition salt thereof.

[26] The compound of any one of the aforementioned [1] to [15] or a pharmaceutically acceptable acid addition salt thereof for use in the treatment or prophylaxis of narcolepsy.

[27] The compound of any one of the aforementioned [1] to [15] or a pharmaceutically acceptable acid addition salt thereof for use in the improvement of sleepiness.

[28] The compound of any one of the aforementioned [1] to [15] or a pharmaceutically acceptable acid addition salt thereof for use in the treatment or prophylaxis of obesity, diabetes or depression.

[29] The compound of any one of the aforementioned [1] to [15] or a pharmaceutically acceptable acid addition salt thereof for use in the treatment or prophylaxis of sepsis, severe sepsis or septic shock.

[30] Use of the compound of any one of the aforementioned [1] to [15] or a pharmaceutically acceptable acid addition salt thereof for the production of an orexin receptor agonist; an anti-narcolepsy agent; an agent for improving sleepiness; a prophylactic or therapeutic agent for obesity, diabetes or depression; or a prophylactic or therapeutic agent for sepsis, severe sepsis or septic shock.

Effect of the Invention

The compound represented by the formula (I) or (I') or a pharmaceutically acceptable acid addition salt thereof of the present invention has an excellent OX2R agonist activity.

BRIEF DESCRIPTION OF THE DRAWINGS

The FIGURE shows a hypnogram for 3 hr after intraventricular administration of a control substance (5% chromophore-containing saline (Vehicle)) or a test compound (compound of Example 40) to a wild-type mouse (WT mouse) in light period.

DESCRIPTION OF EMBODIMENTS

The following terms used in the present specification are as defined below unless otherwise specified.

The "$C_{1-6}$ alkyl" in the present specification means a monovalent straight chain or branched saturated hydrocarbon group having a carbon number of 1 to 6 and composed of a carbon atom and a hydrogen atom. For example, methyl, ethyl, propyl, isopropyl, butyl, isobutyl, sec-butyl, tert-butyl, pentyl, neopentyl, hexyl and the like can be mentioned.

The "$C_{1-6}$ alkoxy" in the present specification means an oxy group to which $C_{1-6}$ alkyl is bonded. For example, methoxy, ethoxy, propoxy, isopropoxy, butoxy, isobutoxy, tert-butoxy and the like can be mentioned.

The "halogen atom" in the present specification means a fluorine atom, a chlorine atom, a bromine atom or an iodine atom.

The "$C_{2-6}$ alkenyl" in the present specification means a monovalent straight chain or branched unsaturated hydrocarbon group having a carbon number of 2 to 6 and at least one double bond, and composed of a carbon atom and a hydrogen atom. For example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like can be mentioned.

The "$C_{2-6}$ alkynyl" in the present specification means a monovalent straight chain or branched unsaturated hydrocarbon group having a carbon number of 2 to 6 and at least one triple bond, and composed of a carbon atom and a hydrogen atom. For example, ethynyl, propynyl, butynyl, pentynyl, hexynyl and the like can be mentioned.

The "$C_{3-10}$ cycloalkyl" in the present specification means a monocyclic or polycyclic aliphatic carbon cyclic group having 3 to 10 carbon atoms. For example, cyclopropyl, cyclobutyl, cyclopentyl, cyclohexyl, cycloheptyl, cyclooctyl, adamantyl and the like can be mentioned.

The "$C_{6-10}$ aryl" in the present specification means a monocyclic or fused aromatic carbon cyclic group having 6 to 10 carbon atoms. For example, phenyl, 1-naphthyl, 2-naphthyl and the like can be mentioned.

The "5- to 10-membered heteroaryl" in the present specification means a 5- to 10-membered monocyclic or bicyclic aromatic heterocyclic group containing, as a ring-constituting atom besides carbon atom, 1 to 4 hetero atoms of one or two kinds selected from oxygen atom, sulfur atom and nitrogen atom. For example, thienyl, furyl, pyrrolyl, imidazolyl, pyrazolyl, triazolyl, tetrazolyl, oxazolyl, isoxazolyl, triazolyl, isothiazolyl, pyridyl, pyridazinyl, pyrimidinyl, furazanyl, pyrazinyl, thiadiazolyl, oxadiazolyl, benzofuryl, benzothienyl, benzimidazolyl, benzothiazolyl, quinolyl, isoquinolyl, cinnolinyl, quinazolinyl, quinoxalinyl, phthalazinyl, 1H-indazolyl and the like can be mentioned.

The "$C_{1-6}$ haloalkyl" in the present specification means a $C_{1-6}$ alkyl substituted by 1 to 5 (preferably 1 to 3) halogen atoms. For example, trifluoromethyl, 2,2,2-trifluoroethyl, 3,3,3-trifluoropropyl and the like can be mentioned. It is preferably trifluoromethyl.

The "$C_{1-6}$ alkoxy-carbonyl" in the present specification means a carbonyl group bonded to $C_{1-6}$ alkoxy. For example, methoxycarbonyl, ethoxycarbonyl, propoxycarbonyl, isopropoxycarbonyl, butoxycarbonyl, isobutoxycarbonyl, tert-butoxycarbonyl and the like can be mentioned.

The "$C_{6-10}$ arylamino" in the present specification means an amino substituted by $C_{6-10}$ aryl. For example, phenylamino, 1-naphthylamino, 2-naphthylamino and the like can be mentioned. It is preferably phenylamino.

The "$C_{1-6}$ alkyl optionally substituted by —OH" in the present specification means $C_{1-6}$ alkyl optionally substituted by one —OH. For example, hydroxymethyl, 2-hydroxyethyl, 3-hydroxypropyl and the like can be mentioned.

The "di($C_{1-6}$ alkylamino" in the present specification means an amino substituted by two $C_{1-6}$ alkyl. For example, dimethylamino, diethylamino, dipropylamino, diisopropylamino, N-ethyl-N-methylamino and the like can be mentioned.

The "$C_{1-6}$ alkoxy-carbonylamino" in the present specification means an amino substituted by $C_{1-6}$ alkoxy-carbonyl. For example, methoxycarbonylamino, ethoxycarbonylamino, propoxycarbonylamino, isopropoxycarbonylamino, butoxycarbonylamino, isobutoxycarbonylamino, tert-butoxycarbonylamino and the like can be mentioned.

The "$C_{6-10}$ aryl-$C_{1-6}$ alkyl" in the present specification means $C_{1-6}$ alkyl substituted by $C_{6-10}$ aryl. For example, benzyl, phenethyl and the like can be mentioned. It is preferably, benzyl.

The "$C_{2-6}$ alkenyl-carbonyl" in the present specification means a carbonyl group bonded to $C_{2-6}$ alkenyl. For example, acryloyl, methacryloyl and the like can be mentioned.

The "$C_{2-6}$ alkenyl-carbonylamino" in the present specification means an amino substituted by $C_{2-6}$ alkenyl-carbonyl. For example, acryloylamino, methacryloylamino and the like can be mentioned.

The "$C_{6-10}$ aryl-$C_{1-6}$ alkylaminocarbonyl" in the present specification means an aminocarbonyl substituted by $C_{6-10}$ aryl-$C_{1-6}$ alkyl. For example, benzylaminocarbonyl, phenethylaminocarbonyl and the like can be mentioned. It is preferably benzylaminocarbonyl.

The "$C_{6-10}$ aryl-carbonyl" in the present specification means a carbonyl group bonded to $C_{6-10}$ aryl. For example, benzoyl, 1-naphthoyl, 2-naphthoyl and the like can be mentioned. It is preferably benzoyl.

In the present specification, as the 5- to 7-membered heterocycle further containing one nitrogen atom, which is formed by $R^{13}$ and $R^{14}$, bonded to each other, together with the nitrogen atom bonded thereto, imidazolidine, piperazine or 1,4-diazepane can be mentioned.

In the present specification, as the 5- to 7-membered heterocycle formed by $R^{17}$ and $R^{18}$, bonded to each other, together with the nitrogen atoms bonded thereto and adjacent C(=O), imidazolidin-2-one, hexahydropyrimidin-2-one or 1,3-diazepan-2-one can be mentioned.

As the "hydrocarbon group" of the "optionally substituted hydrocarbon group" in the present specification, $C_{1-6}$ alkyl, $C_{2-6}$ alkenyl, $C_{2-6}$ alkynyl, $C_{3-10}$ cycloalkyl, $C_{6-10}$ aryl and the like can be mentioned.

As the "heterocyclic group" of the "optionally substituted heterocyclic group" in the present specification, 5- to 10-membered heteroaryl, 4- to 10-membered nonaromatic heterocyclic group and the like can be mentioned.

The "4- to 10-membered nonaromatic heterocyclic group" in the present specification means a 4- to 10-membered monocyclic or bicyclic saturated or unsaturated nonaromatic heterocyclic group containing, as a ring-constituting atom besides carbon atom, 1 to 4 hetero atoms of one or two kinds selected from oxygen atom, sulfur atom and nitrogen atom. For example, azetidinyl, oxetanyl, pyrrolidinyl, tetrahydrofuryl, imidazolidinyl, pyrazolidinyl, piperidyl, tetrahydropyranyl, tetrahydrothiopyranyl, piperazinyl, morpholinyl, thiomorpholinyl, azepanyl, oxazepanyl, diazepanyl, pyrrolinyl, imidazolinyl, pyrazolinyl and the like can be mentioned.

As the "group bonded via an oxygen atom" in the present specification, an oxy group (—O—) bonded to an optionally substituted hydrocarbon group or optionally substituted heterocyclic group and the like can be mentioned.

As the "group bonded via a sulfur atom" in the present specification, a thio group (—S—), sulfinyl group (—SO—) or sulfonyl group (—SO$_2$—) bonded to an optionally substituted hydrocarbon group, an optionally substituted heterocyclic group, or a group bonded via a nitrogen atom and the like can be mentioned.

As the "group bonded via a nitrogen atom" in the present specification, amino bonded to an optionally substituted hydrocarbon group, amino bonded to an optionally substituted heterocyclic group and the like can be mentioned.

Being "optionally substituted" in the present specification means, for example, being optionally substituted by 1 to 5, preferably 1 to 3, substituents selected from the following substituent group.

Substituent Group
halogen atom,
—NO$_2$,
—CN,
—OH,
oxo (=O),
$C_{1-6}$ alkyl,
$C_{1-6}$ haloalkyl,
$C_{1-6}$ alkoxy,
$C_{2-6}$ alkenyl,
$C_{2-6}$ alkynyl,
$C_{3-10}$ cycloalkyl,
$C_{6-10}$ aryl,
$C_{6-10}$ aryl-$C_{1-6}$ alkyl,
5- to 10-membered heteroaryl,
4- to 10-membered nonaromatic heterocyclic group,
—NR$^{21a}$R$^{21b}$
wherein R$^{21a}$ and R$^{21b}$ are each independently a hydrogen atom, $C_{1-6}$ alkyl, $C_{1-6}$ alkoxy-carbonyl, $C_{2-6}$ alkenyl, $C_{2-6}$ alkynyl, $C_{3-10}$ cycloalkyl, $C_{6-10}$ aryl, $C_{6-10}$ aryl-$C_{1-6}$ alkyl, 5- to 10-membered heteroaryl or 4- to 10-membered nonaromatic heterocyclic group,
—C(=O)OR$^{21c}$
wherein R$^{21c}$ is a hydrogen atom, $C_{1-6}$ alkyl, $C_{2-6}$ alkenyl, $C_{2-6}$ alkynyl, $C_{3-10}$ cycloalkyl, $C_{6-10}$ aryl or $C_{6-10}$ aryl-$C_{1-6}$ alkyl,
—C(=O)NR$^{21d}$R$^{21e}$
wherein R$^{21d}$ and R$^{21e}$ are each independently a hydrogen atom, $C_{1-6}$ alkyl, $C_{2-6}$ alkenyl, $C_{2-6}$ alkynyl, $C_{3-10}$ cycloalkyl, $C_{6-10}$ aryl, $C_{6-10}$ aryl-$C_{1-6}$ alkyl, 5- to 10-membered heteroaryl or 4- to 10-membered nonaromatic heterocyclic group,
—NH—C(=NR$^{21f}$)—NHR$^{21g}$
wherein R$^{21f}$ is a hydrogen atom or $C_{1-6}$ alkoxy-carbonyl and R$^{21g}$ is a hydrogen atom or $C_{1-6}$ alkoxy-carbonyl,
—OR$^{21h}$
wherein R$^{21h}$ is $C_{1-6}$ haloalkyl, $C_{2-6}$ alkenyl, $C_{2-6}$ alkynyl, $C_{3-10}$ cycloalkyl, $C_{6-10}$ aryl, $C_{6-10}$ aryl-$C_{1-6}$ alkyl, 5- to 10-membered heteroaryl or 4- to 10-membered nonaromatic heterocyclic group,
—C(=O)R$^{21i}$
wherein R$^{21i}$ is a hydrogen atom, $C_{1-6}$ alkyl, $C_{2-6}$ alkenyl, $C_{2-6}$ alkynyl, $C_{3-10}$ cycloalkyl, $C_{6-10}$ aryl, $C_{6-10}$ aryl-$C_{1-6}$ alkyl, 5- to 10-membered heteroaryl or 4- to 10-membered nonaromatic heterocyclic group,
=N—R$^{21j}$
wherein R$^{21j}$ is a hydrogen atom, —OH or $C_{1-6}$ alkoxy,
—S(O)$_n$—R$^{21k}$
wherein R$^{21k}$ is —OH, $C_{1-6}$ alkyl, $C_{2-6}$ alkenyl, $C_{2-6}$ alkynyl, $C_{3-10}$ cycloalkyl, $C_{6-10}$ aryl, $C_{6-10}$ aryl-$C_{1-6}$ alkyl, 5- to 10-membered heteroaryl or 4- to 10-membered nonaromatic heterocyclic group,
and n is 0, 1 or 2,
—SO$_2$—NR$^{21m}$R$^{21n}$
wherein R$^{21m}$ and R$^{21n}$ are each independently a hydrogen atom, $C_{1-6}$ alkyl, $C_{2-6}$ alkenyl, $C_{2-6}$ alkynyl, $C_{3-10}$ cycloalkyl, $C_{6-10}$ aryl, $C_{6-10}$ aryl-$C_{1-6}$ alkyl, 5- to 10-membered heteroaryl or 4- to 10-membered nonaromatic heterocyclic group, and
$C_{1-3}$ alkylenedioxy (e.g., methylenedioxy).

The "anti-narcolepsy agent" in the present specification means an agent for the treatment or prophylaxis of narcolepsy.

The "agent for improving sleepiness" in the present specification means a medicament for improving daytime sleepiness due to shift work, jet lag, insomnia, sleep apnea syndrome and the like.

The definition of each symbol in the formulas and preferable embodiments of the present invention are explained in the following.

$R^1$ is a hydrogen atom, $C_{1-6}$ alkoxy, —OH, $C_{1-6}$ alkyl or a halogen atom.

Examples of $R^1$ include a hydrogen atom, methoxy, ethoxy, propoxy, —OH, methyl, chlorine atom and the like.

$R^1$ is preferably $C_{1-6}$ alkoxy (e.g., methoxy, ethoxy, propoxy), particularly preferably methoxy.

W is (1) a group represented by the formula (iii):

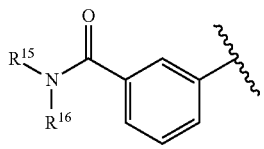

or (2) —C(=O)NR$^{Wa}$R$^{Wb}$.

W is preferably a group represented by the formula (iii):

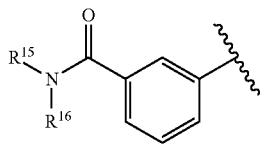

wherein $R^{15}$ is $C_{1-6}$ alkyl (e.g., methyl) and $R^{16}$ is alkyl (e.g., methyl).

In another embodiment, W is preferably —C(=O)NR$^{Wa}$R$^{Wb}$ wherein R$^{Wa}$ is $C_{1-6}$ alkyl (e.g., methyl, ethyl, propyl, 2,2-dimethylpropyl) (wherein $C_{1-6}$ alkyl is optionally substituted by phenyl, pyridyl, $C_{1-6}$ alkoxy-carbonylamino (e.g., tert-butoxycarbonylamino) or di($C_{1-6}$ alkyl) amino (e.g., dimethylamino)) or phenyl (wherein phenyl is optionally substituted by di($C_{1-6}$ alkyl)amino (e.g., dimethylamino)), and R$^{Wb}$ is a hydrogen atom or $C_{1-6}$ alkyl (e.g., ethyl)).

X is —C($R^5$)= or —N=, and $R^5$ is a hydrogen atom or $C_{1-6}$ alkoxy.

Examples of $R^5$ include a hydrogen atom and methoxy.

$R^5$ is preferably a hydrogen atom.

X is preferably —C($R^5$)=, particularly preferably —CH=.

Any one of $R^2$, $R^3$ and $R^4$ is $R^6$ and the remaining two are each a hydrogen atom.

As combinations of $R^2$, $R^3$ and $R^4$, the following combinations can be mentioned.

(1) $R^2$ is $R^6$, and $R^3$ and $R^4$ are each a hydrogen atom.
(2) $R^3$ is $R^6$, and $R^2$ and $R^4$ are each a hydrogen atom.
(3) $R^4$ is $R^6$, and $R^2$ and $R^3$ are each a hydrogen atom.

Of these, the combination wherein $R^2$ is $R^6$, and $R^3$ and $R^4$ are each a hydrogen atom is preferable.

$R^6$ is
(1) —NR$^{17}$—Y$^1$—R$^7$,
(2) —NH—Y$^2$—R$^{10}$,
(3) a group represented by the formula (ii):

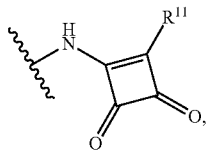

(4) —N=N—R$^{12}$, or
(5) —NR$^{13}$R$^{14}$.

$R^6$ is preferably
(1) —NH—Y$^1$—R$^7$,
(2) —NH—Y$^2$—R$^{10}$,
(3) a group represented by the formula (ii), or
(4) —N=N—R$^{12}$,
particularly preferably —NH—Y$^1$—R$^7$.

When $R^6$ is —NR$^{17}$—Y$^1$—R$^7$,
Y$^1$ is —C(=O)NR$^{18}$—, —C(=S)NH—, —C(=NH)NH—, —C(=O)O—, —C(=O)—, —SO$_2$— or —SO$_2$—NR$^8$—, preferably, —C(=O)NH—, —C(=S)NH—, —C(=NH)NH— or —C(=O)O—, particularly preferably —C(=O)NH—.

$R^8$ is a hydrogen atom or $C_{1-6}$ alkyl (e.g., methyl).

$R^{17}$ is a hydrogen atom or $C_{1-6}$ alkyl (e.g., methyl), $R^{18}$ is a hydrogen atom or $C_{1-6}$ alkyl (e.g., methyl), or $R^{17}$ and $R^{18}$ are optionally bonded to each other to form, together with the nitrogen atoms bonded thereto and adjacent C(=O), a 5- to 7-membered heterocycle (e.g., imidazolidin-2-one, hexahydropyrimidin-2-one, 1,3-diazepan-2-one).

$R^{17}$ and $R^{18}$ are each preferably a hydrogen atom.

$R^7$ is
(a) $C_{6-10}$ aryl (e.g., phenyl, 1-naphthyl, 2-naphthyl),
(b) 5- to 10-membered heteroaryl (e.g., pyridyl, thienyl, thiazolyl),
(c) $C_{1-6}$ alkyl (e.g., methyl, tert-butyl), or
(d) $C_{2-6}$ alkenyl (e.g., vinyl)
wherein $C_{1-6}$ alkyl and $C_{2-6}$ alkenyl are optionally substituted by one substituent selected from phenyl, furyl and diphenylmethylsulfinyl,
$C_{6-10}$ aryl and 5- to 10-membered heteroaryl are optionally substituted by optionally selected $R^9$ in the number of 1 to 4 (preferably 1 to 3, more preferably 1 or 2), $R^9$ are each independently
a halogen atom (e.g., bromine atom),
—NO$_2$,
—OH,
$C_{1-6}$ alkyl (e.g., methyl),
$C_{1-6}$ haloalkyl (e.g., trifluoromethyl),
$C_{1-6}$ alkoxy (e.g., methoxy),
5- to 10-membered heteroaryl (e.g., pyridyl),
—NR$^{9a}$R$^{9b}$ wherein R$^{9a}$ is a hydrogen atom, $C_{1-6}$ alkyl (e.g., methyl) or $C_{1-6}$ alkoxy-carbonyl (e.g., tert-butoxycarbonyl), and R$^{9b}$ is a hydrogen atom or $C_{1-6}$ alkyl (e.g., methyl),
—C(=O)OR$^{9c}$ wherein R$^{9c}$ is a hydrogen atom or $C_{1-6}$ alkyl (e.g., methyl),
—C(=O)NR$^{9d}$R$^{9e}$ wherein R$^{9d}$ is a hydrogen atom or $C_{1-6}$ alkyl (e.g., methyl), and R$^{9e}$ is a hydrogen atom or $C_{1-6}$ alkyl (e.g., methyl), or
—NH—C(=NR$^{9f}$)—NHR$^{9g}$ wherein R$^{9f}$ is a hydrogen atom or $C_{1-6}$ alkoxy-carbonyl (e.g., tert-butoxycarbonyl), and R$^{9g}$ is a hydrogen atom or $C_{1-6}$ alkoxy-carbonyl (e.g., tert-butoxycarbonyl), or
$R^9$ in the number of 2 are joined to form methylenedioxy.

$R^7$ is preferably
(a) $C_{6-10}$ aryl (e.g., phenyl, 1-naphthyl, 2-naphthyl), or
(b) 5- to 10-membered heteroaryl (e.g., pyridyl, thienyl, thiazolyl)
wherein $C_{6-10}$ aryl and 5- to 10-membered heteroaryl are optionally substituted by optionally selected $R^9$ in the number of 1 to 4 (preferably 1 to 3, more preferably 1 or 2), and $R^9$ is as defined above.

$R^7$ is particularly preferably phenyl substituted by —NR$^{9a}$R$^{9b}$ wherein R$^{9a}$ is $C_{1-6}$ alkyl (e.g., methyl) and R$^{9b}$ is a hydrogen atom or $C_{1-6}$ alkyl (e.g., methyl).

When $R^6$ is —NH—Y$^2$—R$^{10}$, Y$^2$ is —CH$_2$— or a single bond.

$R^{10}$ is (a) $C_{6-10}$ aryl (e.g., phenyl), or
(b) 5- to 10-membered heteroaryl (e.g., pyridyl, thienyl, thiazolyl)

wherein $C_{6-10}$ aryl and 5- to 10-membered heteroaryl are optionally substituted by optionally selected $R^9$ in the number of 1 to 4, and $R^9$ is as defined above.

$R^{10}$ is preferably $C_{6-10}$ aryl (e.g., phenyl)

wherein $C_{6-10}$ aryl is optionally substituted by optionally selected $R^9$ in the number of 1 to 4 (preferably 1 to 3, more preferably 1 or 2), $R^9$ are each independently a halogen atom (e.g., bromine atom),

—OH, $C_{1-6}$ alkyl (e.g., methyl), $C_{1-6}$ haloalkyl (e.g., trifluoromethyl), $C_{1-6}$ alkoxy (e.g., methoxy), or —C(=O)NR$^{9d}$R$^{9e}$ wherein $R^{9d}$ is a hydrogen atom or $C_{1-6}$ alkyl (e.g., methyl), and $R^{9e}$ is a hydrogen atom or $C_{1-6}$ alkyl (e.g., methyl), or $R^9$ in the number of 2 are joined to form methylenedioxy.

When $R^6$ is a group represented by the formula (ii), $R^{11}$ is $C_{1-6}$ alkoxy (e.g., methoxy) or $C_{6-10}$ arylamino (e.g., phenylamino) (wherein the $C_{6-10}$ aryl moiety of $C_{6-10}$ arylamino is optionally substituted by 1 to 3 substituents selected from $C_{1-6}$ alkyl (e.g., methyl) and $C_{1-6}$ alkoxy (e.g., methoxy).

When $R^6$ is —N=N—$R^{12}$, $R^{12}$ is $C_{6-10}$ aryl (e.g., phenyl) optionally substituted by 1 to 3 substituents selected from (a) $C_{1-6}$ alkyl (e.g., methyl) optionally substituted by —OH, (b) —OH, (c) di($C_{1-6}$ alkyl)amino (e.g., dimethylamino) and (d) $C_{1-6}$ alkoxy-carbonylamino (e.g., tert-butoxycarbonylamino).

When $R^6$ is —NR$^{13}$R$^{14}$, $R^{13}$ is a hydrogen atom, $C_{1-6}$ alkyl (e.g., methyl), $C_{6-10}$ aryl-$C_{1-6}$ alkyl (e.g., benzyl) or $C_{2-6}$ alkenyl-carbonyl (e.g., acryloyl), and $R^{14}$ is a hydrogen atom or $C_{1-6}$ alkyl (e.g., methyl, ethyl) wherein $C_{1-6}$ alkyl is optionally substituted by one substituent selected from (a) $C_{1-6}$ alkoxy-carbonylamino (e.g., tert-butoxycarbonylamino), (b) $C_{2-6}$ alkenyl-carbonylamino (e.g., acryloylamino) and (c) $C_{6-10}$ aryl-$C_{1-6}$ alkylaminocarbonyl (e.g., benzylaminocarbonyl) optionally substituted by $C_{1-6}$ alkyl (e.g., methyl), or $R^{13}$ and $R^{14}$ are bonded to each other to form, together with the nitrogen atom bonded thereto, a 5- to 7-membered heterocycle further containing one nitrogen atom (e.g., imidazolidine) wherein 5- to 7-membered heterocycle is optionally substituted by $C_{6-10}$ aryl-carbonyl (e.g., benzoyl) optionally substituted by $C_{1-6}$ alkyl (e.g., methyl). When $R^{14}$ is ethyl substituted by $C_{2-6}$ alkenyl-carbonylamino, $R^{13}$ is not a hydrogen atom.

$R^{14}$ is preferably a hydrogen atom or $C_{1-6}$ alkyl (e.g., methyl, ethyl) wherein $C_{1-6}$ alkyl is optionally substituted by one substituent selected from (a) $C_{1-6}$ alkoxy-carbonylamino (e.g., tert-butoxycarbonylamino) and (b) $C_{6-10}$ aryl-$C_{1-6}$ alkylaminocarbonyl (e.g., benzylaminocarbonyl) optionally substituted by $C_{1-6}$ alkyl (e.g., methyl).

As a preferable example of the compound represented by the above-mentioned formula (I) of the present invention, the following compounds can be mentioned.

A compound represented by the formula (I-A):

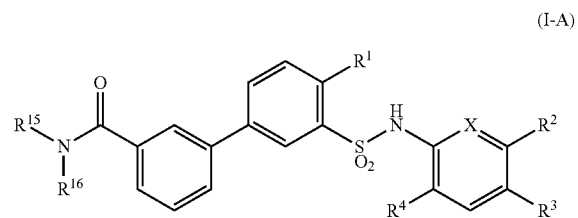

wherein each symbol is as defined in the aforementioned [1], or a pharmaceutically acceptable acid addition salt thereof.

A compound represented by the formula (I-B):

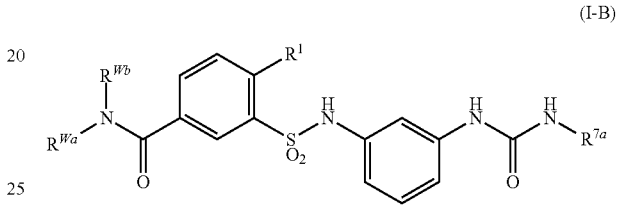

wherein $R^{7a}$ is phenyl substituted by —NR$^{9a}$R$^{9b}$ (wherein $R^{9a}$ is $C_{1-6}$ alkyl and $R^{9b}$ is $C_{1-6}$ alkyl), and each of other symbols is as defined in the aforementioned [1], or a pharmaceutically acceptable acid addition salt thereof.

A compound represented by any of the following formulas (I-C) to (I-L) or a pharmaceutically acceptable acid addition salt thereof.

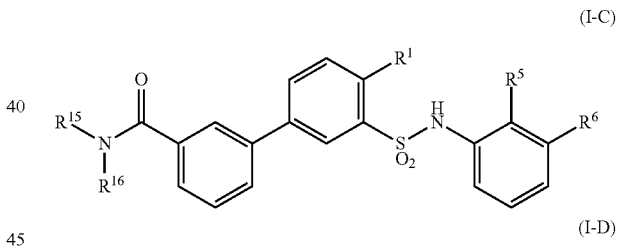

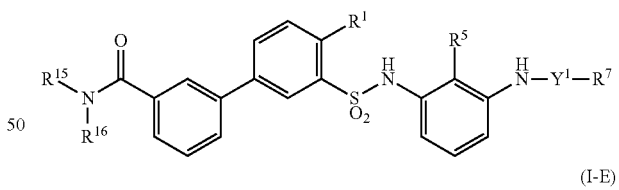

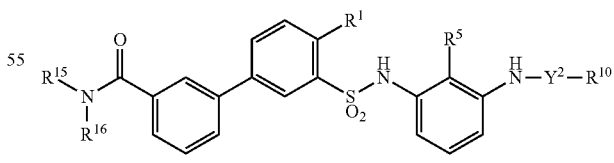

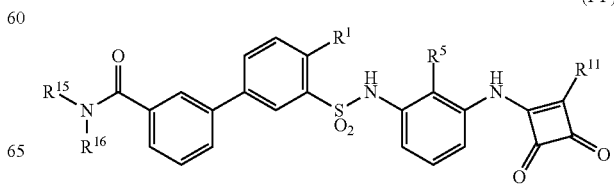

-continued (I-G)
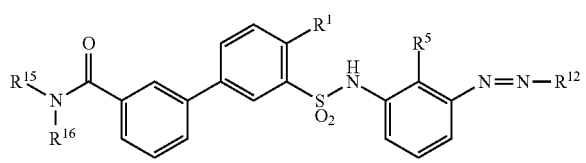

(I-H)
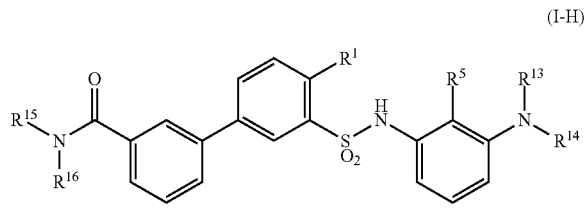

(I-J)
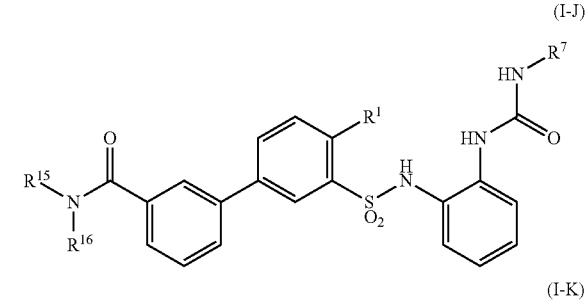

(I-K)
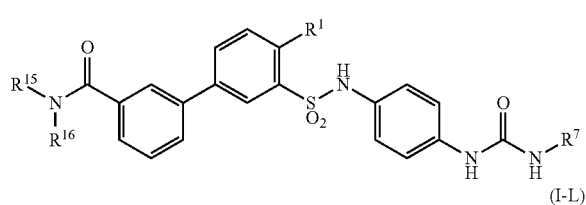

(I-L)
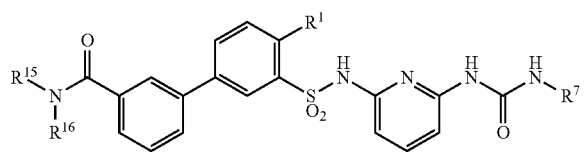

wherein each symbol is as defined in the aforementioned [1].

In the formula (I-D),
$Y^1$ is preferably —C(=O)NH—, —C(=S)NH—, —C(=NH)NH— or —C(=O)O—, particularly preferably —C(=O)NH—.

In the formulas (I-D), (I-J), (I-K) and (I-L), $R^7$ is preferably
(a) $C_{6-10}$ aryl (e.g., phenyl, 1-naphthyl, 2-naphthyl), or
(b) 5- to 10-membered heteroaryl (e.g., pyridyl, thienyl, thiazolyl)
wherein $C_{6-10}$ aryl and 5- to 10-membered heteroaryl are optionally substituted by optionally selected $R^9$ in the number of 1 to 4, and $R^9$ is as defined above.

$R^7$ is particularly preferably phenyl substituted by —$NR^{9a}R^{9b}$ wherein $R^{9a}$ is $C_{1-6}$ alkyl and $R^{9b}$ is $C_{1-6}$ alkyl.

[Compound I-A1]

A compound of the formula (I-A) wherein
$R^1$ is a hydrogen atom, $C_{1-6}$ alkoxy, —OH, $C_{1-6}$ alkyl or a halogen atom,
X is —C($R^5$)= or —N=,
$R^5$ is a hydrogen atom or $C_{1-6}$ alkoxy,
any one of $R^2$, $R^3$ and $R^4$ is $R^6$ and the remaining two are each a hydrogen atom, $R^6$ is
(1) —$NR^{17}$—$Y^1$—$R^7$
wherein $Y^1$ is —C(=O)$NR^{18}$—, —C(=S)NH—, —C(=NH)NH—, —C(=O)O—, —C(=O)—, —$SO_2$— or —$SO_2$—$NR^8$—,
$R^8$ is a hydrogen atom or $C_{1-6}$ alkyl,
$R^{17}$ is a hydrogen atom or $C_{1-6}$ alkyl,
$R^{18}$ is a hydrogen atom or $C_{1-6}$ alkyl, or
$R^{17}$ and $R^{18}$ are optionally bonded to each other to form, together with the nitrogen atoms bonded thereto and adjacent C(=O), a 5- to 7-membered heterocycle (e.g., imidazolidin-2-one, hexahydropyrimidin-2-one or 1,3-diazepan-2-one),
$R^7$ is
(a) $C_{6-10}$ aryl (e.g., phenyl, 1-naphthyl, 2-naphthyl),
(b) 5- to 10-membered heteroaryl (e.g., pyridyl, thienyl, thiazolyl),
(c) $C_{1-6}$ alkyl, or
(d) $C_{2-6}$ alkenyl
(wherein $C_{1-6}$ alkyl and $C_{2-6}$ alkenyl are optionally substituted by one substituent selected from phenyl, furyl and diphenylmethylsulfinyl,
$C_{6-10}$ aryl and 5- to 10-membered heteroaryl are optionally substituted by optionally selected $R^9$ in the number of 1 to 4 (preferably 1 to 3, more preferably 1 or 2),
$R^9$ are each independently
a halogen atom,
—$NO_2$,
—OH,
$C_{1-6}$ alkyl,
$C_{1-6}$ haloalkyl,
$C_{1-6}$ alkoxy,
5- to 10-membered heteroaryl (e.g., pyridyl),
—$NR^{9a}R^{9b}$ wherein $R^{9a}$ is a hydrogen atom, $C_{1-6}$ alkyl or $C_{1-6}$ alkoxy-carbonyl, and $R^{9b}$ is a hydrogen atom or $C_{1-6}$ alkyl,
—C(=O)$OR^{9c}$ wherein $R^{9c}$ is a hydrogen atom or $C_{1-6}$ alkyl,
—C(=O)$NR^{9d}R^{9e}$ wherein $R^{9d}$ is a hydrogen atom or $C_{1-6}$ alkyl, and $R^{9e}$ is a hydrogen atom or $C_{1-6}$ alkyl, or
—NH—C(=$NR^{9f}$)—$NHR^{9g}$ wherein $R^{9f}$ is a hydrogen atom or $C_{1-6}$ alkoxy-carbonyl, and $R^{9g}$ is a hydrogen atom or $C_{1-6}$ alkoxy-carbonyl, or
$R^9$ in the number of 2 are joined to form methylenedioxy,
(2) —NH—$Y^2$—$R^{10}$
wherein $Y^2$ is —$CH_2$— or a single bond,
$R^{10}$ is $C_{6-10}$ aryl (e.g., phenyl)
wherein $C_{6-10}$ aryl is optionally substituted by optionally selected $R^9$ in the number of 1 to 4 (preferably 1 to 3, more preferably 1 or 2),
$R^9$ are each independently
a halogen atom,
—OH,
$C_{1-6}$ alkyl,
$C_{1-6}$ haloalkyl,
$C_{1-6}$ alkoxy, or
—C(=O)$NR^{9d}R^{9e}$ wherein $R^{9d}$ is $C_{1-6}$ alkyl and $R^{9e}$ is $C_{1-6}$ alkyl, or
$R^9$ in the number of 2 are joined to form methylenedioxy,
(3) the formula (ii):

(ii)
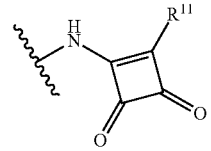

wherein $R^{11}$ is $C_{1-6}$ alkoxy or $C_{6-10}$ arylamino (e.g., phenylamino) (wherein $C_{6-10}$ aryl moiety of the $C_{6-10}$ arylamino is optionally substituted by 1 to 3 substituents selected from $C_{1-6}$ alkyl and $C_{1-6}$ alkoxy), (4) —N=N—$R^{12}$ wherein $R^{12}$ is $C_{6-10}$ aryl (e.g., phenyl) optionally substituted by 1 to 3 substituents selected from (a) $C_{1-6}$ alkyl optionally substituted by —OH, (b) —OH, (c) di($C_{1-6}$ alkyl) amino and (d) $C_{1-6}$ alkoxy-carbonylamino, or (5) —$NR^{13}R^{14}$ wherein $R^{13}$ is a hydrogen atom, $C_{1-6}$ alkyl, $C_{6-10}$ aryl-$C_{1-6}$ alkyl (e.g., benzyl) or $C_{2-6}$ alkenyl-carbonyl, and $R^{14}$ is a hydrogen atom or $C_{1-6}$ alkyl (wherein $C_{1-6}$ alkyl is optionally substituted by 1 to 3 substituents selected from (a) $C_{1-6}$ alkoxy-carbonylamino, (b) $C_{2-6}$ alkenyl-carbonylamino and (c) $C_{6-10}$ aryl-$C_{1-6}$ alkylaminocarbonyl (e.g., benzylaminocarbonyl) optionally substituted by $C_{1-6}$ alkyl), or $R^{13}$ and $R^{14}$ are bonded to each other to form, together with the nitrogen atom bonded thereto, a 5- to 7-membered heterocycle further containing one nitrogen atom (e.g., imidazolidine) (wherein 5- to 7-membered heterocycle is optionally substituted by $C_{6-10}$ aryl-carbonyl (e.g., benzoyl) optionally substituted by $C_{1-6}$ alkyl), provided that when $R^{14}$ is ethyl substituted by $C_{2-6}$ alkenyl-carbonylamino, $R^{13}$ is not a hydrogen atom, $R^{15}$ is $C_{1-6}$ alkyl, and $R^{16}$ is $C_{1-6}$ alkyl, or a pharmaceutically acceptable acid addition salt thereof. Preferably, $R^{17}$ and $R^{18}$ are each a hydrogen atom.

[Compound I-B1]

A compound of the formula (I-B) wherein $R^1$ is $C_{1-6}$ alkoxy, $R^{7a}$ is phenyl substituted by —$NR^{9a}R^{9b}$ wherein $R^{9a}$ is $C_{1-6}$ alkyl and $R^{9b}$ is $C_{1-6}$ alkyl, $R^{Wa}$ is $C_{1-6}$ alkyl (wherein $C_{1-6}$ alkyl is optionally substituted by phenyl, pyridyl, $C_{1-6}$ alkoxy-carbonylamino or di($C_{1-6}$ alkyl)amino) or phenyl (wherein phenyl is optionally substituted by di($C_{1-6}$ alkyl)amino), and $R^{Wb}$ is a hydrogen atom or $C_{1-6}$ alkyl, or a pharmaceutically acceptable acid addition salt thereof.

[Compound I-C1]

A compound of the formula (I-C) wherein $R^1$ is a hydrogen atom, $C_{1-6}$ alkoxy, —OH, $C_{1-6}$ alkyl or a halogen atom, $R^5$ is a hydrogen atom or $C_{1-6}$ alkoxy, $R^6$ is (1) —$NR^{17}$—$Y^1$—$R^7$ wherein $Y^1$ is —C(=O)$NR^{18}$—, —C(=S)NH—, —C(=NH)NH—, —C(=O)O—, —C(=O)—, —SO$_2$— or —SO$_2$—$NR^8$—, $R^8$ is a hydrogen atom or $C_{1-6}$ alkyl, $R^{17}$ is a hydrogen atom or $C_{1-6}$ alkyl, $R^{18}$ is a hydrogen atom or $C_{1-6}$ alkyl, or $R^{17}$ and $R^{18}$ are optionally bonded to each other to form, together with the nitrogen atoms bonded thereto and adjacent C(=O), a 5- to 7-membered heterocycle (e.g., imidazolidin-2-one, hexahydropyrimidin-2-one or 1,3-diazepan-2-one), $R^7$ is (a) $C_{6-10}$ aryl (e.g., phenyl, 1-naphthyl, 2-naphthyl), (b) 5- to 10-membered heteroaryl (e.g., pyridyl, thienyl, thiazolyl), (c) $C_{1-6}$ alkyl, or (d) $C_{2-6}$ alkenyl wherein $C_{1-6}$ alkyl and $C_{2-6}$ alkenyl are optionally substituted by one substituent selected from phenyl, furyl and diphenylmethylsulfinyl, $C_{6-10}$ aryl and 5- to 10-membered heteroaryl are optionally substituted by optionally selected $R^9$ in the number of 1 to 4 (preferably 1 to 3, more preferably 1 or 2), $R^9$ are each independently a halogen atom,

—NO$_2$,

—OH, $C_{1-6}$ alkyl, $C_{1-6}$ haloalkyl, $C_{1-6}$ alkoxy, 5- to 10-membered heteroaryl (e.g., pyridyl), —$NR^{9a}R^{9b}$ wherein $R^{9a}$ is a hydrogen atom, $C_{1-6}$ alkyl or $C_{1-6}$ alkoxy-carbonyl and $R^{9b}$ is a hydrogen atom or $C_{1-6}$ alkyl, —C(=O)$OR^{9c}$ wherein $R^{9c}$ is a hydrogen atom or $C_{1-6}$ alkyl, —C(=O)$NR^{9d}R^{9e}$ wherein $R^{9d}$ is a hydrogen atom or $C_{1-6}$ alkyl and $R^{9e}$ is a hydrogen atom or $C_{1-6}$ alkyl, or —NH—C(=$NR^{9f}$)—$NHR^{9g}$ wherein $R^{9f}$ is a hydrogen atom or $C_{1-6}$ alkoxy-carbonyl and $R^{9g}$ is a hydrogen atom or $C_{1-6}$ alkoxy-carbonyl, or $R^9$ in the number of 2 are joined to form methylenedioxy, (2) —NH—$Y^2$—$R^{10}$ wherein $Y^2$ is —CH$_2$— or a single bond, $R^{10}$ is $C_{6-10}$ aryl (e.g., phenyl)

wherein $C_{6-10}$ aryl is optionally substituted by optionally selected $R^9$ in the number of 1 to 4 (preferably 1 to 3, more preferably 1 or 2), $R^9$ are each independently a halogen atom,

—OH, $C_{1-6}$ alkyl, $C_{1-6}$ haloalkyl, $C_{1-6}$ alkoxy, or

—C(=O)$NR^{9d}R^{9e}$ wherein $R^{9d}$ is $C_{1-6}$ alkyl and $R^{9e}$ is $C_{1-6}$ alkyl, or $R^9$ in the number of 2 are joined to form methylenedioxy, (3) a group represented by the formula (ii):

$$\begin{array}{c} \text{(ii)} \end{array}$$

wherein $R^{11}$ is $C_{1-6}$ alkoxy or $C_{6-10}$ arylamino (e.g., phenylamino) wherein the $C_{6-10}$ aryl moiety of $C_{6-10}$ arylamino is optionally substituted by 1 to 3 substituents selected from $C_{1-6}$ alkyl and $C_{1-6}$ alkoxy, (4) —N=N—$R^{12}$ wherein $R^{12}$ is $C_{6-10}$ aryl (e.g., phenyl) optionally substituted 1 to 3 substituents selected from (a) $C_{1-6}$ alkyl optionally substituted by —OH, (b) —OH, (c) di($C_{1-6}$ alkyl)amino and (d) $C_{1-6}$ alkoxy-carbonylamino, or (5) —$NR^{13}R^{14}$ wherein $R^{13}$ is a hydrogen atom, $C_{1-6}$ alkyl, $C_{6-10}$ aryl-$C_{1-6}$ alkyl (e.g., benzyl) or $C_{2-6}$ alkenyl-carbonyl, and $R^{14}$ is a hydrogen atom or $C_{1-6}$ alkyl wherein $C_{1-6}$ alkyl is optionally substituted by one substituent selected from (a) $C_{1-6}$ alkoxy-carbonylamino, (b) $C_{2-6}$ alkenyl-carbonylamino and (c) $C_{6-10}$ aryl-$C_{1-6}$ alkylaminocarbonyl (e.g., benzylaminocarbonyl) optionally substituted by $C_{1-6}$ alkyl, or $R^{13}$ and $R^{14}$ are bonded to each other to form, together with the nitrogen atom bonded thereto, a 5- to 7-membered heterocycle further containing one nitrogen atom (e.g., imidazolidine) (wherein 5- to 7-membered heterocycle is optionally substituted by $C_{6-10}$ aryl-carbonyl (e.g., benzoyl) optionally substituted by $C_{1-6}$ alkyl), provided that when $R^{14}$ is ethyl substituted by $C_{2-6}$ alkenyl-carbonylamino, $R^{13}$ is not a hydrogen atom,
$R^{15}$ is $C_{1-6}$ alkyl, and $R^{16}$ is $C_{1-6}$ alkyl,
or a pharmaceutically acceptable acid addition salt thereof.

[Compound I-D1]

A compound of the formula (I-D) wherein
$R^1$ is a hydrogen atom, $C_{1-6}$ alkoxy, —OH, $C_{1-6}$ alkyl or a halogen atom,
$R^5$ is a hydrogen atom or $C_{1-6}$ alkoxy,
$Y^1$ is —C(=O)NR$^{18}$—, —C(=S)NH—, —C(=NH)NH—, —C(=O)O—, —C(=O)—, —SO$_2$— or —SO$_2$—NR$^8$—,
$R^8$ is a hydrogen atom or $C_{1-6}$ alkyl,
$R^{18}$ is a hydrogen atom,
$R^7$ is
(a) $C_{6-10}$ aryl (e.g., phenyl, 1-naphthyl, 2-naphthyl),
(b) 5- to 10-membered heteroaryl (e.g., pyridyl, thienyl, thiazolyl),
(c) $C_{1-6}$ alkyl, or
(d) $C_{2-6}$ alkenyl
wherein $C_{1-6}$ alkyl and $C_{2-6}$ alkenyl are optionally substituted by one substituent selected from phenyl, furyl and diphenylmethylsulfinyl,
$C_{6-10}$ aryl and 5- to 10-membered heteroaryl are optionally substituted by optionally selected $R^9$ in the number of 1 to 4 (preferably 1 to 3, more preferably 1 or 2),
$R^9$ are each independently
a halogen atom,
—NO$_2$,
—OH,
$C_{1-6}$ alkyl,
$C_{1-6}$ haloalkyl,
$C_{1-6}$ alkoxy,
5- to 10-membered heteroaryl (e.g., pyridyl),
—NR$^{9a}$R$^{9b}$ wherein $R^{9a}$ is a hydrogen atom, $C_{1-6}$ alkyl or $C_{1-6}$ alkoxy-carbonyl and $R^{9b}$ is a hydrogen atom or $C_{1-6}$ alkyl,
—C(=O)OR$^{9c}$ wherein $R^{9c}$ is a hydrogen atom or $C_{1-6}$ alkyl,
—C(=O)NR$^{9d}$R$^{9e}$ wherein $R^{9d}$ is a hydrogen atom or $C_{1-6}$ alkyl and $R^{9e}$ is a hydrogen atom or $C_{1-6}$ alkyl, or
—NH—C(=NR$^{9f}$)—NHR$^{9g}$ wherein $R^{9f}$ is a hydrogen atom or $C_{1-6}$ alkoxy-carbonyl and $R^{9g}$ is a hydrogen atom or $C_{1-6}$ alkoxy-carbonyl, or
$R^9$ in the number of 2 are joined to form methylenedioxy,
$R^{15}$ is $C_{1-6}$ alkyl, and $R^{16}$ is $C_{1-6}$ alkyl,
or a pharmaceutically acceptable acid addition salt thereof.

[Compound I-D2]

A compound of the formula (I-D) wherein
$R^1$ is a hydrogen atom, $C_{1-6}$ alkoxy, —OH, $C_{1-6}$ alkyl or a halogen atom,
$R^5$ is a hydrogen atom or $C_{1-6}$ alkoxy,
$Y^1$ is —C(=O)NR$^{18}$—, —C(=S)NH— or —C(=NH)NH—,
$R^8$ is a hydrogen atom or $C_{1-6}$ alkyl,
$R^{18}$ is a hydrogen atom,
$R^7$ is
(a) $C_{6-10}$ aryl (e.g., phenyl), or
(b) 5- to 10-membered heteroaryl (e.g., pyridyl, thienyl)
wherein $C_{6-10}$ aryl and 5- to 10-membered heteroaryl are optionally substituted by optionally selected $R^9$ in the number of 1 to 4 (preferably 1 to 3, more preferably 1 or 2),
$R^9$ are each independently
a halogen atom,
—NO$_2$,
—OH,
$C_{1-6}$ alkyl,
$C_{1-6}$ haloalkyl,
$C_{1-6}$ alkoxy,
5- to 10-membered heteroaryl (e.g., pyridyl),
—NR$^{9a}$R$^{9b}$ wherein $R^{9a}$ is a hydrogen atom, $C_{1-6}$ alkyl or $C_{1-6}$ alkoxy-carbonyl and $R^{9b}$ is a hydrogen atom or $C_{1-6}$ alkyl,
—C(=O)OR$^{9c}$ wherein $R^{9c}$ is a hydrogen atom or $C_{1-6}$ alkyl,
—C(=O)NR$^{9d}$R$^{9e}$ wherein $R^{9d}$ is a hydrogen atom or $C_{1-6}$ alkyl and $R^{9e}$ is a hydrogen atom or $C_{1-6}$ alkyl, or
—NH—C(=NR$^{9f}$)—NHR$^{9g}$ wherein $R^{9f}$ is a hydrogen atom or $C_{1-6}$ alkoxy-carbonyl and $R^{9g}$ is a hydrogen atom or $C_{1-6}$ alkoxy-carbonyl, or
$R^9$ in the number of 2 are joined to form methylenedioxy,
$R^{15}$ is $C_{1-6}$ alkyl, and $R^{16}$ is $C_{1-6}$ alkyl,
or a pharmaceutically acceptable acid addition salt thereof.

[Compound I-E1]

A compound of the formula (I-E) wherein
$R^1$ is $C_{1-6}$ alkoxy,
$R^5$ is a hydrogen atom,
$Y^2$ is —CH$_2$— or a single bond,
$R^{10}$ is $C_{6-10}$ aryl (e.g., phenyl)
wherein $C_{6-10}$ aryl is optionally substituted by optionally selected $R^9$ in the number of 1 to 4 (preferably 1 to 3, more preferably 1 or 2),
$R^9$ are each independently
a halogen atom,
—OH,
$C_{1-6}$ alkyl,
$C_{1-6}$ haloalkyl,
$C_{1-6}$ alkoxy, or
—C(=O)NR$^{9d}$R$^{9e}$ wherein $R^{9d}$ is $C_{1-6}$ alkyl and $R^{9e}$ is $C_{1-6}$ alkyl, or
$R^9$ in the number of 2 are joined to form methylenedioxy,
$R^{15}$ is $C_{1-6}$ alkyl and $R^{16}$ is $C_{1-6}$ alkyl,
or a pharmaceutically acceptable acid addition salt thereof.

[Compound I-F1]

A compound of the formula (I-F) wherein
$R^1$ is $C_{1-6}$ alkoxy,
$R^5$ is a hydrogen atom,
$R^{11}$ is $C_{1-6}$ alkoxy or $C_{6-10}$ arylamino (e.g., phenylamino) wherein the $C_{6-10}$ aryl moiety of $C_{6-10}$ arylamino is optionally substituted by one substituent selected from $C_{1-6}$ alkyl and $C_{1-6}$ alkoxy,
$R^{15}$ is $C_{1-6}$ alkyl and $R^{16}$ is $C_{1-6}$ alkyl,
or a pharmaceutically acceptable acid addition salt thereof.

[Compound I-G1]

A compound of the formula (I-G) wherein
$R^1$ is $C_{1-6}$ alkoxy,
$R^5$ is a hydrogen atom,
$R^{12}$ is $C_{6-10}$ aryl (e.g., phenyl) optionally substituted by 1 or 2 substituents selected from (a) $C_{1-6}$ alkyl optionally substituted by —OH, (b) —OH, (c) di($C_{1-6}$ alkyl)amino and (d) $C_{1-6}$ alkoxy-carbonylamino,
$R^{15}$ is $C_{1-6}$ alkyl, and $R^{16}$ is $C_{1-6}$ alkyl,
or a pharmaceutically acceptable acid addition salt thereof.

[Compound I-H1]

A compound of the formula (I-H) wherein
$R^1$ is $C_{1-6}$ alkoxy,
$R^5$ is a hydrogen atom,
$R^{13}$ is a hydrogen atom, $C_{1-6}$ alkyl, $C_{6-10}$ aryl-$C_{1-6}$ alkyl (e.g., benzyl) or $C_{2-6}$ alkenyl-carbonyl and $R^{14}$ is a hydrogen atom or $C_{1-6}$ alkyl wherein $C_{1-6}$ alkyl is optionally substituted by one substituent selected from (a) $C_{1-6}$ alkoxy-carbonylamino, (b) $C_{2-6}$ alkenyl-carbonylamino and (c) $C_{6-10}$ aryl-$C_{1-6}$ alkylaminocarbonyl (e.g., benzylaminocarbonyl) optionally substituted by $C_{1-6}$ alkyl, or $R^{13}$ and $R^{14}$ are bonded to each other to form, together with the nitrogen atom bonded thereto, a 5- to 7-membered heterocycle further containing one nitrogen atom (e.g., imidazolidine) wherein 5- to 7-membered heterocycle is optionally substituted by $C_{6-10}$ aryl-carbonyl (e.g., benzoyl) optionally substituted by $C_{1-6}$ alkyl, provided that when $R^{14}$ is ethyl substituted by $C_{2-6}$ alkenyl-carbonylamino, $R^{13}$ is not a hydrogen atom, $R^{15}$ is $C_{1-6}$ alkyl, and $R^{16}$ is $C_{1-6}$ alkyl, or a pharmaceutically acceptable acid addition salt thereof.

[Compound I-J1]

A compound of the formula (I-J) wherein $R^1$ is $C_{1-6}$ alkoxy, $R^7$ is phenyl substituted by —$NR^{9a}R^{9b}$ wherein $R^{9a}$ is $C_{1-6}$ alkyl and $R^{9b}$ is $C_{1-6}$ alkyl, $R^{15}$ is $C_{1-6}$ alkyl, and $R^{16}$ is $C_{1-6}$ alkyl, or a pharmaceutically acceptable acid addition salt thereof.

[Compound I-K1]

A compound of the formula (I-K) wherein $R^1$ is $C_{1-6}$ alkoxy, $R^7$ is phenyl substituted by —$NR^{9a}R^{9b}$ wherein $R^{9a}$ is $C_{1-6}$ alkyl and $R^{9b}$ is $C_{1-6}$ alkyl, $R^{15}$ is $C_{1-6}$ alkyl, and $R^{16}$ is $C_{1-6}$ alkyl, or a pharmaceutically acceptable acid addition salt thereof.

[Compound I-L1]

A compound of the formula (I-L) wherein $R^1$ is $C_{1-6}$ alkoxy, $R^7$ is phenyl substituted by —$NR^{9a}R^{9b}$ wherein $R^{9a}$ is $C_{1-6}$ alkyl and $R^{9b}$ is $C_{1-6}$ alkyl, $R^{15}$ is $C_{1-6}$ alkyl, and $R^{16}$ is $C_{1-6}$ alkyl, or a pharmaceutically acceptable acid addition salt thereof.

As a pharmaceutically acceptable acid addition salt of the compound of the formula (I) or (I') of the present invention, inorganic acid salts such as hydrochloride, sulfate, nitrate, hydrobromide, hydroiodide, phosphate and the like, organic carbonates such as acetate, lactate, citrate, oxalate, glutarate, malate, tartrate, fumarate, mandelate, maleate, benzoate, phthalate and the like, organic sulfonates such as methanesulfonate, ethanesulfonate, benzenesulfonate, p-toluenesulfonate, camphorsulfonate and the like, and the like can be mentioned; however, these are not limitative. Of these, hydrochloride, hydrobromide, phosphate, tartrate, methanesulfonate or camphorsulfonate is preferable, and hydrochloride, tartrate or methanesulfonate is further preferably used and hydrochloride is particularly preferably used; however, these are also not limitative.

The compound of the above-mentioned formula (I) or (I') of the present invention can be produced by an appropriate method based on the characteristics derived from the basic skeleton and substituents thereof. While the starting materials and reagents to be used for the production of these compounds are generally available or can be synthesized by a method known to those of ordinary skill in the art, which follows the procedures described in reference documents such as Organic Reactions (Wiley & Sons), Fieser and Fieser's Reagent for Organic Synthesis (Wiley & Sons) and the like.

As a specific production method of the compound of the above-mentioned formula (I) or (I') of the present invention, for example, the methods shown in Schemes 1 to 18 can be mentioned.

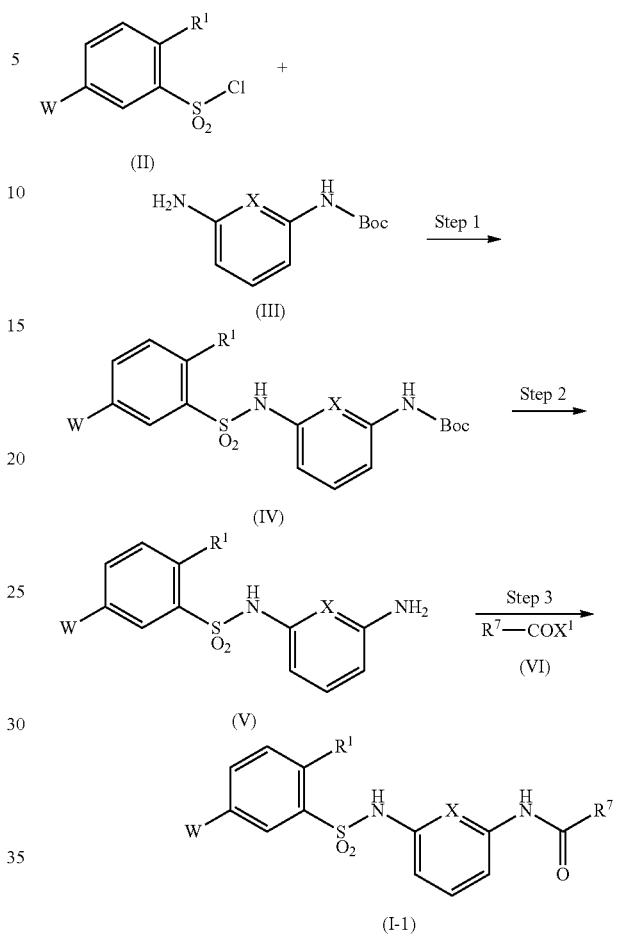

Scheme 1 wherein $R^1$, $R^7$, X and W are as defined above, $X^1$ is a halogen atom such as chlorine atom, bromine atom and the like or a hydroxy group, and Boc is a tert-butoxycarbonyl group.

Step 1

Compound (IV) can be obtained by, for example, amidating sulfonyl chloride compound (II) with amine compound (III).

As the solvent, halogenated hydrocarbon solvents such as dichloromethane, chloroform, 1,2-dichloroethane and the like, ether solvents such as diethyl ether, tetrahydrofuran (THF), 1,2-dimethoxyethane (DME), dioxane and the like, aprotic polar solvents such as N,N-dimethylformamide (DMF), dimethyl sulfoxide (DMSO) and the like or a mixed solvent thereof can be used. Generally, dichloromethane or THF is preferably used. The sulfonyl chloride compound (II) is used in an amount of 0.5-20 equivalents, preferably 1.0-10 equivalents, relative to amine compound (III).

Examples of the base include sodium carbonate, potassium carbonate, cesium carbonate, potassium phosphate, sodium hydroxide, potassium hydroxide, barium hydroxide, triethylamine, diisopropylethylamine, pyridine, 4-dimethylaminopyridine and the like, and diisopropylethylamine, triethylamine or pyridine is preferably used.

The reaction temperature is generally −40-150° C., preferably 0-80° C. While the reaction time is appropriately selected according to the conditions such as reaction temperature and the like, it is generally about 10 min-48 hr. While the concentration of substrate (II) in the reaction system is not particularly limited, it is generally preferably 0.001 mmol/L-1 mol/L.

Step 2

Amine compound (V) can be obtained by, for example, deprotection of a tert-butoxycarbonyl (Boc) group of compound (IV) under acidic conditions.

As the solvent, halogenated hydrocarbon solvents such as dichloromethane, chloroform, 1,2-dichloroethane and the like, ether solvents such as THF, DME, dioxane and the like, alcohol solvents such as methanol, ethanol, propanol and the like or a mixed solvent thereof can be used. In general, dichloromethane or dioxane is preferably used.

As the acid, organic acids such as trifluoroacetic acid, methanesulfonic acid, p-toluenesulfonic acid, trifluoromethanesulfonic acid and the like, or inorganic acids such as hydrochloric acid, hydrobromic acid, hydroiodic acid, sulfuric acid, nitric acid, phosphoric acid and the like can be used. In general, trifluoroacetic acid or hydrochloric acid is preferably used. In another method, a hydrogen chloride-methanol solution, a hydrogen chloride-THF solution, a hydrogen chloride-ethyl acetate solution, or a hydrogen chloride-dioxane solution obtained by dissolving hydrogen chloride in an organic solvent is each independently used. In this case, particularly, preferable results are obtained by using a hydrogen chloride-methanol solution or a hydrogen chloride-THF solution. The acid is used in an amount of 1.0-100 equivalents, preferably 3.0-10 equivalents, relative to compound (IV).

The reaction temperature is generally −40-150° C., preferably 0-80° C. While the reaction time is appropriately selected according to the conditions such as reaction temperature and the like, it is generally about 20 min-48 hr. While the concentration of substrate (IV) in the reaction system is not particularly limited, it is generally preferably 0.001 mmol/L-1 mol/L.

Step 3

Compound (I-1) can be obtained by, for example, amidation of amine compound (V) with acyl halide compound (VI) wherein $X^1$ is a halogen atom.

As the solvent, halogenated hydrocarbon solvents such as dichloromethane, chloroform, 1,2-dichloroethane and the like, ether solvents such as diethyl ether, THF, DME, dioxane and the like, aprotic polar solvents such as DMF, DMSO and the like or a mixed solvent thereof can be used. In general, dichloromethane or THF is preferably used. The acyl halide compound (VI) is used in an amount of 0.5-20 equivalents, preferably 1.0-10 equivalents, relative to amine compound (V).

Examples of the base include sodium carbonate, potassium carbonate, cesium carbonate, potassium phosphate, sodium hydroxide, potassium hydroxide, barium hydroxide, triethylamine, diisopropylethylamine, pyridine, 4-dimethylaminopyridine and the like, and diisopropylethylamine, triethylamine or pyridine is preferably used.

The reaction temperature is generally −40-150° C., preferably 0-80° C. While the reaction time is appropriately selected according to the conditions such as reaction temperature and the like, it is generally about 10 min-48 hr. While the concentration of substrate (V) in the reaction system is not particularly limited, it is generally preferably 0.001 mmol/L-1 mol/L.

In addition, compound (I-1) can be obtained by, for example, amidation of amine compound (V) with carboxylic acid (VI) wherein $X^1$ is a hydroxy group.

As the solvent, halogenated hydrocarbon solvents such as dichloromethane, chloroform, 1,2-dichloroethane and the like, ether solvents such as diethyl ether, THF, DME, dioxane and the like, aprotic polar solvents such as DMF, DMSO, ethyl acetate and the like, alcohol solvents such as methanol, ethanol, propanol and the like or a mixed solvent thereof can be used. Generally, dichloromethane or THF is preferably used. The carboxylic acid (VI) is used in an amount of 0.5-20 equivalents, preferably 0.5-10 equivalents, relative to amine compound (V).

As the condensing agent, dicyclohexylcarbodiimide, 1-ethyl-3-(3-dimethylaminopropyl)carbodiimide hydrochloride (EDCI), benzotriazol-1-yloxytris(dimethylamino) phosphonium hexafluorophosphate (BOP), N,N'-carbonyldiimidazole (CDI), 4-(4,6-dimethoxy-1,3,5-triazin-2-yl)-4-methylmorpholinium chloride (DMT-MM), {[(1-cyano-2-ethoxy-2-oxoethylidene)amino]oxy}-4-morpholinomethylene}dimethylammonium hexafluorophosphate (COMU), O-(7-azabenzotriazol-1-yl)-N,N,N',N'-tetramethyluronium hexafluorophosphate (HATU) and the like can be used, and particularly, BOP or HATU is preferably used. The condensing agent is used in an amount of 1.0-100 equivalents, preferably 1.0-10 equivalents, relative to amine compound (XXI).

When a base is used, triethylamine, diisopropylethylamine, pyridine, N-methylmorpholine and the like can be used, and triethylamine or diisopropylethylamine is preferably used. The base is used in an amount of 3.0-100 equivalents, preferably 3.0-10 equivalents, relative to amine compound (V).

The reaction temperature is generally −40-150° C., preferably 0-60° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

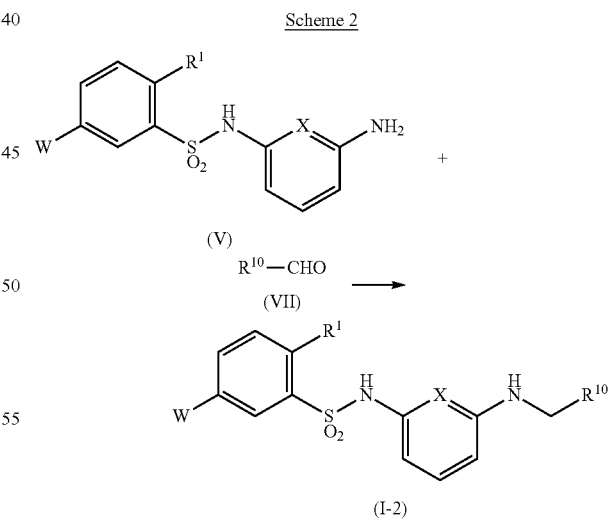

Scheme 2 wherein $R^1$, $R^{10}$, X and W are as defined above.

Compound (I-2) can be obtained by, for example, reductive alkylation of amine compound (V) with aldehyde compound (VII).

As the solvent, halogenated hydrocarbon solvents such as dichloromethane, chloroform, 1,2-dichloroethane and the like, ether solvents such as diethyl ether, THF, DME, dioxane and the like, aprotic polar solvents such as DMF, DMSO and the like, alcohol solvents such as methanol, ethanol, propanol and the like, acetic acid, water or a mixed solvent thereof can be used. The aldehyde compound (VII) is used in an amount of 0.5-20 equivalents, preferably 1.0-10 equivalents, relative to amine compound (V).

Examples of the reducing agent include sodium borohydride, lithium borohydride, sodium cyanoborohydride, sodium triacetoxyborohydride, 2-picoline-borane complex and the like.

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 10 min-48 hr. While the concentration of substrate (V) in the reaction system is not particularly limited, it is generally preferably 0.001 mmol/L-1 mol/L.

Scheme 3

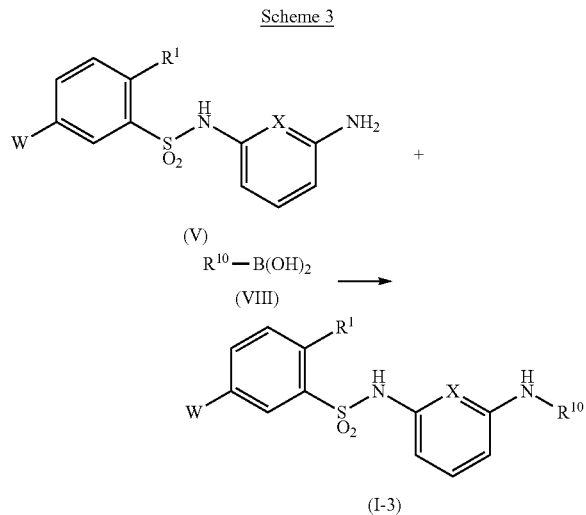

wherein $R^1$, $R^{10}$, X and W is as defined above.

Compound (I-3) can be obtained by, for example, subjecting amine compound (V) to a coupling reaction with boronic acid compound (VIII) in the presence of a copper catalyst.

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, alcohol solvents such as methanol, ethanol, propanol and the like, aromatic hydrocarbon solvents such as benzene, toluene, xylene and the like or a mixed solvent thereof can be used. The boronic acid compound (VIII) is used in an amount of 1.0-20 equivalents, preferably 1.0-10 equivalents, relative to amine compound (V).

As the copper catalyst, copper acetate (II) and the like can be mentioned. The copper catalyst is used in an amount of 0.001-1 equivalents, preferably 0.005-0.5 equivalents, relative to amine compound (V).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

Scheme 4

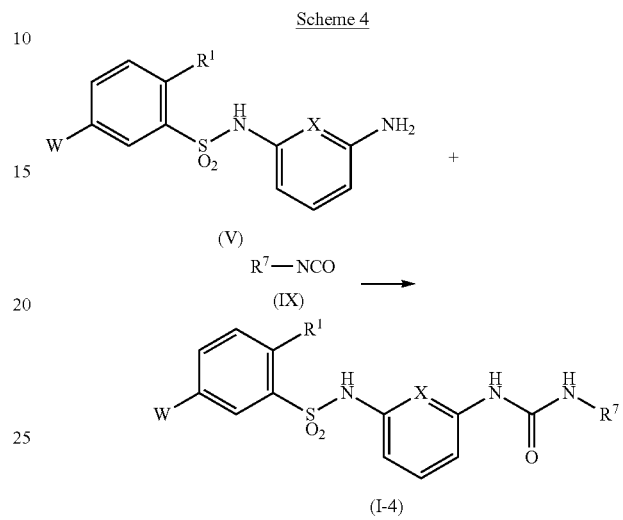

wherein $R^1$, $R^7$, X and W are as defined above.

Compound (I-4) can be obtained by reacting, for example, amine compound (V) with isocyanate (IX) or isocyanate (IX) developed from carboxylic acid $R^7$—$CO_2H$ (IX-1).

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, aromatic hydrocarbon solvents such as benzene, toluene, xylene and the like or a mixed solvent thereof can be used. Isocyanate (IX) is used in an amount of 1.0-20 equivalents, preferably 1.0-10 equivalents, relative to amine compound (V).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

When isocyanate (IX) is developed from carboxylic acid (IX-1), for example, it can be obtained by converting carboxylic acid (IX-1) to an acid azide with diphenylphosphoryl azide (DPPA) and subjecting the same to Curtius rearrangement reaction under heating conditions.

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, aromatic hydrocarbon solvents such as benzene, toluene, xylene and the like or a mixed solvent thereof can be used. The carboxylic acid (IX-1) is used in an amount of 1.0-30 equivalents, preferably 1.0-10 equivalents, relative to amine compound (V). DPPA is used in an amount of 1.0-30 equivalents, preferably 1.0-10 equivalents, relative to carboxylic acid (IX-1).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

Scheme 5

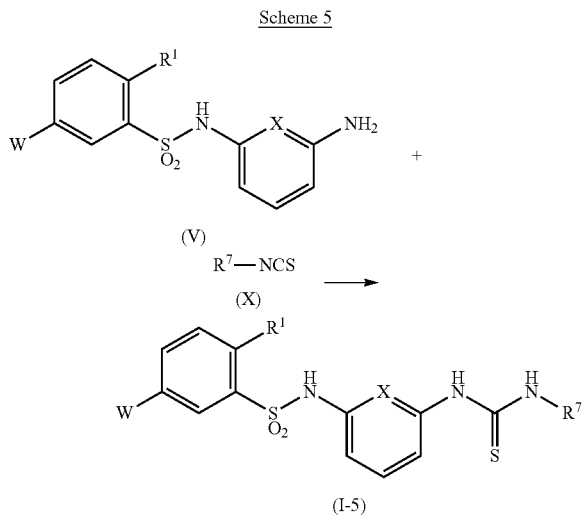

wherein $R^1$, $R^7$, X and W are as defined above.

Compound (I-5) can be obtained by reacting, for example, amine compound (V) with isothiocyanate (X).

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, aromatic hydrocarbon solvents such as benzene, toluene, xylene and the like or a mixed solvent thereof can be used. Isothiocyanate (X) is used in an amount of 1.0-20 equivalents, preferably 1.0-10 equivalents, relative to amine compound (V).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

Scheme 6

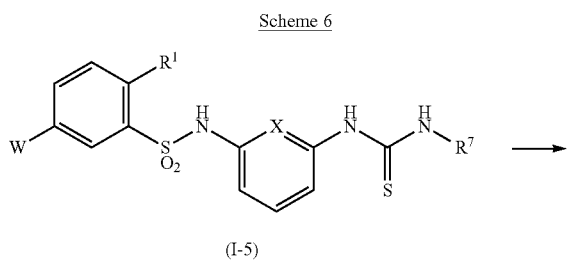

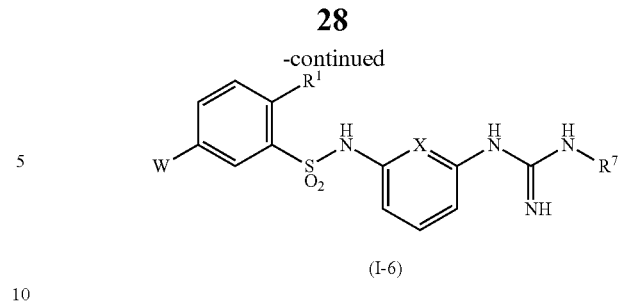

wherein $R^1$, $R^7$, X and W are as defined above.

Compound (I-6) can be obtained by reacting, for example, compound (I-5) with ammonia and 2-iodoxybenzoic acid (IBX).

As the solvent, nitrile solvents such as acetonitrile and the like can be used. As ammonia, an aqueous ammonia solution can be used. Ammonia and IBX are used in an amount of 1.0-20 equivalents, preferably 1.0-10 equivalents, relative to compound (I-6).

The reaction temperature is generally −40-150° C., preferably 0-80° C. While the reaction time is appropriately selected according to the conditions such as reaction temperature and the like, it is generally about 20 min-48 hr. While the concentration of the substrate (I-6) in the reaction system is not particularly limited, it is generally preferably 0.001 mmol/L-1 mol/L.

Scheme 7

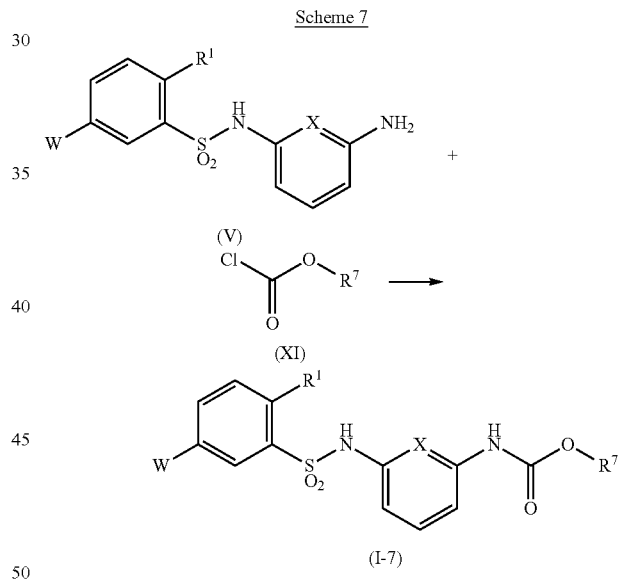

wherein $R^1$, $R^7$, X and W are as defined above.

Compound (I-7) can be obtained by reacting, for example, amine compound (V) with chloroformic acid ester (XI).

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, aromatic hydrocarbon solvents such as benzene, toluene, xylene and the like or a mixed solvent thereof can be used. The chloroformic acid ester (XI) is used in an amount of 1.0-20 equivalents, preferably 1.0-10 equivalents, relative to amine compound (V).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

Step 2

Compound (I-9) can be obtained by reacting, for example, compound (I-8) wherein $R^{11a}$ is methoxy with amine compound (XIII).

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, alcohol solvents such as methanol, ethanol, propanol and the like, aromatic hydrocarbon solvents such as benzene, toluene, xylene and the like or a mixed solvent thereof can be used. The amine compound (XIII) is used in an amount of 1.0-20 equivalents, preferably 1.0-10 equivalents, relative to compound (I-8).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (I-8) in the reaction system is not particularly limited, it is generally preferably 0.001 mmol/L-1 mol/L.

Scheme 8

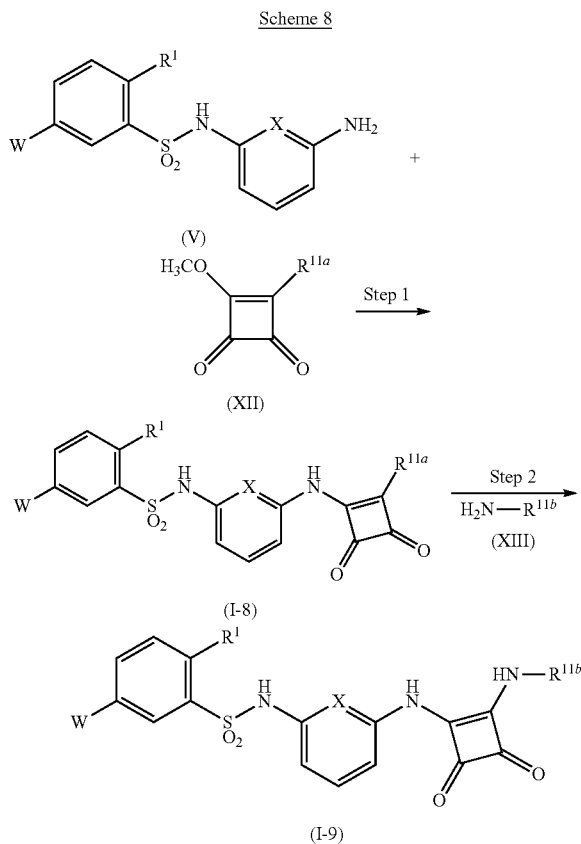

wherein $R^1$, X and W are as defined above, $R^{11a}$ is $C_{1-6}$ alkoxy, and $R^{11b}$ is $C_{6-10}$ aryl optionally substituted by 1 to 3 substituents selected from $C_{1-6}$ alkyl and $C_{1-6}$ alkoxy.

Step 1

Compound (I-8) can be obtained by reacting, for example, amine compound (V) with cyclobutene compound (XII).

As the solvent, halogenated hydrocarbon solvents such as dichloromethane, chloroform, 1,2-dichloroethane and the like, ether solvents such as THF, DME, dioxane and the like, aprotic polar solvents such as DMF, DMSO and the like, alcohol solvents such as methanol, ethanol, propanol and the like, aromatic hydrocarbon solvents such as benzene, toluene, xylene and the like or a mixed solvent thereof can be used. The cyclobutene compound (XII) is used in an amount of 1.0-20 equivalents, preferably 1.0-10 equivalents, relative to amine compound (V).

When a base is used, triethylamine, diisopropylethylamine, pyridine, N-methylmorpholine and the like can be used, and triethylamine or diisopropylethylamine is preferably used.

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

Scheme 9

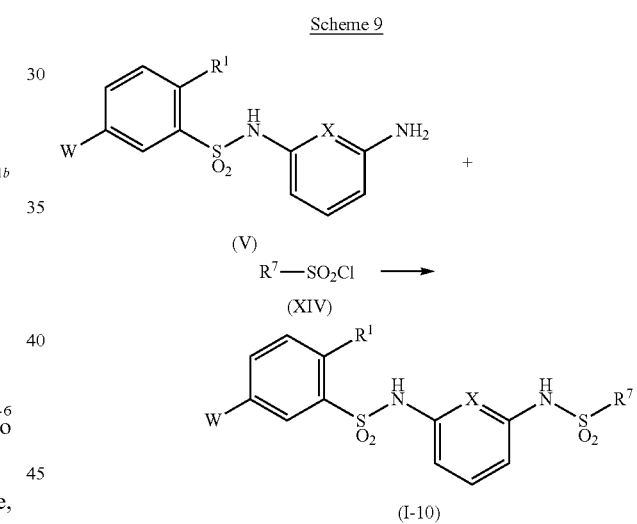

wherein $R^1$, $R^7$, X and W are as defined above.

Compound (I-10) can be obtained by, for example, amidation of amine compound (V) with sulfonyl chloride compound (XIV).

Amidation can be performed by a method similar to Scheme 1, Step 1.

Scheme 10

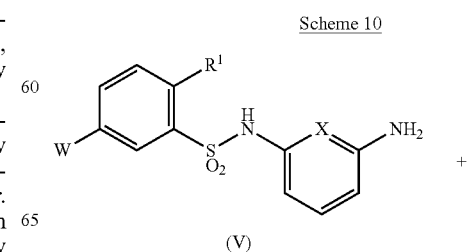

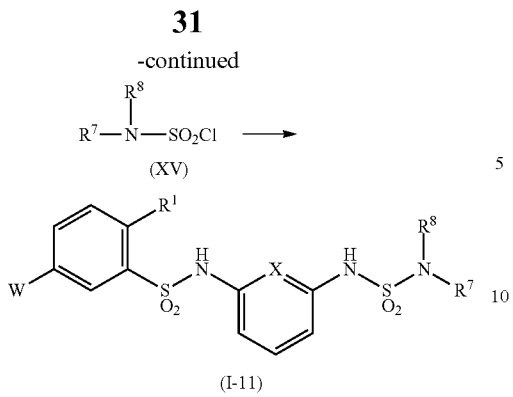

(I-11)

wherein $R^1$, $R^7$, $R^8$, X and W are as defined above.

Compound (I-11) can be obtained by, for example, amidation of amine compound (V) with sulfonyl chloride compound (XV).

Amidation can be performed by a method similar to Scheme 1, Step 1.

Scheme 11

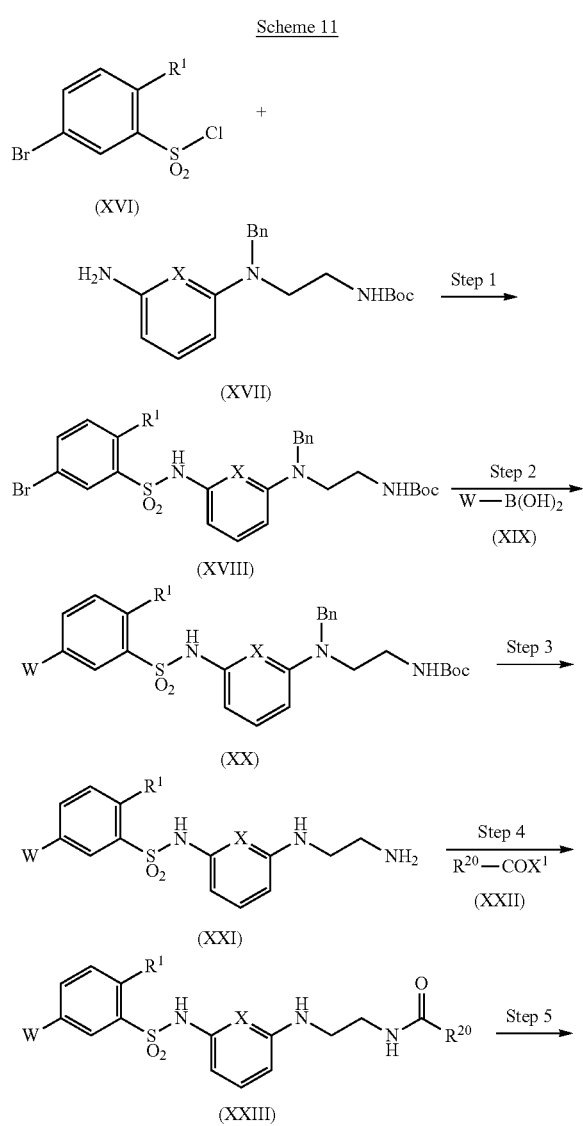

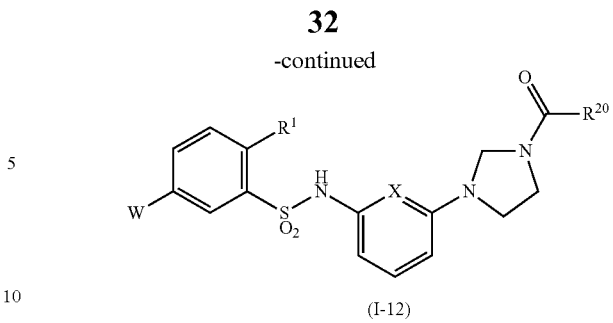

(I-12)

wherein $R^1$, X, W and $X^1$ are as defined above, $R^{20}$ is $C_{6-10}$ aryl optionally substituted by $C_{1-6}$ alkyl, and Bn is a benzyl group.

Step 1

Compound (XVIII) can be obtained by, for example, amidation of sulfonyl chloride compound (XVI) with amine compound (XVII).

Amidation can be performed by a method similar to Scheme 1, Step 1.

Step 2

Compound (XX) can be obtained by, for example, Suzuki coupling of compound (XVIII) with boronic acid compound (XIX).

The Suzuki coupling reaction is performed in the presence of a palladium catalyst and a base, in the presence or absence of a phosphine ligand in a suitable solvent.

As the solvent, ether solvents such as THF, DME, dioxane and the like, aprotic polar solvents such as DMF, DMSO and the like, alcohol solvents such as methanol, ethanol, propanol and the like, aromatic hydrocarbon solvents such as benzene, toluene, xylene and the like, water or a mixed solvent thereof can be used. In general, dioxane, DME, a mixed solvent of dioxane and water or a mixed solvent of DME and water is preferably used.

As boronic acid compound (XIX), not only boronic acid but also boronates such as boronic acid pinacol ester, N-methyliminodiacetic acid (MIDA) boronate and the like, or potassium trifluoroborate salt can be used. Particularly, boronic acid or boronic acid pinacol ester is preferably used. The boronic acid compound (XIX) is used in an amount of 1.0-20 equivalents, preferably 1.0-10 equivalents, relative to compound (XVIII).

Examples of the palladium catalyst include tetrakis(triphenylphosphine)palladium, palladium acetate, bis(triphenylphosphine)palladium dichloride, bis(dibenzylideneacetone)palladium, bis(diphenylphosphino)ferrocene palladium dichloride and the like, and tetrakis(triphenylphosphine)palladium or bis(diphenylphosphino)ferrocene palladium dichloride is preferably used. The palladium catalyst is used in an amount of 0.001-1 equivalent, preferably 0.005-0.5 equivalent, relative to compound (XVIII).

Examples of the base include sodium carbonate, potassium carbonate, cesium carbonate, potassium phosphate, sodium hydroxide, potassium hydroxide, barium hydroxide, triethylamine, diisopropylethylamine and the like, and sodium carbonate or potassium carbonate is preferably used.

The reaction temperature is generally −40-150° C., preferably 20-110° C. While the reaction time is appropriately selected according to the conditions such as reaction temperature and the like, it is generally about 20 min-48 hr. While the concentration of substrate (XIX) in the reaction system is not particularly limited, it is generally preferably 0.001 mmol/L-1 mol/L.

Step 3

Amine compound (XXI) can be obtained by, for example, deprotecting the benzyl group of compound (XX) by hydrogenolysis and the like, and deprotecting the tert-butoxycarbonyl (Boc) group of the obtained compound under acidic conditions.

Hydrogenolysis is performed in the presence of a palladium catalyst and under hydrogen atmosphere in a suitable solvent.

As the solvent, ether solvents such as THF, DME, dioxane and the like, aprotic polar solvents such as DMF, DMSO, ethyl acetate and the like, alcohol solvents such as methanol, ethanol, propanol and the like, aromatic hydrocarbon solvents such as benzene, toluene, xylene and the like, acetic acid, water or a mixed solvent thereof can be used. Generally, toluene, THF or methanol is preferably used.

Examples of the palladium catalyst include palladium (Pd), palladium carbon (Pd/C), palladium hydroxide (Pd(OH)$_2$), palladium hydroxide carbon (Pd(OH)$_2$/C) and the like, and palladium carbon (Pd/C) is preferably used. The palladium catalyst is used in an amount of 0.001-1 equivalents, preferably 0.005-0.5 equivalents, relative to compound (XX).

The reaction temperature is generally −40-150° C., preferably 20-110° C. While the reaction time is appropriately selected according to the conditions such as reaction temperature and the like, it is generally about 20 min-48 hr. While the concentration of substrate (XX) in the reaction system is not particularly limited, it is generally preferably 0.001 mmol/L-1 mol/L.

The deprotection of the tert-butoxycarbonyl (Boc) group can be performed by a method similar to Scheme 1, Step 2.

Step 4

Compound (XXIII) can be obtained by, for example, amidation of amine compound (XXI) with acyl halide (XXII) wherein X$^1$ is a halogen atom or carboxylic acid (XXII) wherein X$^1$ is a hydroxy group.

Amidation can be performed by a method similar to Scheme 1, Step 3.

Step 5

Compound (I-12) can be obtained by, for example, reacting compound (XXIII) with para-formaldehyde.

As the solvent, carboxylic acid solvents such as acetic acid and the like can be used. Para-formaldehyde is used in an amount of 1.0-20 equivalents, preferably 1.0-10 equivalents, relative to compound (XXIII).

The reaction temperature is generally −40-150° C., preferably 0-80° C. While the reaction time is appropriately selected according to the conditions such as reaction temperature and the like, it is generally about 20 min-48 hr. While the concentration of substrate (XXIII) in the reaction system is not particularly limited, it is generally preferably 0.001 mmol/L-1 mol/L.

Scheme 12

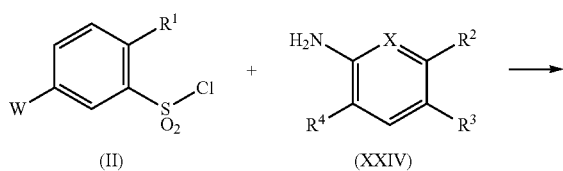

(II)    (XXIV)

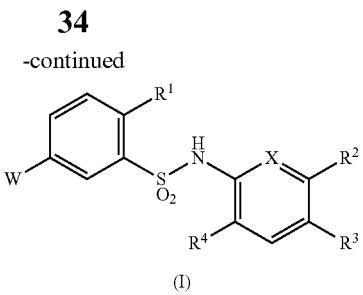

(I)

wherein R$^1$, R$^2$, R$^3$, R$^4$, X and W are as defined above.

Compound (I) can be obtained by, for example, amidation of sulfonyl chloride compound (II) with amine compound (XXIV).

Amidation can be performed by a method similar to Scheme 1, Step 1.

Scheme 13

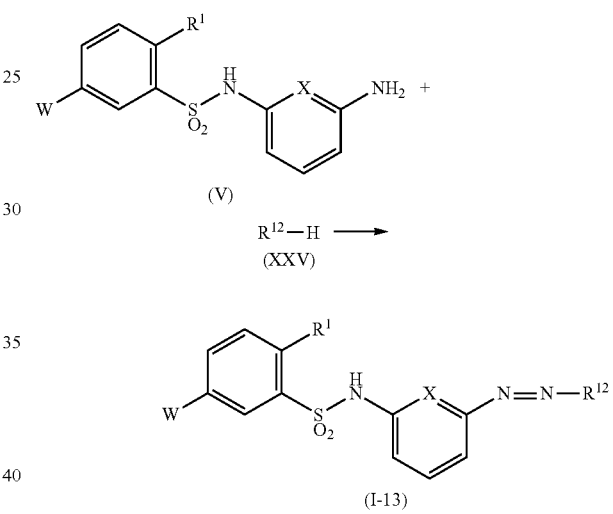

wherein R$^1$, R$^{12}$, X and W are as defined above.

Compound (I-13) can be obtained by, for example, diazotization of amine compound (V) and subjecting the obtained diazonium salt to a diazocoupling reaction with compound (XXV).

The diazotization can be performed by reacting amine compound (V) with a nitrite salt such as sodium nitrite and the like in an aqueous acidic solution. The nitrite salt is used in an amount of 1.0-20 equivalents, preferably 1.0-10 equivalents, relative to amine compound (V).

The diazocoupling reaction can be performed by reacting the obtained diazonium salt with compound (XXV). The compound (XXV) is used in an amount of 1.0-20 equivalents, preferably 1.0-10 equivalents, relative to amine compound (V).

The reaction temperature is generally −40-150° C., preferably 0-80° C. While the reaction time is appropriately selected according to the conditions such as reaction temperature and the like, it is generally about 20 min-48 hr. While the concentration of substrate (V) in the reaction system is not particularly limited, it is generally preferably 0.001 mmol/L-1 mol/L.

Scheme 14

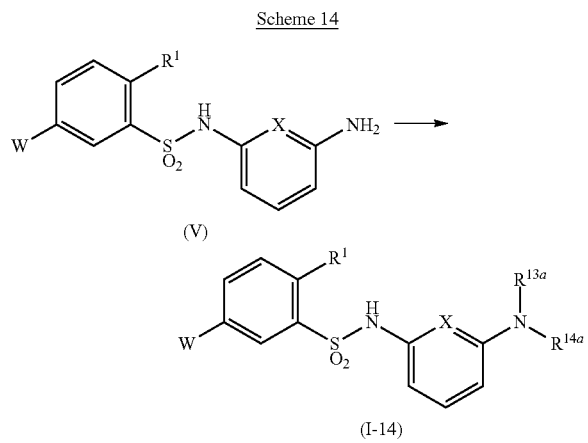

wherein $R^1$, X and W are as defined above, $R^{13a}$ is $C_{1-6}$ alkyl, $C_{6-10}$ aryl-$C_{1-6}$ alkyl or $C_{2-6}$ alkenyl-carbonyl and $R^{14a}$ is $C_{1-6}$ alkyl optionally substituted by one substituent selected from (a) $C_{1-6}$ alkoxy-carbonylamino, (b) $C_{2-6}$ alkenyl-carbonylamino and (c) $C_{6-10}$ aryl-$C_{1-6}$ alkylaminocarbonyl optionally substituted by $C_{1-6}$ alkyl.

Compound (I-14) can be obtained, for example, by acylation and/or alkylation of amine compound (V).

Acylation can be performed by a method similar to Scheme 1, Step 3. Alkylation can be performed by a method similar to the reductive alkylation of Scheme 2.

Scheme 15

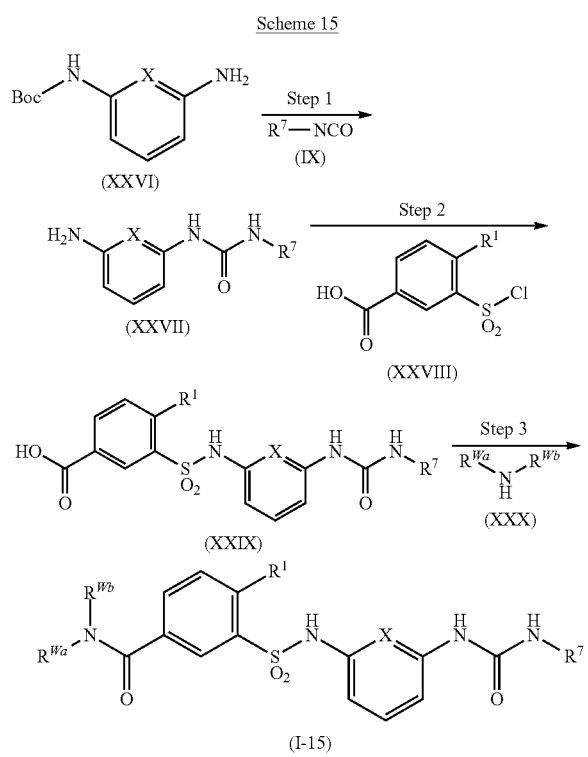

wherein $R^1$, $R^7$, $R^{Wa}$, $R^{Wb}$ and X are as defined above.

Step 1

Compound (XXVII) can be obtained by, for example, reacting compound (XXVI) with isocyanate (IX), and deprotecting the tert-butoxycarbonyl (Boc) group of the obtained compound.

The reaction of compound (XXVI) and isocyanate (IX) can be performed by a method similar to Scheme 4. The deprotection of the tert-butoxycarbonyl (Boc) group can be performed by a method similar to Scheme 1, Step 2.

Step 2

Compound (XXIX) can be obtained, for example, by amidation of compound (XXVII) with sulfonyl chloride compound (XXX).

Amidation can be performed by a method similar to Scheme 1, Step 1.

Step 3

Compound (I-15) can be obtained, for example, by amidation of compound (XXIX) with amine compound (XXX).

Amidation can be performed by a method similar to Scheme 11, Step 4.

Scheme 16

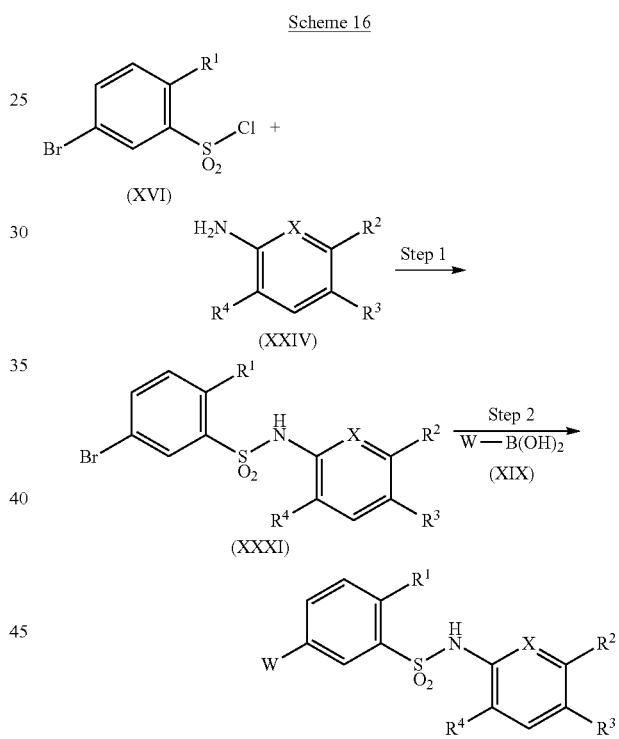

wherein $R^1$, $R^2$, $R^3$, $R^4$, X and W are as defined above.

Step 1

Compound (XXXI) can be obtained, for example, by amidation of sulfonyl chloride compound (XVI) with compound (XXIV).

Amidation can be performed by a method similar to Scheme 1, Step 1.

Step 2

Compound (I) can be obtained, for example, by Suzuki coupling of compound (XXXI) with boronic acid compound (XIX).

The Suzuki coupling can be performed by a method similar to Scheme 11, Step 2.

Scheme 17

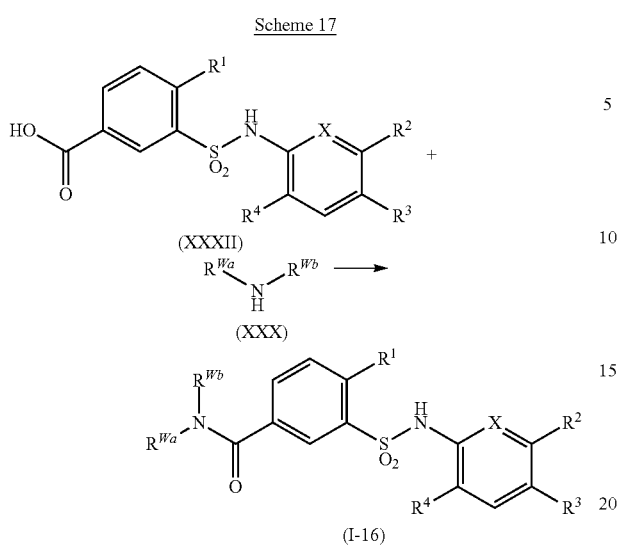

wherein $R^1$, $R^2$, $R^3$, $R^4$, $R^{Wa}$, $R^{Wb}$ and X are as defined above.

Compound (I-16) can be obtained, for example, by amidation of compound (XXXII) with amine compound (XXX).

Amidation can be performed by a method similar to Scheme 11, Step 4.

Step 2
Compound (XXXV) can be obtained, for example, by amidation of sulfonyl chloride compound (XVI) with compound (XXXIV).

Amidation can be performed by a method similar to Scheme 1, Step 1.

Step 3
Compound (I') can be obtained, for example, by Suzuki coupling of compound (XXXV) with boronic acid compound (XXXVI).

The Suzuki coupling can be performed by a method similar to Scheme 11, Step 2.

Compound (I) wherein $R^3$ is $R^6$, and $R^2$ and $R^4$ are each a hydrogen atom can be obtained by a method similar to one mentioned above by using the following amine compound (III-1) instead of amine compound (III).

Compound (I) wherein $R^4$ is $R^6$, and $R^2$ and $R^3$ are each a hydrogen atom can be obtained by a method similar to one mentioned above by using the following amine compound (III-2) instead of amine compound (III).

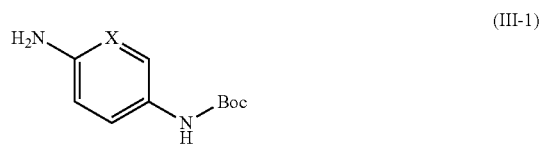
(III-1)

Scheme 18

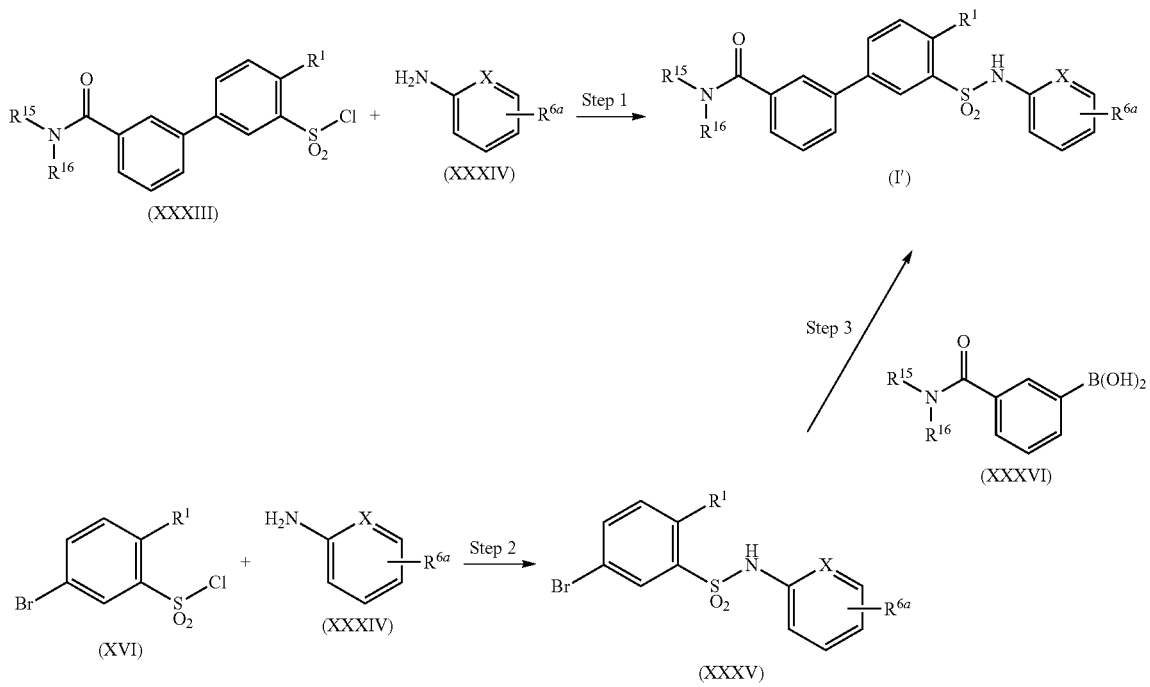

wherein $R^1$, $R^{6a}$, $R^{15}$, $R^{16}$ and X are as defined above.

Step 1
Compound (I') can be obtained, for example, by amidation of sulfonyl chloride compound (XXXIII) with compound (XXXIV).

Amidation can be performed by a method similar to Scheme 1, Step 1.

-continued

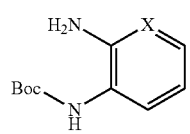
(III-2)

wherein X are as defined above.

An orexin receptor agonist containing the compound of the present invention is effective for not only human but also mammals other than human, for example, mouse, rat, hamster, rabbit, cat, dog, bovine, sheep, monkey and the like.

Also, the compound of the present invention is used not only as an agent for the prophylaxis or treatment of narcolepsy as mentioned above but also can be used in a method of preventing or treating narcolepsy, or for the production of a medicament for the prophylaxis or treatment of narcolepsy.

Furthermore, the compound of the present invention can also be used as an agent for improving sleepiness, or a prophylactic or therapeutic agent for obesity, diabetes, depression, sepsis, severe sepsis, septic shock and the like.

When the compound of the present invention is clinically used as an agent for the prophylaxis or treatment of narcolepsy, an agent for improving sleepiness or a prophylactic or therapeutic agent for obesity, diabetes, depression, sepsis, severe sepsis, septic shock and the like, the medicament may be a free form of the compound of the present invention or an acid addition salt thereof, or additives such as excipient, stabilizer, preservative, buffering agent, solubilizing agent, emulsifier, diluent, isotonicity agent and the like may be mixed as appropriate. Examples of the administration form include oral preparations such as tablet, capsule, granule, powder, syrup and the like, parenteral agents such as injection, suppository, liquid and the like, topical administration of ointment, cream, adhesive preparation and the like, and the like.

The agent for the prophylaxis or treatment of narcolepsy, the agent for improving sleepiness, or the prophylactic or therapeutic agent for obesity, diabetes, depression, sepsis, severe sepsis, septic shock and the like of the present invention desirably contains 0.001-90 wt %, preferably 0.01-70 wt %, of the above-mentioned active ingredient. The amount thereof to be used is appropriately determined according to the symptom, age, body weight, and administration method. In the case of injection for an adult, the amount of the active ingredient is 0.1 µg-1 g per day, 1 µg-1 g in the case of an oral preparation, and 1 µg-10 g in the case of an adhesive preparation, each of which can be administered in one to several portions.

In addition, the agent for the prophylaxis or treatment of narcolepsy or the agent for improving sleepiness of the present invention can also be used in combination with an agent for the prophylaxis or treatment of strong sleepiness and dozing during the day, an agent for the prophylaxis or treatment of deep sleep disorder, or an agent for the prophylaxis or treatment of cataplexy.

As an agent for the prophylaxis or treatment of strong sleepiness and dozing during the day, central nervous system stimulants such as methylphenidate, pemoline, modafinil and the like, and the like can be mentioned.

As an agent for the prophylaxis or treatment of deep sleep disorder, sleep inducing drugs such as triazolam, vegetamin B and the like, antianxiety drug and the like can be mentioned.

As an agent for the prophylaxis or treatment of cataplexy, tricyclic antidepressants such as clomipramine hydrochloride, brotizolam, imipramine hydrochloride and the like, selective serotonin reuptake inhibitors (SSRI) such as fluvoxamine maleate, paroxetine, hydrochloride and the like, serotonin and noradrenaline reuptake inhibitors (SNRI) such as milnacipran hydrochloride, duloxetine hydrochloride and the like, and the like can be mentioned.

EXAMPLES

The present invention is specifically explained in the following by referring to Examples. In the following Examples, the following abbreviations are used.

Boc: tert-butoxycarbonyl
Bn: benzyl
DIPEA: N,N-diisopropylethylamine
DME: 1,2-dimethoxyethane
DMF: N,N-dimethylformamide
DPPA: diphenylphosphoryl azide
HATU: O-(7-azabenzotriazol-1-yl)-N,N,N',N'-tetramethyluronium hexafluorophosphate
IBX: 2-iodoxybenzoic acid
BOP: benzotriazol-1-yloxytris(dimethylamino)phosphonium hexafluorophosphate
Me: methyl
Ph: phenyl
TEA: triethylamine
TFA: 2,2,2-trifluoroacetic acid Compound names were determined using ChemBioDraw Ultra ver.12.0.3 of Cambridge Corporation.

The "room temperature" in the following Examples and Production Examples mean generally from about 10° C. to about 35° C. Unless particularly indicated, % shows weight percent.

Production Example (1)

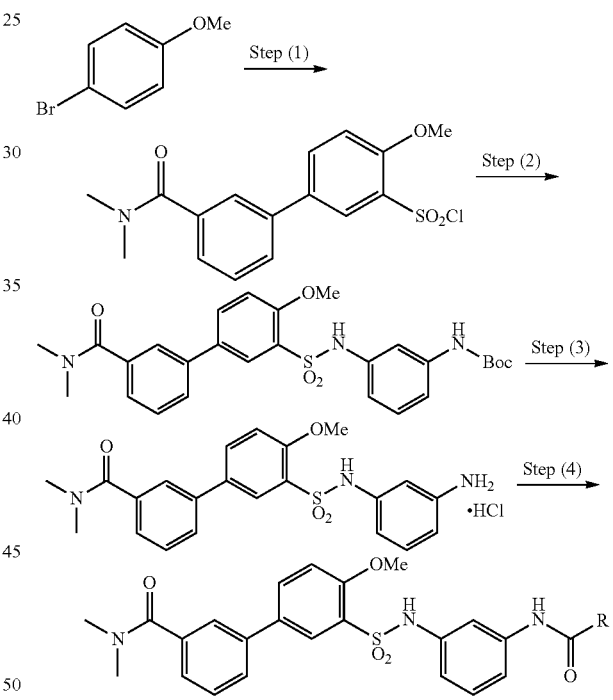

(1) 3'-(dimethylcarbamoyl)-4-methoxy-[1,1'-biphenyl]-3-sulfonyl chloride

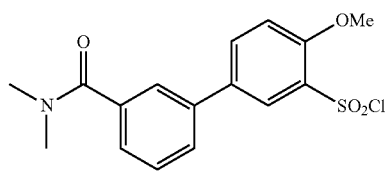 [SMILES: COc1ccc(-c2cccc(C(=O)N(C)C)c2)cc1S(=O)(=O)Cl]

(i) Under an argon atmosphere, to a solution of 4-bromoanisole (1.0 mL) in DME (20.0 mL) were added 3-(N,N-dimethylaminocarbonyl)phenylboronic acid (1.60 g), sodium carbonate (1.80 g), water (2.0 mL) and tetrakis(triphenylphosphine)palladium (250.0 mg), and the mixture was heated under reflux overnight. The reaction mixture was filtered through celite, and the filtrate was concentrated. To the obtained residue was added pure water and the mixture was extracted with chloroform. The organic layer was dried over sodium sulfate and filtered, and the filtrate was concentrated under reduced pressure. The obtained residue was purified by silica gel column chromatography (eluent: ethyl acetate/hexane=1/2→1/1) to give 4'-methoxy-N,N-dimethyl-[1,1'-biphenyl]-3-carboxamide (1.72 g).

(ii) Under an argon atmosphere, to chlorosulfonic acid (870 μL) was slowly added a solution of 4'-methoxy-N,N-dimethyl-[1,1'-biphenyl]-3-carboxamide (1.10 g) in dichloromethane (4.0 mL), and the mixture was stirred under ice-cooling for 10 min. The reaction mixture was warmed to room temperature and stirred for 2 hr. Thionyl chloride (950 μL) and DMF (1.70 mL) were added, and the mixture was stirred at room temperature overnight. The reaction mixture was poured into ice and the mixture was stirred for 1 hr and extracted with chloroform. The organic layer was dried over sodium sulfate and filtered, and the filtrate was concentrated under reduced pressure. The obtained residue was purified by silica gel column chromatography (eluent: ethyl acetate/hexane=1/1→1/0) to give 3'-(dimethylcarbamoyl)-4-methoxy-[1,1'-biphenyl]-3-sulfonyl chloride (1.40 g).

(2) tert-butyl (3-(3'-(dimethylcarbamoyl)-4-methoxy-[1,1'-biphenyl]-3-ylsulfonamido)phenyl) carbamate

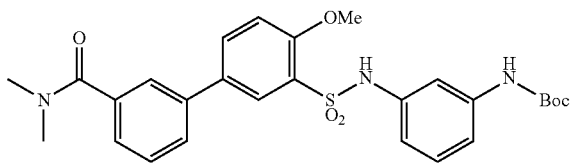 [SMILES: COc1ccc(-c2cccc(C(=O)N(C)C)c2)cc1S(=O)(=O)Nc1cccc(NC(=O)OC(C)(C)C)c1]

Under an argon atmosphere, to a solution of tert-butyl (3-aminophenyl)carbamate (1.22 g) in dichloromethane (4.0 mL) was added a solution of DIPEA (2.80 mL) and 3'-(dimethylcarbamoyl)-4-methoxy-[1,1'-biphenyl]-3-sulfonyl chloride (1.88 g) in dichloromethane (4.0 mL), and the mixture was stirred at room temperature for 4 hr. The resulting white solid was collected by filtration, and the residue was washed with 25% dichloromethane-containing hexane solution. The filtrate was concentrated under reduced pressure, 25% dichloromethane-containing hexane solution was added and the resulting white solid was similarly collected by filtration and washed. The obtained solid was dried in vacuo to give tert-butyl (3-(3'-(dimethylcarbamoyl)-4-methoxy-[1,1'-biphenyl]-3-ylsulfonamido)phenyl)carbamate (2.51 g).

(3) 3'-(N-(3-aminophenyl)sulfamoyl)-4'-methoxy-N,N-dimethyl-[1,1'-biphenyl]-3-carboxamide hydrochloride

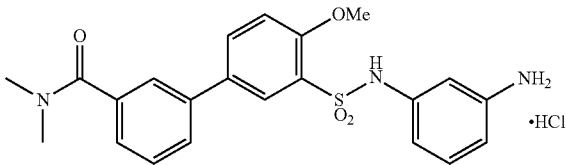 [SMILES: COc1ccc(-c2cccc(C(=O)N(C)C)c2)cc1S(=O)(=O)Nc1cccc(N)c1 ; Cl]

To a suspension of tert-butyl (3-(3'-(dimethylcarbamoyl)-4-methoxy-[1,1'-biphenyl]-3-ylsulfonamido)phenyl)carbamate (2.42 g) in diethyl ether (18.8 mL) was added 10% hydrogen chloride-methanol solution (47.0 mL), and the mixture was stirred at 60° C. for 12 hr. The resulting white solid was collected by filtration, and washed with diethyl ether. The filtrate was concentrated under reduced pressure and diethyl ether was added to the residue. The resulting white solid was similarly collected by filtration and washed. The obtained solid was dried in vacuo to give 3'-(N-(3-aminophenyl)sulfamoyl)-4'-methoxy-N,N-dimethyl-[1,1'-biphenyl]-3-carboxamide hydrochloride (1.99 g).

(4) 3'-(N-(3-benzamidophenyl)sulfamoyl)-4'-methoxy-N,N-dimethyl-[1,1'-biphenyl]-3-carboxamide

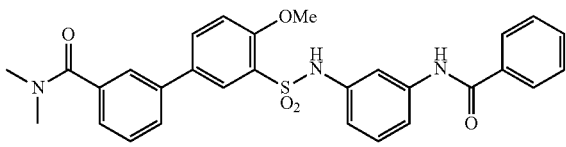 [SMILES: COc1ccc(-c2cccc(C(=O)N(C)C)c2)cc1S(=O)(=O)Nc1cccc(NC(=O)c2ccccc2)c1]

Under an argon atmosphere, to a solution of 3'-(N-(3-aminophenyl)sulfamoyl)-4'-methoxy-N,N-dimethyl-[1,1'-biphenyl]-3-carboxamide hydrochloride (20.0 mg) in anhydrous pyridine (1.0 mL) was added benzoyl chloride (6.03 μg) under ice-cooling, and the mixture was warmed to room temperature and stirred for 5 hr. The reaction mixture was diluted with ethyl acetate, and extracted with 1 M aqueous hydrochloric acid solution. The organic layer was washed with saturated aqueous sodium hydrogen carbonate solution and saturated brine, dried over sodium sulfate and filtered, and the filtrate was concentrated under reduced pressure. The obtained residue was purified by silica gel column chromatography (eluent: hexane/ethyl acetate=1/0→20/1) to give 3'-(N-(3-benzamidophenyl)sulfamoyl)-4'-methoxy-N,N-dimethyl-[1,1'-biphenyl]-3-carboxamide (21.8 mg).

The compounds described in the following Tables 1 and 2 were also synthesized similarly from acid chloride or carboxylic acid having the corresponding R group.

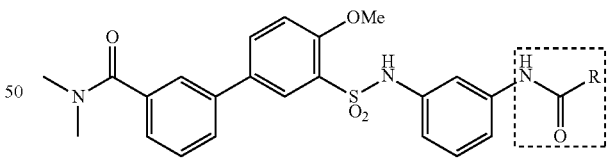

TABLE 1

| Ex. No. | NHCOR moiety structure | $^1$H-NMR |
|---|---|---|
| 1 |  | 1H NMR (400 MHz, Pyridine-d5) δ 12.13 (brs, 1H), 11.03 (brs, 1H), 8.83 (dd, J = 2.0 Hz, 1H), 8.67 (d, J = 2.4 Hz, 1H), 8.13-8.07 (m, 2H), 7.83 (dd, J = 1.5 Hz, 1H), 7.67 (dd, J = 8.6, 2.4 Hz, 1H), 7.60 (dd, J = 8.5 Hz, 2H), 7.51 (d, J = 7.6 Hz, 2H), 7.45-7.32 (m, 4H), 7.27 (dd, J = 8.1 Hz, 1H), 7.09 (d, J = 8.7 Hz, 1H), 3.72 (s, 3H), 3.05 (brs, 3H), 2.79 (brs, 3H). |

TABLE 1-continued

| Ex. No. | NHCOR moiety structure | ¹H-NMR |
|---|---|---|
| 2 | (2-bromobenzamide, N-methyl) | 1H NMR (400 MHz, Chloroform-d) δ 8.04 (d, J = 2.4 Hz, 1H), 7.70 (dd, J = 8.6, 2.4 Hz, 1H), 7.66 (s, 1H), 7.62-7.58 (m, 2H), 7.56 (dd, J = 7.7, 1.4 Hz, 1H), 7.54-7.51 (m, 2H), 7.42 (dd, J = 48.2, 7.8 Hz, 1H), 7.37 (t, J = 7.4 Hz, 1H), 7.35-7.27 (m, 2H), 7.21-7.16 (m, 2H), 7.09 (d, J = 8.7 Hz, 1H), 7.05 (s, 1H), 7.02-6.95 (m, 1H), 4.12 (s, 4H), 3.09 (s, 3H), 2.98 (s, 3H). |
| 3 | (3-bromobenzamide, N-methyl) | 1H NMR (400 MHz, Chloroform-d) δ 8.04 (d, J = 2.4 Hz, 1H), 7.93 (d, J = 8.7 Hz, 1H), 7.85 (s, 1H), 7.71-7.65 (m, 3H), 7.62-7.56 (m, 3H), 7.54-7.49 (m, 2H), 7.44-7.38 (m, 1H), 7.35-7.30 (m, 1H), 7.19 (t, J = 8.0 Hz, 1H), 7.08 (d, J = 8.6 Hz, 1H), 7.05 (s, 1H), 6.89 (ddd, J = 7.9, 2.0, 0.9 Hz, 1H), 4.11 (s, 3H), 3.10 (s, 3H), 2.97 (s, 3H). |
| 4 | (isonicotinamide, N-methyl) | 1H NMR (400 MHz, Chloroform-d) δ 8.77 (d, J = 6.0 Hz, 2H), 8.08 (d, J = 0.5 Hz, 1H), 8.04 (d, J = 2.4 Hz, 1H), 8.02 (brs, 1H), 7.70 (dd, J = 8.6, 2.1 Hz, 1H), 7.66 (d, J = 6.2 Hz, 2H), 7.58 (dd, J = 2.1 Hz, 1H), 7.55-7.50 (m, 2H), 7.41 (dd, J = 7.9 Hz, 1H), 7.35-7.30 (m, 1H), 7.20 (dd, J = 8.0 Hz, 1H), 7.09 (d, J = 8.6 Hz, 1H), 7.05 (brs, 1H), 6.93-6.87 (m, 1H), 4.11 (s, 3H), 3.10 (s, 3H), 2.98 (s, 3H). |
| 5 | (benzo[d][1,3]dioxole-5-carboxamide, N-methyl) | 1H NMR (400 MHz, Methanol-d4) δ 8.11 (d, J = 2.4 Hz, 1H), 7.83-7.77 (m, 2H), 7.67 (d, J = 8.0 Hz, 1H), 7.60 (dd, J = 1.6 Hz, 1H), 7.53-7.44 (m, 2H), 7.38 (dt, J = 7.6, 1.2 Hz, 1H), 7.35 (d, J = 1.8 Hz, 1H), 7.24-7.13 (m, 3H), 6.95-6.89 (m, 2H), 6.06 (s, 2H), 4.04 (s, 3H), 3.11 (s, 3H), 3.01 (s, 3H). |
| 6 | (2-(dimethylamino)benzamide, N-methyl) | 1H NMR (400 MHz, Chloroform-d) δ 12.30 (s, 1H), 8.20 (dd, J = 7.8, 1.6 Hz, 1H), 8.07 (d, J = 2.3 Hz, 1H), 7.73-7.66 (m, 3H), 7.54 (dd, J = 4.2, 2.4 Hz, 3H), 7.51-7.45 (m, 1H), 7.42 (t, J = 8.0 Hz, 1H), 7.34 (d, J = 7.6 Hz, 1H), 7.29 (d, J = 7.3 Hz, 1H), 7.18 (d, J = 5.2 Hz, 1H), 7.09 (d, J = 8.7 Hz, 1H), 7.02 (s, 1H), 6.94 (td, J = 4.1, 2.1 Hz, 1H), 4.15 (s, 3H), 3.11 (s, 3H), 2.97 (s, 3H), 2.76 (s, 6H). |
| 7 | (3-(dimethylamino)benzamide, N-methyl) | 1H NMR (400 MHz, DMSO-d6) δ 10.14 (brs, 1H), 10.09 (s, 1H), 8.04 (d, J = 2.4 Hz, 1H), 7.90 (dd, J = 8.7, 2.4 Hz, 1H), 7.77 (dd, J = 1.9 Hz, 1H), 7.71 (ddd, J = 7.8, 1.4 Hz, 1H), 7.60 (dd, J = 1.6 Hz, 1H), 7.47 (dd, J = 7.7 Hz, 1H), 7.35 (ddd, J = 7.6, 1.2 Hz, 1H), 7.33-7.25 (m, 3H), 7.16-7.10 (m, 3H), 6.93-6.87 (m, 1H), 6.84 (ddd, J = 8.1, 2.0, 0.8 Hz, 1H), 3.95 (s, 3H), 2.96 (s, 3H), 2.93 (s, 6H), 2.87 (s, 3H). |
| 8 | (4-(dimethylamino)benzamide, N-methyl) | 1H NMR (400 MHz, Chloroform-d) δ 8.03 (s, 1H), 7.75-7.63 (m, 4H), 7.59-7.49 (m, 3H), 7.41 (t, J = 7.7 Hz, 1H), 7.35-7.30 (m, 1H), 7.22 (s, 1H), 7.16 (t, J = 8.6 Hz, 1H), 7.08 (d, J = 8.8 Hz, 1H), 6.99 (s, 1H), 6.89 (d, J = 7.5 Hz, 1H), 6.73-6.63 (m, 2H), 4.12 (s, 3H), 3.11 (s, 3H), 3.03 (s, 6H), 2.98 (s, 3H). |

TABLE 1-continued

| Ex. No. | NHCOR moiety structure | ¹H-NMR |
|---|---|---|
| 9 | (2-naphthyl methylamide structure) | 1H NMR (400 MHz, DMSO-d6) δ 10.40 (s, 1H), 10.16 (s, 1H), 8.50 (s, 1H), 8.12-7.97 (m, 4H), 7.94 (dd, J = 8.6, 1.8 Hz, 1H), 7.91 (dd, J = 8.7, 2.4 Hz, 1H), 7.85 (t, J = 2.0 Hz, 1H), 7.73 (ddd, J = 7.8, 1.8, 1.1 Hz, 1H), 7.68-7.59 (m, 3H), 7.48 (t, J = 7.7 Hz, 1H), 7.39 (ddd, J = 8.1, 1.9, 0.8 Hz, 1H), 7.35 (ddd, J = 7.6, 1.3 Hz, 1H), 7.28 (d, J = 8.8 Hz, 1H), 7.17 (t, J = 8.1 Hz, 1H), 6.87 (ddd, J = 8.1, 2.1, 0.9 Hz, 1H), 3.97 (s, 3H), 2.92 (s, 3H), 2.85 (s, 3H). |
| 10 | (1-naphthyl methylamide structure) | 1H NMR (400 MHz, Chloroform-d) δ 8.31-8.22 (m, 1H), 8.06 (d, J = 2.4 Hz, 1H), 7.95 (d, J = 8.3 Hz, 1H), 7.92-7.85 (m, 1H), 7.71 (ddd, J = 16.9, 12.1, 8.1 Hz, 4H), 7.60-7.51 (m, 4H), 7.48 (p, J = 8.1, 7.1 Hz, 1H), 7.41 (t, J = 8.0 Hz, 1H), 7.33 (dt, J = 7.5, 1.3 Hz, 1H), 7.25-7.21 (m, 2H), 7.15-7.07 (m, 2H), 7.01 (ddd, J = 7.3, 2.1 Hz, 1H), 4.15 (s, 3H), 3.08 (s, 3H), 2.97 (s, 3H). |

TABLE 2

| Ex. No. | NHCOR moiety structure | ¹H-NMR |
|---|---|---|
| 11 | (4-methyl-2-(pyridin-4-yl)thiazole-5-carboxamide structure) | 1H NMR (400 MHz, DMSO-d6) δ 10.29 (s, 1H), 10.18 (s, 1H), 8.67 (d, J = 4.8 Hz, 1H), 8.15 (d, J = 7.9 Hz, 1H), 8.06 (d, J = 2.3 Hz, 1H), 8.00 (ddd, J = 7.8, 1.7 Hz, 1H), 7.91 (dd, J = 8.6, 2.3 Hz, 1H), 7.72 (d, J = 7.8 Hz, 1H), 7.69-7.60 (m, 2H), 7.59-7.53 (m, 1H), 7.51 (t, J = 7.7 Hz, 1H), 7.38-7.33 (m, 1H), 7.32-7.25 (m, 2H), 7.15 (dd, J = 8.1 Hz, 1H), 6.87 (d, J = 7.7 Hz, 1H), 3.95 (s, 3H), 3.17 (d, J = 5.0 Hz, 3H), 2.95 (s, 3H), 2.89 (s, 3H). |
| 12 | (4-methyl-2-(pyridin-3-yl)thiazole-5-carboxamide structure) | 1H NMR (400 MHz, Chloroform-d) δ 8.73 (s, 1H), 8.72 (s, 1H), 8.06 (d, J = 2.4 Hz, 1H), 7.82-7.73 (m, 3H), 7.71 (dd, J = 8.6, 2.4 Hz, 1H), 7.56-7.50 (m, 3H), 7.41 (dd, J = 8.0 Hz, 1H), 7.34-7.27 (m, 2H), 7.21 (dd, J = 8.2 Hz, 1H), 7.17-7.06 (m, 2H), 6.94-6.87 (m, 1H), 4.11 (s, 3H), 3.11 (s, 3H), 2.98 (s, 3H), 2.75 (s, 3H). |
| 13 | (benzhydrylsulfinyl acetamide structure) | 1H NMR (400 MHz, Chloroform-d): δ 9.09 (s, 1H), 8.06 (d, J = 2.8 Hz, 1H), 7.67 (dd, J = 2.8, 8.0 Hz, 1H), 7.55-7.50 (m, 2H), 7.48-7.29 (m, 12H), 7.10 (t, J = 8.0 Hz, 1H), 7.03-6.97 (m, 3H), 5.18 (s, 1H), 3.99 (s, 3H), 3.59 (d, J = 14.0 Hz, 1H), 3.25 (d, J = 14.0 Hz, 1H), 3.11 (s, 3H), 2.96 (s, 3H), 1.61 (brs, 2H). |
| 14 | (furan-3-yl acrylamide structure) | 1H NMR (400 MHz, Pyridine-d5) δ 12.12 (brs, 1H), 10.96 (s, 1H), 8.83 (t, J = 1.9 Hz, 1H), 8.70 (d, J = 2.4 Hz, 1H), 7.98 (d, J = 15.6 Hz, 1H), 7.96 (s, 1H), 7.91 (dd, J = 1.5 Hz, 1H), 7.68 (dd, J = 8.6, 2.4 Hz, 1H), 7.63-7.59 (m, 1H), 7.56-7.49 (m, 3H), 7.43 (dd, J = 7.7 Hz, 1H), 7.39 (ddd, J = 8.1, 2.0, 0.9 Hz, 1H), 7.23 (dd, J = 8.1 Hz, 1H), 7.08 (d, J = 8.7 Hz, 1H), 6.66 (d, J = 15.4 Hz, 1H), 6.49 (brd, J = 1.9 Hz, 1H), 3.71 (s, 3H), 3.06 (brs, 3H), 2.80 (brs, 3H). |

TABLE 2-continued

| Ex. No. | NHCOR moiety structure | 1H-NMR |
|---|---|---|
| 15 | 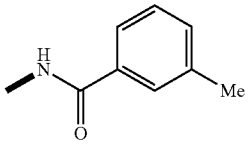 | 1H NMR (400 MHz, Chloroform-d) δ 8.04 (d, J = 2.4 Hz, 1H), 7.90 (s, 1H), 7.69 (dd, J = 8.6, 2.4 Hz, 1H), 7.63 (brs, 1H), 7.62-7.56 (m, 2H), 7.55-7.49 (m, 2H), 7.41 (dd, J = 8.3 Hz, 1H), 7.36-7.31 (m, 2H), 7.29 (ddd, J = 8.6, 2.1, 0.9 Hz, 1H), 7.18 (dd, J = 8.1 Hz, 1H), 7.13 (brs, 1H), 7.08 (d, J = 8.7 Hz, 1H), 6.93 (ddd, J = 8.0, 2.1, 0.9 Hz, 1H), 4.12 (s, 3H), 3.11 (s, 3H), 2.97 (s, 3H), 2.40 (s, 3H). |
| 16 | 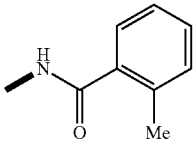 | 1H NMR (400 MHz, Chloroform-d) δ 8.03 (d, J = 2.4 Hz, 1H), 7.75 (brs, 1H), 7.68 (dd, J = 8.6, 2.4 Hz, 1H), 7.58 (brs, 1H), 7.55-7.50 (m, 2H), 7.44-7.34 (m, 2H), 7.34-7.28 (m, 2H), 7.26-7.22 (m, 2H), 7.22-7.12 (m, 3H), 7.07 (d, J = 8.7 Hz, 1H), 6.98-6.92 (m, 1H), 4.09 (s, 3H), 3.08 (s, 3H), 2.97 (s, 3H), 2.40 (s, 3H). |
| 17 | 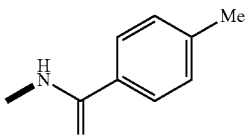 | 1H NMR (400 MHz, Pyridine-d5) δ 12.13 (brs, 1H), 10.96 (brs, 1H), 8.86 (dd, J = 2.0 Hz, 1H), 8.67 (d, J = 2.4 Hz, 1H), 8.06 (d, J = 8.2 Hz, 2H), 7.83 (dd, J = 1.7 Hz, 1H), 7.67 (dd, J = 8.6, 2.4 Hz, 1H), 7.62 (ddd, J = 7.7, 1.5 Hz, 1H), 7.58 (ddd, J = 8.0, 2.1, 0.9 Hz, 1H), 7.53-7.48 (m, 2H), 7.42 (dd, J = 7.6 Hz, 1H), 7.26 (dd, J = 8.1 Hz, 1H), 7.15 (d, J = 7.9 Hz, 2H), 7.08 (d, J = 8.7 Hz, 1H), 3.73 (s, 3H), 3.05 (brs, 3H), 2.79 (brs, 3H), 2.17 (s, 3H). |
| 18 | 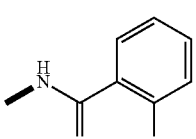 | 1H NMR (400 MHz, Pyridine-d5) δ 12.07 (brs, 1H), 10.44 (brs, 1H), 8.75 (dd, J = 2.0 Hz, 1H), 8.63 (d, J = 2.4 Hz, 1H), 8.12 (dd, J = 7.7, 1.8 Hz, 1H), 7.77 (dd, J = 1.6 Hz, 1H), 7.60 (dd, J = 8.6, 2.4 Hz, 1H), 7.55 (ddd, J = 7.7, 1.9, 1.2 Hz, 1H), 7.49 (ddd, J = 8.0, 2.1, 1.0 Hz, 1H), 7.43 (ddd, J = 7.6, 1.3 Hz, 1H), 7.34 (dd, J = 7.6 Hz, 1H), 7.30 (ddd, J = 7.2, 1.9, 1.8 Hz, 1H), 7.26 (ddd, J = 8.0, 1.9, 1.0 Hz, 1H), 7.17 (dd, J = 8.0 Hz, 1H), 7.01 (d, J = 8.7 Hz, 1H), 6.98 (ddd, J = 7.7, 1.1 Hz, 2H), 3.64 (s, 3H), 3.57 (s, 3H), 2.97 (s, 3H), 2.72 (s, 3H). |
| 19 | 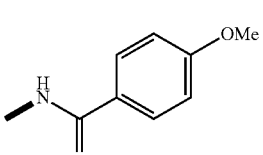 | 1H NMR (400 MHz, Pyridine-d5) δ 12.13 (brs, 1H), 10.89 (s, 1H), 8.86 (dd, J = 2.0 Hz, 1H), 8.68 (d, J = 2.4 Hz, 1H), 8.19 (d, J = 8.9 Hz, 2H), 7.84 (dd, J = 1.5 Hz, 1H), 7.67 (dd, J = 8.6, 2.4 Hz, 1H), 7.65-7.60 (m, 1H), 7.57 (ddd, J = 8.1, 2.1, 0.9 Hz, 1H), 7.54-7.47 (m, 2H), 7.43 (dd, J = 7.6 Hz, 1H), 7.26 (dd, J = 8.1 Hz, 1H), 7.08 (d, J = 8.7 Hz, 1H), 6.99 (d, J = 8.9 Hz, 2H), 3.73 (s, 3H), 3.64 (s, 3H), 3.05 (s, 3H), 2.79 (s, 3H). |

Production Example (2)

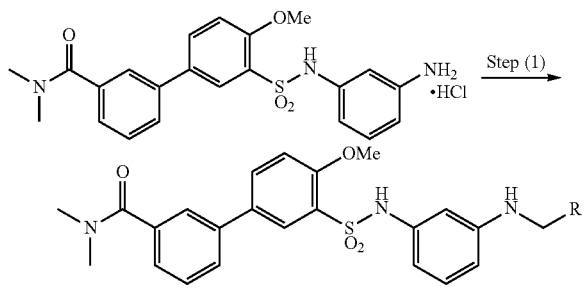

(1) 3'-(N-(3-(benzylamino)phenyl)sulfamoyl)-4'-methoxy-N,N-dimethyl-[1,1'-biphenyl]-3-carboxamide Under an argon atmosphere, to a suspension of 3'-(N-(3-aminophenyl)sulfamoyl)-4'-methoxy-N,N-dimethyl-[1,1'-biphenyl]-3-carboxamide hydrochloride (10.0 mg) in dichloromethane (215 μL) were added TEA (3.0 μL), acetic acid (5.0 μL) and benzaldehyde (2.25 μL), and the mixture was stirred at room temperature for 3.5 hr. Thereto was added sodium triacetoxyborohydride (10 mg), and the mixture was stirred for 14 hr. The reaction mixture was diluted with ethyl acetate, and extracted with 1 M aqueous hydrochloric acid solution. The organic layer was washed with saturated aqueous sodium hydrogen carbonate solution and saturated brine, dried over sodium sulfate and filtered, and the filtrate was concentrated under reduced pressure. The obtained residue was purified by silica gel column chromatography (eluent: ethyl acetate/hexane=0/1→20/1) to give 3'-(N-(3-(benzylamino)phenyl)sulfamoyl)-4'-methoxy-N,N-dimethyl-[1,1'-biphenyl]-3-carboxamide (21.8 mg).

The compounds described in the following Table 3 were also synthesized similarly from aldehyde having the corresponding R group.

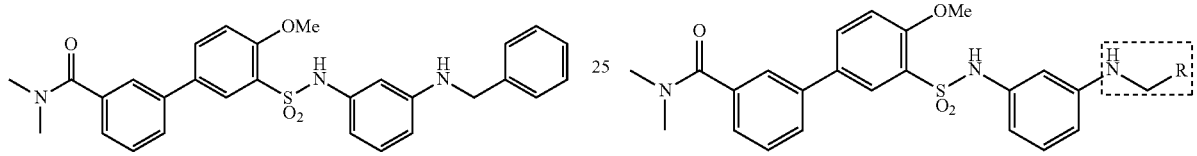

TABLE 3

| Ex. No. | NHCH$_2$R moiety structure | $^1$H-NMR |
|---|---|---|
| 20 | ![benzyl] | 1H NMR (400 MHz, Chloroform-d) δ 8.03 (d, J = 2.3 Hz, 1H), 7.68 (dd, J = 8.6, 2.4 Hz, 1H), 7.61-7.49 (m, 2H), 7.43 (dd, J = 7.6 Hz, 1H), 7.39-7.33 (m, 1H), 7.31-7.21 (m, 5H), 7.01 (d, J = 8.5 Hz, 1H), 6.94 (dd, J = 8.0 Hz, 1H), 6.88 (s, 1H), 6.45-6.39 (m, 1H), 6.39-6.27 (m, 2H), 4.21 (s, 2H), 4.07 (brs, 1H), 3.96 (s, 3H), 3.12 (s, 3H), 2.98 (s, 3H). |
| 21 | ![2-OMe-benzyl] | 1H NMR (400 MHz, Chloroform-d) δ 8.06 (d, J = 2.3 Hz, 1H), 7.69 (dd, J = 8.6, 2.4 Hz, 1H), 7.58-7.50 (m, 2H), 7.43 (dd, J = 7.6 Hz, 1H), 7.35 (ddd, J = 7.5, 1.2 Hz, 1H), 7.19 (d, J = 8.5 Hz, 2H), 7.08 (s, 1H), 7.02 (d, J = 8.7 Hz, 1H), 6.95 (dd, J = 8.0 Hz, 1H), 6.82 (d, J = 8.6 Hz, 2H), 6.43 (dd, J = 2.1 Hz, 1H), 6.39 (dd, J = 7.8, 1.8 Hz, 1H), 6.30 (dd, J = 8.1, 2.2 Hz, 1H), 4.13 (s, 2H), 3.99 (s, 3H), 3.77 (s, 3H), 3.12 (s, 3H), 2.98 (s, 3H). |
| 22 | ![4-OMe-benzyl] | 1H NMR (400 MHz, Chloroform-d) δ 8.05 (d, J = 2.4 Hz, 1H), 7.68 (dd, J = 8.6, 2.4 Hz, 1H), 7.57-7.49 (m, 2H), 7.43 (dd, J = 7.6 Hz, 1H), 7.35 (d, J = 7.6 Hz, 1H), 7.23-7.13 (m, 2H), 7.03 (s, 1H), 6.99 (d, J = 8.6 Hz, 1H), 6.93 (dd, J = 8.0 Hz, 1H), 6.87-6.78 (m, 2H), 6.43 (dd, J = 2.1 Hz, 1H), 6.37 (dd, J = 7.9, 2.0 Hz, 1H), 6.32 (dd, J = 8.2, 2.3 Hz, 1H), 4.21 (s, 2H), 3.96 (s, 3H), 3.81 (s, 3H), 3.12 (s, 3H), 2.98 (s, 3H). |

TABLE 3-continued

| Ex. No. | NHCH₂R moiety structure | ¹H-NMR |
|---|---|---|
| 23 | 3-methoxybenzyl(methyl)amine | 1H NMR (400 MHz, Chloroform-d) δ 8.04 (d, J = 2.4 Hz, 1H), 7.67 (dd, J = 8.6, 2.4 Hz, 1H), 7.57-7.49 (m, 2H), 7.42 (dd, J = 7.6 Hz, 1H), 7.34 (ddd, J = 7.5, 1.3 Hz, 1H), 7.18 (dd, J = 7.8 Hz, 1H), 7.02 (s, 1H), 6.99 (d, J = 8.7 Hz, 1H), 6.93 (dd, J = 8.3 Hz, 1H), 6.86-6.79 (m, 2H), 6.76 (dd, J = 8.2, 2.5 Hz, 1H), 6.42-6.37 (m, 2H), 6.32-6.27 (m, 1H), 4.18 (s, 2H), 4.07 (d, J = 17.4 Hz, 1H), 3.95 (s, 3H), 3.73 (s, 3H), 3.11 (s, 3H), 2.97 (s, 3H). |
| 24 | 2-methylbenzyl(methyl)amine | 1H NMR (400 MHz, Chloroform-d) δ 8.04 (d, J = 2.4 Hz, 1H), 7.69 (dd, J = 8.6, 2.4 Hz, 1H), 7.59-7.49 (m, 2H), 7.42 (dd, J = 7.9 Hz, 1H), 7.35 (ddd, J = 7.5, 1.4 Hz, 1H), 7.20 (d, J = 7.6 Hz, 1H), 7.18-7.14 (m, 2H), 7.12-7.06 (m, 1H), 7.01 (d, J = 8.7 Hz, 1H), 6.96 (dd, J = 8.0 Hz, 1H), 6.85 (s, 1H), 6.40 (dd, J = 2.1 Hz, 1H), 6.37 (ddd, J = 7.8, 2.0, 0.8 Hz, 1H), 6.31 (ddd, J = 8.2, 2.3, 0.8 Hz, 1H), 4.15 (s, 2H), 3.97 (s, 3H), 3.88 (s, 1H), 3.12 (s, 3H), 2.98 (s, 3H), 2.28 (s, 3H). |
| 25 | 3-methylbenzyl(methyl)amine | 1H NMR (400 MHz, Chloroform-d) δ 8.06 (d, J = 2.4 Hz, 1H), 7.68 (dd, J = 8.6, 2.4 Hz, 1H), 7.58-7.55 (m, 1H), 7.55-7.50 (m, 1H), 7.43 (dd, J = 7.6 Hz, 1H), 7.35 (ddd, J = 7.5, 1.4 Hz, 1H), 7.17 (dd, J = 7.5 Hz, 1H), 7.10 (s, 2H), 7.05 (t, J = 6.8 Hz, 2H), 7.01 (d, J = 8.7 Hz, 1H), 6.95 (t, J = 8.0 Hz, 1H), 6.45-6.37 (m, 2H), 6.31 (ddd, J = 8.2, 2.3, 0.9 Hz, 1H), 4.16 (s, 2H), 3.96 (s, 3H), 3.13 (s, 3H), 2.98 (s, 3H), 2.30 (s, 3H). |
| 26 | 2-hydroxybenzyl(methyl)amine | 1H NMR (400 MHz, Chloroform-d) δ 8.43 (brs, 1H), 8.06 (d, J = 2.4 Hz, 1H), 7.66 (dd, J = 8.6, 2.4 Hz, 1H), 7.59 (dd, J = 1.3 Hz, 1H), 7.53 (d, J = 7.8 Hz, 1H), 7.42 (dd, J = 7.6 Hz, 1H), 7.32 (d, J = 7.7 Hz, 1H), 7.12-7.05 (m, 2H), 7.04-6.93 (m, 3H), 6.83-6.73 (m, 2H), 6.57 (dd, J = 2.0 Hz, 1H), 6.44-6.32 (m, 2H), 4.16 (s, 2H), 3.96 (s, 3H), 3.16 (s, 3H), 3.03 (s, 3H). |
| 27 | 4-methylbenzyl(methyl)amine | 1H NMR (400 MHz, Chloroform-d) δ 8.05 (d, J = 2.3 Hz, 1H), 7.68 (dd, J = 8.6, 2.4 Hz, 1H), 7.57-7.48 (m, 2H), 7.42 (dd, J = 7.6 Hz, 1H), 7.34 (ddd, J = 7.4, 1.2 Hz, 1H), 7.14 (d, J = 8.0 Hz, 2H), 7.08 (d, J = 7.9 Hz, 2H), 7.05-6.98 (m, 2H), 6.93 (dd, J = 8.0 Hz, 1H), 6.44-6.35 (m, 2H), 6.29 (dd, J = 8.2, 2.1 Hz, 1H), 4.15 (s, 2H), 4.01 (s, 1H), 3.97 (s, 3H), 3.11 (s, 3H), 2.97 (s, 3H), 2.30 (s, 3H). |
| 28 | 2-bromobenzyl(methyl)amine | 1H NMR (400 MHz, Pyridine-d5) δ 11.65 (s, 1H), 8.59 (d, J = 2.4 Hz, 1H), 7.77 (dd, J = 1.5 Hz, 1H), 7.68 (dd, J = 8.6, 2.4 Hz, 1H), 7.58 (dd, J = 7.8, 1.3 Hz, 1H), 7.55-7.45 (m, 3H), 7.41 (dd, J = 7.6 Hz, 1H), 7.19-7.03 (m, 6H), 6.99 (t, J = 5.9 Hz, 1H), 6.51 (ddd, J = 7.6, 1.8 Hz, 1H), 4.45 (d, J = 5.8 Hz, 2H), 3.60 (s, 3H), 3.07 (s, 3H), 2.80 (s, 3H). |

Production Example (3)

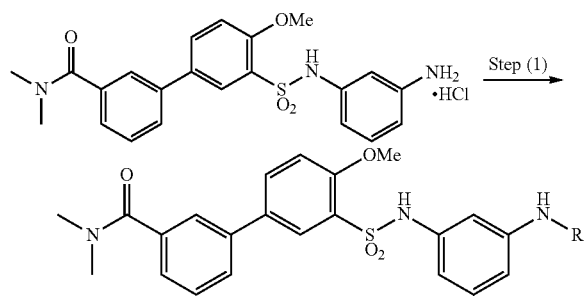

(1) 4'-methoxy-N,N-dimethyl-3'-(N-(3-(phenylamino)phenyl)sulfamoyl)-[1,1'-biphenyl]-3-carboxamide

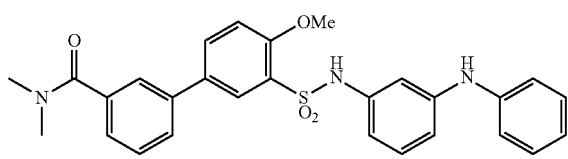 [SMILES: COc1ccc(-c2cccc(C(=O)N(C)C)c2)cc1S(=O)(=O)Nc1cccc(Nc2ccccc2)c1]

To a solution of 3'-(N-(3-aminophenyl)sulfamoyl)-4'-methoxy-N,N-dimethyl-[1,1'-biphenyl]-3-carboxamide hydrochloride (10.0 mg) and phenylboronic acid (5.6 mg) in dichloromethane (2.0 mL) were added TEA (6.4 μL) and copper(II) acetate (4.1 mg), and the mixture was stirred at room temperature overnight. After completion of the reaction, the reaction mixture was directly applied to a silica gel column, and purified by column chromatography (eluent: ethyl acetate/hexane=4/1→1/0) to give 4'-methoxy-N,N-dimethyl-3'-(N-(3-(phenylamino)phenyl)sulfamoyl)-[1,1'-biphenyl]-3-carboxamide (8.8 mg).

The compounds described in the following Table 4 were also synthesized similarly from boronic acid having the corresponding R group.

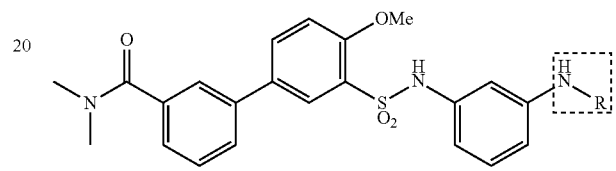

TABLE 4

| Ex. No. | NHR moiety structure | ¹H-NMR |
|---|---|---|
| 29 | *N*-phenyl-4-OMe | 1H NMR (400 MHz, Chloroform-d) δ 8.05 (d, J = 2.4 Hz, 1H), 7.72 (dd, J = 8.6, 2.4 Hz, 1H), 7.55 (dd, J = 1.5 Hz, 1H), 7.53 (ddd, J = 7.7, 1.6 Hz, 1H), 7.44 (dd, J = 7.8 Hz, 1H), 7.36 (ddd, J = 7.5, 1.4 Hz, 1H), 7.06 (d, J = 8.7 Hz, 1H), 7.00 (dd, J = 8.0 Hz, 1H), 6.95 (d, J = 9.0 Hz, 2H), 6.85 (s, 1H), 6.79 (d, J = 9.0 Hz, 2H), 6.65 (dd, J = 2.1 Hz, 1H), 6.56 (ddd, J = 8.2, 2.2, 0.8 Hz, 1H), 6.49 (ddd, J = 7.9, 2.0, 0.8 Hz, 1H), 5.48 (s, 1H), 4.01 (s, 3H), 3.77 (s, 3H), 3.13 (s, 3H), 2.99 (s, 3H). |
| 30 | *N*-phenyl | 1H NMR (400 MHz, Chloroform-d) δ 7.45 (d, J = 2.4 Hz, 1H), 7.12 (dd, J = 8.6, 2.4 Hz, 1H), 6.96-6.89 (m, 2H), 6.83 (dd, J = 7.6 Hz, 1H), 6.75 (ddd, J = 7.5, 1.3 Hz, 1H), 6.62-6.56 (m, 2H), 6.49-6.43 (m, 2H), 6.37-6.28 (m, 4H), 6.23 (dd, J = 2.1 Hz, 1H), 6.12 (ddd, J = 8.1, 2.2, 0.8 Hz, 1H), 5.98 (ddd, J = 7.9, 2.0, 0.8 Hz, 1H), 5.09 (s, 1H), 3.42 (s, 3H), 2.52 (s, 3H), 2.38 (s, 3H). |
| 31 | *N*-phenyl-2-OMe | 1H NMR (400 MHz, Methanol-d4) δ 8.02 (d, J = 2.4 Hz, 1H), 7.83 (dd, J = 8.6, 2.4 Hz, 1H), 7.60 (ddd, J = 7.8, 1.8, 1.2 Hz, 1H), 7.55 (dd, J = 1.5 Hz, 1H), 7.51 (dd, J = 7.7 Hz, 1H), 7.38 (ddd, J = 7.5, 1.3 Hz, 1H), 7.23 (d, J = 8.7 Hz, 1H), 7.02 (dd, J = 7.9 Hz, 1H), 6.99 (dd, J = 7.9, 1.5 Hz, 1H), 6.95 (dd, J = 2.1 Hz, 1H), 6.91 (dd, J = 8.1, 1.3 Hz, 1H), 6.80 (ddd, J = 7.8, 1.6 Hz, 1H), 6.70-6.63 (m, 2H), 6.60 (ddd, J = 8.0, 2.0, 0.9 Hz, 1H), 3.97 (s, 3H), 3.80 (s, 3H), 3.10 (s, 3H), 2.99 (s, 3H). |

TABLE 4-continued

| Ex. No. | NHR moiety structure | ¹H-NMR |
|---|---|---|
| 32 | 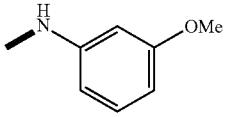 | 1H NMR (400 MHz, Chloroform-d) δ 8.05 (d, J = 2.4 Hz, 1H), 7.72 (dd, J = 8.6, 2.4 Hz, 1H), 7.54 (dd, J = 1.5 Hz, 1H), 7.51 (ddd, J = 7.8, 1.8, 1.3 Hz, 1H), 7.43 (ddd, J = 7.6, 0.5 Hz, 1H), 7.35 (ddd, J = 7.5, 1.4 Hz, 1H), 7.13-7.03 (m, 3H), 6.93 (s, 1H), 6.87 (dd, J = 2.1 Hz, 1H), 6.74 (ddd, J = 8.1, 2.2, 0.8 Hz, 1H), 6.60 (ddd, J = 8.0, 2.1, 0.9 Hz, 1H), 6.57-6.51 (m, 2H), 6.48 (ddd, J = 8.2, 2.4, 0.9 Hz, 1H), 5.71 (s, 1H), 4.05 (s, 3H), 3.76 (s, 3H), 3.12 (s, 3H), 2.98 (s, 3H). |
| 33 | 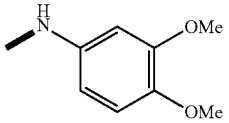 | 1H NMR (400 MHz, Methanol-d4) δ 8.03 (d, J = 2.4 Hz, 1H), 7.83 (dd, J = 8.6, 2.5 Hz, 1H), 7.61 (ddd, J = 7.8, 1.9, 1.2 Hz, 1H), 7.55 (dd, J = 1.8 Hz, 1H), 7.51 (dd, J = 7.7 Hz, 1H), 7.38 (ddd, J = 7.6, 1.2 Hz, 1H), 7.23 (d, J = 8.7 Hz, 1H), 7.04 (dd, J = 8.0 Hz, 1H), 6.98 (dd, J = 2.1 Hz, 1H), 6.74 (dd, J = 8.2 Hz, 1H), 6.68 (ddd, J = 8.1, 2.2, 0.9 Hz, 1H), 6.65-6.60 (m, 2H), 6.50 (dd, J = 8.3, 1.4 Hz, 1H), 3.98 (s, 3H), 3.82 (s, 3H), 3.66 (s, 3H), 3.10 (s, 3H), 2.99 (s, 3H). |
| 34 | 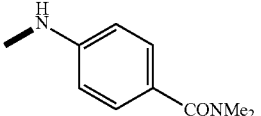 | 1H NMR (400 MHz, Methanol-d4) δ 8.05 (d, J = 2.4 Hz, 1H), 7.84 (dd, J = 8.6, 2.4 Hz, 1H), 7.62 (ddd, J = 7.8, 1.9, 1.2 Hz, 1H), 7.56 (dd, J = 1.5 Hz, 1H), 7.51 (dd, J = 7.6 Hz, 1H), 7.38 (ddd, J = 7.6, 1.3 Hz, 1H), 7.25 (d, J = 8.7 Hz, 1H), 7.19 (d, J = 8.8 Hz, 2H), 7.08-7.05 (m, 2H), 6.91 (d, J = 8.8 Hz, 2H), 6.71 (ddd, J = 8.2, 2.2, 0.9 Hz, 1H), 6.68 (ddd, J = 8.0, 2.0, 0.9 Hz, 1H), 3.99 (s, 3H), 3.10 (s, 3H), 3.05 (s, 6H), 2.98 (s, 3H). |
| 35 | 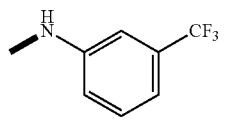 | 1H NMR (400 MHz, Chloroform-d) δ 8.05 (d, J = 2.3 Hz, 1H), 7.73 (dd, J = 8.6, 2.3 Hz, 1H), 7.57-7.50 (m, 2H), 7.43 (dd, J = 7.6 Hz, 1H), 7.35 (brd, J = 7.6 Hz, 1H), 7.17 (dd, J = 8.2 Hz, 1H), 7.14-7.06 (m, 2H), 6.95 (s, 1H), 6.88 (dd, J = 2.0 Hz, 1H), 6.84 (dd, J = 8.5, 2.0 Hz, 1H), 6.81-6.76 (m, 2H), 6.73 (brd, J = 8.1 Hz, 1H), 6.66 (brd, J = 7.9 Hz, 1H), 5.83 (s, 1H), 4.06 (s, 3H), 3.13 (s, 3H), 2.99 (s, 3H). |
| 36 | 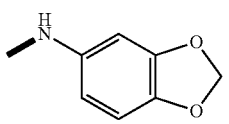 | 1H NMR (400 MHz, Chloroform-d) δ 8.04 (d, J = 2.4 Hz, 1H), 7.72 (dd, J = 8.6, 2.3 Hz, 1H), 7.57-7.50 (m, 2H), 7.44 (dd, J = 7.8 Hz, 1H), 7.36 (ddd, J = 7.6, 1.4 Hz, 1H), 7.09 (d, J = 8.6 Hz, 1H), 7.02 (dd, J = 8.0 Hz, 1H), 6.90 (brs, 1H), 6.70-6.64 (m, 2H), 6.58 (ddd, J = 8.2, 2.2, 0.8 Hz, 1H), 6.56-6.51 (m, 2H), 6.43 (dd, J = 8.2, 2.2 Hz, 1H), 5.92 (s, 2H), 5.51 (brs, 1H), 4.03 (s, 3H), 3.13 (s, 3H), 2.99 (s, 3H). |

Production Example (4)

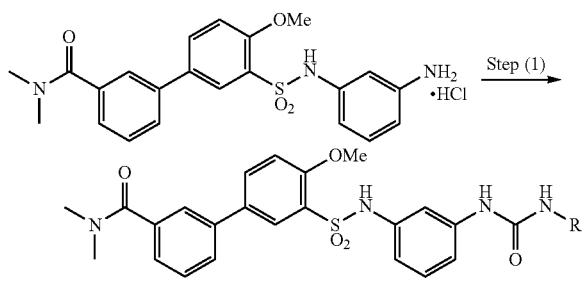

(1) 4'-methoxy-N,N-dimethyl-3'-(N-(3-(3-phenylureido)phenyl)sulfamoyl)-[1,1'-biphenyl]-3-carboxamide Under an argon atmosphere, to a suspension of 3'-(N-(3-aminophenyl)sulfamoyl)-4'-methoxy-N,N-dimethyl-[1,1'-biphenyl]-3-carboxamide hydrochloride (12.0 mg) in dichloromethane (4.0 mL) were added TEA (10.0 μL) and phenyl isocyanate (10.0 μL), and the mixture was stirred at room temperature for 20 hr. The reaction mixture was diluted with 20% methanol-containing chloroform, and extracted with saturated aqueous ammonium chloride solution. The organic layer was washed with saturated brine, dried over sodium sulfate and filtered, and the filtrate was concentrated under reduced pressure. The obtained residue was purified by preparative thin layer chromatography (eluent: chloroform/methanol=10/1) to give 4'-methoxy-N,N-dimethyl-3'-(N-(3-(3-phenylureido)phenyl)sulfamoyl)-[1,1'-biphenyl]-3-carboxamide (3.9 mg).

The compounds described in the following Tables 5-8 were also synthesized similarly from isocyanate having the corresponding R group, isocyanate developed from carboxylic acid having R group or chloroformic acid ester.

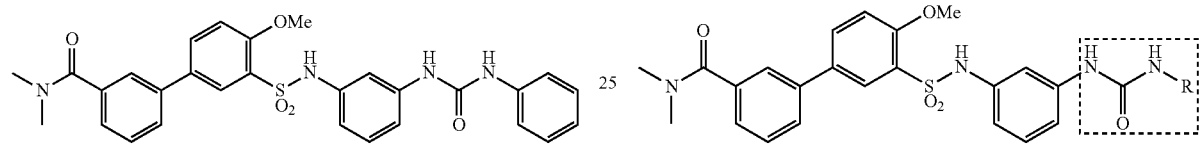

TABLE 5

| Ex. No. | NHCONHR moiety structure | $^1$H-NMR |
|---|---|---|
| 37 | ![structure] | 1H NMR (400 MHz, Methanol-d) δ 8.06 (d, J = 2.0 Hz, 1H), 7.77 (dd, J = 8.8, 2.0 Hz, 1H), 7.64 (m, 1H), 7.55 (t, J = 1.6 Hz, 1H), 7.44 (m, 2H), 7.36 (m, 3H), 7.25 (m, 2H), 7.19 (d, J = 8.8 Hz, 1H), 7.06 (t, J = 8.0 Hz, 1H), 6.99 (m, 2H), 6.78 (m, 1H), 4.00 (s, 3H), 3.07 (s, 3H), 2.99 (s, 3H). |
| 38 | ![structure with Me] | 1H NMR (400 MHz, Methanol-d) δ 8.06 (d, J = 2.4 Hz, 1H), 7.79 (dd, J = 8.4, 2.4 Hz, 1H), 7.66 (m, 1H), 7.55 (t, J = 2.0 Hz, 1H), 7.45 (t, J = 8.0 Hz, 1H), 7.42 (t, J = 2.4 Hz, 1H), 7.35 (m, 1H), 7.20 (m, 2H), 7.16-7.13 (m, 2H), 7.11-7.05 (m, 1H) 7.00-6.98 (m, 1H), 6.83 (d, J = 7.6 Hz, 1H), 6.79-6.77 (m, 1H), 4.01 (s, 3H), 3.08 (s, 3H), 2.98 (s, 3H), 2.29 (s, 3H). |
| 39 | ![structure with NMe2] | 1H NMR (400 MHz, DMSO-d6) δ 10.06 (s, 1H), 8.54 (s, 1H), 8.17 (s, 1H), 8.03 (d, J = 2.4 Hz, 1H), 7.89 (dd, J = 8.8, 2.4 Hz, 1H), 7.70 (d, J = 8.4 Hz, 1H), 7.57 (s, 1H), 7.45 (t, J = 7.6 Hz, 1H), 7.35-7.34 (m, 2H), 7.26 (d, J = 8.8 Hz, 1H), 7.19 (d, J = 9.2 Hz, 2H), 7.05-6.99 (m, 2H), 6.67 (t, J = 8.4 Hz, 3H), 3.94 (s, 3H), 2.97 (s, 3H), 2.88 (s, 3H), 2.81 (s, 6H). |
| 40 | ![structure with NMe2] | 1H NMR (400 MHz, DMSO-d6) δ 10.05 (s, 1H), 8.58 (s, 1H), 8.34 (s, 1H), 7.99 (d, J = 2.4 Hz, 1H), 7.89 (dd, J = 8.8, 2.4 Hz, 1H), 7.68 (d, J = 8.4 Hz, 1H), 7.56 (s, 1H), 7.45 (t, J = 7.6 Hz, 1H), 7.35-7.32 (m, 2H), 7.26 (d, J = 8.4 Hz, 1H), 7.07-7.02 (m, 3H), 6.81 (m, 1H), 6.73-6.69 (m, 1H), 6.68 (d, J = 8.0 Hz, 1H), 6.34 (dd, J = 8.0, 2.0 Hz, 1H), 3.94 (s, 3H), 2.97 (s, 3H), 2.88 (s, 3H), 2.85 (s, 6H). |

TABLE 5-continued

| Ex. No. | NHCONHR moiety structure | ¹H-NMR |
|---|---|---|
| 41 | (structure: methylurea linked to phenyl with ortho-NMe₂) | 1H NMR (400 MHz, Methanol-d) δ 8.08 (d, J = 3.6 Hz, 1H), 8.02 (dd, J = 8.0, 2.0 Hz, 1H), 7.79 (dd, J = 8.8, 2.4 Hz, 1H), 7.67 (d, J = 8.0 Hz, 1H), 7.57 (s, 1H), 7.50 (t, J = 2.0 Hz, 1H), 7.44 (t, J = 8.0 Hz, 1H), 7.35 (d, J = 7.6 Hz, 1H), 7.22-7.17 (m, 2H), 7.08-6.95 (m, 4H), 6.80-6.8 (m, 1H), 4.03 (s, 3H), 3.08 (s, 3H), 2.98 (s, 3H), 2.62 (s, 6H). |
| 42 | (structure: methylurea linked to phenyl with para-Br) | 1H NMR (400 MHz, Pyridine-d5) δ 12.03 (brs, 1H), 9.51 (s, 1H), 9.40 (s, 1H), 8.66 (d, J = 2.0 Hz, 1H), 8.46 (s, 1H), 7.80-7.62 (m, 5H), 7.50-7.39 (m, 5H), 7.22-7.17 (m, 2H), 7.07 (d, J = 8.8 Hz, 1H), 3.71 (s, 3H), 3.05 (s, 3H), 2.79 (s, 3H). |
| 43 | (structure: methylurea linked to phenyl with ortho-Br) | 1H NMR (400 MHz, DMSO-d6) δ 12.02 (s, 1H), 10.54 (s, 1H), 8.66-8.63 (m, 2H), 8.46 (s, 1H), 8.03 (s, 1H), 7.79 (s, 1H), 7.68 (dd, J = 8.8, 2.0 Hz, 1H), 7.63 (d, J = 8.0 Hz, 1H), 7.51-7.46 (m, 3H), 7.41 (t, J = 8.0 Hz, 1H), 7.33 (m, 1H), 7.21 (s, 1H), 7.19 (d, J = 5.6 Hz, 1H), 7.09 (d, J = 8.8 Hz, 1H), 6.87 (m, 1H), 3.71 (s, 3H), 3.05 (s, 3H), 2.79 (s, 3H). |
| 44 | (structure: methylurea linked to phenyl with meta-OMe) | 1H NMR (400 MHz, DMSO-d6) δ 10.07 (s, 1H), 8.67 (s, 1H), 8.54 (s, 1H), 8.00 (d, J = 2.4 Hz, 1H), 7.89 (dd, J = 8.8, 2.4 Hz, 1H), 7.69 (d, J = 8.0 Hz, 1H), 7.57 (s, 1H), 7.46 (t, J = 7.6 Hz, 1H), 7.35-7.31 (m, 2H), 7.26 (d, J = 8.8 Hz, 1H), 7.15 (t, J = 8.4 Hz, 1H), 7.11 (s, 1H), 7.08-7.02 (m, 2H), 6.89 (d, J = 8.4 Hz, 1H), 6.73 (d, J = 6.8 Hz, 1H), 6.54 (dd, J = 8.4, 2.4 Hz, 1H), 3.94 (s, 3H), 3.71 (s, 3H), 2.97 (s, 3H), 2.89 (s, 3H). |
| 45 | (structure: methylurea linked to phenyl with meta-CO₂Me) | 1H NMR (400 MHz, Chloroform-d) δ 8.06 (s, 1H), 7.99 (s, 1H), 7.85 (s, 1H), 7.72 (brs, 1H), 7.59 (d, J = 7.6 Hz, 1H), 7.55-7.50 (m, 3H), 7.40 (d, J = 6.4 Hz, 1H), 7.35-7.17 (m, 5H), 6.96 (d, J = 8.4 Hz, 1H), 6.87 (t, J = 8.0 Hz, 1H), 6.81 (d, J = 7.6 Hz, 1H), 6.67 (d, J = 7.6 Hz, 1H), 3.98 (s, 3H), 3.82 (s, 3H), 3.16 (s, 3H), 3.01 (s, 3H). |
| 46 | (structure: methylurea linked to phenyl with ortho-NO₂) | 1H NMR (400 MHz, Chloroform-d) δ 9.77 (s, 1H), 8.66 (s, 1H), 8.46 (d, J = 8.8 Hz, 1H), 8.08 (dd, J = 8.0, 1.2 Hz, 1H), 8.00 (d, J = 2.4 Hz, 1H), 7.54-7.41 (m, 4H), 7.32-7.26 (m, 4H), 7.09 (d, J = 8.4 Hz, 1H), 7.03-6.95 (m, 3H), 6.78 (d, J = 8.0 Hz, 1H), 4.01 (s, 3H), 3.15 (s, 3H), 3.00 (s, 3H). |

TABLE 6

| Ex. No. | NHCONHR moiety structure | ¹H-NMR |
|---|---|---|
| 47 | (structure: methylurea linked to phenyl with 3,5-di-NO₂) | 1H NMR (400 MHz, DMSO-d6) δ 10.13 (s, 1H), 9.53 (s, 1H), 9.15 (s, 1H), 8.69 (s, 2H), 8.39 (s, 1H), 8.00 (s, 1H), 7.90 (d, J = 8.4 Hz, 1H), 7.67 (d, J = 7.6 Hz, 1H), 7.59 (s, 1H), 7.44 (t, J = 7.2 Hz, 1H), 7.38-7.32 (m, 2H), 7.27 (d, J = 8.8 Hz, 1H), 7.14-7.08 (m, 2H), 6.78 (d, J = 6.8 Hz, 1H), 3.94 (s, 3H), 2.97 (s, 3H), 2.90 (s, 3H). |

TABLE 6-continued

| Ex. No. | NHCONHR moiety structure | $^1$H-NMR |
|---|---|---|
| 48 | (3-CO$_2$H phenyl urea, N-methyl) | 1H NMR (400 MHz, Methanol-d) δ 8.06 (d, J = 2.4 Hz, 1H), 8.02 (s, 1H), 7.77 (dd, J = 8.8, 2.4 Hz, 1H), 7.67-7.63 (m, 3H), 7.55 (s, 1H), 7.46-7.45 (m, 1H), 7.43 (d, J = 7.6 Hz, 1H), 7.37-7.32 (m, 2H), 7.19 (d, J = 8.8 Hz, 1H), 7.07 (t, J = 8.0 Hz, 1H), 6.98 (d, J = 8.8 Hz, 1H), 6.81-6.78 (m, 1H), 4.01 (s, 3H), 3.07 (s, 3H), 2.97 (s, 3H). |
| 49 | (3-CONMe$_2$ phenyl urea, N-methyl) | 1H NMR (400 MHz, Chloroform-d) δ 8.22 (s, 1H), 8.03 (s, 1H), 8.00 (d, J = 2.0 Hz, 1H), 7.61 (dd, J = 8.8, 2.4 Hz, 1H), 7.52-7.49 (m, 2H), 7.37-7.23 (m, 6H), 7.12 (t, J = 8.0 Hz, 1H), 7.01-6.96 (m, 3H), 6.92 (d, J = 8.0 Hz, 1H), 6.71 (m, 1H), 4.01 (s, 3H), 3.12 (s, 3H), 3.10 (s, 3H), 2.99 (s, 3H), 2.95 (s, 3H). |
| 50 | (3-Br phenyl urea, N-methyl) | 1H NMR (400 MHz, Methanol-d) δ 8.07 (d, J = 2.0 Hz, 1H), 7.79 (d, J = 8.8 Hz, 1H), 7.74 (dd, J = 1.6 Hz, 1H), 7.66 (d, J = 8.0 Hz, 1H), 7.56 (s, 1H), 7.48-7.45 (m, 2H), 7.35 (d, J = 8.0 Hz, 1H), 7.27 (dt, J = 8.0, 2.0 Hz, 1H), 7.21 (d, J = 8.8 Hz, 1H), 7.19-7.13 (m, 2H), 7.08 (t, J = 8.0 Hz, 1H), 6.98 (d, J = 9.2 Hz, 1H), 6.80 (m, 1H), 4.02 (s, 3H), 3.09 (s, 3H), 2.99 (s, 3H). |
| 51 | (2-Me phenyl urea, N-methyl) | 1H NMR (400 MHz, Chloroform-d) δ 8.49 (brs, 1H), 8.07 (d, J = 2.4 Hz, 1H), 7.64 (s, 1H), 7.60 (dd, J = 8.8, 2.4 Hz, 1H), 7.54 (s, 1H), 7.48 (d, J = 8.0 Hz, 1H), 7.41 (d, J = 8.4 Hz, 1H), 7.37-7.26 (m, 4H), 7.15-7.03 (m, 3H), 6.99-6.93 (m, 2H), 6.87 (d, J = 8.0 Hz, 1H), 6.62 (d, J = 7.6 Hz, 1H), 3.98 (s, 3H), 3.13 (s, 3H), 3.00 (s, 3H), 2.16 (s, 3H). |
| 52 | (2-OMe phenyl urea, N-methyl) | 1H NMR (400 MHz, Pyridine-d5) δ 12.02 (brs, 1H), 10.22 (s, 1H), 8.82 (d, J = 6.8 Hz, 1H), 8.68 (d, J = 1.6 Hz, 1H), 8.50 (s, 1H), 8.24 (s, 1H), 7.78 (s, 1H), 7.68-7.64 (m, 2H), 7.51-7.40 (m, 3H), 7.20-7.16 (m, 2H), 7.09-7.07 (m, 2H), 6.99 (t, J = 7.2 Hz, 1H), 6.82 (d, J = 7.2 Hz, 1H), 3.72 (s, 3H), 3.34 (s, 3H), 3.05 (s, 3H), 2.78 (s, 3H). |
| 53 | (4-OMe phenyl urea, N-methyl) | 1H NMR (400 MHz, Pyridine-d5) δ 12.02 (brs, 1H), 9.39 (s, 1H), 9.07 (s, 1H), 8.67 (d, J = 2.4 Hz, 1H), 8.52 (s, 1H), 7.80 (s, 1H), 7.71 (d, J = 9.2 Hz, 2H), 7.68-7.63 (m, 2H), 7.50 (d, J = 8.0 Hz, 1H), 7.46-7.40 (m, 2H), 7.18-7.15 (m, 2H), 7.07 (d, J = 8.8 Hz, 1H), 6.98 (d, J = 6.8 Hz, 2H), 3.71 (s, 3H), 3.66 (s, 3H), 3.05 (s, 3H), 2.79 (s, 3H). |
| 54 | (3,4,5-triOMe phenyl urea, N-methyl) | 1H NMR (400 MHz, DMSO-d6) δ 10.06 (s, 1H), 8.64 (s, 1H), 8.47 (s, 1H), 7.98 (s, 1H), 7.89 (d, J = 8.8 Hz, 1H), 7.67 (d, J = 7.6 Hz, 1H), 7.57 (s, 1H), 7.44 (t, J = 7.6 Hz, 1H), 7.33 (d, J = 7.6 Hz, 1H), 7.30-7.26 (m, 2H), 7.09-7.03 (m, 2H), 6.74-6.71 (m, 3H), 3.94 (s, 3H), 3.71 (s, 6H), 3.59 (s, 3H), 2.98 (s, 3H), 2.89 (s, 3H). |
| 55 | (4-NH$_2$ phenyl urea, N-methyl) | 1H NMR (400 MHz, DMSO-d6) δ 8.15 (brs, 1H), 8.01 (d, J = 2.4 Hz, 1H), 7.66-7.60 (m, 2H), 7.43 (t, J = 8.0 Hz, 1H), 7.43 (s, 1H), 7.28 (d, J = 8.0 Hz, 1H), 7.06 (d, J = 8.8 Hz, 1H), 7.01 (d, J = 8.4 Hz, 2H), 6.84-6.73 (m, 3H), 6.46 (d, J = 8.4 Hz, 2H), 6.39 (d, J = 1.6 Hz, 1H), 4.70 (s, 2H), 4.13 (brs, 1H), 3.78 (s, 3H), 2.97 (s, 3H), 2.86 (s, 3H). |

TABLE 6-continued

| Ex. No. | NHCONHR moiety structure | $^1$H-NMR |
|---|---|---|
| 56 | (structure: methylurea linked to 4-methylphenyl) | 1H NMR (400 MHz, DMSO-d6) δ 10.08 (s, 1H), 8.61 (s, 1H), 8.39 (s, 1H), 8.01 (d, J = 2.8 Hz, 1H), 7.89 (dd, J = 8.8, 2.4 Hz, 1H), 7.70 (d, J = 8.4 Hz, 1H), 7.57 (s, 1H), 7.45 (t, J = 7.6 Hz, 1H), 7.36-7.33 (m, 2H), 7.27-7.25 (m, 3H), 7.07-7.00 (m, 4H), 7.70 (dt, J = 7.2, 1.6 Hz, 1H), 3.94 (s, 3H), 2.97 (s, 3H), 2.88 (s, 3H), 2.23 (s, 3H). |
| 57 | (structure: methylurea linked to 3-nitrophenyl) | 1H NMR (400 MHz, DMSO-d6) δ 10.12 (s, 1H), 9.05 (s, 1H), 8.88 (s, 1H), 8.49 (t, J = 2.0 Hz, 1H), 8.01 (d, J = 2.4 Hz, 1H), 7.90 (dd, J = 8.8, 2.0 Hz, 1H), 7.80 (dd, J = 8.0, 2.0 Hz, 1H), 7.69-7.66 (m, 2H), 7.58 (s, 1H), 7.54 (t, J = 8.0 Hz, 1H), 7.44 (t, J = 8.0 Hz, 1H), 7.37 (s, 1H), 7.33 (d, J = 7.6 Hz, 1H), 7.26 (d, J = 8.8 Hz, 1H), 7.10-7.07 (m, 2H), 6.77-6.74 (m, 1H), 3.94 (s, 3H), 2.97 (s, 3H), 2.88 (s, 3H). |

TABLE 7

| Ex. No. | NHCONHR moiety structure | $^1$H-NMR |
|---|---|---|
| 58 | (structure: methylurea linked to 4-(N,N'-diBoc-guanidino)phenyl) | 1H NMR (400 MHz, DMSO-d6) δ 11.45 (s, 1H), 10.07 (brs, 1H), 9.89 (s, 1H), 8.82 (brs, 1H), 8.72 (brs, 1H), 8.02 (s, 1H), 7.89 (dd, J = 8.0, 2.0 Hz, 1H), 7.70 (d, J = 8.0 Hz, 1H), 7.57 (s, 1H), 7.46 (t, J = 7.6 Hz, 1H), 7.41-7.34 (m, 6H), 7.26 (d, J = 8.8 Hz, 1H), 7.05 (t, J = 8.0 Hz, 1H), 6.99 (d, J = 8.0 Hz, 1H), 6.71 (d, J = 8.0 Hz, 1H), 3.94 (s, 3H), 2.97 (s, 3H), 2.88 (s, 3H), 1.51 (s, 9H), 1.39 (s, 9H). |
| 59 | (structure: methylurea linked to 4-(N'-Boc-guanidino)phenyl) | 1H NMR (400 MHz, Methanol-d) δ 8.08 (d, J = 2.4 Hz, 1H), 7.80 (dd, J = 8.4, 2.0 Hz, 1H), 7.67 (d, J = 8.0 Hz, 1H), 7.58 (s, 1H), 7.48 (t, J = 8.0 Hz, 1H), 7.46-7.42 (m, 3H), 7.36 (d, J = 7.2 Hz, 1H), 7.22 (d, J = 8.8 Hz, 1H), 7.17 (d, J = 8.8 Hz, 2H), 7.08 (t, J = 8.0 Hz, 1H), 6.99-6.96 (m, 1H), 6.79-6.77 (m, 1H), 4.02 (s, 3H), 3.09 (s, 3H), 3.00 (s, 3H), 1.50 (s, 9H). |
| 60 | (structure: methylurea linked to 4-guanidinophenyl) | 1H NMR (400 MHz, Methanol-d) δ 8.08 (d, J = 2.4 Hz, 1H), 7.81 (dd, J = 8.4, 2.8 Hz, 1H), 7.68 (dt, J = 7.6, 2.0 Hz, 1H), 7.58 (t, J = 1.6 Hz, 1H), 7.51-7.47 (m, 4H), 7.36 (dt, J = 8.0, 1.6 Hz, 1H), 7.22 (d, J = 8.8 Hz, 1H), 7.18 (d, J = 9.2 Hz, 2H), 7.09 (t, J = 8.4 Hz, 1H), 7.00-6.98 (m, 1H), 6.78-6.75 (m, 1H), 4.02 (s, 3H), 3.09 (s, 3H), 3.00 (s, 3H). |
| 61 | (structure: methylurea linked to 4-nitrophenyl) | 1H NMR (400 MHz, DMSO-d6) δ 10.14 (s, 1H), 9.36 (s, 1H), 8.99 (s, 1H), 8.16 (d, J = 9.2 Hz, 2H), 8.03 (d, J = 2.4 Hz, 1H), 7.90 (dd, J = 8.8, 2.4 Hz, 1H), 7.70 (d, J = 7.6 Hz, 1H), 7.61 (d, J = 9.2 Hz, 2H), 7.59 (s, 1H), 7.46 (t, J = 8.0 Hz, 1H), 7.40 (s, 1H), 7.34 (d, J = 8.0 Hz, 1H), 7.26 (d, J = 8.8 Hz, 1H), 7.09 (t, J = 8.0 Hz, 1H), 7.03 (d, J = 8.0 Hz, 1H), 6.76 (d, J = 8.4 Hz, 1H), 3.94 (s, 3H), 2.97 (s, 3H), 2.88 (s, 3H). |

TABLE 7-continued

| Ex. No. | NHCONHR moiety structure | $^1$H-NMR |
|---|---|---|
| 62 | (structure: methylurea linked to 3-NHBoc phenyl) | 1H NMR (400 MHz, DMSO-d6) δ 10.03 (brs, 1H), 9.31 (s, 1H), 8.55 (s, 1H), 8.51 (s, 1H), 8.00 (d, J = 2.0 Hz, 1H), 7.89 (dd, J = 8.8, 2.4 Hz, 1H), 7.69 (d, J = 7.6 Hz, 1H), 7.57 (s, 1H), 7.51 (s, 1H), 7.45 (t, J = 8.0 Hz, 1H), 7.34-7.32 (m, 2H), 7.26 (d, J = 8.8 Hz, 1H), 7.12-6.99 (m, 5H), 6.72 (d, J = 7.2 Hz, 1H), 3.94 (s, 3H), 2.97 (s, 3H), 2.88 (s, 3H), 1.46 (s, 9H). |
| 63 | (structure: methylurea linked to 3-NH$_2$ phenyl) | 1H NMR (400 MHz, DMSO-d6) δ 10.01 (brs, 1H), 8.31 (brs, 2H), 8.01 (d, J = 2.0 Hz, 1H), 7.74 (brs, 1H), 7.65 (d, J = 7.2 Hz, 1H), 7.50-7.42 (m, 2H), 7.30 (d, J = 7.6 Hz, 1H), 7.14 (brs, 1H), 6.91 (brs, 1H), 6.85 (t, J = 8.0 Hz, 2H), 6.72 (s, 1H), 6.55-6.49 (m, 2H), 6.14 (d, J = 8.0 Hz, 1H), 5.00 (s, 2H), 3.85 (s, 3H), 2.97 (s, 3H), 2.87 (s, 3H). |
| 64 | (structure: methylurea linked to phenyl with N(Boc)=C-NHBoc guanidine) | 1H NMR (400 MHz, DMSO-d6) δ 9.97 (brs, 1H), 8.70 (s, 1H), 8.61 (s, 1H), 8.00 (d, J = 2.4 Hz, 1H), 7.89 (d, J = 8.8 Hz, 1H), 7.69 (d, J = 7.6 Hz, 1H), 7.57 (s, 1H), 7.49 (s, 1H), 7.44 (t, J = 7.6 Hz, 1H), 7.34-7.32 (m, 2H), 7.28-7.20 (m, 4H), 7.05 (m, 2H), 6.73 (m, 1H), 3.94 (s, 3H), 2.97 (s, 3H), 2.88 (s, 3H), 1.50 (brs, 9H), 1.39 (brs, 9H). |
| 65 | (structure: methylurea linked to phenyl with guanidine NH$_2$/NH) | 1H NMR (400 MHz, DMSO-d6) δ 8.33 (brs, 1H), 8.28 (brs, 1H), 8.00 (d, J = 2.4 Hz, 1H), 7.60 (d, J = 7.2 Hz, 2H), 7.46-7.42 (m, 2H), 7.28 (d, J = 7.6 Hz, 1H), 7.07-6.77 (m, 6H), 6.42 (brs, 1H), 6.34 (brs, 1H), 5.08 (brs, 2H), 4.09 (brs, 3H), 3.78 (s, 3H), 2.97 (s, 3H), 2.86 (s, 3H). |
| 66 | (structure: methylurea linked to benzyl) | 1H NMR (400 MHz, DMSO-d6) δ 10.02 (s, 1H), 8.55 (s, 1H), 7.99 (d, J = 2.4 Hz, 1H), 7.89 (dd, J = 8.4, 2.4 Hz, 1H), 7.69 (d, J = 7.6 Hz, 1H), 7.60 (s, 1H), 7.46 (t, J = 8.0 Hz, 1H), 7.34 (d, J = 7.2 Hz, 1H), 7.33-7.20 (m, 7H), 7.02-6.99 (m, 2H), 6.66-6.63 (m, 1H), 6.46 (t, J = 6.4 Hz, 1H), 4.24 (d, J = 6.4 Hz, 2H), 3.92 (s, 3H), 2.97 (s, 3H), 2.89 (s, 3H). |
| 67 | (structure: methylurea linked to 2-thienyl) | 1H NMR (400 MHz, DMSO-d6) δ 10.09 (s, 1H), 9.44 (s, 1H), 8.74 (s, 1H), 8.01 (d, J = 2.4 Hz, 1H), 7.89 (dd, J = 8.4, 2.0 Hz, 1H), 7.68 (d, J = 8.4 Hz, 1H), 7.58 (s, 1H), 7.46 (t, J = 7.6 Hz, 1H), 7.37-7.33 (m, 2H), 7.26 (d, J = 8.4 Hz, 1H), 7.06 (t, J = 8.0 Hz, 1H), 7.01 (d, J = 8.4 Hz, 1H), 6.85 (dd, J = 5.6, 1.2 Hz, 1H), 6.80-6.77 (m, 1H), 6.73 (d, J = 8.0 Hz, 1H), 6.51 (dd, J = 3.6, 1.2 Hz, 1H), 3.94 (s, 3H), 2.98 (s, 3H), 2.89 (s, 3H). |

TABLE 7-continued

| Ex. No. | NHCONHR moiety structure | ¹H-NMR |
|---|---|---|
| 68 | (structure: methyl-NHC(O)NH-pyridin-2-yl) | 1H NMR (400 MHz, DMSO-d6) δ 10.18 (s, 1H), 10.12 (s, 1H), 9.25 (s, 1H), 8.18 (d, J = 3.2 Hz, 1H), 8.02 (d, J = 2.4 Hz, 1H), 7.90 (dd, J = 8.8, 2.4 Hz, 1H), 7.74-7.68 (m, 2H), 7.59 (s, 1H), 7.50-7.43 (m, 3H), 7.35 (d, J = 7.2 Hz, 1H), 7.26 (d, J = 8.8 Hz, 1H), 7.09 (t, J = 8.0 Hz, 1H), 7.04 (d, J = 8.0 Hz, 1H), 6.97 (dd, J = 7.2, 5.2 Hz, 1H), 6.78 (d, J = 8.0 Hz, 1H), 3.94 (s, 3H), 2.98 (s, 3H), 2.88 (s, 3H). |

TABLE 8

| Ex. No. | NHCONHR moiety structure | ¹H-NMR |
|---|---|---|
| 69 | (structure: methyl-NHC(O)NH-pyridin-3-yl) | 1H NMR (400 MHz, DMSO-d6) δ 10.11 (s, 1H), 8.82 (s, 1H), 8.68 (s, 1H), 8.55 (d, J = 2.4 Hz, 1H), 8.17 (dd, J = 8.4, 1.6 Hz, 1H), 8.02 (d, J = 6.4 Hz, 1H), 7.89 (dd, J = 8.8, 2.8 Hz, 1H), 7.88-7.85 (m, 1H), 7.70 (d, J = 8.0 Hz, 1H), 7.58 (s, 1H), 7.46 (t, J = 7.6 Hz, 1H), 7.38 (s, 1H), 7.34 (d, J = 7.6 Hz, 1H), 7.30-7.25 (m, 2H), 7.07 (t, J = 8.0 Hz, 1H), 7.02 (d, J = 8.8 Hz, 1H), 6.73 (d, J = 8.0 Hz, 1H), 3.94 (s, 3H), 2.97 (s, 3H), 2.88 (s, 3H). |
| 70 | (structure: methyl-NHC(O)NH-pyridin-4-yl) | 1H NMR (400 MHz, DMSO-d6) δ 8.95 (s, 1H), 8.88 (s, 1H), 8.33-8.31 (m, 3H), 8.03 (d, J = 2.4 Hz, 1H), 7.90 (dd, J = 8.4, 2.0 Hz, 1H), 7.70 (d, J = 8.0 Hz, 1H), 7.58 (s, 1H), 7.46 (t, J = 8.0 Hz, 1H), 7.40-7.34 (m, 4H), 7.26 (d, J = 9.2 Hz, 1H), 7.08 (t, J = 8.0 Hz, 1H). 6.99 (d, J = 8.4 Hz, 1H), 6.74 (d, J = 7.6 Hz, 1H), 3.94 (s, 3H), 2.97 (s, 3H), 2.88 (s, 3H). |
| 71 | (structure: methyl-NHC(O)NH-(6-NMe2-pyridin-3-yl)) | 1H NMR (400 MHz, DMSO-d6) δ 10.11 (s, 1H), 9.03 (brs, 1H), 8.82 (brs, 1H), 8.14 (d, J = 0.8 Hz, 1H), 8.01 (d, J = 2.4 Hz, 1H), 7.90 (dd, J = 8.8, 2.4 Hz, 1H), 7.77 (d, J = 9.6 Hz, 1H), 7.68 (d, J = 8.4 Hz, 1H), 7.60 (s, 1H), 7.46 (t, J = 8.0 Hz, 1H), 7.37 (s, 1H), 7.35 (d, J = 7.6 Hz, 1H), 7.26 (d, J = 7.6 Hz, 1H), 7.12 (brs, 1H), 7.06 (t, J = 8.0 Hz, 1H), 7.01 (d, J = 8.0 Hz, 1H), 6.72 (d, J = 7.6 Hz, 1H), 3.94 (s, 3H), 3.14 (s, 6H), 2.99 (s, 3H), 2.90 (s, 3H). |
| 72 | (structure: methyl-NHC(O)NH-(4-NHBoc-phenyl)) | 1H NMR (400 MHz, Methanol-d) δ 8.07 (d, J = 2.4 Hz, 1H), 7.79 (dd, J = 8.8, 2.8 Hz, 1H), 7.66 (dt, J = 8.0, 1.6 Hz, 1H), 7.56 (t, J = 1.6 Hz, 1H), 7.46 (t, J = 8.0 Hz, 1H), 7.43 (t, J = 1.6 Hz, 1H), 7.29 (dt, J = 8.0, 1.6 Hz, 1H), 7.31-7.25 (m, 4H), 7.20 (d, J = 8.8 Hz, 1H), 7.06 (t, J = 8.0 Hz, 1H), 6.97-6.94 (m, 1H), 6.79-6.76 (m, 1H), 4.01 (s, 3H), 3.08 (s, 3H), 2.98 (s, 3H), 1.51 (s, 9H). |
| 73 | (structure: methyl-NHC(O)O-CH2-phenyl (benzyl carbamate)) | 1H NMR (400 MHz, DMSO-d6) δ 10.09 (s, 1H), 9.72 (s, 1H), 8.01 (d, J = 2.8 Hz, 1H), 7.89 (dd, J = 8.8, 2.4 Hz, 1H), 7.69 (d, J = 8.0 Hz, 1H), 7.62 (s, 1H), 7.50-7.47 (m, 2H), 7.38-7.30 (m, 6H), 7.25 (d, J = 8.8 Hz, 1H), 7.05 (t, J = 8.0 Hz, 1H), 6.97 (d, J = 8.8 Hz, 1H), 6.73 (d, J = 8.4 Hz, 1H), 5.07 (s, 2H), 3.92 (s, 3H), 2.96 (s, 3H), 2.89 (s, 3H). |

TABLE 8-continued

| Ex. No. | NHCONHR moiety structure | ¹H-NMR |
|---|---|---|
| 74 | (structure) | 1H NMR (400 MHz, DMSO-d6) δ 10.05 (s, 1H), 9.30 (s, 1H), 8.00 (d, J = 2.4 Hz, 1H), 7.90 (dd, J = 8.4, 2.4 Hz, 1H), 7.69 (d, J = 8.4 Hz, 1H), 7.59 (s, 1H), 7.49 (t, J = 8.0 Hz, 1H), 7.43 (s, 1H), 7.35 (d, J = 8.4 Hz, 1H), 7.02 (t, J = 8.0 Hz, 1H), 6.66 (d J = 8.0 Hz, 1H), 3.92 (s, 3H), 2.99 (s, 3H), 2.91 (s, 3H), 1.39 (s, 9H). |

Production Example (5)

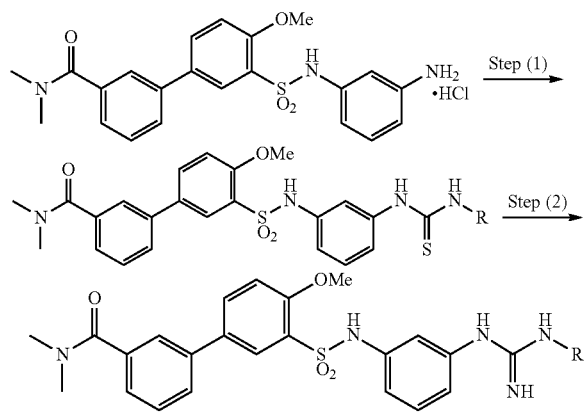

(1) 4'-methoxy-N,N-dimethyl-3'-(N-(3-(3-phenylthioureido)phenyl)sulfamoyl)-[1,1'-biphenyl]-3-carboxamide Under an argon atmosphere, to a solution of 3'-(N-(3-aminophenyl)sulfamoyl)-4'-methoxy-N,N-dimethyl-[1,1'-biphenyl]-3-carboxamide hydrochloride (16.5 mg) in anhydrous benzene (3.0 mL) were added TEA (30.0 µL) and phenyl isothiocyanate (30.0 mg), and the mixture was stirred under reflux at 110° C. for 12 hr. The reaction mixture was diluted with 20% methanol-containing chloroform, and extracted with saturated aqueous ammonium chloride solution. The organic layer was washed with saturated aqueous sodium hydrogen carbonate solution and saturated brine, dried over sodium sulfate and filtered, and the filtrate was concentrated under reduced pressure. The obtained residue was purified by preparative thin layer chromatography (eluent: chloroform/methanol=10/1) to give 4'-methoxy-N,N-dimethyl-3'-(N-(3-(3-phenylthioureido)phenyl)sulfamoyl)-[1,1'-biphenyl]-3-carboxamide (7.1 mg).

The compounds described in the following Table 9 were also synthesized similarly from isothiocyanate having the corresponding R group.

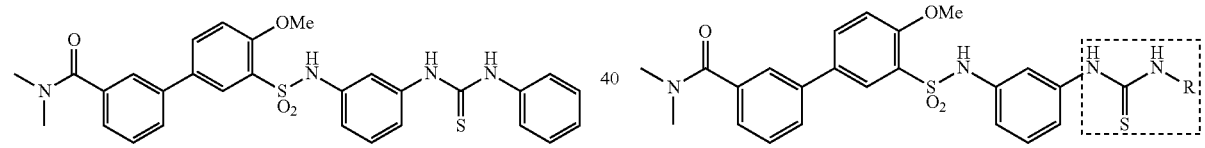

TABLE 9

| Ex. No. | NHCSNHR moiety structure | ¹H-NMR |
|---|---|---|
| 75 | (structure) | 1H NMR (400 MHz, Chloroform-d) δ 8.05 (brs, 1H), 8.00 (d, J = 2.0 Hz, 1H), 7.88 (brs, 1H), 7.65 (d, J = 8.8 Hz, 1H), 7.52 (s, 1H), 7.49 (d, J = 8.0 Hz, 1H), 7.41 (d, J = 7.2 Hz, 1H), 7.38-7.25 (m, 8H), 7.15 (t, J = 8.0 Hz, 1H), 7.03 (d, J = 8.8 Hz, 1H), 6.98 (dd, J = 8.0, 2.0 Hz, 2H), 4.06 (s, 3H), 3.12 (s, 3H), 3.00 (s, 3H). |
| 76 | (structure) | 1H NMR (400 MHz, Chloroform-d) δ 8.01-7.97 (m, 2H), 7.83 (brs, 1H), 7.66 (d, J = 8.4 Hz, 1H), 7.52 (s, 1H), 7.50 (d, J = 7.6 Hz, 1H), 7.42-7.39 (m, 2H), 7.39-7.25 (m, 3H), 7.17-6.98 (m, 7H), 4.07 (s, 3H), 3.13 (s, 3H), 3.00 (s, 3H), 2.34 (s, 3H). |

(2) 4'-methoxy-N,N-dimethyl-3'-(N-(3-(3-phenyl-guanidino)phenyl)sulfamoyl)-[1,1'-biphenyl]-3-carboxamide

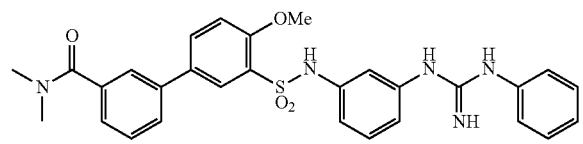 [SMILES: COc1ccc(-c2cccc(C(=O)N(C)C)c2)cc1S(=O)(=O)Nc1cccc(NC(=N)Nc2ccccc2)c1]

Under an argon atmosphere, to a solution of 4'-methoxy-N,N-dimethyl-3'-(N-(3-(3-phenylthioureido)phenyl)sulfamoyl)-[1,1'-biphenyl]-3-carboxamide (10.9 mg) in acetonitrile (2.0 mL) were added 30% aqueous ammonia solution (1.0 mL) and IBX (37.9 mg), and the mixture was stirred at room temperature for 4 hr. The reaction mixture was diluted with 20% methanol-containing chloroform, and extracted with saturated aqueous sodium hydrogen carbonate solution. The organic layer was washed with saturated brine, dried over sodium sulfate and filtered, and the filtrate was concentrated under reduced pressure. The obtained residue was purified by preparative thin layer chromatography (eluent: chloroform/ammonia-saturated methanol=87/13) to give 4'-methoxy-N,N-dimethyl-3'-(N-(3-(3-phenylguanidino)phenyl)sulfamoyl)-[1,1'-biphenyl]-3-carboxamide (5.1 mg).

The compounds described in the following Table 10 were also synthesized similarly from thiourea derivative having the corresponding R group.

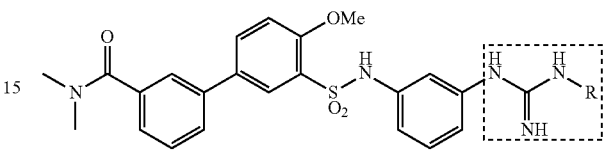

TABLE 10

| Ex. No. | NHCNHNHR moiety structure | $^1$H-NMR |
|---|---|---|
| 77 | (structure: MeNH-C(=NH)-NH-Ph) | 1H NMR (400 MHz, Methanol-d) δ 8.06 (d, J = 2.4 Hz, 1H), 7.80 (dd, J = 8.4, 2.0 Hz, 1H), 7.63 (m, 1H), 7.57 (t, J = 1.6 Hz, 1H), 7.50 (t, J = 8.0 Hz, 1H), 7.37 (m, 1H), 7.29 (t, J = 7.6 Hz, 1H), 7.21 (d, J = 8.4 Hz, 1H), 7.17-7.13 (m, 3H), 7.11-7.06 (m, 2H), 6.87 (m, 1H), 6.81 (d, J = 8.0 Hz, 1H), 3.98 (s, 3H), 3.10 (s, 3H), 3.00 (s, 3H). |
| 78 | (structure: MeNH-C(=NH)-NH-(3-Me-Ph)) | 1H NMR (400 MHz, Chloroform-d) δ 8.02 (d, J = 2.4 Hz, 1H), 7.66 (dd, J = 8.8, 2.4 Hz, 1H), 7.54 (s, 1H), 7.51 (d, J = 8.0 Hz, 1H), 7.40 (t, J = 7.6 Hz, 1H), 7.30 (d, J = 8.0 Hz, 1H), 7.18 (t, J = 7.6 Hz, 1H), 7.12 (t, J = 7.6 Hz, 1H), 7.05-6.98 (m, 3H), 6.95 (s, 1H), 6.91 (d, J = 8.0 Hz, 1H), 6.81 (d, J = 8.0 Hz, 1H), 6.76 (d, J = 8.0 Hz, 1H), 5.32-5.12 (brs, 1H), 4.03 (s, 3H), 3.09 (s, 3H), 2.99 (s, 3H), 2.81-2.08 (brs, 2H), 2.30 (s, 3H). |

Production Example (6)

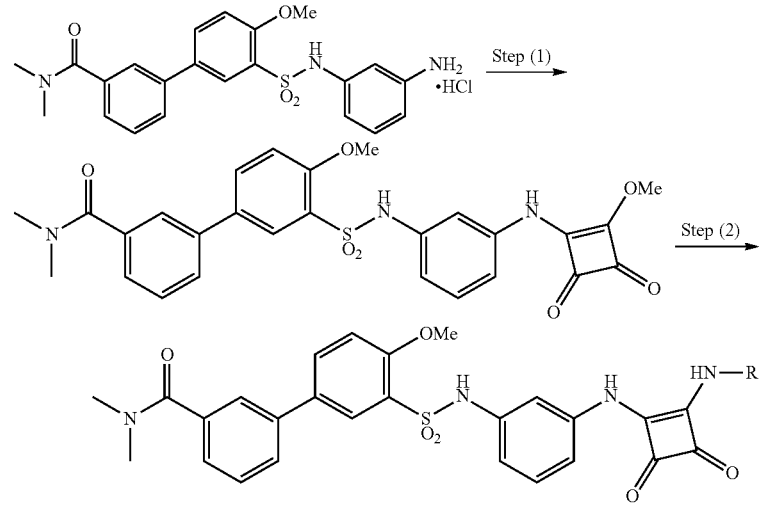

(1) 4'-methoxy-3'-(N-(3-((2-methoxy-3,4-dioxocyclobut-1-en-1-yl)amino)phenyl)sulfamoyl)-N,N-dimethyl-[1,1'-biphenyl]-3-carboxamide

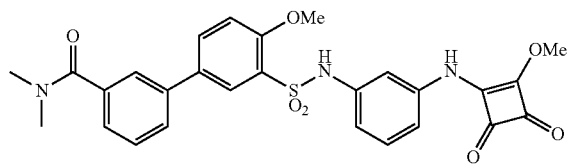 [SMILES: COc1ccc(-c2cccc(C(=O)N(C)C)c2)cc1S(=O)(=O)Nc1cccc(Nc2c(OC)c(=O)c2=O)c1]

Under an argon atmosphere, to a suspension of 3'-(N-(3-aminophenyl)sulfamoyl)-4'-methoxy-N,N-dimethyl-[1,1'-biphenyl]-3-carboxamide hydrochloride (149.0 mg) in methanol (5.0 mL) were added TEA (88.0 μL) and 3,4-dimethoxy-3-cyclobutene-1,2-dione (48.4 mg), and the mixture was stirred at room temperature for 15 hr. The reaction mixture was concentrated under reduced pressure, the obtained residue was crudely purified by silica gel column chromatography (eluent: chloroform/ethyl acetate=4/1), and the crude product was recrystallized from chloroform to give 4'-methoxy-3'-(N-(3-((2-methoxy-3,4-dioxocyclobut-1-en-1-yl)amino)phenyl)sulfamoyl)-N,N-dimethyl-[1,1'-biphenyl]-3-carboxamide (150.2 mg) as colorless needle crystals.

(2) 3'-(N-(3-((3,4-dioxo-2-(m-tolylamino)cyclobut-1-en-1-yl)amino)phenyl)sulfamoyl)-4'-methoxy-N,N-dimethyl-[1,1'-biphenyl]-3-carboxamide

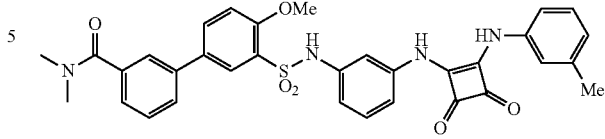

Under an argon atmosphere, a solution of 4'-methoxy-3'-(N-(3-((2-methoxy-3,4-dioxocyclobut-1-en-1-yl)amino)phenyl)sulfamoyl)-N,N-dimethyl-[1,1'-biphenyl]-3-carboxamide (10.1 mg) in ethanol (1.0 mL) were added DIPEA (50.0 μL) and m-toluidine (3.0 μL), and the mixture was stirred with heating under reflux for 8 hr. The reaction mixture was concentrated under reduced pressure, the obtained residue was crudely purified by silica gel column chromatography (eluent: chloroform/ethyl acetate=4/1), and the crude product was recrystallized from chloroform to give 3'-(N-(3-((3,4-dioxo-2-(m-tolylamino)cyclobut-1-en-1-yl)amino)phenyl)sulfamoyl)-4'-methoxy-N,N-dimethyl-[1,1'-biphenyl]-3-carboxamide (150.2 mg) as colorless needle crystals.

The compounds (Examples 81-84) described in the following Table 11 were also synthesized similarly from aniline having the corresponding R group.

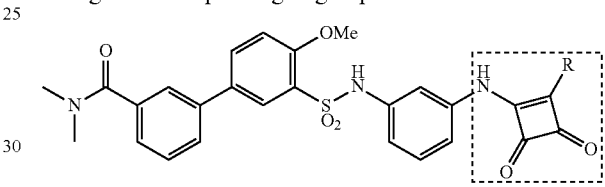

TABLE 11

| Ex. No. | structure of substituent on aniline | ¹H-NMR |
|---|---|---|
| 79 | ![structure] | 1H NMR (400 MHz, Acetone-d6) δ 8.11 (d, J = 2.8 Hz, 1H), 7.88 (dd, J = 8.4, 2.4 Hz, 1H), 7.67 (dt, J = 8.0, 2.0 Hz, 1H), 7.63 (t, J = 1.6 Hz, 1H), 7.51 (t, J = 8.0 Hz, 1H), 7.43 (m, 1H), 7.39 (d, J = 8.4 Hz, 1H), 7.29 (d, J = 8.8 Hz, 1H), 7.23-7.16 (m, 2H), 7.05 (dt, J = 7.6, 2.0 Hz, 1H), 4.44 (s, 3H), 4.06 (s, 3H), 3.03 (s, 6H). |
| 80 | ![structure] | 1H NMR (400 MHz, Methanol-d) δ 8.09 (d, J = 2.4 Hz, 1H), 7.80 (dd, J = 8.4, 2.4 Hz, 1H), 7.63 (d, J = 8.0 Hz, 1H), 7.56 (s, 1H), 7.49 (t, J = 7.6 Hz, 1H), 7.39 (s, 1H), 7.35 (d, J = 7.6 Hz, 1H), 7.30 (s, 1H), 7.27-7.13 (m, 5H), 6.89 (t, J = 8.4 Hz, 2H), 4.02 (s, 3H), 3.09 (s, 3H), 2.99 (s, 6H), 2.31 (s, 3H). |
| 81 | ![structure] | 1H NMR (400 MHz, DMSO-d6) δ 10.26 (s, 1H), 9.78 (s, 1H), 9.71 (s, 1H), 8.02 (d, J = 2.4 Hz, 1H), 7.91 (dd, J = 8.4, 2.0 Hz, 1H), 7.67 (d, J = 7.6 Hz, 1H), 7.58 (s, 1H), 7.49 (t, J = 7.6 Hz, 1H), 7.38-7.34 (m, 4H), 7.28 (d, J = 8.4 Hz, 1H), 7.18 (t, J = 8.0 Hz, 1H), 7.09 (s, 1H), 6.94 (d, J = 8.8 Hz, 2H), 6.81 (d, J = 8.4 Hz, 1H), 3.94 (s, 3H), 3.73 (s, 3H), 2.97 (s, 3H), 2.89 (s, 3H). |

TABLE 11-continued

| Ex. No. | structure of substituent on aniline | ¹H-NMR |
|---|---|---|
| 82 | | 1H NMR (400 MHz, Chloroform-d) δ 9.29 (brs, 1H), 9.21 (s, 1H), 7.94 (s, 1H), 7.56 (d, J = 9.2 Hz, 1H), 7.51 (s, 1H), 7.42 (d, J = 7.6 Hz, 1H), 7.34-7.22 (m, 4H), 7.10-7.01 (m, 3H), 6.89 (m, 1H), 6.78-6.74 (m, 3H), 6.55 (d, J = 7.6 Hz, 1H), 4.05 (s, 3H), 3.74 (s, 3H), 3.18 (s, 3H), 3.04 (s, 3H). |
| 83 | | 1H NMR (400 MHz, Methanol-d) δ 8.10 (s, 1H), 7.90 (m, 1H), 7.80 (d, J = 8.4 Hz, 1H), 7.63 (d, J = 7.2 Hz, 1H), 7.56 (s, 1H), 7.49 (t, J = 7.6 Hz, 1H), 7.40 (s, 1H), 7.35 (d, J = 7.6 Hz, 1H), 7.24-7.16 (m, 3H), 7.07 (m, 1H), 7.01 (m, 1H), 6.95-6.88 (m, 2H), 4.03 (s, 3H), 3.92 (s, 3H), 3.09 (s, 3H), 3.00 (s, 6H). |
| 84 | | 1H NMR (400 MHz, DMSO-d6) δ 10.27 (s, 1H), 9.77 (s, 1H), 9.70 (s, 1H), 7.99 (d, J = 1.6 Hz, 1H), 7.88 (dd, J = 8.4, 2.0 Hz, 1H), 7.64 (d, J = 8.0 Hz, 1H), 7.55 (s, 1H), 7.46 (t, J = 7.6 Hz, 1H), 7.35-7.30 (m, 4H), 7.25 (d, J = 8.8 Hz, 1H), 7.17-7.12 (m, 3H), 7.05 (s, 1H), 6.78 (d, J = 8.0 Hz, 1H), 3.90 (s, 3H), 2.94 (s, 3H), 2.86 (s, 3H), 2.23 (s, 3H). |

Production Example (7)

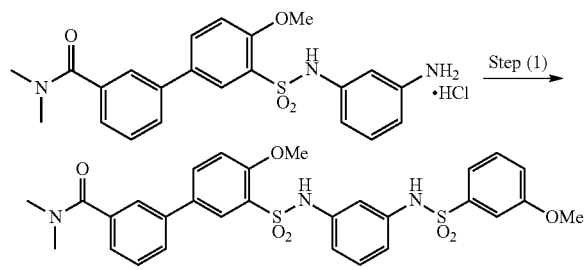

(1) 4'-methoxy-3'-(N-(3-(3-methoxyphenylsulfonamido)phenyl)sulfamoyl)-N,N-dimethyl-[1,1'-biphenyl]-3-carboxamide Under an argon atmosphere, to a solution of 3'-(N-(3-aminophenyl)sulfamoyl)-4'-methoxy-N,N-dimethyl-[1,1'-biphenyl]-3-carboxamide hydrochloride (19.1 mg) in dichloromethane (3.0 mL) were added TEA (23.9 μL) and 3-methoxybenzenesulfonyl chloride (7.0 μL), and the mixture was stirred at room temperature overnight. Thereto was added sodium triacetoxyborohydride (10 mg), and the mixture was further stirred for 14 hr. The reaction mixture was concentrated under reduced pressure, and the residue was diluted with chloroform and extracted with pure water. The organic layer was washed with saturated brine, dried over sodium sulfate and filtered, and the filtrate was concentrated under reduced pressure. The obtained residue was purified by silica gel column chromatography (eluent: ethyl acetate) to give 4'-methoxy-3'-(N-(3-(3-methoxyphenylsulfonamido)phenyl)sulfamoyl)-N,N-dimethyl-[1,1'-biphenyl]-3-carboxamide (19.9 mg).

The compounds described in the following Table 12 were also synthesized similarly from sulfonyl chloride having the corresponding R group.

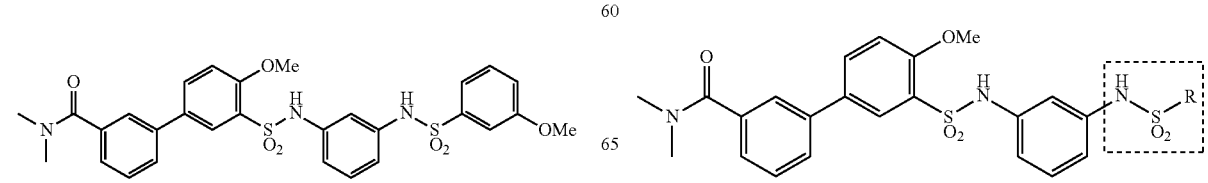

TABLE 12

| Ex. No. | NHSO₂R moiety structure | ¹H-NMR |
|---|---|---|
| 85 | *—N(H)—S(O₂)—(3-OMe-C₆H₄)* | 1H NMR (400 MHz, DMSO-d6) δ 8.17-8.10 (m, 2H), 7.74 (ddd, J = 7.8, 1.9, 1.1 Hz, 1H), 7.68-7.64 (m, 1H), 7.59-7.49 (m, 3H), 7.45-7.39 (m, 2H), 7.37-7.29 (m, 2H), 7.17-7.11 (m, 2H), 7.03-6.99 (m, 1H), 6.94 (t, J = 2.1 Hz, 1H), 3.78 (s, 3H), 3.74 (s, 3H), 3.01 (s, 3H), 2.93 (s, 3H). |
| 86 | *—N(H)—S(O₂)—(3-Br-C₆H₄)* | 1H NMR (400 MHz, Chloroform-d) δ 8.03 (d, J = 2.4 Hz, 1H), 7.92 (t, J = 1.8 Hz, 1H), 7.78 (ddd, J = 8.0, 1.9, 1.0 Hz, 1H), 7.73 (dd, J = 8.6, 2.4 Hz, 1H), 7.68 (ddd, J = 8.0, 1.8, 1.0 Hz, 1H), 7.55-7.49 (m, 2H), 7.42 (ddd, J = 7.6, 0.8 Hz, 1H), 7.39-7.33 (m, 3H), 7.23-7.18 (m, 1H), 7.09 (d, J = 8.7 Hz, 1H), 6.99 (s, 1H), 6.89 (t, J = 2.0 Hz, 1H), 6.64 (ddd, J = 7.8, 2.1, 1.2 Hz, 1H), 4.06 (s, 3H), 3.09 (s, 3H), 2.94 (s, 3H). |
| 87 | *—N(H)—S(O₂)—NMe₂* | 1H NMR (400 MHz, DMSO-d6) δ 9.71 (s, 1H), 7.93 (d, J = 2.4 Hz, 1H), 7.86 (dd, J = 8.7, 2.4 Hz, 1H), 7.63 (dt, J = 7.9, 2.0, 1.2 Hz, 1H), 7.54 (dd, J = 1.6 Hz, 1H), 7.47 (dd, J = 7.6 Hz, 1H), 7.32 (ddd, J = 7.5, 1.3 Hz, 1H), 7.23 (d, J = 8.7 Hz, 1H), 6.73 (dd, J = 8.0 Hz, 1H), 6.37 (dd, J = 2.0 Hz, 1H), 6.22 (ddd, J = 8.0, 1.9, 0.8 Hz, 1H), 6.09 (ddd, J = 8.0, 2.3, 0.7 Hz, 1H), 5.02 (s, 2H), 3.90 (s, 3H), 3.24 (s, 6H), 2.96 (s, 3H), 2.88 (s, 3H). |
| 88 | *—N(H)—S(O₂)—(3-F-C₆H₄)* | 1H NMR (400 MHz, Chloroform-d) δ 8.31 (d, J = 2.4 Hz, 1H), 7.85 (dd, J = 8.6, 2.4 Hz, 1H), 7.68 (d, J = 7.3 Hz, 2H), 7.63 (dt, J = 6.6, 1.6 Hz, 2H), 7.51-7.46 (m, 3H), 7.46-7.41 (m, 3H), 7.39 (dt, J = 7.6, 1.3 Hz, 1H), 7.34-7.28 (m, 1H), 7.16 (ddd, J = 5.9, 3.5, 2.1 Hz, 1H), 7.11 (d, J = 8.7 Hz, 1H), 6.90 (dd, J = 1.3 Hz, 1H), 3.86 (s, 3H), 3.14 (s, 3H), 3.02 (s, 3H). |
| 89 | *—N(H)—S(O₂)—Me* | 1H NMR (400 MHz, Chloroform-d) δ 8.22 (d, J = 2.3 Hz, 1H), 7.82 (dd, J = 8.6, 2.4 Hz, 1H), 7.64-7.52 (m, 4H), 7.52-7.43 (m, 3H), 7.37 (ddd, J = 7.5, 1.2 Hz, 1H), 7.11 (d, J = 8.7 Hz, 1H), 3.90 (s, 3H), 3.32 (s, 3H), 3.14 (s, 3H), 3.01 (s, 3H). |
| 90 | *—N(H)—S(O₂)—N(H)—(3-Me-C₆H₄)* | 1H NMR (400 MHz, DMSO-d6) δ 10.20 (s, 1H), 10.09 (s, 1H), 10.04 (s, 1H), 7.98 (d, J = 2.4 Hz, 1H), 7.88 (dd, J = 8.7, 2.4 Hz, 1H), 7.67 (ddd, J = 7.8, 1.1 Hz, 1H), 7.60 (dd, J = 1.5 Hz, 1H), 7.51 (dd, J = 7.7 Hz, 1H), 7.37 (ddd, J = 7.6, 1.2 Hz, 1H), 7.22 (d, J = 8.8 Hz, 1H), 7.06 (dd, J = 8.2 Hz, 1H), 7.01 (dd, J = 7.7 Hz, 2H), 6.96 (dd, J = 2.0 Hz, 1H), 6.88 (s, 1H), 6.86-6.80 (m, 2H), 6.78-6.69 (m, 2H), 3.86 (s, 3H), 3.01 (s, 3H), 2.91 (s, 3H), 2.18 (s, 3H). |

Production Example (8)

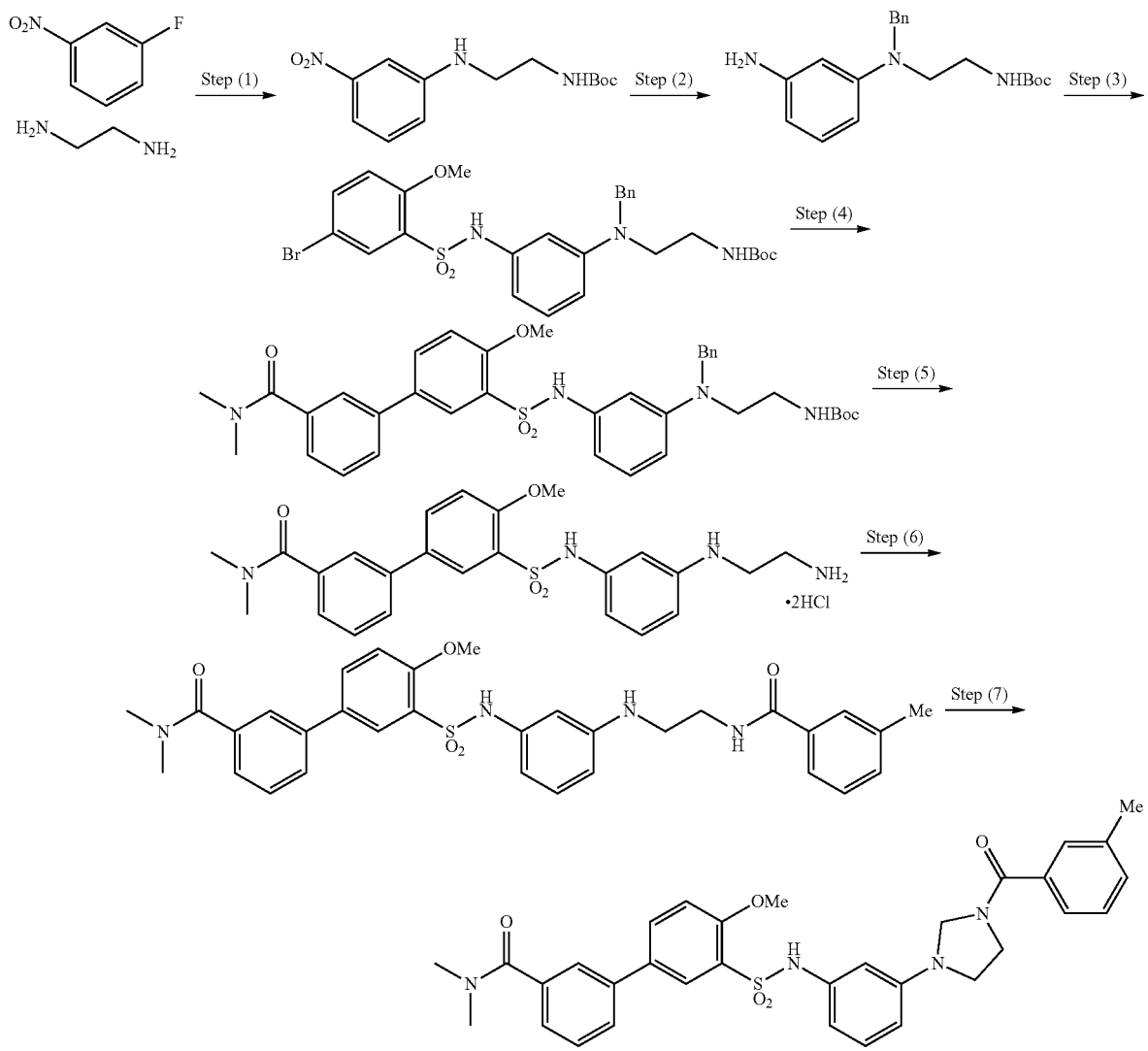

(1) tert-butyl (2-((3-nitrophenyl)amino)ethyl)carbamate

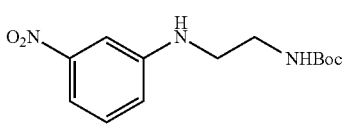 [SMILES: CC(C)(C)OC(=O)NCCNc1cccc([N+](=O)[O-])c1]

Under an argon atmosphere, to 3-fluoronitrobenzene (3.21 mL) was added ethylenediamine (25.0 mL), and the mixture was stirred at 100° C. for 24 hr. To the reaction mixture was added saturated aqueous sodium hydrogen carbonate solution, and the mixture was extracted with chloroform. The organic layer was dried over sodium sulfate and filtered, and the filtrate was concentrated. To a solution of the obtained residue in dichloromethane (50 mL) were added triethylamine (4.60 mL) and di-tert-butyl dicarbonate (6.55 g), and the mixture was stirred at room temperature for 2 hr. To the reaction mixture was added saturated aqueous sodium hydrogen carbonate solution, and the mixture was extracted with chloroform. The organic layer was dried over sodium sulfate and filtered, and the filtrate was concentrated. The obtained residue was purified by silica gel column chromatography (eluent: ethyl acetate/hexane=1/4→1/3) to give tert-butyl (2-((3-nitrophenyl)amino)ethyl)carbamate (5.31 g).

(2) tert-butyl (2-((3-aminophenyl)(benzyl)amino)ethyl)carbamate

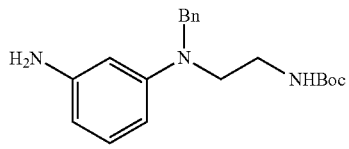 [SMILES: CC(C)(C)OC(=O)NCCN(Cc1ccccc1)c1cccc(N)c1]

(i) Under an argon atmosphere, to a solution of tert-butyl (2-((3-nitrophenyl)amino)ethyl)carbamate (4.46 g) in dichloromethane (30.0 mL) were added 50 wt % aqueous sodium hydroxide solution (10.0 mL), benzyl bromide (2.84 mL) and tetrabutylammonium iodide (587.0 mg), and the mixture was stirred at room temperature for 48 hr. To the reaction mixture was added saturated aqueous sodium hydrogen carbonate solution, and the mixture was extracted with chloroform. The organic layer was dried over sodium sulfate and filtered, and the filtrate was concentrated. The obtained residue was purified by silica gel column chromatography (eluent: ethyl acetate/hexane=1/6→1/4) to give tert-butyl (2-((benzyl)(3-nitrophenyl)amino)ethyl)carbamate (4.62 g).

(ii) Under an argon atmosphere, to a suspension of tert-butyl (2-((benzyl)(3-nitrophenyl)amino)ethyl)carbamate in a mixture of ethanol (50.0 mL) and water (20.0 mL) were added ammonium chloride (6.69 g) and iron powder (4.86 g), and the mixture was heated under reflux for 2 hr. The reaction mixture was filtered through celite, and the filtrate was concentrated. Saturated aqueous sodium hydrogen carbonate solution was added, and the mixture was extracted with chloroform. The organic layer was dried over sodium sulfate and filtered, and the filtrate was concentrated. The obtained residue was purified by amine silica gel column chromatography (eluent: chloroform/ethyl acetate=2/1) to give tert-butyl (2-((3-aminophenyl)(benzyl)amino)ethyl)carbamate (4.58 g).

(3) tert-butyl (2-((benzyl)(3-(5-bromo-2-methoxyphenylsulfonamido)phenyl)amino)ethyl)carbamate

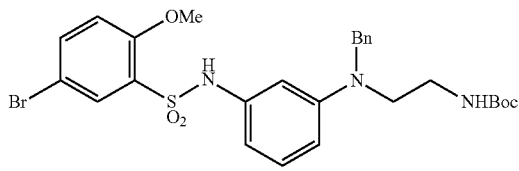 [SMILES: COc1ccc(Br)cc1S(=O)(=O)Nc1cccc(N(CCNC(=O)OC(C)(C)C)Cc2ccccc2)c1]

Under an argon atmosphere, to a solution of tert-butyl (2-((3-aminophenyl)(benzyl)amino)ethyl)carbamate (1.59 g) in dichloromethane (20.0 mL) were added pyridine (413 μL) and 5-bromo-2-methoxybenzenesulfonyl chloride (1.33 g), and the mixture was stirred at room temperature overnight. To the reaction mixture was added saturated aqueous sodium hydrogen carbonate solution, and the mixture was extracted with chloroform. The organic layer was dried over sodium sulfate and filtered, and the filtrate was concentrated. The obtained residue was purified by silica gel column chromatography (eluent: ethyl acetate/hexane=1/2) to give tert-butyl (2-((benzyl)(3-(5-bromo-2-methoxyphenylsulfonamido)phenyl)amino)ethyl)carbamate (2.53 g).

(4) tert-butyl (2-((benzyl)(3-(3'-(dimethylcarbamoyl)-4-methoxy-[1,1'-biphenyl]-3-ylsulfonamido)phenyl)amino)ethyl)carbamate

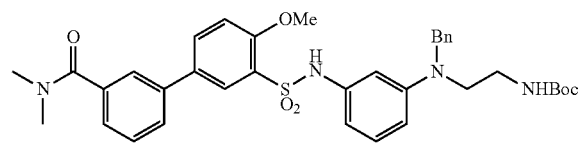 [SMILES: COc1ccc(-c2cccc(C(=O)N(C)C)c2)cc1S(=O)(=O)Nc1cccc(N(CCNC(=O)OC(C)(C)C)Cc2ccccc2)c1]

Under an argon atmosphere, to a solution of tert-butyl (2-((benzyl)(3-(5-bromo-2-methoxyphenylsulfonamido)phenyl)amino)ethyl)carbamate (4.66 g) in DME (80.0 mL) were added 3-(N,N-dimethylaminocarbonyl)phenylboronic acid (3.56 g), sodium carbonate (1.80 g), water (8.0 mL) and tetrakis(triphenylphosphine)palladium (463.2 mg), and the mixture was heated under reflux overnight. The reaction mixture was filtered through celite, and the filtrate was concentrated. The obtained residue was purified by silica gel column chromatography (eluent: ethyl acetate/hexane=7/5→1/1) to give tert-butyl (2-((benzyl)(3-(3'-(dimethylcarbamoyl)-4-methoxy-[1,1'-biphenyl]-3-ylsulfonamido)phenyl)amino)ethyl)carbamate (4.85 g).

(5) 3'-(N-(3-((2-aminoethyl)amino)phenyl)sulfamoyl)-4'-methoxy-N,N-dimethyl-[1,1'-biphenyl]-3-carboxamide dihydrochloride

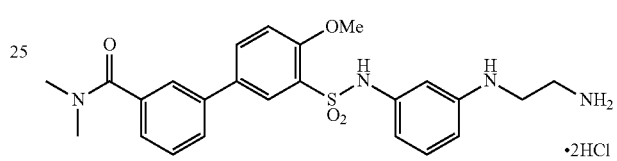

(i) To a solution of tert-butyl (2-((benzyl)(3-(3'-(dimethylcarbamoyl)-4-methoxy-[1,1'-biphenyl]-3-ylsulfonamido)phenyl)amino)ethyl)carbamate (1.50 g) in methanol (30.0 mL) was added palladium hydroxide (221.0 mg), and the mixture was stirred under a hydrogen atmosphere at room temperature for 3 hr. The reaction mixture was filtered through celite, and the filtrate was concentrated. The obtained residue was purified by silica gel column chromatography (eluent: ethyl acetate) to give tert-butyl (2-((3-(3'-(dimethylaminocarbamoyl)-4-methoxy-[1,1'-biphenyl]-3-ylsulfonamido)phenyl)amino)ethyl)carbamate (950.0 mg).

(ii) To tert-butyl (2-((3-(3'-(dimethylaminocarbamoyl)-4-methoxy-[1,1'-biphenyl]-3-ylsulfonamido)phenyl)amino)ethyl)carbamate (203.0 mg) was added 10% hydrogen chloride-methanol solution (4.0 mL), and the mixture was stirred at 50° C. for 2 hr. The reaction mixture was concentrated to give 3'-(N-(3-((2-aminoethyl)amino)phenyl)sulfamoyl)-4'-methoxy-N,N-dimethyl-[1,1'-biphenyl]-3-carboxamide dihydrochloride (187.0 mg).

(6) 4'-methoxy-N,N-dimethyl-3'-(N-(3-((2-(3-methylbenzamido)ethyl)amino)phenyl)sulfamoyl)-[1,1'-biphenyl]-3-carboxamide

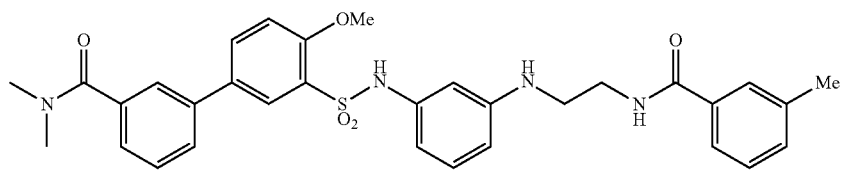 [SMILES: COc1ccc(-c2cccc(C(=O)N(C)C)c2)cc1S(=O)(=O)Nc1cccc(NCCNC(=O)c2cccc(C)c2)c1]

Under an argon atmosphere, to a solution of 3'-(N-(3-((2-aminoethyl)amino)phenyl)sulfamoyl)-4'-methoxy-N,N-dimethyl-[1,1'-biphenyl]-3-carboxamide dihydrochloride (127.8 mg) in dichloromethane (14.0 mL) were added 3-toluic acid (32.1 mg), TEA (108.0 μL) and BOP (114.8 mg), and the mixture was stirred at room temperature overnight. To the reaction mixture was added saturated aqueous sodium hydrogen carbonate solution, and the mixture was extracted with chloroform. The organic layer was washed with 1N hydrochloric acid and saturated brine, dried over sodium sulfate and filtered, and the filtrate was concentrated. The obtained residue was purified by silica gel column chromatography (eluent: ethyl acetate) to give 4'-methoxy-N,N-dimethyl-3'-(N-(3-((2-(3-methylbenzamido)ethyl)amino)phenyl)sulfamoyl)-[1,1'-biphenyl]-3-carboxamide (19.5 mg).

(7) 4'-methoxy-N,N-dimethyl-3'-(N-(3-(3-(3-methylbenzoyl)imidazolidin-1-yl)phenyl)sulfamoyl)-[1,1'-biphenyl]-3-carboxamide

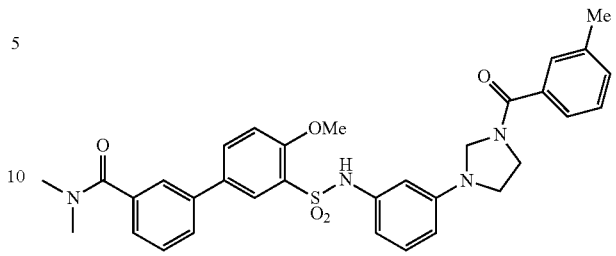

Under an argon atmosphere, to a solution of 4'-methoxy-N,N-dimethyl-3'-(N-(3-((2-(3-methylbenzamido)ethyl)amino)phenyl)sulfamoyl)-[1,1'-biphenyl]-3-carboxamide (19.5 mg) in acetic acid (1.0 mL) was added para-formaldehyde (30.0 mg), and the mixture was stirred at room temperature overnight. The reaction mixture was concentrated under reduced pressure, and the residue was purified by silica gel column chromatography (eluent: ethyl acetate) to give 4'-methoxy-N,N-dimethyl-3'-(N-(3-(3-(3-methylbenzoyl)imidazolidin-1-yl)phenyl)sulfamoyl)-[1,1'-biphenyl]-3-carboxamide (14.5 mg).

Production Example (9)

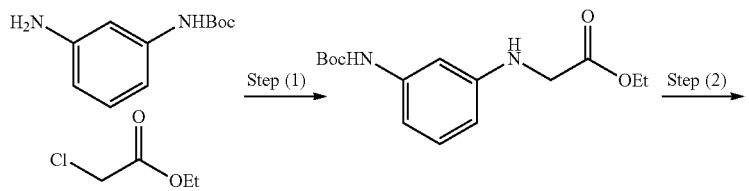

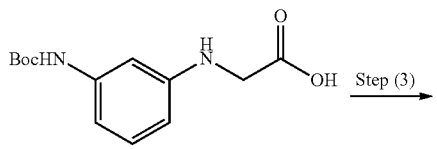

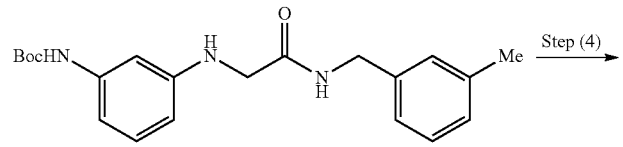

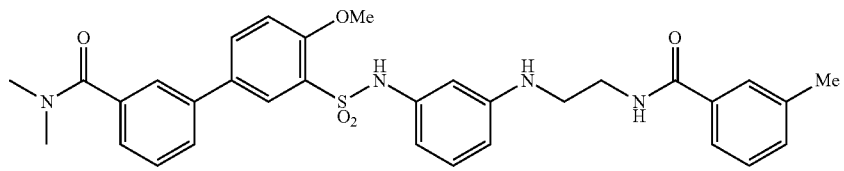

(1) ethyl 2-((3-((tert-butoxycarbonyl)amino)phenyl)amino)acetate

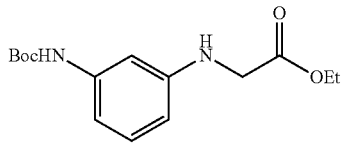 [SMILES: CCOC(=O)CNc1cccc(NC(=O)OC(C)(C)C)c1]

Under an argon atmosphere, to a solution of tert-butyl (3-aminophenyl)carbamate (1.22 g) in ethanol (10.0 mL) were added sodium acetate (790.0 mg) and ethyl chloroacetate (562 μL), and the mixture was stirred at room temperature for 12 hr. The reaction mixture was concentrated under reduced pressure, and the residue was diluted with chloroform and extracted with pure water. The organic layer was washed with saturated brine, dried over sodium sulfate and filtered, and the filtrate was concentrated under reduced pressure. The obtained residue was purified by silica gel column chromatography (eluent: hexane/ethyl acetate=4/1→3/2) to give ethyl 2-((3-((tert-butoxycarbonyl)amino)phenyl)amino)acetate (1.40 g).

(2) 2-((3-((tert-butoxycarbonyl)amino)phenyl)amino)acetic acid

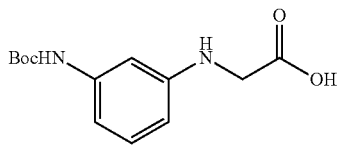

To a solution of ethyl 2-((3-((tert-butoxycarbonyl)amino)phenyl)amino)acetate (103.3 mg) in ethanol (10.0 mL) was added 1N aqueous sodium hydroxide solution (3.5 mL), and the mixture was stirred at room temperature for 6 hr. To the reaction mixture was added 1N aqueous hydrochloric acid solution, and the mixture was extracted with ethyl acetate. The organic layer was washed with saturated brine, dried over magnesium sulfate and filtered, and the filtrate was concentrated under reduced pressure to give 2-((3-((tert-butoxycarbonyl)amino)phenyl)amino)acetic acid (99.1 mg). The present compound was used for the next reaction without further purification.

(3) tert-butyl (3-((2-((3-methylbenzyl)amino)-2-oxoethyl)amino)phenyl)carbamate

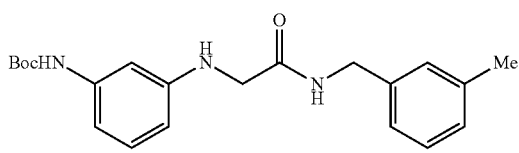 [SMILES: Cc1cccc(CNC(=O)CNc2cccc(NC(=O)OC(C)(C)C)c2)c1]

Under an argon atmosphere, to a solution of 2-((3-((tert-butoxycarbonyl)amino)phenyl)amino)acetic acid (15.0 mg) in dichloromethane (5.0 mL) were added DIPEA (87.0 μL) and HATU (190.0 mg), and the mixture was stirred at room temperature for 10 min. 3-Methylbenzylamine (12.0 μL) was added, and the mixture was further stirred for 10 hr. The reaction mixture was concentrated under reduced pressure, and the residue was diluted with chloroform, and extracted with saturated aqueous sodium hydrogen carbonate solution. The organic layer was washed with saturated brine, dried over sodium sulfate and filtered, and the filtrate was concentrated under reduced pressure. The obtained residue was purified by silica gel column chromatography (eluent: hexane/ethyl acetate=4/1→1/1) to give tert-butyl (3-((2-((3-methylbenzyl)amino)-2-oxoethyl)amino)phenyl)carbamate (13.0 mg).

(4) 4'-methoxy-N,N-dimethyl-3'-(N-(3-((2-((3-methylbenzyl)amino)-2-oxoethyl)amino)phenyl)sulfamoyl)-[1,1'-biphenyl]-3-carboxamide

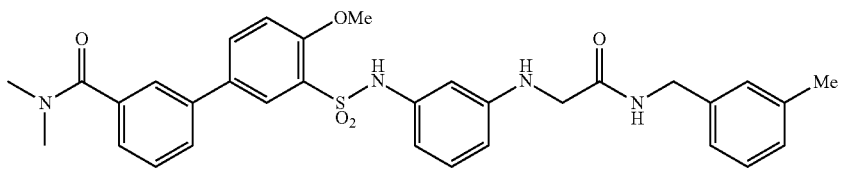 [SMILES: COc1ccc(-c2cccc(C(=O)N(C)C)c2)cc1S(=O)(=O)Nc1cccc(NCC(=O)NCc2cccc(C)c2)c1]

(i) Under an argon atmosphere, to a solution of tert-butyl (3-((2-((3-methylbenzyl)amino)-2-oxoethyl)amino)phenyl)carbamate (13.0 mg) in dichloromethane (2.0 mL) was added TFA (200 μL), and the mixture was stirred at room temperature for 2 hr. The reaction mixture was concentrated under reduced pressure to give 2-((3-aminophenyl)amino)-N-(3-methylbenzyl)acetamide TFA salt (13.0 mg). The present compound was used for the next reaction without further purification.

(ii) Under an argon atmosphere, to a solution of 2-((3-aminophenyl)amino)-N-(3-methylbenzyl)acetamide TFA salt (6.8 mg) in pyridine (1.0 mL) was added 3'-(dimethylcarbamoyl)-4-methoxy-[1,1'-biphenyl]-3-sulfonyl chloride (6.0 mg), and the mixture was stirred at room temperature for 16 hr. The reaction mixture was concentrated under reduced pressure, and the obtained residue was purified by silica gel column chromatography (eluent: hexane/ethyl acetate=1/9→0/1) to give 4'-methoxy-N,N-dimethyl-3'-(N-(3-((2-((3-methylbenzyl)amino)-2-oxoethyl)amino)phenyl)sulfamoyl)-[1,1'-biphenyl]-3-carboxamide (7.0 mg).

Production Example (10)

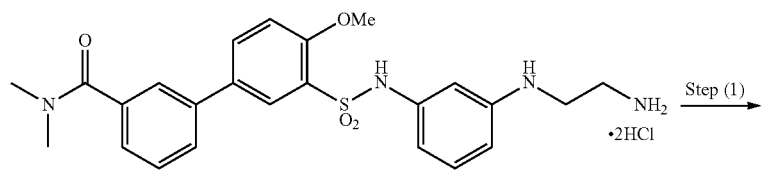

(1) 3'-(N-(3-(N-(2-acrylamidoethyl)acrylamido)phenyl)sulfamoyl)-4'-methoxy-N,N-dimethyl-[1,1'-biphenyl]-3-carboxamide

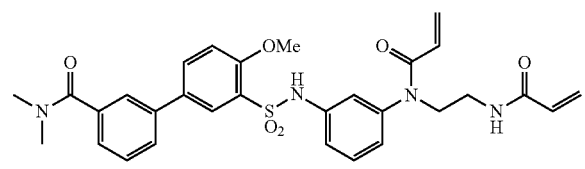 [SMILES: C=CC(=O)NCCN(C(=O)C=C)c1cccc(NS(=O)(=O)c2cc(-c3cccc(C(=O)N(C)C)c3)ccc2OC)c1]

Under an argon atmosphere, to a solution of 3'-(N-(3-((2-aminoethyl)amino)phenyl)sulfamoyl)-4'-methoxy-N,N-dimethyl-[1,1'-biphenyl]-3-carboxamide dihydrochloride (100.0 mg) in dichloromethane (1.0 mL) were added DIPEA (64.0 µL) and acryloyl chloride (30.0 µL), and the mixture was stirred at room temperature overnight. The reaction mixture was concentrated under reduced pressure, and the residue was purified by silica gel column chromatography (eluent: ethyl acetate/methanol=1/0→9/1) to give 3'-(N-(3-(N-(2-acrylamidoethyl)acrylamido)phenyl)sulfamoyl)-4'-methoxy-N,N-dimethyl-[1,1'-biphenyl]-3-carboxamide (103.0 mg).

Production Example (11)

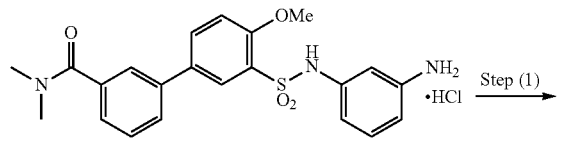

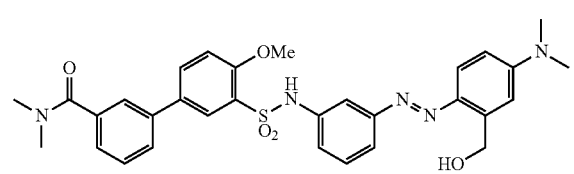

(1) (E)-3'-(N-(3-((4-(dimethylamino)-2-(hydroxymethyl)phenyl)diazenyl)phenyl)sulfamoyl)-4'-methoxy-N,N-dimethyl-[1,1-biphenyl]-3-carboxamide To a mixture of 3'-(N-(3-aminophenyl)sulfamoyl)-4'-methoxy-N,N-dimethyl-[1,1'-biphenyl]-3-carboxamide hydrochloride (30.0 mg), sulfuric acid on silica gel (50.0 mg) and sodium nitrite (10.0 mg) was added pure water (50.0 µL), and the mixture was stirred for 10 min until the release of gas ceased. Thereto was added 3-(dimethylaminobenzyl)alcohol (10.0 mg), and the mixture was stirred at room temperature for 1 hr. The reaction mixture was dried in vacuo, and purified by silica gel column chromatography (eluent: hexane/ethyl acetate=1/0→2/1) to give (E)-3'-(N-(3-((4-(dimethylamino)-2-(hydroxymethyl)phenyl)diazenyl)phenyl)sulfamoyl)-4'-methoxy-N,N-dimethyl-[1,1-biphenyl]-3-carboxamide (10.9 mg).

The compound of Example 98 described in the following Table 13 was also synthesized similarly from corresponding benzene derivative.

Production Example (12)

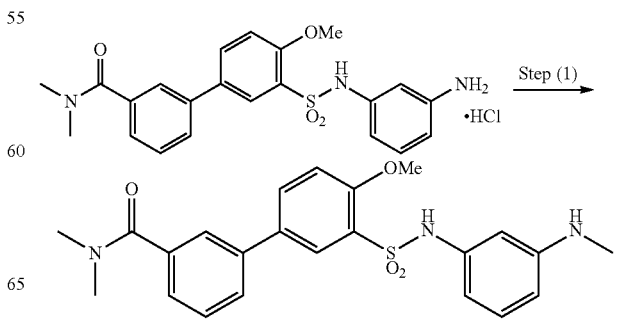

89

(1) 4'-methoxy-N,N-dimethyl-3'-(N-(3-(methyl-amino)phenyl)sulfamoyl)-[1,1'-biphenyl]-3-carboxamide

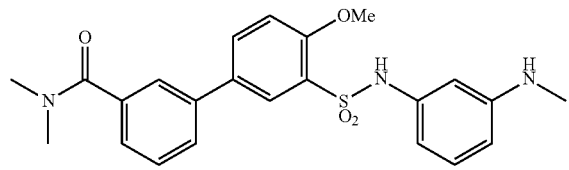

To a suspension of 3'-(N-(3-aminophenyl)sulfamoyl)-4'-methoxy-N,N-dimethyl-[1,1'-biphenyl]-3-carboxamide hydrochloride (100.0 mg) in methanol (15.0 mL) were added TEA (100.0 μL), para-formaldehyde (10.0 mg) and 5% palladium-activated carbon (9.20 mg), and the mixture was stirred with heating under reflux under a hydrogen atmosphere for 3 hr. The reaction mixture was filtered through celite, and the filtrate was concentrated. The obtained residue was purified by preparative thin layer chromatography (eluent: chloroform/methanol=20/1) to give 4'-methoxy-N,N-dimethyl-3'-(N-(3-(methylamino)phenyl)sulfamoyl)-[1,1'-biphenyl]-3-carboxamide (74.8 mg).

Production Example (13)

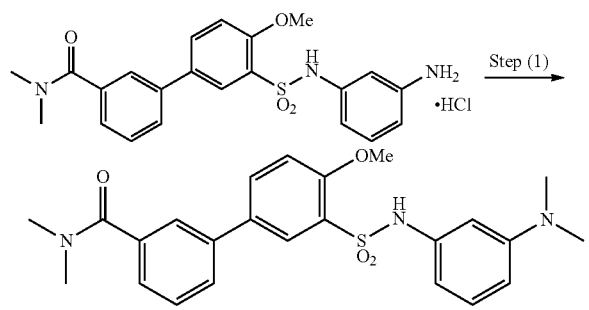

90

(1) 3'-(N-(3-(dimethylamino)phenyl)sulfamoyl)-4'-methoxy-N,N-dimethyl-[1,1'-biphenyl]-3-carboxamide

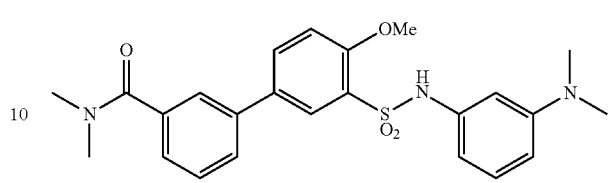

To a suspension of 3'-(N-(3-aminophenyl)sulfamoyl)-4'-methoxy-N,N-dimethyl-[1,1'-biphenyl]-3-carboxamide hydrochloride (17.0 mg) in ethanol (1.50 mL) were added TEA (20.0 μL), 30% aqueous formalin solution (14.0 μL) and 5% palladium-activated carbon (9.20 mg), and the mixture was stirred under a hydrogen atmosphere with heating under reflux for 40 hr. To the reaction mixture was added acetic acid (20.0 μL), and the mixture was further stirred for 12 hr. The reaction mixture was filtered through celite, and the filtrate was diluted with chloroform, and extracted with saturated aqueous sodium hydrogen carbonate solution. The organic layer was washed with saturated brine, dried over sodium sulfate and filtered, and the filtrate was concentrated under reduced pressure. The obtained residue was purified by preparative thin layer chromatography (eluent: chloroform/methanol=40/1) to give 3'-(N-(3-(dimethylamino)phenyl)sulfamoyl)-4'-methoxy-N,N-dimethyl-[1,1'-biphenyl]-3-carboxamide (14.0 mg).

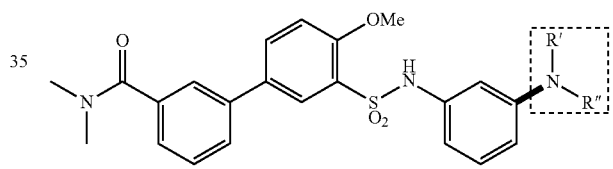

TABLE 13

| Ex. No. | structure of substituent on aniline | ¹H-NMR |
|---|---|---|
| 91 | (benzyl-N(Me)-CH₂CH₂-NH-C(O)O-tBu) | 1H NMR (400 MHz, Chloroform-d) δ 7.98 (d, J = 2.4 Hz, 1H), 7.67 (dd, J = 8.4, 2.0 Hz, 1H), 7.53 (s, 1H), 7.51 (d, J = 8.8 Hz, 1H), 7.42 (t, J = 7.6 Hz, 1H), 7.34 (d, J = 7.6 Hz, 1H), 7.22-7.14 (m, 3H), 7.05 (d, J = 7.6 Hz, 2H), 7.00-6.94 (m, 2H), 6.87 (s, 1H), 6.44 (t, J = 7.6 Hz, 2H), 6.38 (s, 1H), 4.63 (m, 1H), 4.44 (s, 2H), 3.87 (s, 3H), 3.45-3.42 (m, 2H), 3.24-3.19 (m, 2H), 3.12 (s, 3H), 2.98 (s, 3H), 1.38 (s, 9H). |
| 92 | (MeNH-CH₂-C(O)-NH-CH₂-(3-Me-phenyl)) | 1H NMR (400 MHz, Chloroform-d) δ 8.06 (d, J = 2.4 Hz, 1H), 7.70 (dd, J = 8.6, 2.4 Hz, 1H), 7.56 (dd, J = 1.5 Hz, 1H), 7.52 (ddd, J = 7.8, 1.5 Hz, 1H), 7.42 (dd, J = 7.6 Hz, 1H), 7.32 (ddd, J = 7.5, 1.3 Hz, 1H), 7.14 (dd, J = 7.8 Hz, 1H), 7.07 (d, J = 8.7 Hz, 1H), 7.05-6.98 (m, 2H), 6.97-6.89 (m, 4H), 6.47 (dd, J = 7.5, 2.1 Hz, 1H), 6.37 (dd, J = 2.1 Hz, 1H), 6.32 (dd, J = 8.4, 2.5 Hz, 1H), 4.36 (d, J = 5.9 Hz, 2H), 4.05 (s, 3H), 3.70 (d, J = 4.3 Hz, 2H), 3.12 (s, 3H), 2.99 (s, 3H), 2.25 (s, 3H). |

TABLE 13-continued

| Ex. No. | structure of substituent on aniline | ¹H-NMR |
|---|---|---|
| 93 | 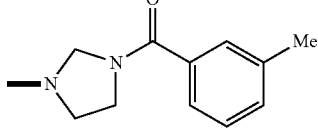 | 1H NMR (400 MHz, Chloroform-d) δ 8.02 (brs, J = 16.5 Hz, 1H), 7.77-7.62 (brm, 1H), 7.59-7.47 (brm, 2H), 7.42 (d, J = 7.7 Hz, 1H), 7.37-7.23 (brm, 5H), 7.16 (brd, J = 11.0 Hz, 1H), 7.10-6.94 (brm, 2H), 6.55-6.39 (brm, 2H), 6.39-6.27 (brm, 1H), 4.86 (brs, 1H), 4.58 (brs, 1H), 4.10-3.92 (brm, 4H), 3.78 (dd, J = 7.1 Hz, 1H), 3.42 (brs, J = 6.6 Hz, 2H), 3.10 (brs, 3H), 2.98 (s, 3H), 2.37 (s, 3H). |
| 94 | 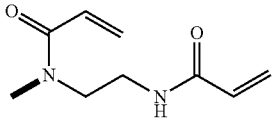 | 1H NMR (400 MHz, Chloroform-d) δ 8.04 (d, J = 2.4 Hz, 1H), 7.96 (brs, 1H), 7.70 (dd, J = 8.6, 2.4 Hz, 1H), 7.54-7.48 (m, 2H), 7.42 (dd, J = 7.8 Hz, 1H), 7.33 (ddd, J = 7.5, 1.3 Hz, 1H), 7.22 (d, J = 7.8 Hz, 1H), 7.17 (ddd, J = 8.2, 1.5 Hz, 1H), 7.05 (d, J = 8.7 Hz, 1H), 6.95 (dd, J = 1.8 Hz, 1H), 6.87-6.79 (m, 2H), 6.25-5.99 (m, 3H), 5.67 (dd, J = 16.7, 10.3 Hz, 1H), 5.59-5.49 (m, 1H), 5.32 (d, J = 10.3 Hz, 1H), 4.00 (s, 3H), 3.82 (t, J = 5.9 Hz, 2H), 3.35 (q, J = 5.2 Hz, 2H), 3.11 (s, 3H), 2.98 (s, 3H). |
| 95 |  | 1H NMR (400 MHz, Chloroform-d) δ 8.06 (d, J = 2.4 Hz, 1H), 7.70 (dd, J = 8.6, 2.4 Hz, 1H), 7.57-7.51 (m, 2H), 7.43 (ddd, J = 7.4, 1.2 Hz, 1H), 7.35 (ddd, J = 7.5, 1.4 Hz, 1H), 7.07 (d, J = 8.7 Hz, 1H), 6.96 (dd, J = 8.0 Hz, 1H), 6.90 (brs, 1H), 6.44 (dd, J = 2.2 Hz, 1H), 6.36-6.24 (m, 2H), 4.07 (s, 3H), 3.13 (s, 3H), 3.00 (s, 3H), 2.74 (s, 3H). |
| 96 |  | 1H NMR (400 MHz, Chloroform-d) δ 8.07 (d, J = 2.4 Hz, 1H), 7.69 (dd, J = 8.6, 2.4 Hz, 1H), 7.55-7.49 (m, 2H), 7.43 (ddd, J = 7.4, 1.0 Hz, 1H), 7.35 (ddd, J = 7.5, 1.4 Hz, 1H), 7.06 (d, J = 8.7 Hz, 1H), 7.04-6.97 (m, 2H), 6.51 (dd, J = 2.2 Hz, 1H), 6.44-6.38 (m, 1H), 6.38-6.31 (m, 1H), 4.06 (s, 3H), 3.13 (s, 3H), 2.99 (s, 3H), 2.85 (s, 6H). |
| 97 | 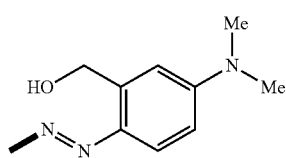 | 1H NMR (400 MHz, Chloroform-d) δ 8.08 (d, J = 2.4 Hz, 1H), 7.80 (d, J = 9.3 Hz, 1H), 7.70 (dd, J = 8.6, 2.4 Hz, 1H), 7.56-7.49 (m, 3H), 7.44-7.39 (m, 2H), 7.36-7.31 (m, 2H), 7.26-7.22 (m, 1H), 7.16 (s, 1H), 7.09 (d, J = 8.7 Hz, 1H), 6.68-6.61 (m, 2H), 4.89 (s, 2H), 4.11 (s, 3H), 3.10 (s, 9H), 2.97 (s, 3H). |
| 98 | 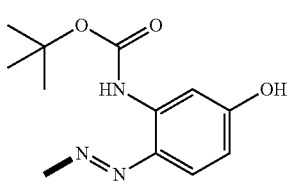 | 1H NMR (400 MHz, Chloroform-d) δ 9.73 (s, 1H), 8.08 (d, J = 2.3 Hz, 1H), 7.89 (d, J = 2.5 Hz, 1H), 7.71-7.62 (m, 2H), 7.54-7.46 (m, 4H), 7.39 (dd, J = 7.6 Hz, 1H), 7.36-7.28 (m, 3H), 7.20 (brd, J = 7.3 Hz, 1H), 7.11-6.98 (m, 2H), 6.53 (dd, J = 8.9, 2.6 Hz, 1H), 4.05 (s, 3H), 3.12 (s, 3H), 2.98 (s, 3H), 1.50 (s, 9H). |

TABLE 13-continued

| Ex. No. | structure of substituent on aniline | $^1$H-NMR |
|---|---|---|
| 99 | H₃C-NH-H | 1H NMR (400 MHz, DMSO-d6) δ 10.33 (brs, 1H), 8.01 (d, J = 2.4 Hz, 1H), 7.93 (dd, J = 8.7, 2.4 Hz, 1H), 7.69 (ddd, J = 7.8, 1.9, 1.1 Hz, 1H), 7.60 (dd, J = 1.6 Hz, 1H), 7.52 (dd, J = 7.7 Hz, 1H), 7.37 (ddd, J = 7..6, 1.3 Hz, 1H), 7.28 (d, J = 8.8 Hz, 1H), 7.17 (dd, J = 8.0 Hz, 1H), 6.99 (brs, 1H), 6.90 (brd, J = 8.5 Hz, 1H), 6.72 (brd, J = 7.8 Hz, 1H), 3.92 (s, 3H), 3.00 (s, 3H), 2.92 (s, 3H). |

Production Example (14)

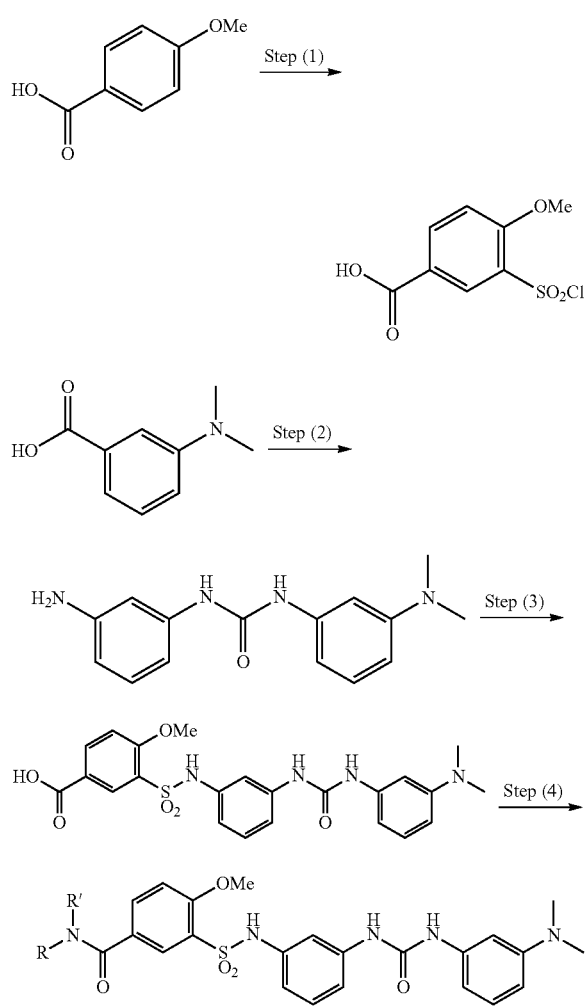

(1) 3-(chlorosulfonyl)-4-methoxybenzoic acid

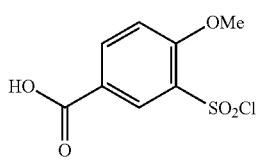

Under an argon atmosphere, to chlorosulfonic acid (2.20 mL) was slowly added 4-methoxybenzoic acid (1.00 g) under ice-cooling, and the mixture was stirred for 10 min. Thereafter, the reaction mixture was heated to 65° C. and stirred for 2 hr. The reaction mixture was allowed to cool, poured into ice and stirred for 1 hr. The resulting white solid was collected by filtration and washed with cold water. The obtained solid was dried in vacuo to give 3-(chlorosulfonyl)-4-methoxybenzoic acid (966.0 mg). The present compound was used for the next reaction without further purification.

(2) 1-(3-aminophenyl)-3-(3-(dimethylamino)phenyl)urea

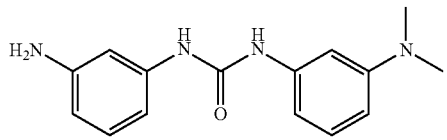 [SMILES: CN(C)c1cccc(NC(=O)Nc2cccc(N)c2)c1]

(i) Under an argon atmosphere, to a solution of 3-dimethylaminobenzoic acid (1.59 g) in benzene (10.0 mL) were added TEA (2.60 mL) and DPPA (4.0 mL), and the mixture was stirred under reflux at 110° C. for 1 hr. To the reaction mixture was added tert-butyl (3-aminophenyl)carbamate (1.31 g), and the mixture was further stirred under reflux for 10 hr. The reaction mixture was allowed to cool and concentrated under reduced pressure, and the residue was purified by silica gel column chromatography (eluent: ethyl acetate/chloroform=0/1→5/1) to give tert-butyl (3-(3-(3-(dimethylamino)phenyl)ureido)phenyl)carbamate (3.43 g).

(ii) Under an argon atmosphere, to a suspension of tert-butyl (3-(3-(3-(dimethylamino)phenyl)ureido)phenyl)carbamate (1.0 g) in dichloromethane (10.0 mL) was added TFA (600 μL), and the mixture was stirred overnight. The reaction mixture was concentrated under reduced pressure, and the residue was diluted with 25% methanol-containing chloroform and extracted with saturated aqueous sodium hydrogen carbonate solution. The organic layer was washed with saturated brine, dried over sodium sulfate and filtered, and the filtrate was concentrated under reduced pressure. The obtained residue was purified by silica gel column chromatography (eluent: chloroform/ethyl acetate=2/1) to give 1-(3-aminophenyl)-3-(3-(dimethylamino)phenyl)urea (715.3 mg).

(3) 3-(N-(3-(3-(3-(dimethylamino)phenyl)ureido) phenyl)sulfamoyl)-4-methoxybenzoic acid

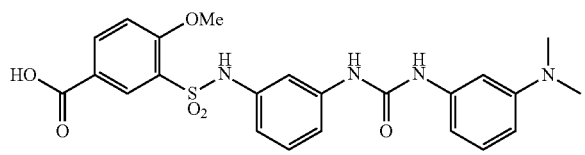 [SMILES: COc1ccc(C(=O)O)cc1S(=O)(=O)Nc1cccc(NC(=O)Nc2cccc(N(C)C)c2)c1]

Under an argon atmosphere, pyridine (7.5 mL) was added to a suspension of 1-(3-aminophenyl)-3-(3-(dimethylamino) phenyl)urea (797.1 mg) in dichloromethane (7.5 mL) and completely dissolved by agitating at 60° C. under reflux. The reaction mixture was allowed to cool, a solution of 3-(chlorosulfonyl)-4-methoxybenzoic acid (672.9 mg) in 50% pyridine-containing dichloromethane (15 mL) was slowly added dropwise, and the mixture was stirred at room temperature for 15 hr. Furthermore, 3-(chlorosulfonyl)-4-methoxybenzoic acid (448.8 mg) was added and the mixture was stirred at room temperature for 19 hr. The reaction mixture was concentrated under reduced pressure, and the obtained residue was purified by silica gel column chromatography (eluent: chloroform/ethyl acetate/methanol=2/1/0→1/1/0→1/1/0.4) to give 3-(N-(3-(3-(3-(dimethylamino)phenyl) ureido)phenyl)sulfamoyl)-4-methoxybenzoic acid (905.6 mg).

(4) N-benzyl-3-(N-(3-(3-(3-(dimethylamino)phenyl) ureido)phenyl)sulfamoyl)-4-methoxybenzamide

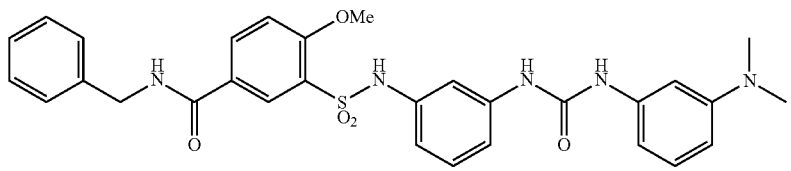 [SMILES: COc1ccc(C(=O)NCc2ccccc2)cc1S(=O)(=O)Nc1cccc(NC(=O)Nc2cccc(N(C)C)c2)c1]

Under an argon atmosphere, to a solution of 3-(N-(3-(3-(3-(dimethylamino)phenyl)ureido)phenyl)sulfamoyl)-4-methoxybenzoic acid (15.4 mg) in dichloromethane (3.0 mL) were added TEA (20.1 μL) and HATU (25.9 mg), and the mixture was stirred at room temperature for 10 min. Benzylamine (4.0 μL) was added and the mixture was further stirred for 12 hr. The reaction mixture was concentrated under reduced pressure, and the residue was diluted with chloroform and extracted with saturated aqueous sodium hydrogen carbonate solution. The organic layer was washed with saturated brine, dried over sodium sulfate and filtered, and the filtrate was concentrated under reduced pressure. The obtained residue was purified by preparative thin layer chromatography (eluent: chloroform/ethyl acetate=1/2) to give N-benzyl-3-(N-(3-(3-(3-(dimethylamino)phenyl)ureido)phenyl)sulfamoyl)-4-methoxybenzamide (3.9 mg).

The compounds described in the following Table 14 were also synthesized similarly from amine having the corresponding R and R' groups.

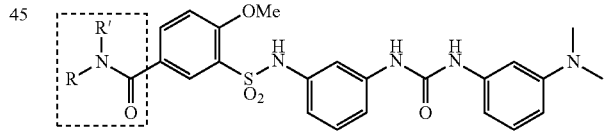

TABLE 14

| Ex. No. | amide substituent structure | $^1$H-NMR |
|---|---|---|
| 100 | ![structure] | 1H NMR (400 MHz, Methanol-d4) δ 8.40 (d, J = 2.3 Hz, 1H), 8.03 (dd, J = 8.7, 2.3 Hz, 1H), 7.50 (dd, J = 2.0 Hz, 1H), 7.33-7.17 (m, 6H), 7.09 (ddd, J = 10.9, 8.1 Hz, 2H), 6.95 (ddd, J = 8.2, 2.1, 1.0 Hz, 1H), 6.90 (dd, J = 2.1 Hz, 1H), 6.75 (ddd, J = 8.0, 2.1, 1.0 Hz, 1H), 6.70 (ddd, J = 7.9, 1.9, 0.8 Hz, 1H), 6.48 (dd, J = 8.3, 2.5 Hz, 1H), 4.44 (s, 2H), 4.05 (s, 3H), 2.92 (s, 6H). |

TABLE 14-continued

| Ex. No. | amide substituent structure | ¹H-NMR |
|---|---|---|
| 101 | (benzyl, N-ethyl acetamide) | 1H NMR (400 MHz, Methanol-d4) δ 7.84 (d, J = 2.0 Hz, 1H), 7.65-7.46 (m, 1H), 7.39-6.81 (m, 11H), 6.78-6.59 (m, 2H), 6.44 (dd, J = 7.9, 2.4 Hz, 1H), 4.63 (brs, 1.2H), 4.31 (brs, 0.8H), 4.00 (s, 3H), 3.41 (brs, 0.8H), 3.06 (brs, 1.2H), 2.89 (s, 6H), 1.11 (brs, 1.2H), 0.95 (brs, 1.8H). |
| 102 | (pyridin-3-ylmethyl, N-ethyl acetamide) | 1H NMR (400 MHz, DMSO-d6) δ 10.11 (brs, 1H), 8.61-8.43 (m, 2H), 7.75 (d, J = 2.1 Hz, 1H), 7.62 (brs, 2H), 7.35 (dd, J = 7.7, 4.8 Hz, 1H), 7.21 (d, J = 7.3 Hz, 2H), 7.13-6.94 (m, 3H), 6.86 (s, 1H), 6.75-6.59 (m, 2H), 6.35 (dd, J = 8.3, 2.3 Hz, 1H), 4.61 (s, 1H), 3.94 (s, 3H), 3.09 (brs, 2H), 2.86 (s, 6H), 0.95 (brs, 3H). |
| 103 | (pyridin-3-ylmethyl acetamide) | 1H NMR (400 MHz, DMSO-d6) δ 10.03 (brs, 1H), 9.16 (dd, J = 5.9 Hz, 1H), 8.64 (s, 1H), 8.52 (d, J = 1.9 Hz, 1H), 8.48-8.39 (m, 2H), 8.31 (d, J = 2.3 Hz, 1H), 8.08 (dd, J = 8.7, 2.2 Hz, 1H), 7.68 (ddd, J = 7.9, 1.9 Hz, 1H), 7.32 (dd, J = 7.8, 4.7 Hz, 1H), 7.29-7.20 (m, 2H), 7.12-7.02 (m, 3H), 6.85 (t, J = 2.1 Hz, 1H), 6.74-6.64 (m, 2H), 6.35 (dd, J = 8.3, 2.3 Hz, 1H), 4.44 (d, J = 5.7 Hz, 2H), 3.97 (s, 3H), 2.86 (s, 6H). |
| 104 | (Boc-NH-propyl acetamide) | 1H NMR (400 MHz, Chloroform-d) δ 8.36 (brs, 1H), 8.04-7.79 (m, 2H), 7.73-7.48 (m, 4H), 7.08 (dd, J = 8.1 Hz, 1H), 6.94 (dd, J = 8.0 Hz, 1H), 6.87 (brd, J = 8.6 Hz, 1H), 6.80 (brd, J = 8.3 Hz, 1H), 6.72 (brs, 1H), 6.65 (brd, J = 6.9 Hz, 1H), 6.56 (brd, J = 7.9 Hz, 1H), 6.42 (dd, J = 8.4, 1.9 Hz, 1H), 5.15 (brs, 1H), 3.90 (s, 3H), 3.30 (q, J = 5.4 Hz, 2H), 3.09 (d, J = 6.1 Hz, 2H), 2.85 (s, 6H), 1.69-1.51 (m, 2H), 1.42 (s, 9H). |
| 105 | (Boc-NH-ethyl acetamide) | 1H NMR (400 MHz, Chloroform-d) δ 8.38 (brs, 1H), 8.05-7.41 (m, 6H), 7.10 (dd, J = 8.0 Hz, 1H), 6.94 (dd, J = 8.0 Hz, 1H), 6.90-6.64 (m, 3H), 6.64-6.35 (m, 3H), 5.26 (s, 1H), 3.89 (s, 3H), 3.39 (brd, J = 5.4 Hz, 2H), 3.26 (brd, 2H), 2.87 (s, 6H), 1.38 (s, 9H). |
| 106 | (3-(dimethylamino)phenyl acetamide) | 1H NMR (400 MHz, Chloroform-d) δ 8.80 (brs, 1H), 8.41 (d, J = 1.6 Hz, 1H), 8.10-7.87 (m, 2H), 7.65 (brs, 1H), 7.30 (brs, 1H), 7.18-7.04 (m, 4H), 7.00-6.91 (m, 2H), 6.87 (d, J = 8.8 Hz, 1H), 6.71 (d, J = 7.6 Hz, 1H), 6.62 (brd, J = 9.0 Hz, 1H), 6.56 (brs, 1H), 6.51-6.40 (m, 3H), 3.90 (s, 3H), 2.88 (s, 6H), 2.83 (s, 6H). |
| 107 | (Me2N-CH2-C(Me)2-CH2-NH acetamide) | 1H NMR (400 MHz, Methanol-d4) δ 8.21 (d, J = 2.4 Hz, 1H), 8.01 (dd, J = 8.7, 2.4 Hz, 1H), 7.40 (dd, J = 2.1 Hz, 1H), 7.22 (d, J = 8.8 Hz, 1H), 7.10 (d, J = 8.0 Hz, 1H), 7.04 (dd, J = 8.0 Hz, 1H), 6.96 (ddd, J = 8.2, 2.0, 1.0 Hz, 1H), 6.90 (dd, J = 2.2 Hz, 1H), 6.76 (ddd, J = 8.0, 2.1, 1.0 Hz, 1H), 6.68 (ddd, J = 7.9, 1.9, 0.7 Hz, 1H), 6.47 (ddd, J = 8.3, 2.5, 0.6 Hz, 1H), 4.05 (s, 3H), 3.22 (s, 2H), 2.91 (s, 6H), 2.35 (s, 6H), 2.31 (s, 2H), 0.93 (s, 6H). |

Production Example (15)

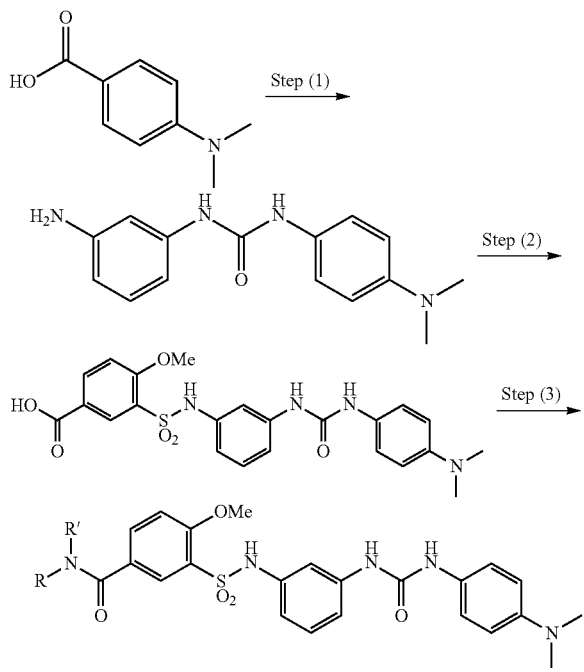

(1) 1-(3-aminophenyl)-3-(4-(dimethylamino)phenyl)urea

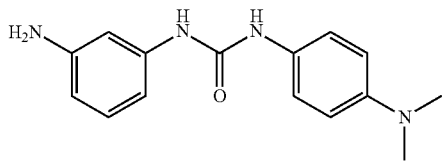 [SMILES: CN(C)c1ccc(NC(=O)Nc2cccc(N)c2)cc1]

(i) Under an argon atmosphere, to a solution of 4-dimethylaminobenzoic acid (1.60 g) in benzene (10.0 mL) were added TEA (2.60 mL) and DPPA (4.10 mL), and the mixture was stirred at 110° C. under reflux for 1 hr. To the reaction mixture was further added tert-butyl (3-aminophenyl)carbamate (1.35 g), and the mixture was further stirred under reflux for 10 hr. The reaction mixture was allowed to cool and concentrated under reduced pressure, and the residue was purified by silica gel column chromatography (eluent: ethyl acetate/chloroform=0/1→4/1) to give tert-butyl (3-(3-(4-(dimethylamino)phenyl)ureido)phenyl)carbamate (1.90 g).

(ii) Under an argon atmosphere, to a suspension of tert-butyl (3-(3-(4-(dimethylamino)phenyl)ureido)phenyl)carbamate (1.90 g) in dichloromethane (10.0 mL) was added TFA (2.00 mL), and the mixture was stirred overnight. The reaction mixture was concentrated under reduced pressure, and the residue was diluted with 15% methanol-containing chloroform, and extracted with saturated aqueous sodium hydrogen carbonate solution. The organic layer was washed with saturated brine, dried over sodium sulfate and filtered, and the filtrate was concentrated under reduced pressure to give 1-(3-aminophenyl)-3-(4-(dimethylamino)phenyl)urea (1.02 g). The present compound was used for the next reaction without further purification.

(2) 3-(N-(3-(3-(4-(dimethylamino)phenyl)ureido)phenyl)sulfamoyl)-4-methoxybenzoic acid

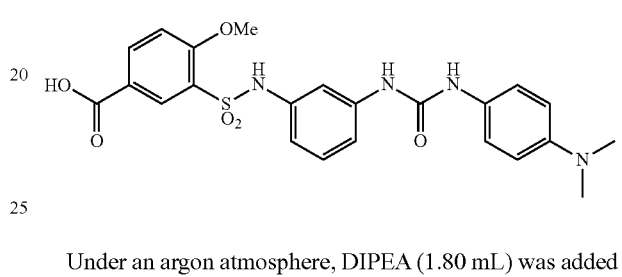

Under an argon atmosphere, DIPEA (1.80 mL) was added to a suspension of 1-(3-aminophenyl)-3-(4-(dimethylamino)phenyl)urea (916.7 mg) in dichloromethane (10.0 mL) and completely dissolved. Thereto was slowly added 3-(chlorosulfonyl)-4-methoxybenzoic acid (1.09 g), and the mixture was stirred at room temperature for 3 hr. The reaction mixture was concentrated under reduced pressure, and the obtained residue was purified by silica gel column chromatography (eluent: chloroform/methanol=20/1→10/1) to give 3-(N-(3-(3-(4-(dimethylamino)phenyl)ureido)phenyl)sulfamoyl)-4-methoxybenzoic acid (1.26 g).

(3) N-benzyl-3-(N-(3-(3-(4-(dimethylamino)phenyl)ureido)phenyl)sulfamoyl)-4-methoxybenzamide

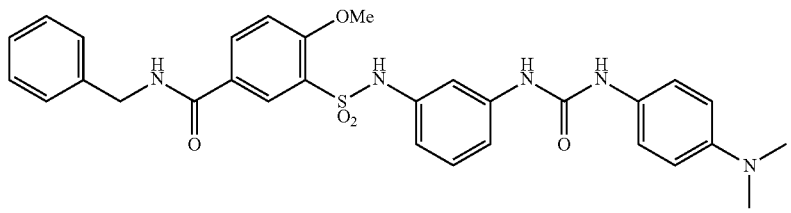 [SMILES: COc1ccc(C(=O)NCc2ccccc2)cc1S(=O)(=O)Nc1cccc(NC(=O)Nc2ccc(N(C)C)cc2)c1]

Under an argon atmosphere, to a solution of 3-(N-(3-(3-(4-(dimethylamino)phenyl)ureido)phenyl)sulfamoyl)-4-methoxybenzoic acid (22.8 mg) in dichloromethane (5.0 mL) were added TEA (40.0 μL) and HATU (37.8 mg), and the mixture was stirred at room temperature for 10 min. Thereto was added benzylamine (5.7 μL), and the mixture was further stirred for 15 hr. The reaction mixture was concentrated under reduced pressure, and the residue was diluted with chloroform and extracted with saturated aqueous sodium hydrogen carbonate solution. The organic layer was washed with saturated brine, dried over sodium sulfate and filtered, and the filtrate was concentrated under reduced pressure. The obtained residue was purified by preparative thin layer chromatography (eluent: chloroform/ethyl acetate=1/2) to give N-benzyl-3-(N-(3-(3-(4-(dimethylamino)phenyl)ureido)phenyl)sulfamoyl)-4-methoxybenzamide (2.80 mg).

The compounds described in the following Table 15 were also synthesized similarly from amine having the corresponding R and R' groups.

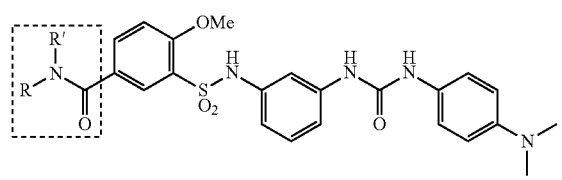

Production Example (16)

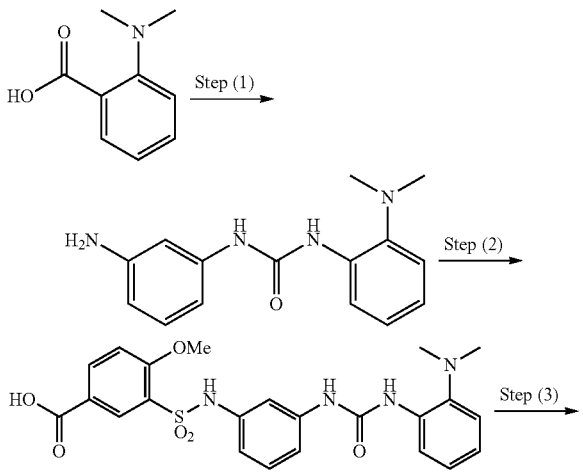

TABLE 15

| Ex. No. | amide substituent structure | $^1$H-NMR |
|---|---|---|
| 108 | | 1H NMR (400 MHz, Methanol-d4) δ 8.38 (d, J = 2.3 Hz, 1H), 8.00 (dd, J = 8.7, 2.4 Hz, 1H), 7.52 (dd, J = 2.0 Hz, 1H), 7.32-7.23 (m, 4H), 7.20 (t, J = 8.8 Hz, 4H), 7.05 (dd, J = 8.1 Hz, 1H), 6.87 (ddd, J = 8.1, 2.1, 0.9 Hz, 1H), 6.76-6.68 (m, 3H), 4.36 (s, 2H), 4.02 (s, 3H), 2.85 (s, 6H). |
| 109 | | 1H NMR (400 MHz, Methanol-d4) δ 8.44-8.36 (m, 3H), 8.00 (dd, J = 8.7, 2.4 Hz, 1H), 7.70 (ddd, J = 7.9, 1.9 Hz, 1H), 7.64 (dd, J = 2.1 Hz, 1H), 7.36 (dd, J = 7.8, 4.9 Hz, 1H), 7.25-7.16 (m, 3H), 7.05 (dd, J = 8.1 Hz, 1H), 6.80 (ddd, J = 8.2, 2.0, 0.9 Hz, 1H), 6.72 (d, J = 9.0 Hz, 2H), 6.68 (ddd, J = 8.0, 2.1, 0.8 Hz, 1H), 4.32 (s, 2H), 4.03 (s, 3H), 2.85 (s, 6H). |
| 110 | | 1H NMR (400 MHz, Methanol-d4) δ 7.87 (d, J = 2.2 Hz, 1H), 7.62 (brs, 1H), 7.38-7.17 (m, 8H), 7.15-6.87 (m, 3H), 6.78 (d, J = 9.0 Hz, 2H), 6.72 (brs, 1H), 4.71 (brs, 1.2H), 4.35 (brs, 0.8H), 4.03 (s, 3H), 3.43 (brs, 0.8H), 3.09 (brs, 1.2H), 2.88 (s, 6H), 1.14 (brs, 1.2H), 0.98 (brs, 1.8H). |
| 111 | | 1H NMR (400 MHz, Methanol-d4) δ 8.67-8.36 (m, 2H), 7.88-7.73 (m, 1H), 7.61 (brs, 1H), 7.40 (dd, J = 7.9, 5.2 Hz, 1H), 7.34 (dd, J = 2.1 Hz, 1H), 7.28-7.08 (m, 4H), 7.00 (brs, 2H), 6.84-6.65 (m, 3H), 4.70 (brs, 2H), 4.03 (s, 3H), 3.17 (brs, 2H), 2.88 (s, 6H), 1.05 (brs, 3H). |

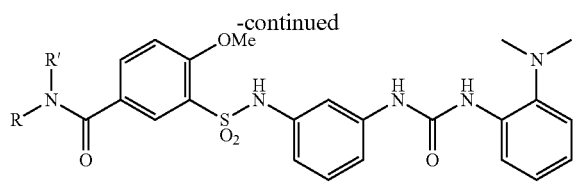

(1) 1-(3-aminophenyl)-3-(2-(dimethylamino)phenyl)urea

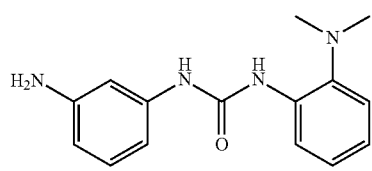 [SMILES: CN(C)c1ccccc1NC(=O)Nc1cccc(N)c1]

(i) Under an argon atmosphere, to a solution of 2-dimethylaminobenzoic acid (900.0 mg) in benzene (8.0 mL) were added TEA (1.49 mL) and DPPA (2.30 mL), and the mixture was stirred at 110° C. under reflux for 5 hr. To the reaction mixture was added tert-butyl (3-aminophenyl)carbamate (655.7 mg), and the mixture was stirred under reflux for 2 hr. The reaction mixture was allowed to cool and concentrated under reduced pressure, and the residue was purified by silica gel column chromatography (eluent: ethyl acetate/chloroform=0/1→4/1) to give tert-butyl (3-(3-(2-(dimethylamino)phenyl)ureido)phenyl)carbamate (1.12 g).

(ii) Under an argon atmosphere, to a suspension of tert-butyl (3-(3-(2-(dimethylamino)phenyl)ureido)phenyl)carbamate (1.00 g) in dichloromethane (10.0 mL) was added TFA (2.00 mL), and the mixture was stirred overnight. The reaction mixture was concentrated under reduced pressure, and the residue was diluted with 15% methanol-containing chloroform and extracted with saturated aqueous sodium hydrogen carbonate solution. The organic layer was washed with saturated brine, dried over sodium sulfate and filtered, and the filtrate was concentrated under reduced pressure to give 1-(3-aminophenyl)-3-(2-(dimethylamino)phenyl)urea (725.8 mg). The present compound was used for the next reaction without further purification.

(2) 3-(N-(3-(3-(2-(dimethylamino)phenyl)ureido)phenyl)sulfamoyl)-4-methoxybenzoic acid

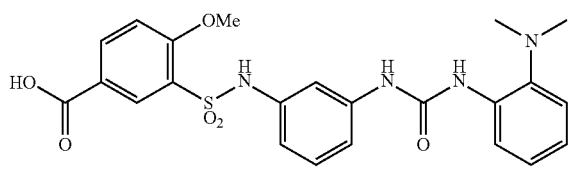 [SMILES: COc1ccc(C(=O)O)cc1S(=O)(=O)Nc1cccc(NC(=O)Nc2ccccc2N(C)C)c1]

Under an argon atmosphere, pyridine (10.0 mL) was added to a suspension of 1-(3-aminophenyl)-3-(2-(dimethylamino)phenyl)urea (686.6 mg) in dichloromethane (10.0 mL) and completely dissolved. Thereto was slowly added 3-(chlorosulfonyl)-4-methoxybenzoic acid (524.4 mg), and the mixture was heated under reflux at 50° C. for 3 hr. The reaction mixture was concentrated under reduced pressure, and the obtained residue was purified by silica gel column chromatography (eluent: chloroform/ethyl acetate=1/0→1/1) to give 3-(N-(3-(3-(2-(dimethylamino)phenyl)ureido)phenyl)sulfamoyl)-4-methoxybenzoic acid (258.6 mg).

(3) tert-butyl (3-(3-(N-(3-(3-(2-(dimethylamino)phenyl)ureido)phenyl)sulfamoyl)-4-methoxybenzamido)propyl)carbamate

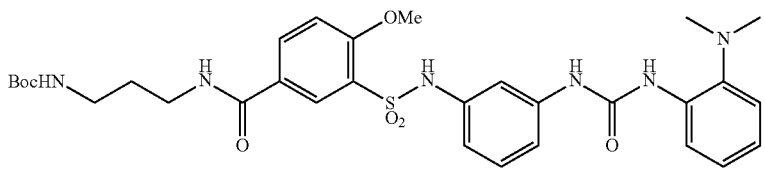 [SMILES: COc1ccc(C(=O)NCCCNC(=O)OC(C)(C)C)cc1S(=O)(=O)Nc1cccc(NC(=O)Nc2ccccc2N(C)C)c1]

Under an argon atmosphere, to a solution of 3-(N-(3-(3-(2-(dimethylamino)phenyl)ureido)phenyl)sulfamoyl)-4-methoxybenzoic acid (17.7 mg) in dichloromethane (3.0 mL) were added TEA (20.0 μL) and HATU (35.2 mg), and the mixture was stirred at room temperature for 10 min. Thereto was added N-(tert-butoxycarbonyl)-1,3-diaminopropane (7.0 μL), and the mixture was further stirred for 8 hr. The reaction mixture was concentrated under reduced pressure, and the residue was diluted with chloroform and extracted with saturated aqueous sodium hydrogen carbonate solution. The organic layer was washed with saturated brine, dried over sodium sulfate and filtered, and the filtrate was concentrated under reduced pressure. The obtained residue was purified by preparative thin layer chromatography (eluent: chloroform/ethyl acetate=1/1) to give tert-butyl (3-(3-(N-(3-(3-(2-(dimethylamino)phenyl)ureido)phenyl)sulfamoyl)-4-methoxybenzamido)propyl)carbamate (17.9 mg).

The compounds described in the following Table 16 were also synthesized similarly from amine having the corresponding R and R' groups.

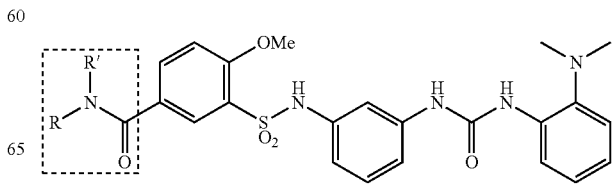

TABLE 16

| Ex. No. | amide substituent structure | ¹H-NMR |
|---|---|---|
| 112 | (structure: tBuO-C(O)-NH-CH₂CH₂CH₂-NH-C(O)-) | 1H NMR (400 MHz, Methanol-d4) δ 8.35 (d, J = 2.3 Hz, 1H), 8.02 (dd, J = 8.0, 1.5 Hz, 1H), 7.99 (dd, J = 8.7, 2.3 Hz, 1H), 7.48 (brs, 1H), 7.24-7.14 (m, 2H), 7.12-7.03 (m, 2H), 7.03-6.95 (m, 2H), 6.75 (brd, J = 7.9 Hz, 1H), 6.55 (brs, 1H), 4.04 (s, 3H), 3.35-3.25 (m, 2H), 3.04 (q, J = 6.5 Hz, 2H), 2.64 (s, 6H), 1.66 (p, J = 6.8 Hz, 2H), 1.41 (s, 9H). |
| 113 | (structure: pyridin-3-ylmethyl-N(Et)-C(O)-) | ¹H NMR (400 MHz, Methanol-d₄) δ 8.50 (brs, 1H), 8.43 (d, J = 5.9 Hz, 1H), 8.02 (d, J = 7.8 Hz, 1H), 7.88 (d, J = 1.9 Hz, 1H), 7.81 (brs, 1H), 7.62 (brs, 1H), 7.44-7.34 (m, 2H), 7.22 (brd, J = 8.8 Hz, 1H), 7.19 (dd, J = 7.8, 1.5 Hz, 1H), 7.12-7.00 (m, 3H), 6.97 (ddd, J = 7.6, 1.6 Hz, 1H), 6.73 (brs, 1H), 4.69 (brs, 2H), 4.04 (s, 3H), 3.17 (brs, 1H), 2.63 (s, 6H), 1.06 (brs, 3H). |
| 114 | (structure: Me₂N-C(O)-) | ¹H NMR (400 MHz, DMSO-d₆) δ 10.11 (brs, 1H), 9.45 (s, 1H), 8.32 (s, 1H), 8.07 (dd, J = 8.1, 1.4 Hz, 1H), 7.77 (d, J = 2.2 Hz, 1H), 7.61 (dd, J = 8.6, 2.2 Hz, 1H), 7.27 (dd, J = 1.8 Hz, 1H), 7.21 (d, J = 8.7 Hz, 1H), 7.17 (dd, J = 7.9, 1.4 Hz, 1H), 7.14 (ddd, J = 8.2, 1.9, 0.9 Hz, 1H), 7.04 (dd, J = 8.0 Hz, 1H), 7.01 (ddd, J = 8.0, 1.5 Hz, 1H), 6.93 (ddd, J = 7.6, 1.6 Hz, 1H), 6.67 (ddd, J = 8.0, 1.9, 0.9 Hz, 1H), 3.94 (s, 3H), 2.86 (brd, J = 33.6 Hz, 6H), 2.60 (s, 6H). |

Production Example (17)

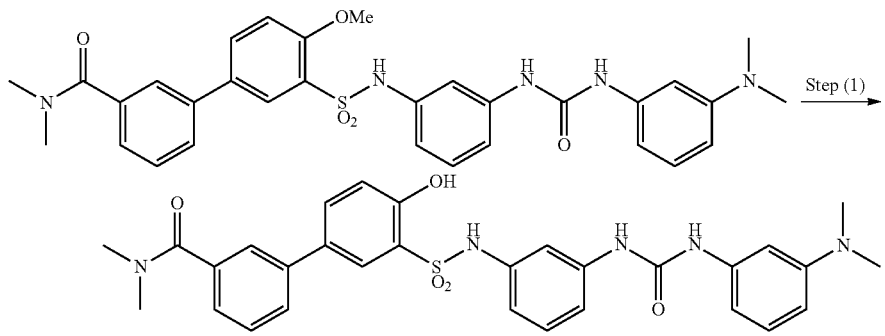

Step (1)

(1) 3'-(N-(3-(3-(3-(dimethylamino)phenyl)ureido)phenyl)sulfamoyl)-4'-hydroxy-N,N-dimethyl-[1,1'-biphenyl]-3-carboxamide

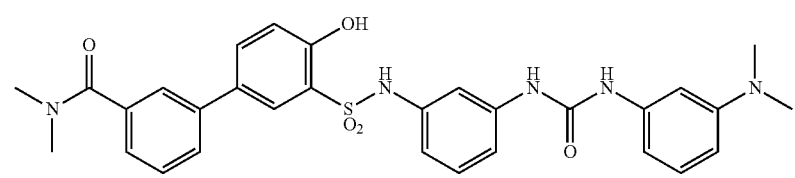

Under an argon atmosphere, to a suspension of 3'-(N-(3-(3-(3-(dimethylamino)phenyl)ureido)phenyl)sulfamoyl)-4'-methoxy-N,N-dimethyl-[1,1'-biphenyl]-3-carboxamide (6.5 mg) in dichloromethane (15.0 mL) was added boron tribromide (100.0 μL) under ice-cooling, and the mixture was stirred at room temperature for 12 hr. The reaction mixture was diluted with 20% methanol-containing chloroform and extracted with saturated aqueous sodium hydrogen carbonate solution under ice-cooling. The organic layer was washed with saturated brine, dried over sodium sulfate and filtered, and the filtrate was concentrated under reduced pressure. The obtained residue was purified by preparative thin layer chromatography (eluent: chloroform/methanol=10/1) to give 3'-(N-(3-(3-(3-(dimethylamino)phenyl)ureido)phenyl)sulfamoyl)-4'-hydroxy-N,N-dimethyl-[1,1'-biphenyl]-3-carboxamide (1.9 mg).

Production Example (18)

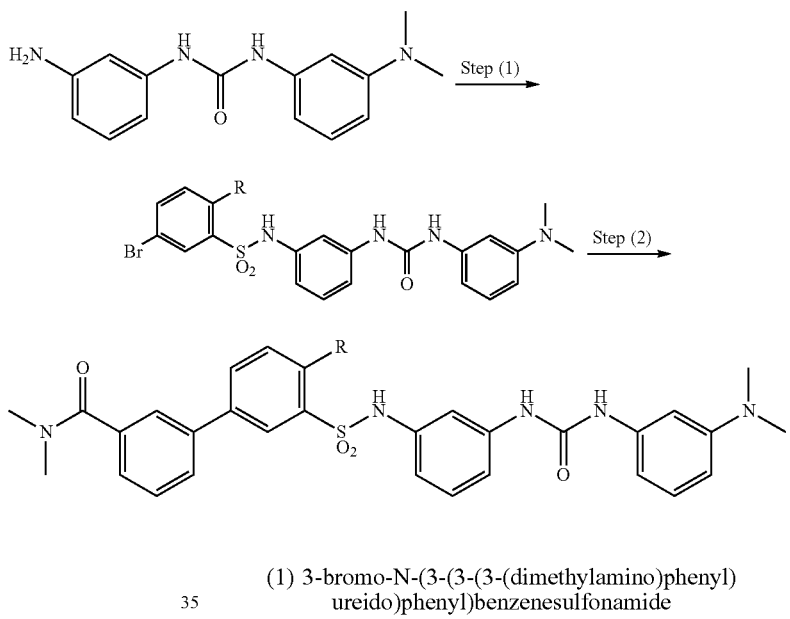

(1) 3-bromo-N-(3-(3-(3-(dimethylamino)phenyl)ureido)phenyl)benzenesulfonamide

Under an argon atmosphere, to a solution of 1-(3-aminophenyl)-3-(3-(dimethylamino)phenyl)urea (348.0 mg) in dehydrated dichloromethane (6.4 mL) were added pyridine (2.6 mL) and 3-bromobenzenesulfonyl chloride (223.0 μL), and the mixture was stirred at room temperature for 45 min. The reaction mixture was concentrated under reduced pressure, and the obtained residue was purified by silica gel column chromatography (eluent: chloroform/ethyl acetate/methanol=5/1/0→1/1/0→10/0/1) to give 3-bromo-N-(3-(3-(3-(dimethylamino)phenyl)ureido)phenyl)benzenesulfonamide (21.8 mg).

(2) 3'-(N-(3-(3-(3-(dimethylamino)phenyl)ureido)phenyl)sulfamoyl)-N,N-dimethyl-[1,1'-biphenyl]-3-carboxamide

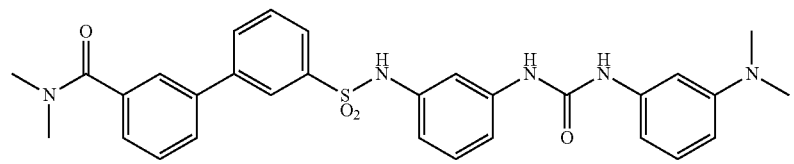

Under an argon atmosphere, to a solution of 3-bromo-N-(3-(3-(3-(dimethylamino)phenyl)ureido)phenyl)benzenesulfonamide (19.6 mg) in DME (3.0 mL) were added 3-(N,N-dimethylaminocarbonyl)phenylboronic acid (13.3 mg), sodium carbonate (8.5 mg), water (0.10 mL) and tetrakis(triphenylphosphine)palladium (2.3 mg), and the mixture was heated under reflux for 3 hr. To the reaction mixture was added saturated aqueous sodium hydrogen carbonate solution, and the mixture was extracted with chloroform. The organic layer was dried over sodium sulfate and filtered, and the filtrate was concentrated. The obtained residue was purified by preparative thin layer chromatography (eluent: chloroform/ethyl acetate=1/1) to give 3'-(N-(3-(3-(3-(dimethylamino)phenyl)ureido)phenyl)sulfamoyl)-N,N-dimethyl-[1,1'-biphenyl]-3-carboxamide (19.7 mg).

The compounds (Examples 117 and 118) described in the following Table 17 were also synthesized similarly from sulfonyl chloride having the corresponding R group.

Production Example (19)

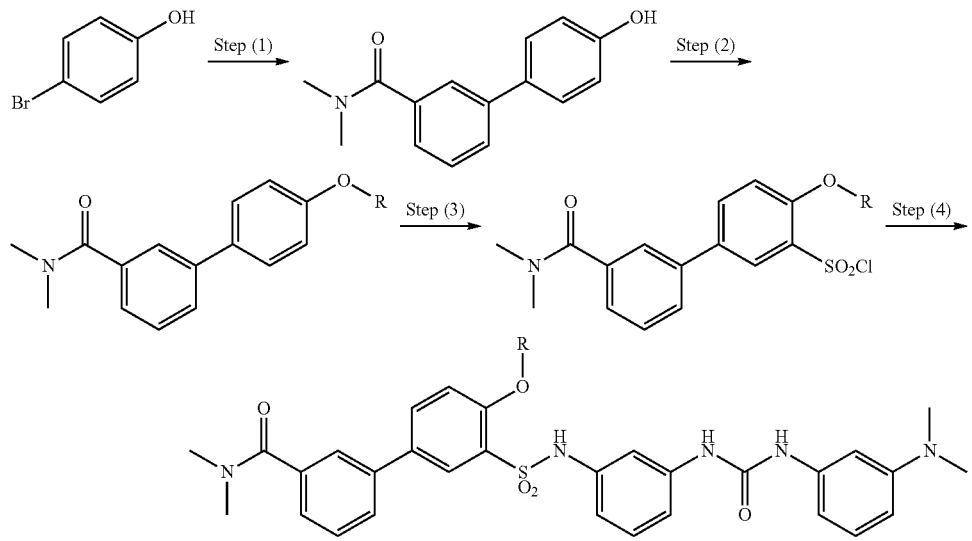

(1) 4'-hydroxy-N,N-dimethyl-[1,1'-biphenyl]-3-carboxamide

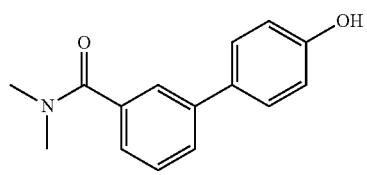 [SMILES: CN(C)C(=O)c1cccc(-c2ccc(O)cc2)c1]

Under an argon atmosphere, to a solution of 4-bromophenol (1.03 g) in DME (25.0 mL) were added 3-(N,N-dimethylaminocarbonyl)phenylboronic acid (1.04 g), sodium carbonate (1.12 g), water (2.50 mL) and tetrakis(triphenylphosphine)palladium (219.3 mg), and the mixture was heated under reflux for 16 hr. To the reaction mixture was added pure water, and the mixture was extracted with chloroform. The organic layer was dried over sodium sulfate and filtered, and the filtrate was concentrated. The obtained residue was purified by silica gel column chromatography (eluent: hexane/ethyl acetate=4/1→1/1) to give 4'-hydroxy-N,N-dimethyl-[1,1'-biphenyl]-3-carboxamide (459.8 mg).

(2) 4'-ethoxy-N,N-dimethyl-[1,1'-biphenyl]-3-carboxamide

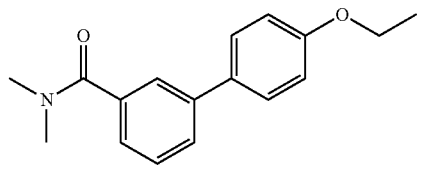 [SMILES: CCOc1ccc(-c2cccc(C(=O)N(C)C)c2)cc1]

Under an argon atmosphere, to a solution of 4'-hydroxy-N,N-dimethyl-[1,1'-biphenyl]-3-carboxamide (60.9 mg) in acetone (5.0 mL) were added potassium carbonate (350.3 mg) and ethyl iodide (44.0 μL), and the mixture was stirred at room temperature for 22 hr. To the reaction mixture was added pure water, and the mixture was extracted with chloroform. The organic layer was dried over sodium sulfate and filtered, and the filtrate was concentrated. The obtained residue was purified by preparative thin layer chromatography (eluent: chloroform/ethyl acetate=1/1) to give 4'-ethoxy-N,N-dimethyl-[1,1'-biphenyl]-3-carboxamide (68.2 mg).

(3) 3'-(dimethylcarbamoyl)-4-ethoxy-[1,1'-biphenyl]-3-sulfonyl chloride

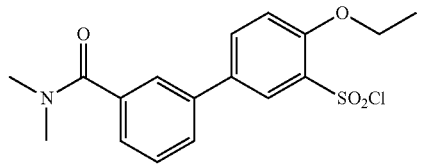 [SMILES: CCOc1ccc(-c2cccc(C(=O)N(C)C)c2)cc1S(=O)(=O)Cl]

Under an argon atmosphere, to chlorosulfonic acid (150.0 μL) was slowly added a solution of 4'-ethoxy-N,N-dimethyl-

[1,1'-biphenyl]-3-carboxamide (61.1 mg) in dichloromethane (2.0 mL), and the mixture was stirred under ice-cooling for 10 min. The reaction mixture was warmed to room temperature and stirred for 1 hr, thionyl chloride (320.0 µL) and DMF (50 µL) were added, and the mixture was stirred at 60° C. for 2 hr. The reaction mixture was allowed to cool, poured into ice, stirred for 20 min, and extracted with chloroform. The organic layer was dried over sodium sulfate and filtered, and the filtrate was concentrated under reduced pressure. The obtained residue was purified by silica gel column chromatography (eluent: ethyl acetate/hexane=1/2) to give 3'-(dimethylcarbamoyl)-4-ethoxy-[1,1'-biphenyl]-3-sulfonyl chloride (79.7 mg).

(4) 3'-(N-(3-(3-(3-(dimethylamino)phenyl)ureido)phenyl)sulfamoyl)-4'-ethoxy-N,N-dimethyl-[1,1'-biphenyl]-3-carboxamide

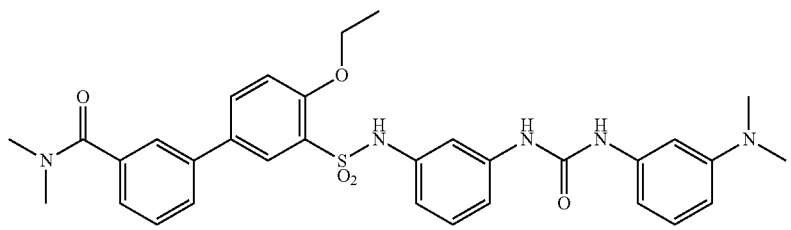

Under an argon atmosphere, to a solution of 1-(3-aminophenyl)-3-(3-(dimethylamino)phenyl)urea TFA salt (9.3 mg) in dehydrated dichloromethane (2.0 mL) were added pyridine (130.0 µL) and 3'-(dimethylcarbamoyl)-4-ethoxy-[1,1'-biphenyl]-3-sulfonyl chloride (14.3 mg), and the mixture was stirred at room temperature overnight. The reaction mixture was concentrated under reduced pressure, and the obtained residue was purified by preparative thin layer chromatography (eluent: chloroform/ammonia-saturated chloroform=40/1) to give 3'-(N-(3-(3-(3-(dimethylamino)phenyl)ureido)phenyl)sulfamoyl)-4'-ethoxy-N,N-dimethyl-[1,1'-biphenyl]-3-carboxamide (15.4 mg).

The compound of Example 120 described in the following Table 17 was also synthesized similarly from alkylhalide having the corresponding R group.

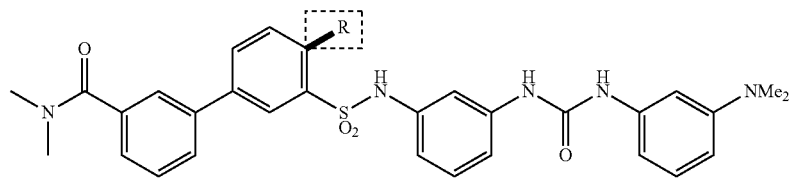

TABLE 17

| Ex. No. | R moiety structure | $^1$H-NMR |
|---|---|---|
| 115 | ⟋OH | 1H NMR (400 MHz, Chloroform-d) δ 7.76 (s, 1H), 7.60 (d, J = 8.8 Hz, 1H), 7.58 (s, 1H), 7.40-7.38 (m, 3H), 7.32-7.24 (m, 4H), 7.06-6.97 (m, 3H), 6.91-6.87 (m, 2H), 6.83 (d, J = 7.6 Hz, 1H), 6.75 (s, 1H), 6.48 (d, J = 7.6 Hz, 1H), 6.39 (dd, J = 8.0, 2.0 Hz, 1H), 3.14 (s, 3H), 2.99 (s, 3H), 2.83 (s, 6H). |
| 116 | ⟋H | 1H NMR (400 MHz, Chloroform-d) δ 7.90-7.83 (m, 2H), 7.75 (brd, J = 8.0 Hz, 1H), 7.60 (brd, J = 7.9 Hz, 1H), 7.53-7.47 (m, 3H), 7.41 (dd, J = 7.8 Hz, 1H), 7.38-7.33 (m, 2H), 7.12-7.03 (m, 2H), 6.99 (brs, J = 8.1 Hz, 1H), 6.86 (brd, J = 8.2 Hz, 1H), 6.73 (brs, 1H), 6.50 (dd, J = 7.7, 1.4 Hz, 1H), 6.45 (dd, J = 8.3, 2.3 Hz, 1H), 3.15 (s, 3H), 3.00 (s, 3H), 2.87 (s, 6H). |

TABLE 17-continued

| Ex. No. | R moiety structure | 1H-NMR |
|---|---|---|
| 117 | Me | 1H NMR (400 MHz, Chloroform-d) δ 8.76 (brs, 1H), 8.15 (s, 1H), 7.93 (s, 1H), 7.61-7.45 (m, 4H), 7.45-7.30 (m, 3H), 7.24-7.20 (m, 1H), 7.07 (dd, J = 8.1 Hz, 1H), 6.96 (dd, J = 8.1 Hz, 1H), 6.84 (d, J = 7.9 Hz, 1H), 6.77 (d, J = 7.4 Hz, 1H), 6.71 (s, 1H), 6.51 (d, J = 7.7 Hz, 1H), 6.43 (dd, J = 8.3, 2.1 Hz, 1H), 3.13 (s, 3H), 2.99 (s, 3H), 2.84 (s, 6H), 2.62 (s, 3H). |
| 118 | Cl | 1H NMR (400 MHz, DMSO-d6) δ 10.70 (s, 1H), 8.65 (s, 1H), 8.38 (s, 1H), 8.26 (d, J = 2.2 Hz, 1H), 7.94 (dd, J = 8.4, 2.3 Hz, 1H), 7.79 (d, J = 7.7 Hz, 1H), 7.72 (d, J = 8.3 Hz, 1H), 7.65 (s, 1H), 7.51-7.40 (m, 3H), 7.14-6.99 (m, 3H), 6.82-6.78 (m, 1H), 6.72 (ddd, J = 15.8, 8.0, 1.7 Hz, 2H), 6.36 (dd, J = 8.4, 2.3 Hz, 1H), 2.98 (s, 3H), 2.89 (s, 3H), 2.85 (s, 6H). |
| 119 | O | 1H NMR (400 MHz, DMSO-d6) δ 9.97 (s, 1H), 8.61 (s, 1H), 8.37 (s, 1H), 8.32 (s, 1H), 8.04 (d, J = 2.4 Hz, 1H), 7.88 (dd, J = 8.7, 2.4 Hz, 1H), 7.71 (ddd, J = 7.8, 1.4 Hz, 1H), 7.58 (dd, J = 1.5 Hz, 1H), 7.46 (dd, J = 7.7 Hz, 1H), 7.39-7.32 (m, 2H), 7.27 (d, J = 8.8 Hz, 1H), 7.10-6.99 (m, 3H), 6.83 (t, J = 2.1 Hz, 1H), 6.72 (ddd, J = 7.3, 2.0 Hz, 1H), 6.69 (dd, J = 8.0, 1.2 Hz, 1H), 6.35 (dd, J = 8.2, 2.3 Hz, 1H), 4.25 (q, J = 7.0 Hz, 2H), 2.98 (s, 3H), 2.89 (s, 3H), 2.86 (s, 6H), 1.38 (t, J = 7.0 Hz, 3H). |
| 120 | O | 1H NMR (400 MHz, Chloroform-d) δ 7.98 (d, J = 2.3 Hz, 1H), 7.68 (d, J = 4.8 Hz, 2H), 7.55-7.46 (m, 2H), 7.42 (d, J = 7.6 Hz, 1H), 7.36-7.26 (m, 4H), 7.00 (dd, J = 8.1 Hz, 1H), 6.92 (d, J = 8.7 Hz, 1H), 6.88 (dd, J = 8.1 Hz, 1H), 6.79-6.67 (m, 3H), 6.47 (d, J = 7.8 Hz, 1H), 6.35 (dd, J = 8.3, 2.1 Hz, 1H), 4.10 (t, J = 6.7 Hz, 2H), 3.13 (s, 3H), 2.97 (s, 3H), 2.80 (s, 6H), 1.92 (h, J = 7.2 Hz, 2H), 1.06 (t, J = 7.4 Hz, 3H). |

Production Example (20)

(1) 2-methoxy-3-nitrobenzoic acid

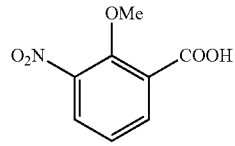 [SMILES: COc1c(C(=O)O)cccc1[N+](=O)[O-]]

(i) Under an argon atmosphere, to a solution of 2-hydroxy-3-nitrobenzoic acid (1.0 g) in acetone (20.0 mL) were added potassium carbonate (3.70 g) and methyl iodide (1.70 mL), and the mixture was stirred at room temperature overnight. To the reaction mixture was added pure water, and the mixture was extracted with ethyl acetate. The organic layer was dried over sodium sulfate and filtered, and the filtrate was concentrated and dried to give methyl 2-methoxy-3-nitrobenzoate (1.10 g). The present compound was used for the next reaction without further purification.

(ii) To a solution of methyl 2-methoxy-3-nitrobenzoate (1.10 g) in ethanol (20.0 mL) was added 1N aqueous sodium hydroxide solution (20.0 mL), and the mixture was stirred at room temperature overnight. To the reaction mixture was added 1N aqueous hydrochloric acid solution, and the mixture was extracted with ethyl acetate. The organic layer was washed with saturated brine, dried over magnesium sulfate and filtered, and the filtrate was concentrated under reduced pressure to give 2-methoxy-3-nitrobenzoic acid (980 mg). The present compound was used for the next reaction without further purification.

(2) 1-(3-amino-2-methoxyphenyl)-3-(3-(dimethylamino)phenyl)urea

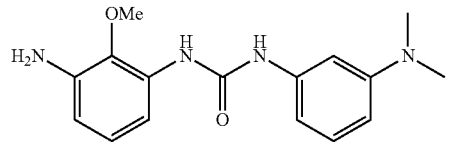 [SMILES: COc1c(N)cccc1NC(=O)Nc1cccc(N(C)C)c1]

(i) Under an argon atmosphere, to a solution of 2-methoxy-3-nitrobenzoic acid (100.0 mg) in toluene (5.0 mL) were

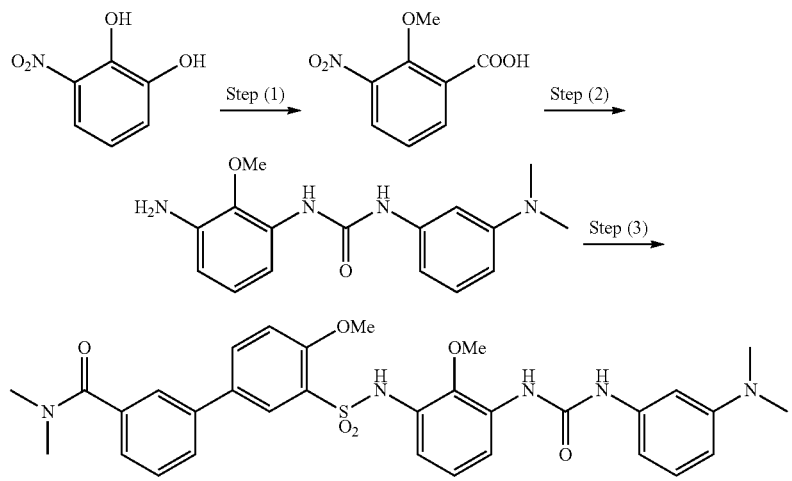

added TEA (140.0 μL) and DPPA (216.0 μL), and the mixture was stirred at 110° C. under reflux for 2 hr. To the reaction mixture was added N,N-dimethyl-1,3-phenylenediamine (106.0 mg), and the mixture was further stirred under reflux for 2 hr. The reaction mixture was allowed to cool, concentrated under reduced pressure, and the residue was purified by silica gel column chromatography (eluent: hexane/ethyl acetate=9/1→1/1→chloroform/methanol=9/1) to give 1-(3-nitro-2-methoxyphenyl)-3-(3-(dimethylamino)phenyl)urea (98.5 mg).

(ii) To a solution of 1-(3-nitro-2-methoxyphenyl)-3-(3-(dimethylamino)phenyl)urea (98.5 mg) in methanol (10.0 mL) was added 5% palladium-activated carbon (10.30 mg), and the mixture was stirred under a hydrogen atmosphere at room temperature overnight. The reaction mixture was filtered through celite and the filtrate was concentrated. The obtained residue was purified by silica gel column chromatography (eluent: hexane/ethyl acetate=9/1→1/4) to give 1-(3-amino-2-methoxyphenyl)-3-(3-(dimethylamino)phenyl)urea (80.5 mg).

(3) 3'-(N-(3-(3-(3-(dimethylamino)phenyl)ureido)-2-methoxyphenyl)sulfamoyl)-4'-methoxy-N,N-dimethyl-[1,1'-biphenyl]-3-carboxamide

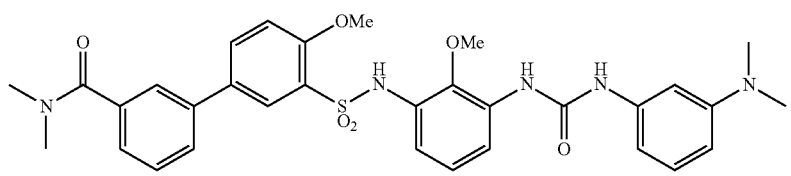

Under an argon atmosphere, to a solution of 1-(3-amino-2-methoxyphenyl)-3-(3-(dimethylamino)phenyl)urea (18.0 mg) in dichloromethane (1.0 mL) were added pyridine (100.0 μL) and 3'-(dimethylcarbamoyl)-4-methoxy-[1,1'-biphenyl]-3-sulfonyl chloride (16.0 mg), and the mixture was stirred at room temperature overnight. The reaction mixture was concentrated under reduced pressure, and the obtained residue was purified by silica gel column chromatography (eluent: chloroform/methanol=49/1→4/1) to give 3'-(N-(3-(3-(3-(dimethylamino)phenyl)ureido)-2-methoxyphenyl)sulfamoyl)-4'-methoxy-N,N-dimethyl-[1,1'-biphenyl]-3-carboxamide (26.8 mg).

Example 121, Example 122 and Example 124 were respectively synthesized by a method similar to Production Example (4) using the corresponding tert-butyl (2-aminophenyl)carbamate, tert-butyl (4-aminophenyl)carbamate and tert-butyl (6-aminopyridin-2-yl)carbamate.

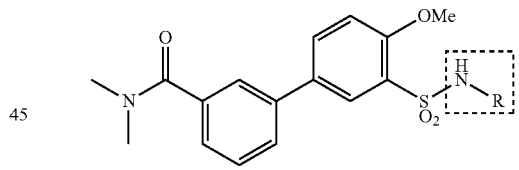

TABLE 18

| Ex. No. | R moiety structure | $^1$H-NMR |
|---|---|---|
| 121 | ![structure] | 1H NMR (400 MHz, Chloroform-d) δ 8.28 (s, 0.7H), 7.97-7.93 (m, 1H), 7.79 (s, 0.7H), 7.73 (dd, J = 8.6, 2.4 Hz, 0.3H), 7.67 (s, 0.7H), 7.58 (dd, J = 8.6, 2.4 Hz, 0.7H), 7.55 (s, 0.7H), 7.53-7.47 (m, 0.6H), 7.47-7.40 (m, 0.7H), 7.41-7.34 (m, 1H), 7.33-7.29 (m, 1H), 7.23 (d, J = 1.7 Hz, 0.3H), 7.18 (dd, J = 7.8, 1.4 Hz, 0.7H), 7.15 (d, J = 8.7 Hz, 0.3H), 7.05 (dd, J = 8.1 Hz, 0.7H), 7.00-6.88 (m, 3.3H), 6.69 (dd, J = 8.0, 1.2 Hz, 0.3H), 6.64 (brs, 0.3H), 6.57 (dd, J = 7.9, 1.4 Hz, 0.3H), 6.53-6.37 (m, 1.7H), 4.10 (s, 0.9H), 3.89 (s, 2.1H), 3.15 (s, 2.1H), 3.11 (s, 0.9H), 3.01 (s, 2.1H), 2.96 (s, 0.9H), 2.87 (s, 6H). |

| Ex. No. | R moiety structure | ¹H-NMR |
|---|---|---|
| 122 | | 1H NMR (400 MHz, DMSO-d6) δ 9.82 (brs, 1H), 8.52-8.42 (m, 2H), 7.94-7.86 (m, 2H), 7.65 (d, J = 8.0 Hz, 1H), 7.56 (s, 1H), 7.50 (dd, J = 7.7 Hz, 1H), 7.36 (d, J = 7.8 Hz, 1H), 7.32-7.20 (m, 4H), 7.07-6.97 (m, 2H), 6.89-6.81 (m, 1H), 6.64 (d, J = 8.1 Hz, 1H), 6.35-6.31 (m, 1H), 3.96 (s, 3H), 2.99 (s, 3H), 2.91 (s, 3H), 2.84 (s, 6H). |
| 123 | | 1H NMR (400 MHz, Chloroform-d) δ 8.11 (d, J = 2.4 Hz, 1H), 7.77 (dd, J = 8.3, 1.4 Hz, 1H), 7.71 (brs, 1H), 7.67 (dd, J = 1.6 Hz, 1H), 7.61 (dd, J = 8.7, 2.4 Hz, 1H), 7.56 (ddd, J = 8.0, 1.7, 1.3 Hz, 1H), 7.54-7.49 (m, 2H), 7.44 (t, J = 7.7 Hz, 1H), 7.34 (ddd, J = 7.6, 1.3 Hz, 1H), 7.20 (dd, J = 8.3, 1.4 Hz, 1H), 7.14 (dd, J = 8.1 Hz, 1H), 6.97-6.88 (m, 3H), 6.57 (dd, J = 7.6, 1.5 Hz, 1H), 6.47 (dd, J = 8.4, 2.4 Hz, 1H), 3.86 (s, 3H), 3H), 3.70 (s, 3H), 3.20 (s, 3H), 3.05 (s, 3H), 2.92 (s, 6H). |
| 124 | | 1H NMR (400 MHz, DMSO-d6) δ 9.33 (brs, 1H), 8.01 (d, J = 3.1 Hz, 1H), 7.89 (dd, J = 8.7, 2.2 Hz, 1H), 7.61-7.48 (m, 2H), 7.38-7.27 (m, 3H), 7.23 (d, J = 8.8 Hz, 1H), 7.15-7.00 (m, 3H), 6.70 (brs, 1H), 6.57 (d, J = 8.0 Hz, 1H), 6.44 (dd, J = 8.7, 2.7 Hz, 1H), 3.86 (s, 3H), 2.98 (s, 3H), 2.87 (d, J = 7.5 Hz, 9H). |

Production Example (21)

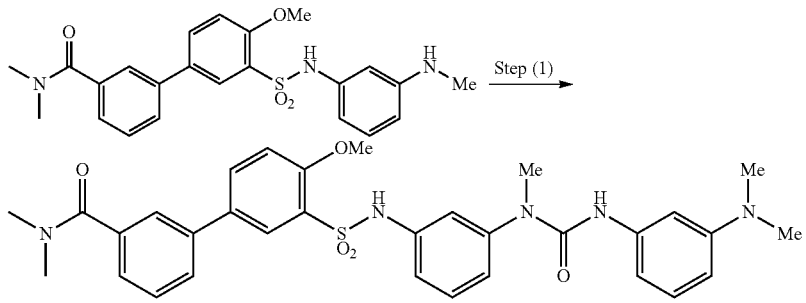

(1) 3'-(N-(3-(3-(3-(dimethylamino)phenyl)-1-methylureido)phenyl)sulfamoyl)-4'-methoxy-N,N-dimethyl-[1,1'-biphenyl]-3-carboxamide

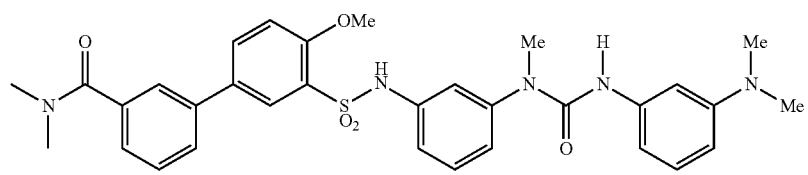 [SMILES: COc1ccc(-c2cccc(C(=O)N(C)C)c2)cc1S(=O)(=O)Nc1cccc(N(C)C(=O)Nc2cccc(N(C)C)c2)c1]

Under an argon atmosphere, to a solution of 3-dimethylaminobenzoic acid (34.0 mg) in benzene (3.0 mL) were added TEA (57.0 μL) and DPPA (88.0 μL), and the mixture was stirred at 110° C. under reflux for 30 min. To the reaction mixture was added 4'-methoxy-N,N-dimethyl-3'-(N-(3-(methylamino)phenyl)sulfamoyl)-[1,1'-biphenyl]-3-carboxamide (45.0 mg), and the mixture was stirred under reflux for 12 hr. The reaction mixture was allowed to cool, saturated aqueous sodium hydrogen carbonate solution was added and the mixture was extracted with chloroform. The organic layer was washed with saturated brine, dried over sodium sulfate and filtered, and the filtrate was concentrated under reduced pressure. The obtained residue was purified by preparative thin layer chromatography (eluent: chloroform/methanol=30/1) to give 3'-(N-(3-(3-(3-(dimethylamino)phenyl)-1-methylureido)phenyl)sulfamoyl)-4'-methoxy-N,N-dimethyl-[1,1'-biphenyl]-3-carboxamide (14.0 mg).

Production Example (22)

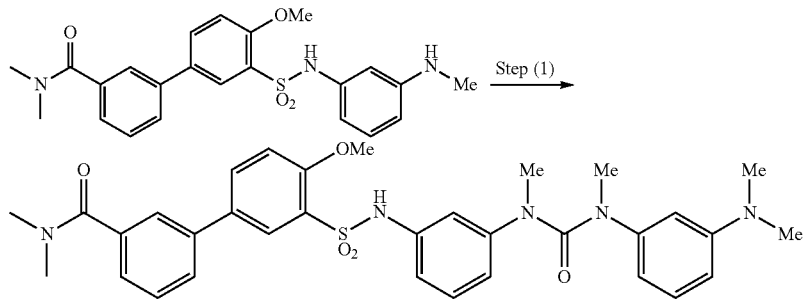

(1) 3'-(N-(3-(3-(3-(dimethylamino)phenyl)-1,3-dimethylureido)phenyl)sulfamoyl)-4'-methoxy-N,N-dimethyl-[1,1'-biphenyl]-3-carboxamide

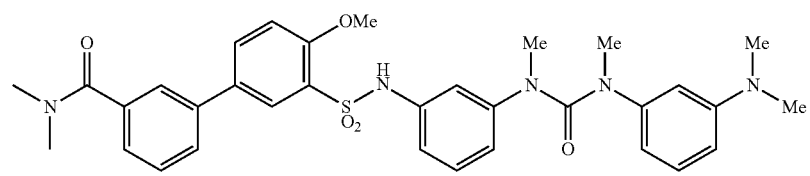 [SMILES: COc1ccc(-c2cccc(C(=O)N(C)C)c2)cc1S(=O)(=O)Nc1cccc(N(C)C(=O)N(C)c2cccc(N(C)C)c2)c1]

Under an argon atmosphere, to a solution of trimethylphenylenediamine (35.0 mg) in 1,2-dichloroethane (2.0 mL) were added DIPEA (52.0 μL) and triphosgene (22.0 mg), and the mixture was stirred at room temperature for 30 min. To the reaction mixture was added a solution of 4'-methoxy-N,N-dimethyl-3'-(N-(3-(methylamino)phenyl)sulfamoyl)-[1,1'-biphenyl]-3-carboxamide (33.0 mg) in 1,2-dichloroethane (2.0 mL), and the mixture was stirred with heating under reflux for 5 hr. The reaction mixture was allowed to cool, saturated aqueous sodium hydrogen carbonate solution was added and the mixture was extracted with chloroform. The organic layer was washed with saturated brine, dried over sodium sulfate and filtered, and the filtrate was concentrated under reduced pressure. The obtained residue was purified by preparative thin layer chromatography (eluent: chloroform/methanol=20/1) to give 3'-(N-(3-(3-(3-(dimethylamino)phenyl)-1,3-dimethylureido)phenyl)sulfamoyl)-4'-methoxy-N,N-dimethyl-[1,1'-biphenyl]-3-carboxamide (38.1 mg).

Production Example (23)

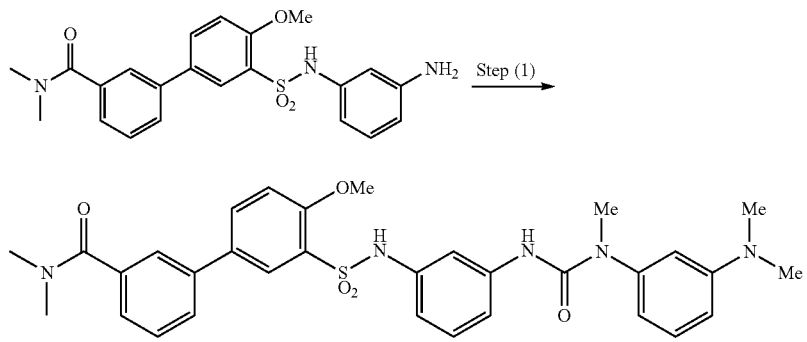

(1) 3'-(N-(3-(3-(3-(dimethylamino)phenyl)-3-methylureido)phenyl)sulfamoyl)-4'-methoxy-N,N-dimethyl-[1,1'-biphenyl]-3-carboxamide

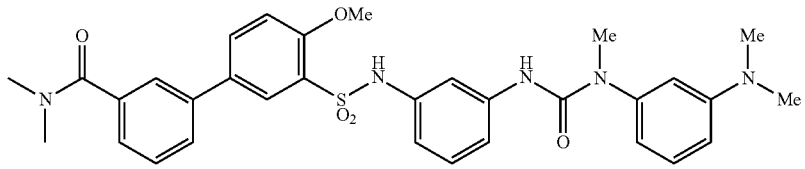 [SMILES: COc1ccc(-c2cccc(C(=O)N(C)C)c2)cc1S(=O)(=O)Nc1cccc(NC(=O)N(C)c2cccc(N(C)C)c2)c1]

Under an argon atmosphere, to a solution of triphosgene (24.0 mg) in 1,2-dichloroethane (2.0 mL) was added a solution of DIPEA (52.0 μL) and trimethylphenylenediamine (39.0 mg) in 1,2-dichloroethane (1.0 mL), and the mixture was stirred at room temperature for 30 min. To the reaction mixture was added a solution of 3'-(N-(3-aminophenyl)sulfamoyl)-4'-methoxy-N,N-dimethyl-[1,1'-biphenyl]-3-carboxamide hydrochloride (38.0 mg) in 1,2-dichloroethane (2.0 mL)/DIPEA (29.0 μL), and the mixture was stirred with heating under reflux for 7 hr. The reaction mixture was allowed to cool, saturated aqueous sodium hydrogen carbonate solution was added and the mixture was extracted with chloroform. The organic layer was washed with saturated brine, dried over sodium sulfate and filtered, and the filtrate was concentrated under reduced pressure. The obtained residue was purified by preparative thin layer chromatography (eluent: chloroform/methanol=20/1) to give 3'-(N-(3-(3-(3-(dimethylamino)phenyl)-3-methylureido)phenyl)sulfamoyl)-4'-methoxy-N,N-dimethyl-[1,1'-biphenyl]-3-carboxamide (25.2 mg).

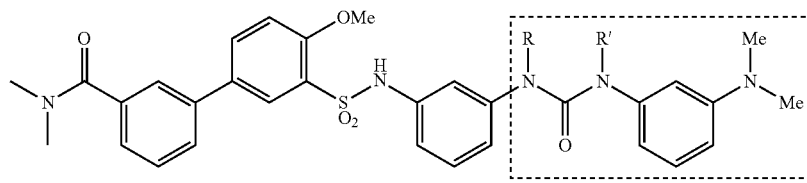

TABLE 19

| Ex. No. | urea moiety structure | $^1$H-NMR |
|---|---|---|
| 125 | Me, H, Me (N-C(O)-N-Ar-N(Me)-Ar-NMe$_2$) | 1H NMR (400 MHz, Chloroform-d) δ 8.07 (d, J = 2.4 Hz, 1H), 7.68 (dd, J = 8.6, 2.4 Hz, 1H), 7.55-7.53 (m, 1H), 7.48 (ddd, J = 7.7, 1.6 Hz, 1H), 7.42 (ddd, J = 7.6, 0.5 Hz, 1H), 7.38-7.30 (m, 2H), 7.16 (ddd, J = 8.1, 2.0, 1.1 Hz, 2H), 7.07-6.96 (m, 4H), 6.92 (dd, J = 2.2 Hz, 1H), 6.37 (ddd, J = 8.3, 2.5, 0.8 Hz, 1H), 6.22 (ddd, J = 7.9, 2.0, 0.8 Hz, 1H), 6.03 (s, 1H), 4.03 (s, 3H), 3.22 (s, 3H), 3.13 (s, 3H), 2.98 (s, 3H), 2.90 (s, 6H). |
| 126 | Me, Me, Me | 1H NMR (400 MHz, Chloroform-d) δ 8.06 (dd, J = 2.3, 0.8 Hz, 1H), 7.72 (ddd, J = 8.6, 2.4, 0.8 Hz, 1H), 7.56-7.49 (m, 2H), 7.43 (dd, J = 7.6 Hz, 1H), 7.38-7.33 (m, 1H), 7.17 (s, 1H), 7.07 (d, J = 8.7 Hz, 1H), 6.87 (dd, J = 8.2 Hz, 1H), 6.80-6.74 (m, 1H), 6.71 (dd, J = 8.1 Hz, 1H), 6.64 (brs, 1H), 6.46 (dddd, J = 8.0, 1.0 Hz, 1H), 6.27 (dd, J = 8.4, 2.5 Hz, 1H), 6.10 (brs, 1H), 5.89-5.82 (m, 1H), 4.05 (s, 3H), 3.12 (s, 3H), 3.07 (s, 3H), 3.01 (s, 3H), 2.96 (s, 3H), 2.77 (s, 6H). |
| 127 | H, Me, Me | 1H NMR (400 MHz, Chloroform-d) δ 8.01 (d, J = 2.4 Hz, 1H), 7.67 (dd, J = 8.6, 2.4 Hz, 1H), 7.55-7.49 (m, 2H), 7.41 (dd, J = 8.3, 7.6 Hz, 1H), 7.33 (ddd, J = 7.6, 1.4 Hz, 1H), 7.29-7.21 (m, 2H), 7.15 (s, 1H), 7.04 (d, J = 8.7 Hz, 1H), 7.00 (dd, J = 8.1 Hz, 1H), 6.82 (ddd, J = 8.1, 2.1, 0.9 Hz, 1H), 6.76 (ddd, J = 8.1, 2.1, 0.9 Hz, 1H), 6.66 (ddd, J = 8.5, 2.5, 0.8 Hz, 1H), 6.54 (ddd, J = 7.6, 1.9, 0.8 Hz, 1H), 6.52 (dd, J = 2.2 Hz, 1H), 6.39 (s, 1H), 4.05 (s, 3H), 3.26 (s, 3H), 3.11 (s, 3H), 2.97 (s, 3H), 2.94 (s, 6H). |

Production Example (24)

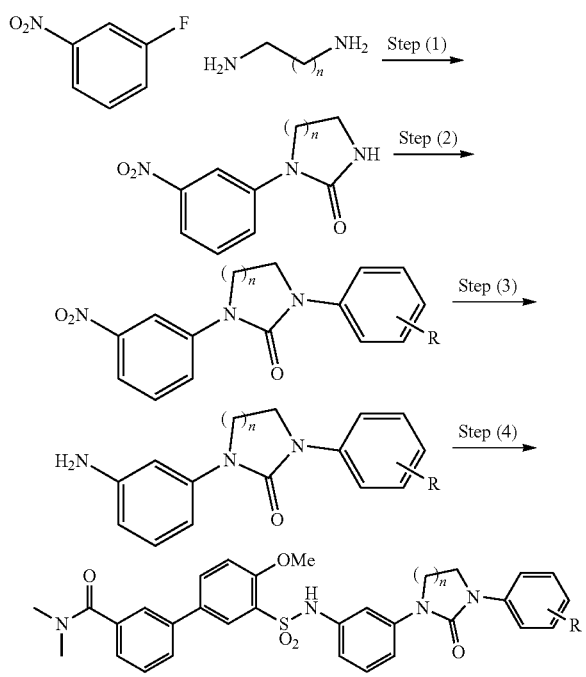

(1) 1-(3-nitrophenyl)imidazolidin-2-one

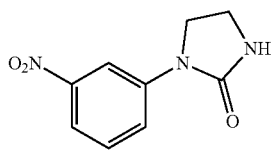 [SMILES: O=C1NCCN1c1cccc([N+](=O)[O-])c1]

Under an argon atmosphere, to 3-fluoronitrobenzene (2.20 mL) was added ethylenediamine (2.20 mL), and the mixture was stirred at 100° C. for 16 hr. To the reaction mixture was added water, and the mixture was extracted with chloroform. The organic layer was dried over sodium sulfate and filtered, and the filtrate was concentrated. To a solution of the obtained residue in dry THF (100 mL) was added carbonyldiimidazole (7.56 g) under ice-cooling, and the mixture was stirred for 1 hr. To the reaction mixture was added saturated brine, and the mixture was extracted with ethyl acetate. The organic layer was dried over magnesium sulfate and filtered, and the filtrate was concentrated. The obtained residue was purified by silica gel column chromatography (eluent: methanol/chloroform=5/95) and then recrystallized (ethyl acetate/chloroform=1:1) to give 1-(3-nitrophenyl)imidazolidin-2-one (5.31 g).

(2) 1-(3-nitrophenyl)-3-phenylimidazolidin-2-one

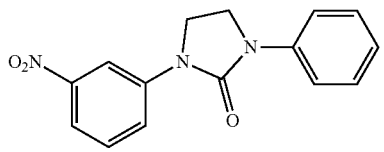

Under an argon atmosphere, to a solution of 1-(3-nitrophenyl)imidazolidin-2-one (200 mg) in anhydrous toluene (1.6 mL) were added copper iodide (18.3 mg), N,N'-dimethylcyclohexane-1,2-diamine (31.0 μL), anhydrous potassium carbonate (333 mg) and bromobenzene (110 μL), and the mixture was stirred with heating under reflux for 22 hr. The reaction mixture was allowed to cool, chloroform was added, and the mixture was filtered through celite and washed with chloroform. The filtrate was washed with distilled water and saturated brine, dried over magnesium sulfate and filtered, and the filtrate was concentrated under reduced pressure. The obtained residue was purified by silica gel column chromatography (eluent: chloroform) to give 1-(3-nitrophenyl)-3-phenylimidazolidin-2-one (258 mg).

(3) 1-(3-aminophenyl)-3-phenylimidazolidin-2-one

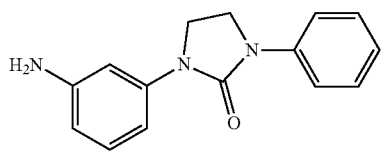 [SMILES: O=C1N(c2ccccc2)CCN1c1cccc([N+](=O)[O-])c1]

To a solution of 1-(3-nitrophenyl)-3-phenylimidazolidin-2-one (237 mg) in ethanol (30.0 mL) was added 5% palladium-activated carbon (89.0 mg), and the mixture was stirred under a hydrogen atmosphere at 50° C. for 2 hr. The reaction mixture was allowed to cool and filtered through celite, and the filtrate was concentrated. The obtained residue was purified by silica gel column chromatography (eluent: methanol/chloroform=2/98) to give 1-(3-aminophenyl)-3-phenylimidazolidin-2-one (178 mg).

(4) 4'-methoxy-N,N-dimethyl-3'-(N-(3-(2-oxo-3-phenylimidazolidin-1-yl)phenyl)sulfamoyl)-[1,1'-biphenyl]-3-carboxamide

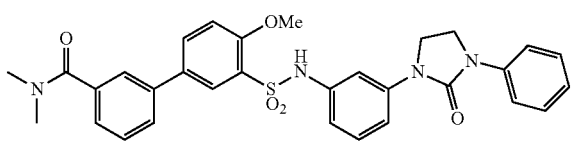 [SMILES: COc1ccc(-c2cccc(C(=O)N(C)C)c2)cc1S(=O)(=O)Nc1cccc(N2CCN(c3ccccc3)C2=O)c1]

Under an argon atmosphere, to a solution of 1-(3-aminophenyl)-3-phenylimidazolidin-2-one (30.0 mg) in anhydrous pyridine (1.0 mL) was added 3'-(dimethylcarbamoyl)-4-methoxy-[1,1'-biphenyl]-3-sulfonyl chloride (43.0 mg), and the mixture was stirred with heating under reflux for 30 min. The reaction mixture was allowed to cool, distilled water was added and the mixture was extracted with chloroform. The organic layer was washed with saturated brine, dried over magnesium sulfate and filtered, and the filtrate was concentrated under reduced pressure. The obtained residue was dissolved in chloroform, hexane was added under ice-cooling, and the resulting precipitate was collected by filtration to give 4'-methoxy-N,N-dimethyl-3'-(N-(3-(2-oxo-3-phenylimidazolidin-1-yl)phenyl)sulfamoyl)-[1,1'-biphenyl]-3-carboxamide (53.5 mg).

The compounds (Examples 129-136) described in the following Table 20 were also synthesized similarly from diamine having the corresponding carbon number (n=1-3) and bromobenzene having R group.

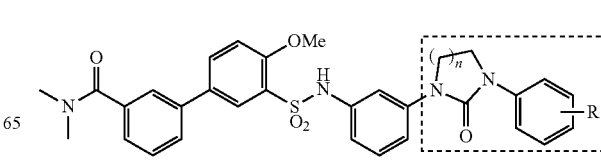

TABLE 20

| Ex. No. | urea moiety structure | ¹H-NMR |
|---|---|---|
| 128 | 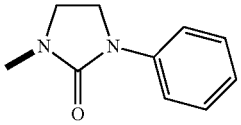 | 1H NMR (400 MHz, Chloroform-d) δ 8.04 (d, J = 2.3 Hz, 1H), 7.69 (dd, J = 8.6, 2.3 Hz, 1H), 7.62-7.47 (m, 5H), 7.40 (dd, J = 7.6 Hz, 1H), 7.38-7.30 (m, 3H), 7.19 (dd, J = 7.5 Hz, 2H), 7.09 (dd, J = 7.6 Hz, 2H), 6.98 (s, 1H), 6.85 (ddd, J = 6.8, 1.7 Hz, 1H), 4.11 (s, 3H), 3.98-3.82 (m, 4H), 3.10 (s, 3H), 2.97 (s, 3H). |
| 129 | 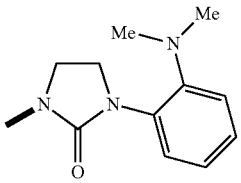 | 1H NMR (400 MHz, DMSO-d6) δ 10.11 (brs, 1H), 8.02 (s, 1H), 7.89 (d, J = 8.7 Hz, 1H), 7.70 (d, J = 7.2 Hz, 1H), 7.60 (s, 1H), 7.56 (s, 1H), 7.45-7.31 (m, 2H), 7.26 (d, J = 8.6 Hz, 1H), 7.19 (d, J = 7.9 Hz, 2H), 7.17-7.07 (m, 2H), 7.03 (d, J = 8.3 Hz, 1H), 6.96 (dd, J = 7.5 Hz, 1H), 6.79 (d, J = 7.2 Hz, 1H), 3.94 (s, 3H), 3.88-3.78 (m, 2H), 3.78-3.68 (m, 2H), 2.98 (s, 3H), 2.90 (s, 3H), 2.62 (s, 6H). |
| 130 | 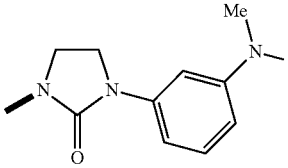 | 1H NMR (400 MHz, DMSO-d6) δ 10.12 (s, 1H), 8.02 (d, J = 2.2 Hz, 1H), 7.90 (dd, J = 8.6, 2.2 Hz, 1H), 7.70 (d, J = 7.8 Hz, 1H), 7.59 (d, J = 14.3 Hz, 2H), 7.45 (dd, J = 7.7 Hz, 1H), 7.35 (d, J = 7.6 Hz, 1H), 7.27 (d, J = 8.7 Hz, 1H), 7.19-7.09 (m, 3H), 7.00 (brs, 1H), 6.83 (d, J = 7.8 Hz, 2H), 6.46 (dd, J = 8.4, 2.2 Hz, 1H), 3.96 (s, 3H), 3.89 (dd, J = 9.6, 6.2 Hz, 2H), 3.79 (dd, J = 9.0, 5.8 Hz, 2H), 2.98 (s, 3H), 2.90 (s, 3H), 2.89 (s, 6H). |
| 131 | 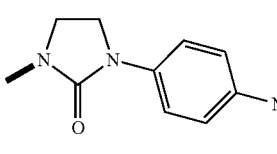 | 1H NMR (400 MHz, DMSO-d6) δ 10.11 (s, 1H), 8.04 (s, 1H), 7.90 (d, J = 8.6 Hz, 1H), 7.71 (d, J = 7.6 Hz, 1H), 7.67-7.52 (m, 2H), 7.45 (dd, J = 7.6 Hz, 1H), 7.40-7.29 (m, 3H), 7.27 (d, J = 8.6 Hz, 1H), 7.14 (dd, J = 8.0 Hz, 1H), 7.06 (d, J = 8.0 Hz, 1H), 6.79 (d, J = 7.7 Hz, 1H), 6.77-6.66 (m, 2H), 3.95 (s, 3H), 3.88-3.65 (m, 4H), 2.98 (s, 3H), 2.90 (s, 3H), 2.87 (s, 6H). |
| 132 | 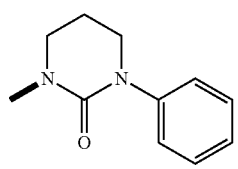 | ¹H NMR (400 MHz, Chloroform-d) δ 8.05 (d, J = 2.0 Hz, 1H), 7.74 (s, 1H), 7.64 (dd, J = 8.6, 2.0 Hz, 1H), 7.55-7.47 (m, 2H), 7.39 (dd, J = 7.5 Hz, 1H), 7.36-7.23 (m, 5H), 7.18-7.10 (m, 2H), 7.08-7.02 (m, 2H), 7.00 (d, J = 8.7 Hz, 1H), 6.81 (brd, J = 6.4 Hz, 1H), 3.88 (s, 3H), 3.74 (t, J = 5.8 Hz, 2H), 3.65 (t, J = 5.8 Hz, 2H), 3.11 (s, 3H), 2.97 (s, 3H), 2.16 (p, J = 5.8 Hz, 2H). |
| 133 | 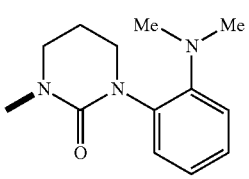 | 1H NMR (400 MHz, Chloroform-d) δ 8.04 (d, J = 2.4 Hz, 1H), 7.67 (ddd, J = 8.6, 2.2 Hz, 1H), 7.55-7.49 (m, 2H), 7.38 (dd, J = 8.0 Hz, 1H), 7.35-7.31 (m, 1H), 7.20-7.06 (m, 5H), 7.03 (dd, J = 8.7, 2.8 Hz, 1H), 6.98 (d, J = 8.4 Hz, 1H), 6.90 (dd, J = 7.5 Hz, 1H), 6.84-6.77 (m, 1H), 3.98 (s, 3H), 3.93 (brs, 1H), 3.78 (brs, 1H), 3.66 (brs, 1H), 3.34 (brs, 1H), 3.11 (s, 3H), 2.97 (s, 3H), 2.76 (s, 6H), 2.18 (brs, 1H), 1.68 (brs, 1H). |

TABLE 20-continued

| Ex. No. | urea moiety structure | ¹H-NMR |
|---|---|---|
| 134 | | ¹H NMR (400 MHz, Chloroform-d) δ 8.05 (d, J = 2.3 Hz, 1H), 7.68 (ddd, J = 8.7, 1.7 Hz, 1H), 7.58-7.51 (m, 2H), 7.40 (dd, J = 7.9 Hz, 1H), 7.34 (d, J = 7.6 Hz, 1H), 7.19 (dd, J = 8.0 Hz, 2H), 7.15-7.01 (m, 4H), 6.88-6.79 (m, 1H), 6.69 (brs, 1H), 6.63 (brd, J = 7.7 Hz, 1H), 6.59 (brd, J = 8.0 Hz, 1H), 4.00 (s, 3H), 3.75 (t, J = 5.9 Hz, 2H), 3.70 (t, J = 5.1 Hz, 2H), 3.12 (s, 3H), 2.98 (s, 3H), 2.91 (s, 6H), 2.19 (p, J = 5.5 Hz, 2H). |
| 135 | | 1H NMR (400 MHz, Chloroform-d) δ 8.04 (d, J = 2.3 Hz, 1H), 7.69 (dd, J = 8.6, 2.4 Hz, 1H), 7.56-7.50 (m, 2H), 7.40 (dd, J = 7.3 Hz, 1H), 7.33 (ddd, J = 7.7, 1.3 Hz, 1H), 7.15-7.03 (m, 6H), 6.96-6.88 (m, 1H), 6.82 (ddd, J = 6.5, 2.1 Hz, 1H), 6.68 (d, J = 8.9 Hz, 2H), 4.03 (s, 3H), 3.72 (brd, J = 6.7 Hz, 2H), 3.68 (brd, J = 6.2 Hz, 2H), 3.11 (s, 3H), 2.98 (s, 3H), 2.91 (s, 6H), 2.17 (p, J = 5.9 Hz, 2H). |
| 136 | | 1H NMR (400 MHz, Chloroform-d) δ 8.04 (d, J = 2.1 Hz, 1H), 7.69 (d, J = 8.5 Hz, 1H), 7.52 (brs, 2H), 7.40 (dd, J = 7.8 Hz, 1H), 7.33 (d, J = 7.2 Hz, 1H), 7.18 (dd, J = 8.0 Hz, 1H), 7.15-6.99 (m, 4H), 6.89 (brs, 1H), 6.80 (brd, J = 7.1 Hz, 1H), 6.65-6.51 (m, 3H), 4.04 (s, 3H), 3.71 (brd, J = 14.9 Hz, 4H), 3.11 (s, 3H), 2.97 (s, 3H), 2.92 (s, 6H), 1.79 (brs, 4H). |

Experimental Example 1

Evaluation of Agonist Activity Against OX1R and OX2R

NAFT-luciferase gene and human OX1R gene were constitutively expressed in CHO cell, which is a cell line derived from Chinese hamster ovary to establish a cell line (CHOOX1R) and NAFT-luciferase gene and human OX2R gene were constitutively expressed in CHO cell to establish a cell line (CHOOX2R). The respective cells were seeded in a 96-well Multiplate at 10,000 cells/well and cultured in a 5% FBS (Thermo Scientific)-added DMEM medium (Sigma-Aldrich) for 48 hr. The medium was removed, an assay buffer (20 mM HEPES (Sigma-Aldrich), Hanks' balanced salt solution (Gibco), 0.1% BSA (Sigma-Aldrich), 2.5 mM probenecid acid (Wako Pure Chemical Industries, Ltd.)) (100 μL) containing 5 μM Fura-2AM (Cayman Chemical) was added, and the cells were incubated for 60 min. The buffer containing Fura-2AM was removed, and an assay buffer (75 μL) was added. An assay buffer (25 μL) containing a test compound was added thereto to start the reaction. Changes in the intracellular calcium ion concentration due to the reaction were measured by measuring the fluorescence intensity ratio by dual wavelength excitation at 340 and 380 nm, by using FDSS7000 (Hamamatsu Photonics K.K.). The test compound was dissolved in DMSO to 10 mM, and diluted with the assay buffer to a final concentration of $10^{-7}$M to $10^{-5}$M (final concentration of DMSO 1%). The agonist activity values of the respective compounds are shown in Table 21-Table 27.

TABLE 21

| Ex. No. | concentration | Response (%) OX1R | Response (%) OX2R |
|---|---|---|---|
| 1 | 0.1 μM | <5 | <5 |
| | 1.0 μM | <5 | 6 |
| | 10 μM | <5 | 67 |
| 2 | 0.1 μM | 13 | <5 |
| | 1.0 μM | 11 | 26 |
| | 10 μM | 32 | 74 |
| 3 | 0.1 μM | 14 | <5 |
| | 1.0 μM | 9 | 6 |
| | 10 μM | 12 | 23 |
| 4 | 0.1 μM | 10 | <5 |
| | 1.0 μM | 8 | <5 |
| | 10 μM | <5 | 16 |
| 5 | 0.1 μM | 8 | 10 |
| | 1.0 μM | 8 | 8 |
| | 10 μM | 7 | 19 |
| 6 | 0.1 μM | 7 | 9 |
| | 1.0 μM | 7 | 17 |
| | 10 μM | 6 | 32 |
| 7 | 0.1 μM | 6 | 8 |
| | 1.0 μM | 8 | 10 |
| | 10 μM | 27 | 24 |
| 8 | 0.1 μM | 9 | 8 |
| | 1.0 μM | 8 | 13 |
| | 10 μM | 27 | 61 |
| 9 | 0.1 μM | 5 | <5 |
| | 1.0 μM | 6 | 41 |
| | 10 μM | 5 | 47 |
| 10 | 0.1 μM | 5 | 14 |
| | 1.0 μM | 6 | 80 |
| | 10 μM | 11 | 98 |

TABLE 21-continued

| Ex. No. | concentration | Response (%) OX1R | Response (%) OX2R |
|---|---|---|---|
| 11 | 0.1 μM | <5 | <5 |
| | 1.0 μM | <5 | <5 |
| | 10 μM | 8 | 9 |
| 12 | 0.1 μM | <5 | <5 |
| | 1.0 μM | 11 | 9 |
| | 10 μM | 59 | 48 |
| 13 | 0.1 μM | <5 | 11 |
| | 1.0 μM | 63 | 117 |
| | 10 μM | 107 | 109 |
| 14 | 0.1 μM | <5 | <5 |
| | 1.0 μM | <5 | 18 |
| | 10 μM | <5 | 74 |
| 15 | 0.1 μM | <5 | 12 |
| | 1.0 μM | <5 | 81 |
| | 10 μM | <5 | 114 |
| 16 | 0.1 μM | <5 | <5 |
| | 1.0 μM | <5 | 19 |
| | 10 μM | 10 | 82 |
| 17 | 0.1 μM | <5 | <5 |
| | 1.0 μM | <5 | 9 |
| | 10 μM | 13 | 41 |
| 18 | 0.1 μM | <5 | <5 |
| | 1.0 μM | <5 | 6 |
| | 10 μM | 15 | 44 |
| 19 | 0.1 μM | <5 | <5 |
| | 1.0 μM | <5 | 10 |
| | 10 μM | <5 | 58 |
| 20 | 0.1 μM | <5 | <5 |
| | 1.0 μM | <5 | 51 |
| | 10 μM | 17 | 78 |

TABLE 22

| Ex. No. | concentration | Response (%) OX1R | Response (%) OX2R |
|---|---|---|---|
| 21 | 0.1 μM | <5 | <5 |
| | 1.0 μM | <5 | 37 |
| | 10 μM | 12 | 54 |
| 22 | 0.1 μM | <5 | 57 |
| | 1.0 μM | 47 | 61 |
| | 10 μM | 82 | 48 |
| 23 | 0.1 μM | <5 | 54 |
| | 1.0 μM | 10 | 95 |
| | 10 μM | 51 | 86 |
| 24 | 0.1 μM | <5 | <5 |
| | 1.0 μM | <5 | 72 |
| | 10 μM | 6 | 93 |
| 25 | 0.1 μM | <5 | 21 |
| | 1.0 μM | <5 | 88 |
| | 10 μM | 32 | 97 |
| 26 | 0.1 μM | <5 | <5 |
| | 1.0 μM | <5 | 51 |
| | 10 μM | 9 | 101 |
| 27 | 0.1 μM | <5 | 90 |
| | 1.0 μM | 24 | 126 |
| | 10 μM | 70 | 92 |
| 28 | 0.1 μM | <5 | 6 |
| | 1.0 μM | <5 | 54 |
| | 10 μM | <5 | 81 |
| 29 | 0.1 μM | <5 | 11 |
| | 1.0 μM | <5 | 84 |
| | 10 μM | <5 | 81 |
| 30 | 0.1 μM | <5 | <5 |
| | 1.0 μM | <5 | <5 |
| | 10 μM | <5 | 39 |
| 31 | 0.1 μM | <5 | <5 |
| | 1.0 μM | <5 | 10 |
| | 10 μM | <5 | 72 |
| 32 | 0.1 μM | <5 | 13 |
| | 1.0 μM | <5 | 79 |
| | 10 μM | 14 | 88 |

TABLE 22-continued

| Ex. No. | concentration | Response (%) OX1R | Response (%) OX2R |
|---|---|---|---|
| 33 | 0.1 μM | <5 | 37 |
| | 1.0 μM | <5 | 92 |
| | 10 μM | 50 | 87 |
| 34 | 0.1 μM | <5 | <5 |
| | 1.0 μM | <5 | 52 |
| | 10 μM | <5 | 95 |
| 35 | 0.1 μM | <5 | <5 |
| | 1.0 μM | <5 | 35 |
| | 10 μM | <5 | 63 |
| 36 | 0.1 μM | <5 | <5 |
| | 1.0 μM | <5 | 63 |
| | 10 μM | 10 | 93 |
| 37 | 0.1 μM | <5 | 55 |
| | 1.0 μM | <5 | 88 |
| | 10 μM | <5 | 81 |
| 38 | 0.1 μM | <5 | 68 |
| | 1.0 μM | <5 | 82 |
| | 10 μM | <5 | 71 |
| 39 | 0.1 μM | <5 | 73 |
| | 1.0 μM | <5 | 59 |
| | 10 μM | 32 | 53 |
| 40 | 0.1 μM | <5 | 77 |
| | 1.0 μM | <5 | 60 |
| | 10 μM | <5 | 52 |

TABLE 23

| Ex. No. | concentration | Response (%) OX1R | Response (%) OX2R |
|---|---|---|---|
| 41 | 0.1 μM | <5 | 17 |
| | 1.0 μM | <5 | 93 |
| | 10 μM | <5 | 102 |
| 42 | 0.1 μM | <5 | 93 |
| | 1.0 μM | <5 | 109 |
| | 10 μM | <5 | 95 |
| 43 | 0.1 μM | <5 | 102 |
| | 1.0 μM | <5 | 105 |
| | 10 μM | 10 | 104 |
| 44 | 0.1 μM | <5 | 100 |
| | 1.0 μM | <5 | 104 |
| | 10 μM | 10 | 95 |
| 45 | 0.1 μM | <5 | 82 |
| | 1.0 μM | <5 | 97 |
| | 10 μM | <5 | 100 |
| 46 | 0.1 μM | <5 | 74 |
| | 1.0 μM | <5 | 101 |
| | 10 μM | 8 | 115 |
| 47 | 0.1 μM | <5 | 7 |
| | 1.0 μM | <5 | 81 |
| | 10 μM | <5 | 102 |
| 48 | 0.1 μM | <5 | <5 |
| | 1.0 μM | <5 | <5 |
| | 10 μM | <5 | 14 |
| 49 | 0.1 μM | <5 | 26 |
| | 1.0 μM | <5 | 89 |
| | 10 μM | <5 | 92 |
| 50 | 0.1 μM | <5 | 100 |
| | 1.0 μM | <5 | 94 |
| | 10 μM | <5 | 97 |
| 51 | 0.1 μM | <5 | 93 |
| | 1.0 μM | 36 | 85 |
| | 10 μM | 67 | 88 |
| 52 | 0.1 μM | <5 | 43 |
| | 1.0 μM | <6 | 81 |
| | 10 μM | <7 | 78 |
| 53 | 0.1 μM | <8 | 98 |
| | 1.0 μM | 6 | 95 |
| | 10 μM | 26 | 100 |
| 54 | 0.1 μM | <5 | 91 |
| | 1.0 μM | <5 | 71 |
| | 10 μM | 10 | 61 |

TABLE 23-continued

| Ex. No. | concentration | Response (%) OX1R | OX2R |
|---|---|---|---|
| 55 | 0.1 μM | <5 | <5 |
|  | 1.0 μM | <5 | 54 |
|  | 10 μM | <5 | 105 |
| 56 | 0.1 μM | <5 | 95 |
|  | 1.0 μM | <5 | 96 |
|  | 10 μM | 19 | 82 |
| 57 | 0.1 μM | <5 | 91 |
|  | 1.0 μM | <5 | 92 |
|  | 10 μM | <5 | 60 |
| 58 | 0.1 μM | <5 | <5 |
|  | 1.0 μM | <5 | <5 |
|  | 10 μM | <5 | 63 |
| 59 | 0.1 μM | <5 | <5 |
|  | 1.0 μM | <5 | 18 |
|  | 10 μM | <5 | 52 |
| 60 | 0.1 μM | <5 | <5 |
|  | 1.0 μM | <5 | <5 |
|  | 10 μM | <5 | 31 |

TABLE 24

| Ex. No. | concentration | Response (%) OX1R | OX2R |
|---|---|---|---|
| 61 | 0.1 μM | <5 | 24 |
|  | 1.0 μM | <5 | 105 |
|  | 10 μM | 7 | 99 |
| 62 | 0.1 μM | 9 | 6 |
|  | 1.0 μM | 8 | 7 |
|  | 10 μM | 13 | 9 |
| 63 | 0.1 μM | 9 | 8 |
|  | 1.0 μM | 9 | 55 |
|  | 10 μM | 7 | 66 |
| 64 | 0.1 μM | <5 | <5 |
|  | 1.0 μM | <5 | <5 |
|  | 10 μM | <5 | <5 |
| 65 | 0.1 μM | <5 | <5 |
|  | 1.0 μM | <5 | <5 |
|  | 10 μM | <5 | 6 |
| 66 | 0.1 μM | 6 | 79 |
|  | 1.0 μM | 6 | 70 |
|  | 10 μM | 7 | 60 |
| 67 | 0.1 μM | 6 | 15 |
|  | 1.0 μM | 8 | 83 |
|  | 10 μM | 9 | 103 |
| 68 | 0.1 μM | 6 | 10 |
|  | 1.0 μM | 6 | 10 |
|  | 10 μM | 6 | 57 |
| 69 | 0.1 μM | 6 | 7 |
|  | 1.0 μM | 6 | 90 |
|  | 10 μM | 6 | 127 |
| 70 | 0.1 μM | 6 | 9 |
|  | 1.0 μM | 6 | 9 |
|  | 10 μM | 6 | 46 |
| 71 | 0.1 μM | 6 | 106 |
|  | 1.0 μM | <5 | 97 |
|  | 10 μM | 10 | 113 |
| 72 | 0.1 μM | <5 | 7 |
|  | 1.0 μM | <5 | 59 |
|  | 10 μM | <5 | 79 |
| 73 | 0.1 μM | 6 | 25 |
|  | 1.0 μM | 6 | 49 |
|  | 10 μM | <5 | 11 |
| 74 | 0.1 μM | 6 | 15 |
|  | 1.0 μM | 7 | 13 |
|  | 10 μM | 7 | 64 |
| 75 | 0.1 μM | <5 | 61 |
|  | 1.0 μM | <5 | 94 |
|  | 10 μM | 30 | 95 |
| 76 | 0.1 μM | <5 | 93 |
|  | 1.0 μM | 20 | 90 |
|  | 10 μM | 55 | 89 |

TABLE 24-continued

| Ex. No. | concentration | Response (%) OX1R | OX2R |
|---|---|---|---|
| 77 | 0.1 μM | <5 | <5 |
|  | 1.0 μM | <5 | 51 |
|  | 10 μM | <5 | 99 |
| 78 | 0.1 μM | <5 | 23 |
|  | 1.0 μM | <5 | 89 |
|  | 10 μM | 14 | 86 |
| 79 | 0.1 μM | <5 | <5 |
|  | 1.0 μM | <5 | <5 |
|  | 10 μM | <5 | 51 |
| 80 | 0.1 μM | <5 | <5 |
|  | 1.0 μM | <5 | <5 |
|  | 10 μM | <5 | 23 |

TABLE 25

| Ex. No. | concentration | Response (%) OX1R | OX2R |
|---|---|---|---|
| 81 | 0.1 μM | <5 | <5 |
|  | 1.0 μM | <5 | <5 |
|  | 10 μM | 7 | 27 |
| 82 | 0.1 μM | <5 | <5 |
|  | 1.0 μM | <5 | <5 |
|  | 10 μM | 7 | 16 |
| 83 | 0.1 μM | <5 | <5 |
|  | 1.0 μM | <5 | <5 |
|  | 10 μM | 9 | 11 |
| 84 | 0.1 μM | <5 | 6 |
|  | 1.0 μM | <5 | 6 |
|  | 10 μM | 10 | 21 |
| 85 | 0.1 μM | <5 | <5 |
|  | 1.0 μM | <5 | <5 |
|  | 10 μM | <5 | 12 |
| 86 | 0.1 μM | <5 | <5 |
|  | 1.0 μM | <5 | <5 |
|  | 10 μM | <5 | 11 |
| 87 | 0.1 μM | <5 | <5 |
|  | 1.0 μM | <5 | 10 |
|  | 10 μM | <5 | 56 |
| 88 | 0.1 μM | 7 | 15 |
|  | 1.0 μM | 7 | 13 |
|  | 10 μM | 9 | 13 |
| 89 | 0.1 μM | <5 | 7 |
|  | 1.0 μM | <5 | 8 |
|  | 10 μM | <5 | 31 |
| 90 | 0.1 μM | <5 | <5 |
|  | 1.0 μM | <5 | 56 |
|  | 10 μM | <5 | 89 |
| 91 | 0.1 μM | <5 | <5 |
|  | 1.0 μM | <5 | <5 |
|  | 10 μM | <5 | 35 |
| 92 | 0.1 μM | <5 | 35 |
|  | 1.0 μM | 6 | 95 |
|  | 10 μM | 30 | 95 |
| 93 | 0.1 μM | 10 | 16 |
|  | 1.0 μM | 9 | 77 |
|  | 10 μM | 20 | 85 |
| 94 | 0.1 μM | <5 | <5 |
|  | 1.0 μM | <5 | <5 |
|  | 10 μM | <5 | 46 |
| 95 | 0.1 μM | <5 | <5 |
|  | 1.0 μM | <5 | 11 |
|  | 10 μM | <5 | 68 |
| 96 | 0.1 μM | <5 | <5 |
|  | 1.0 μM | <5 | <5 |
|  | 10 μM | <5 | 67 |
| 97 | 0.1 μM | <5 | 25 |
|  | 1.0 μM | <5 | 84 |
|  | 10 μM | 11 | 108 |
| 98 | 0.1 μM | 8 | 13 |
|  | 1.0 μM | 8 | 11 |
|  | 10 μM | 9 | 67 |

TABLE 25-continued

| Ex. No. | concentration | Response (%) OX1R | Response (%) OX2R |
|---|---|---|---|
| 99 | 0.1 μM | 8 | 19 |
|  | 1.0 μM | 8 | 14 |
|  | 10 μM | 9 | 76 |
| 100 | 0.1 μM | <5 | <5 |
|  | 1.0 μM | <5 | 7 |
|  | 10 μM | <5 | 49 |

TABLE 26

| Ex. No. | concentration | Response (%) OX1R | Response (%) OX2R |
|---|---|---|---|
| 101 | 0.1 μM | <5 | 20 |
|  | 1.0 μM | <5 | 89 |
|  | 10 μM | <5 | 111 |
| 102 | 0.1 μM | <5 | 61 |
|  | 1.0 μM | <5 | 97 |
|  | 10 μM | <5 | 100 |
| 103 | 0.1 μM | <5 | 4 |
|  | 1.0 μM | <5 | 27 |
|  | 10 μM | <5 | 84 |
| 104 | 0.1 μM | 7 | 7 |
|  | 1.0 μM | 6 | 79 |
|  | 10 μM | 7 | 99 |
| 105 | 0.1 μM | 8 | 9 |
|  | 1.0 μM | 7 | 32 |
|  | 10 μM | 8 | 92 |
| 106 | 0.1 μM | 8 | 9 |
|  | 1.0 μM | 7 | 7 |
|  | 10 μM | 8 | 46 |
| 107 | 0.1 μM | <5 | 7 |
|  | 1.0 μM | <5 | 9 |
|  | 10 μM | <5 | 80 |
| 108 | 0.1 μM | <5 | 6 |
|  | 1.0 μM | <5 | 6 |
|  | 10 μM | <5 | 24 |
| 109 | 0.1 μM | 8 | 7 |
|  | 1.0 μM | 9 | 6 |
|  | 10 μM | 7 | 39 |
| 110 | 0.1 μM | <5 | 38 |
|  | 1.0 μM | <5 | 86 |
|  | 10 μM | <5 | 109 |
| 111 | 0.1 μM | <5 | 32 |
|  | 1.0 μM | <5 | 88 |
|  | 10 μM | <5 | 100 |
| 112 | 0.1 μM | <5 | <5 |
|  | 1.0 μM | <5 | 26 |
|  | 10 μM | <5 | 69 |
| 113 | 0.1 μM | <5 | <5 |
|  | 1.0 μM | <5 | 6 |
|  | 10 μM | <5 | 73 |
| 114 | 0.1 μM | <5 | <5 |
|  | 1.0 μM | <5 | <5 |
|  | 10 μM | <5 | 28 |
| 115 | 0.1 μM | <5 | <5 |
|  | 1.0 μM | <5 | 8 |
|  | 10 μM | <5 | 62 |
| 116 | 0.1 μM | 6 | 7 |
|  | 1.0 μM | 9 | 6 |
|  | 10 μM | 7 | 7 |
| 117 | 0.1 μM | <5 | <5 |
|  | 1.0 μM | <5 | 16 |
|  | 10 μM | <5 | 44 |
| 118 | 0.1 μM | 9 | 11 |
|  | 1.0 μM | 8 | 36 |
|  | 10 μM | 9 | 71 |
| 119 | 0.1 μM | <5 | 49 |
|  | 1.0 μM | <5 | 85 |
|  | 10 μM | <5 | 98 |
| 120 | 0.1 μM | <5 | 29 |
|  | 1.0 μM | <5 | 84 |
|  | 10 μM | <5 | 103 |

TABLE 27

| Ex. No. | concentration | Response (%) OX1R | Response (%) OX2R |
|---|---|---|---|
| 121 | 0.1 μM | <5 | 7 |
|  | 1.0 μM | <5 | 47 |
|  | 10 μM | 10 | 104 |
| 122 | 0.1 μM | <5 | 7 |
|  | 1.0 μM | <5 | 7 |
|  | 10 μM | <5 | 10 |
| 123 | 0.1 μM | <5 | 63 |
|  | 1.0 μM | 6 | 111 |
|  | 10 μM | <5 | 111 |
| 124 | 0.1 μM | 8 | 9 |
|  | 1.0 μM | 7 | 78 |
|  | 10 μM | 8 | 147 |
| 125 | 0.1 μM | <5 | 42 |
|  | 1.0 μM | <5 | 78 |
|  | 10 μM | <5 | 79 |
| 126 | 0.1 μM | 5 | 7 |
|  | 1.0 μM | 5 | 37 |
|  | 10 μM | <5 | 85 |
| 127 | 0.1 μM | <5 | 106 |
|  | 1.0 μM | 7 | 90 |
|  | 10 μM | 56 | 73 |
| 128 | 0.1 μM | <5 | 10 |
|  | 1.0 μM | <5 | 77 |
|  | 10 μM | 6 | 105 |
| 129 | 0.1 μM | <5 | 85 |
|  | 1.0 μM | 41 | 93 |
|  | 10 μM | 81 | 92 |
| 130 | 0.1 μM | <5 | 64 |
|  | 1.0 μM | <5 | 99 |
|  | 10 μM | 6 | 106 |
| 131 | 0.1 μM | <5 | 43 |
|  | 1.0 μM | <5 | 96 |
|  | 10 μM | 18 | 101 |
| 132 | 0.1 μM | <5 | 42 |
|  | 1.0 μM | <5 | 100 |
|  | 10 μM | 46 | 101 |
| 133 | 0.1 μM | 25 | 107 |
|  | 1.0 μM | 86 | 81 |
|  | 10 μM | 84 | 72 |
| 134 | 0.1 μM | 9 | 101 |
|  | 1.0 μM | 13 | 76 |
|  | 10 μM | 84 | 75 |
| 135 | 0.1 μM | 8 | 94 |
|  | 1.0 μM | 14 | 66 |
|  | 10 μM | 83 | 64 |
| 136 | 0.1 μM | <5 | 144 |
|  | 1.0 μM | 78 | 97 |
|  | 10 μM | 110 | 94 |

(As used herein, Response in Table 21 to Table 27 is a value obtained by dividing the agonist activity value, when the test compound is evaluated with orexin-A as a full-agonist (maximum value of agonist activity: 100%), at 10 μM, 1.0 μM, 0.1 μM by the agonist activity value of orexin-A.)

Experimental Example 2

Awakening Effect on Wild-Type Mouse by Light Period Intraventricular Administration of the Compound of the Present Invention As the experiment animal, C57BL/6 lineage wild-type mouse (male) was used. The mice before and after 9-week-old (±1 week) underwent surgery for embedding electroencephalogram electrodes into the skull (Bregma: X=1.5; Y=0.6, Lambda: X=1.5; Y=0) and inserting electromyogram electrodes into the trapezius muscle under isoflurane anesthesia. The mice for intraventricular administration also underwent cannula embedding into lateral cerebral ventricle (Bregma: X=−0.9; Y=−0.3). From two weeks thereafter, the administration and electroencephalogram measurement were started. The experiment was conducted under a light-dark cycle environment in which the light period started at 9 (ZT0) and the dark period started at 21 (ZT12).

The test compound (compound of Example 40) (10 nmol; dissolved in 5% chromophore-containing saline) (5 μl) was injected at ZT6 into the lateral cerebral ventricle of wild-type mice under isoflurane anesthesia through cannula by using a microsyringe pump at a flow rate of 0.5 μl/min, and electroencephalogram and electromyogram was measured thereafter. The administration was started with 5% chromophore-containing saline (Vehicle) as a control, and then the test compound was administered. In each case, one day after the administration was set as a recovery period. The results are shown in the FIGURE.

When the test compound was intraventricularly administered in the light period (ZT6), which is a sleep period for mouse, the conscious time increased in the wild-type mouse as compared to the Vehicle administration.

INDUSTRIAL APPLICABILITY

The compound of the present invention shows an orexin receptor agonist activity, and is useful as a prophylactic or therapeutic agent for narcolepsy and the like.

This application is based on a patent application No. 2015-119785 filed in Japan (filing date: Jun. 12, 2015), the entire contents of which are incorporated by reference herein.

The invention claimed is:

1. A compound represented by the formula (I):

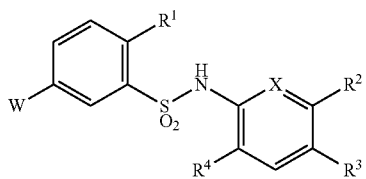

wherein
$R^1$ is a hydrogen atom, $C_{1-6}$ alkoxy, —OH, $C_{1-6}$ alkyl or a halogen atom,
X is —C($R^5$)= or —N=,
$R^5$ is a hydrogen atom or $C_{1-6}$ alkoxy,
any one of $R^2$, $R^3$ and $R^4$ is $R^6$ and the remaining two are each a hydrogen atom,
$R^6$ is
(1) —$NR^{17}$—$Y^1$—$R^7$
wherein $Y^1$ is —C(=O)$NR^{18}$—, —C(=S)NH—, —C(=NH)NH—, —C(=O)O—, —C(=O)—, —$SO_2$— or —$SO_2$—$NR^8$—,
$R^8$ is a hydrogen atom or $C_{1-6}$ alkyl,
$R^{17}$ is a hydrogen atom or $C_{1-6}$ alkyl,
$R^{18}$ is a hydrogen atom or $C_{1-6}$ alkyl, or
$R^{17}$ and $R^{18}$ are optionally bonded to each other to form, together with the nitrogen atoms bonded thereto and adjacent C(=O), a 5- to 7-membered heterocycle,
$R^7$ is
(a) $C_{6-10}$ aryl,
(b) 5- to 10-membered heteroaryl,
(c) $C_{1-6}$ alkyl, or
(d) $C_{2-6}$ alkenyl
wherein $C_{1-6}$ alkyl and $C_{2-6}$ alkenyl are optionally substituted by one substituent selected from phenyl, furyl and diphenylmethylsulfinyl, $C_{6-10}$ aryl and 5- to 10-membered heteroaryl are optionally substituted by optionally selected $R^9$ in the number of 1 to 4,
$R^9$ are each independently
a halogen atom,
—$NO_2$,
—OH,
$C_{1-6}$ alkyl,
$C_{1-6}$ haloalkyl,
$C_{1-6}$ alkoxy,
5- to 10-membered heteroaryl,
—$NR^{9a}R^{9b}$ wherein $R^{9a}$ is a hydrogen atom, $C_{1-6}$ alkyl or $C_{1-6}$ alkoxy-carbonyl, and $R^{9b}$ is a hydrogen atom or $C_{1-6}$ alkyl,
—C(=O)$OR^{9c}$ wherein $R^{9c}$ is a hydrogen atom or $C_{1-6}$ alkyl,
—C(=O)$NR^{9d}R^{9e}$ wherein $R^{9d}$ is a hydrogen atom or $C_{1-6}$ alkyl, and $R^{9e}$ is a hydrogen atom or $C_{1-6}$ alkyl, or
—NH—C(=$NR^{9f}$)—$NHR^{9g}$ wherein $R^{9f}$ is a hydrogen atom or $C_{1-6}$ alkoxy-carbonyl, and $R^{9g}$ is a hydrogen atom or $C_{1-6}$ alkoxy-carbonyl, or
$R^9$ in the number of 2 are joined to form methylenedioxy,
(2) —NH—$Y^2$—$R^{10}$
wherein $Y^2$ is —$CH_2$— or a single bond, and
$R^{10}$ is
(a) $C_{6-10}$ aryl, or
(b) 5- to 10-membered heteroaryl
wherein $C_{6-10}$ aryl and 5- to 10-membered heteroaryl are optionally substituted by optionally selected $R^9$ in the number of 1 to 4, and $R^9$ is as defined above,
(3) a group represented by the formula (ii):

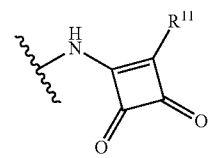

wherein $R^{11}$ is $C_{1-6}$ alkoxy or $C_{6-10}$ arylamino (wherein $C_{6-10}$ aryl moiety of the $C_{6-10}$ arylamino is optionally substituted by 1 to 3 substituents selected from $C_{1-6}$ alkyl and $C_{1-6}$ alkoxy),
(4) —N=N—$R^{12}$
wherein $R^{12}$ is $C_{6-10}$ aryl optionally substituted by 1 to 3 substituents selected from (a) $C_{1-6}$ alkyl optionally substituted by —OH, (b) —OH, (c) di($C_{1-6}$ alkyl)amino and (d) $C_{1-6}$ alkoxy-carbonylamino, or
(5) —$NR^{13}R^{14}$
wherein $R^{13}$ is a hydrogen atom, $C_{1-6}$ alkyl, $C_{6-10}$ aryl-$C_{1-6}$ alkyl or $C_{2-6}$ alkenyl-carbonyl, and
$R^{14}$ is a hydrogen atom or $C_{1-6}$ alkyl (wherein $C_{1-6}$ alkyl is optionally substituted by one substituent selected from (a) $C_{2-6}$ alkenyl-carbonylamino and (b) $C_{6-10}$ aryl-$C_{1-6}$ alkylaminocarbonyl optionally substituted by $C_{1-6}$ alkyl), or $R^{13}$ and $R^{14}$ are bonded to each other to form, together with the nitrogen atom bonded thereto, a 5- to 7-membered heterocycle further containing one nitrogen atom (wherein 5- to 7-membered heterocycle is optionally substituted by $C_{6-10}$ aryl-carbonyl optionally substituted by $C_{1-6}$ alkyl), provided that when $R^{14}$ is ethyl substituted by $C_{2-6}$ alkenyl-carbonylamino, $R^{13}$ is not a hydrogen atom, and W is a group represented by the formula (iii):

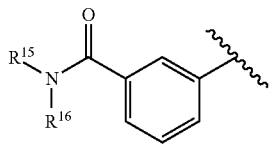

(iii)

wherein $R^{15}$ is $C_{1-6}$ alkyl, and $R^{16}$ is $C_{1-6}$ alkyl, or a pharmaceutically acceptable acid addition salt thereof.

2. The compound according to claim 1 wherein $R^{17}$ and $R^{18}$ are each a hydrogen atom, or a pharmaceutically acceptable acid addition salt thereof.

3. The compound according to claim 1 wherein X is $-C(R^5)=$, wherein $R^5$ is a hydrogen atom or $C_{1-6}$ alkoxy, or a pharmaceutically acceptable acid addition salt thereof.

4. The compound according to claim 1 wherein $R^2$ is $R^6$ (wherein $R^6$ is as defined in claim 1), and $R^3$ and $R^4$ are each a hydrogen atom, or a pharmaceutically acceptable acid addition salt thereof.

5. The compound according to claim 1 wherein $R^6$ is $-NR^{17}-Y^1-R^7$ (wherein $R^{17}$, $Y^1$ and $R^7$ are as defined in claim 1), or a pharmaceutically acceptable acid addition salt thereof.

6. The compound according to claim 1 wherein $R^6$ is $-NH-Y^2-R^{10}$ (wherein $Y^2$ and $R^{10}$ are as defined in claim 1), or a pharmaceutically acceptable acid addition salt thereof.

7. The compound according to claim 1 wherein $R^6$ is a group represented by the formula (ii):

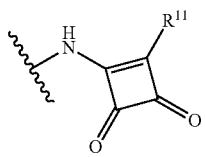

(ii)

wherein $R^{11}$ is as defined in claim 1, or a pharmaceutically acceptable acid addition salt thereof.

8. The compound according to claim 1 wherein $R^6$ is $-N=N-R^{12}$ (wherein $R^{12}$ is as defined in claim 1), or a pharmaceutically acceptable acid addition salt thereof.

9. The compound according to claim 1 wherein $R^6$ is $-NR^{13}R^{14}$ (wherein $R^{13}$ and $R^{14}$ are as defined in claim 1), or a pharmaceutically acceptable acid addition salt thereof.

10. The compound according to claim 1 wherein W is a group represented by the formula (iii):

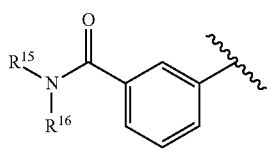

(iii)

wherein $R^{15}$ is $C_{1-6}$ alkyl and $R^{16}$ is $C_{1-6}$ alkyl,

X is $-C(R^5)=$ wherein $R^5$ is a hydrogen atom or $C_{1-6}$ alkoxy, $R^2$ is $-NH-Y^1-R^7$ wherein $Y^1$ and $R^7$ are as defined in claim 1, and $R^3$ and $R^4$ are each a hydrogen atom, or a pharmaceutically acceptable acid addition salt thereof.

11. The compound according to claim 10 wherein $Y^1$ is $-C(=O)NH-$, $-C(=S)NH-$, $-C(=NH)NH-$ or $-C(=O)O-$, or a pharmaceutically acceptable acid addition salt thereof.

12. A compound represented by the formula (I-B):

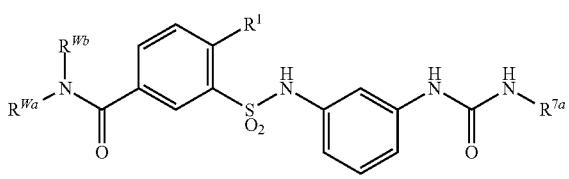

(I-B)

wherein $R^{7a}$ is phenyl substituted by $-NR^{9a}R^{9b}$ (wherein $R^{9a}$ is $C_{1-6}$ alkyl and $R^{9b}$ is $C_{1-6}$ alkyl), $R^1$ is a hydrogen atom, $C_{1-6}$ alkoxy, $-OH$, $C_{1-6}$ alkyl or a halogen atom, $R^{Wa}$ is $C_{1-6}$ alkyl (wherein $C_{1-6}$ alkyl is optionally substituted by phenyl, pyridyl, $C_{1-6}$ alkoxy-carbonylamino or di($C_{1-6}$ alkyl)amino) or phenyl (wherein phenyl is optionally substituted by di($C_{1-6}$ alkyl)amino), and $R^{Wb}$ is a hydrogen atom or $C_{1-6}$ alkyl, or a pharmaceutically acceptable acid addition salt thereof.

13. A compound represented by the formula (I'):

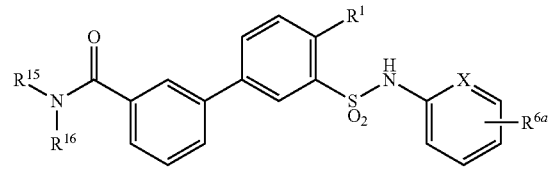

(I')

wherein $R^1$ is a hydrogen atom, $C_{1-6}$ alkoxy, $-OH$, $C_{1-6}$ alkyl or a halogen atom, X is $-C(R^5)=$ or $-N=$, $R^5$ is a hydrogen atom or $C_{1-6}$ alkoxy, $R^{6a}$ is an optionally substituted hydrocarbon group, an optionally substituted heterocyclic group, a group bonded via an oxygen atom, or a group bonded via a sulfur atom, $R^{15}$ is $C_{1-6}$ alkyl, and $R^{16}$ is $C_{1-6}$ alkyl, or a pharmaceutically acceptable acid addition salt thereof.

14. A medicament comprising the compound according to claim 1 or a pharmaceutically acceptable acid addition salt thereof.

15. A method of treating or preventing narcolepsy narcolepsy, obesity, diabetes, depression, sepsis, severe sepsis or septic shock comprising administering an effective amount of the compound according to claim 1 or a pharmaceutically acceptable acid addition salt thereof.

16. A method of improving sleepiness comprising administering an effective amount of the compound according to claim 1 or a pharmaceutically acceptable acid addition salt thereof.

17. A medicament comprising the compound according to claim 13 or a pharmaceutically acceptable acid addition salt thereof.

18. A method of treating or preventing narcolepsy, obesity, diabetes, depression, sepsis, severe sepsis or septic shock, or improving sleepiness comprising administering an effective amount of the compound according to claim 13 or a pharmaceutically acceptable acid addition salt thereof.

19. A medicament comprising the compound according to claim 12 or a pharmaceutically acceptable acid addition salt thereof.

20. A method of treating or preventing narcolepsy, obesity, diabetes, depression, sepsis, severe sepsis or septic shock, or improving sleepiness comprising administering an effective amount of the compound according to claim 12 or a pharmaceutically acceptable acid addition salt thereof.

* * * * *